(12) United States Patent
Yamazaki et al.

(10) Patent No.: US 8,552,170 B2
(45) Date of Patent: Oct. 8, 2013

(54) EXPRESSION VECTOR FOR ESTABLISHING HIGHLY PRODUCTIVE CELL AND THE HIGHLY PRODUCTIVE CELL

(75) Inventors: Tomomi Yamazaki, Tsuruga (JP); Kenji Masuda, Tsuruga (JP); Shigeaki Nishii, Tsuruga (JP); Bunsei Kawakami, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 75 days.

(21) Appl. No.: 13/122,119

(22) PCT Filed: Jun. 4, 2010

(86) PCT No.: PCT/JP2010/003759
§ 371 (c)(1),
(2), (4) Date: Mar. 31, 2011

(87) PCT Pub. No.: WO2010/140387
PCT Pub. Date: Dec. 9, 2010

(65) Prior Publication Data
US 2011/0281286 A1 Nov. 17, 2011

(30) Foreign Application Priority Data

| Jun. 5, 2009 | (JP) | 2009-136512 |
| Jun. 19, 2009 | (JP) | 2009-146703 |
| Dec. 28, 2009 | (JP) | 2009-297963 |
| Feb. 4, 2010 | (JP) | 2010-023321 |
| Feb. 10, 2010 | (JP) | 2010-027317 |
| Apr. 21, 2010 | (JP) | 2010-098246 |
| Apr. 21, 2010 | (JP) | 2010-098247 |
| Jun. 1, 2010 | (JP) | 2010-126179 |

(51) Int. Cl.
*C07H 21/04* (2006.01)
*C12N 15/85* (2006.01)
*C12P 21/00* (2006.01)

(52) U.S. Cl.
USPC .......... 536/24.1; 435/325; 435/70.1; 435/455

(58) Field of Classification Search
None
See application file for complete search history.

(56) References Cited

U.S. PATENT DOCUMENTS

| 5,627,033 A | 5/1997 | Smith et al. |
| 7,344,886 B2 | 3/2008 | Enenkel et al. |

FOREIGN PATENT DOCUMENTS

| EP | 0 481 790 A2 | 4/1992 |
| JP | 2001-037478 A | 2/2001 |
| JP | 2007-503837 A | 3/2007 |
| WO | WO 01/032901 A1 | 5/2001 |
| WO | WO 2004/050884 A2 | 6/2004 |
| WO | WO 2005/024015 A1 | 3/2005 |

OTHER PUBLICATIONS

Jenks, Trends in Comparative Endocrinology and Neurobiology, 2009. Ann. N. Y. Acad. Sci. vol. 1163, pp. 17-30.*
Dickmeis, Briefings in Functional Genomics and Proteomics, 2005. vol. 3, No. 4, pp. 332-350.*
Kwaks et al., *Journal of Biotechnology*, 115(1): 35-46 (2005).
Majors et al., *Biotechnology and Bioengineering*, 101(3): 567-578 (2008).
Ng et al., *Metabolic Engineering*, 9(3): 304-316 (2007).
Pham et al., *Bio Techniques*, 45(2): 155-162 (2008).
Pon et al., *Cell Biochemistry and Biophysics*, 29(1/02): 159-178 (1998).
Romanos et al., *Yeast*, 8: 423-488 (1992).
Schmidt et al., *Phytochemistry Reviews*, 7(3): 539-552 (2008).
Voon et al., *Nucleic Acids Research*, 33(3): e27 (Feb. 16, 2005).
Wang et al., *Applied Microbiology and Biotechnology*, 76(3): 651-657 (2007).
European Patent Office, Extended European Search Report in European Patent Application No. 10783175.2 (Jul. 23, 2012).
International Bureau of WIPO, International Preliminary Report on Patentability in International Patent Application PCT/JP2010/003759 (Jan. 26, 2012).
Allison et al., *Bioprocessing Journal*, Mar/Apr. 2003: 33-40 (2003).
Bakheet et al., *Nucleic Acids Research*, 29(1): 246-254 (2001).
Bao et al., *Nucleic Acids Research*, 36: D83-D87 (2008).
Blasco, *Nature Reviews Genetics*, 8: 299-309 (Apr. 2007).
Butler, *Appl. Microbiol. Biotechnol.*, 68: 283-291 (2005).
Gonzalo et al., *Nature Cell Biology*, 8(4): 416-424 and S3 (Apr. 2006).
Houdebine, *Current Opinion in Biotechnology*, 13: 625-629 (2002).
Izumi et al., *Journal of Cellular Biochemistry*, 76: 280-289 (1999).
Kim et al., *Journal of Biotechnology*, 107: 95-105 (2004).
Kwaks et al., *Trends in Biotechnology*, 24(3): 137-142 (2006).
Lagnado et al., *Molecular and Cellular Biology*, 14(12): 7984-7995 (Dec. 1994).
Miloux et al., *Gene*, 149: 341-344 (1994).
Niwa et al., *Gene*, 108: 193-200 (1991).
Perrod et al., *Cell. Mol. Life Sci.*, 60: 2303-2318 (2003).
Pikaart et al., *Genes & Development*, 12: 2852-2862 (1998).
Wakimoto, *Cell*, 93: 321-324 (May 1, 1998).
Zubiaga et al., *Molecular and Cellular Biology*, 15(4): 2219-2230 (Apr. 1995).
International Search Report for International Patent Application PCT/JP2010/003759 (Jul. 6, 2010) English.

* cited by examiner

*Primary Examiner* — Celine Qian
(74) *Attorney, Agent, or Firm* — Leydig, Voit & Mayer, Ltd.

(57) ABSTRACT

The present invention provides an expression vector which is effective in an efficient establishment of transformed cells which express the aimed protein gene in a high level. An expression vector which has a cassette for expressing the drug selective marker gene containing mRNA destabilizing sequence, at least one element for stabilizing the gene expression and a cassette for expressing the gene of the aimed protein. Preferably, the mRNA destabilizing sequence is derived from AT-rich sequence existing in the 3'-untranslated region of cytokine, interleukin or proto-oncogene, and the element for stabilizing the gene expression is derived from Chinese hamster genome.

17 Claims, 63 Drawing Sheets pBS-CMV-SNAPm-Pur pBS-CMV-SNAPm-Pur・N4 pBS-CMV-SNAPm-Pur pBS-CMV-SNAPm-Pur・N4 pEF1α-SNAP26m-Pur-RE2

· Pur: 5 μg/mL    · Pur: 7.5 μg/mL    · Pur: 10 μg/mL pEF1α-SNAP26m-Pur·N4

· Pur: 5 μg/mL    · Pur: 7.5 μg/mL    · Pur: 10 μg/mL pEF1α-SNAP26m-Neo-RE2 pEF1α-SNAP26m-Neo・N4 pEF1α-SNAP26m-Pur-RE2    pEF1α-SNAP26m-Pur·N2 pEF1α-SNAP26m-Pur·N4    pEF1α-SNAP26m-Pur·N6 pEF1α-SNAP26m-Pur·N8 pEF1α-SNAP26m-Pur-RE2

- Pur: 5 μg/mL
- Pur: 7.5 μg/mL
- Pur: 10 μg/mL pEF1α-SNAP26m-Pur-1.1k/1.1k

- Pur: 5 μg/mL
- Pur: 7.5 μg/mL
- Pur: 10 μg/mL pEF1α-SNAP26m-Pur·N4

- Pur: 5 μg/mL
- Pur: 7.5 μg/mL
- Pur: 10 μg/mL pEF1α-SNAP26m-Pur·N4-1.1k/1.1k

- Pur: 5 μg/mL
- Pur: 7.5 μg/mL
- Pur: 10 μg/mL pEF1α-SNAP26m-Hyg-RE2 pEF1α-SNAP26m-Hyg-1.1k/1.1k pEF1α-SNAP26m-Hyg·N4 pEF1α-SNAP26m-Hyg·N4-1.1k/1.1k pEF1α-SNAP26m-Neo-RE2 pEF1α-SNAP26m-Neo-1.1k/1.1k pEF1α-SNAP26m-Neo・N4 pEF1α-SNAP26m-Neo・N4-1.1k/1.1k pEF1α-SNAP26m-Pur-1.1k/1.1k pEF1α-SNAP26m-Pur·N2-1.1k/1.1k pEF1α-SNAP26m-Pur·N4-1.1k/1.1k pEF1α-SNAP26m-Pur·N6-1.1k/1.1k pEF1α-SNAP26m-Pur·N8-1.1k/1.1k

*Restriction enzyme BsiW I, Sal I, and Sma I sites within Pur have been deleted.

pEF1α-SNAP26m-Pur·N4-1.1k/1.1k

・Pur: 7.5 μg/mL     ・Pur: 10 μg/mL pEH(M-SNAP26m-N)

・Pur: 7.5 μg/mL     ・Pur: 10 μg/mL pEH(B-SNAP26m-N)

・Pur: 7.5 μg/mL     ・Pur: 10 μg/mL

```
                             SEQUENCE LISTING

<160> NUMBER OF SEQ ID NOS: 123

<210> SEQ ID NO 1
<211> LENGTH: 654
<212> TYPE: DNA
<213> ORGANISM: cytomegarovirus

<400> SEQUENCE: 1
gatgtacggg ccagatatac gcgttgacat tgattattga ctagttatta atagtaatca      60
attacggggt cattagttca tagcccatat atggagttcc gcgttacata acttacggta     120
aatggcccgc ctggctgacc gcccaacgac ccccgcccat tgacgtcaat aatgacgtat     180
gttcccatag taacgccaat agggactttc cattgacgtc aatgggtgga gtatttacgg     240
taaactgccc acttggcagt acatcaagtg tatcatatgc caagtacgcc ccctattgac     300
gtcaatgacg gtaaatggcc cgcctggcat tatgcccagt acatgacctt atgggacttt     360
cctacttggc agtacatcta cgtattagtc atcgctatta ccatggtgat gcggttttgg     420
cagtacatca atgggcgtgg atagcggttt gactcacggg gatttccaag tctccacccc     480
attgacgtca atgggagttt gttttggcac caaaatcaac gggactttcc aaaatgtcgt     540
aacaactccg ccccattgac gcaaatgggc ggtaggcgtg tacggtggga ggtctatata     600
agcagagctc tctggctaac tagagaaccc actgcttact ggcttatcga aatt          654

<210> SEQ ID NO 2
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 2
atcgaattca ccatggacaa agactg                                          26

<210> SEQ ID NO 3
<211> LENGTH: 38
<212> TYPE: DNA
<213> ORGANISM: Artificial Sequence
<220> FEATURE:
<223> OTHER INFORMATION: Synthetic

<400> SEQUENCE: 3
ctatgcggcc gctcatggcg cgcctatacc tgcaggac                             38

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
gggatcgatg tacgggccag atatacgcg                                       29

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
ctgggatcca taccacattt gtagaggttt tacttg                               36

<210> SEQ ID NO 6
<211> LENGTH: 29
<212> TYPE: DNA
<213> ORGANISM: Artificial Sequence
<220> FEATURE:
<223> OTHER INFORMATION: Synthetic

<400> SEQUENCE: 6
ttatcaggca ccgggcttgc gggtcatgc                                       29

<210> SEQ ID NO 7
<211> LENGTH: 79
<212> TYPE: DNA
<213> ORGANISM: Artificial Sequence
<220> FEATURE:
<223> OTHER INFORMATION: Synthetic

<400> SEQUENCE: 7
ttatttattg atccttattt attgatcctt atttattgat ccttatttat taaggcccgc     60
cccacgaccc gcagcgccc                                                  79

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
gggggatcct gtggaatgtc tctacgttag gg                                   32
```

```
<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
ggggagctcc agacatgata agatacattg atg                                  33

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
cgctagctga gatctcttcg tgaggctccg                                      30

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
gtcgacagtc gagccatgtg agcaaaaggc                                      30

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
gactcgaggc gtatggtgca ctctcagtac                                      30

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
cttcgtacgt ggatccttat cgctatcgat tc                                   32

<210> SEQ ID NO 14
<211> LENGTH: 35
<212> TYPE: DNA
<213> ORGANISM: Artificial Sequence
<220> FEATURE:
<223> OTHER INFORMATION: Synthetic

<400> SEQUENCE: 14
gggcttaagc caccatgacc gagtacaagc ccacg                                35

<210> SEQ ID NO 15
<211> LENGTH: 34
<212> TYPE: DNA
<213> ORGANISM: Artificial Sequence
<220> FEATURE:
<223> OTHER INFORMATION: Synthetic

<400> SEQUENCE: 15
```

```
gcttcgaagg gcgctgcggg tcgtggggcg ggcc                          34
```

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16

```
ggttcgaaat gaccgaccaa gc                                       22
```

<210> SEQ ID NO 17
<211> LENGTH: 26
<212> TYPE: DNA
<213> ORGANISM: Artificial Sequence
<220> FEATURE:
<223> OTHER INFORMATION: Synthetic

<400> SEQUENCE: 17

```
tcaggcaccg ggcttgcggg tcatgc                                   26
```

<210> SEQ ID NO 18
<211> LENGTH: 33
<212> TYPE: DNA
<213> ORGANISM: Artificial Sequence
<220> FEATURE:
<223> OTHER INFORMATION: Synthetic

<400> SEQUENCE: 18

```
gatggcttaa gatgaaaaag cctgaactca ccg                           33
```

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19

```
gtaggttcga atcagttagc ctcccccatc tcc                           33
```

<210> SEQ ID NO 20
<211> LENGTH: 26
<212> TYPE: DNA
<213> ORGANISM: Artificial Sequence
<220> FEATURE:
<223> OTHER INFORMATION: Synthetic

<400> SEQUENCE: 20

```
atcacgcgta ccatggacaa agactg                                   26
```

<210> SEQ ID NO 21
<211> LENGTH: 54
<212> TYPE: DNA
<213> ORGANISM: Artificial Sequence
<220> FEATURE:
<223> OTHER INFORMATION: Synthetic

<400> SEQUENCE: 21

```
ttatttattg atccttattt attttcgaaa tgaccgacca agcgacgccc aacc    54
```

<210> SEQ ID NO 22
<211> LENGTH: 56
<212> TYPE: DNA
<213> ORGANISM: Artificial Sequence

```
<220> FEATURE:
<223> OTHER INFORMATION: Synthetic

<400> SEQUENCE: 22
ggatcaataa ataaggatca ataaataatc agttagcctc ccccatctcc cgatcc        56

<210> SEQ ID NO 23
<211> LENGTH: 56
<212> TYPE: DNA
<213> ORGANISM: Artificial Sequence
<220> FEATURE:
<223> OTHER INFORMATION: Synthetic

<400> SEQUENCE: 23
ggatcaataa ataaggatca ataaataatc agaagaactc gtcaagaagg cgatag        56

<210> SEQ ID NO 24
<211> LENGTH: 44
<212> TYPE: DNA
<213> ORGANISM: Artificial Sequence
<220> FEATURE:
<223> OTHER INFORMATION: Synthetic

<400> SEQUENCE: 24
ggatcaataa ataaggatca ataaataata atcaggcacc gggc                    44

<210> SEQ ID NO 25
<211> LENGTH: 72
<212> TYPE: DNA
<213> ORGANISM: Artificial Sequence
<220> FEATURE:
<223> OTHER INFORMATION: Synthetic

<400> SEQUENCE: 25
ggatcaataa ataaggatca ataaataagg atcaataaat aaggatcaat aaataataat   60
caggcaccgg gc                                                        72

<210> SEQ ID NO 26
<211> LENGTH: 91450
<212> TYPE: DNA
<213> ORGANISM: Chinese hamster

<400> SEQUENCE: 26
aagcttggat aaacatggtc tcctggtcat gggagcaact gtgatcacaa agtcacagac    60
cagtgtctcc ctgaagatat tcctatattc ctagggacag gccagccaag ggatagtcag   120
gggtacccat gtgggttaaa agtaccctc tccatcattt ctggatcctt acaggattct    180
gggctgggga agagatttcg tgaagttgac tttctggagg aaaatcaaca gccgagggg    240 aactgctttta ctccagatct gcaggggagg gcctaaacta gaatccagga acagggtgtc   300
atcacatgtc atcatataag gccttgggac agacttcaaa cactggtcat ctgcttcccg   360
gcaatagctc ttcccaccca ccctaggtcc ttgcaaagag cgaacagagt taacgggaga   420
cgcagcggca tttattaagg tctggcagat gaggtgaagg tggagctagg cataggcaca   480
cctagggcgg ggtgccagag gctcccttgg aggaggtccc cttccgtccc tgcttccacc   540
caacacccac cccagctgcc tcccacctgc tcctgcctcc cagagcacag caccaagaac   600
acaggatccc agctcagggc agagcccagg cttctgtctc ccatggcggg agaagtgggg   660
tgttctggga acccccttgg ccctgctgcc ataataaagt taggaagccc ctttgtctgt   720
ccccagaaca gaacaagcac tggttctctg tggtgggggtg gccaagctga accccctgagg   780 gcagaggtga atgacagcaa attcattgct gcctttagac ttgtcctgcc tcactgtcct   840
```

```
tcccgaagac tgcttttgg ccgagtctgg ccaggagtaa gatggaataa tgacgatgtg    900
accccagaga cttgtatggg catcaacatg agggcttccc caacgccgaa tctgttgata    960
tgtacatcgg gcagcccac ccatggcaag ggaaagccac tggtacctaa taagaatatc   1020
cacctttgtg gctaaagggc tgagcagggc cagccagttc tgggaggtag gcagggctct   1080
catccaagtg ggacaaaggg actgtgtcct cctcgctgac tggccggtca aactcagcct   1140
tcagagctgg acgctgatta tccgggaagg ccagagagaa cagggcctcg ggctcacaca   1200
caaacttgta cacgtagcgc tcaccagcca cctgtggaga gagggctgtc aggccaacat   1260 gcatacc ctg cctcagtagg gaatgtagag gatcccgtcc ttctcatagg tcacaaaaac   1320
acaccaggaa cccc ttccct tgcttttcca cactggttct tctttaaacc agcacgcttt   1380
ggaacagccc agtcactgtt taacaacttc acagaggaac cttgggtttt ataatttctg   1440
ttcccacaaa cctaagaaac tccctgtctc tccctccctc tctctcttcc tccctccctc   1500
cctcctctta accctccctt gatctctcct catggccatg ctaagacctc agtccgacct   1560
tctgcataat gcctttctca taatagtatc gaagtgaacg gctcagcttg tcatagttca   1620
tggctggcct gttcttctgg atgccccaga gcctggcgac ctaggacaa gagacaaagc    1680 atttgggtgg agatgccatt tccaaggaaa attgggagga aaggagtgga aagagcattt   1740
gagattcttg gtgtaatcta gacttgttac catacaactg actcaggctt ggcaactagg   1800
tcaggcagat ggaggatgcc ggtgaaggca agtgccctgt ttctcctctc aaggctccta   1860
aggtgctgcg gaggaggggt gggaacaacc aagacccacc tcttcaggtt caattagttt   1920
aaactccatc ccccggcctg tccaagcaat gaaatgcgca ttcgttgggt catccagcag   1980
ggccaccaga aactgccaca gttgcaaggc acccggcgc tggtagggtg gcccctcccg    2040
gaaagctcca accccttcct gtttgatgtc tcctgggaaa gtggaaatag gtgtgaggta   2100
catatcccct aaccaacctc cttcccttcc ccgtggggtg tccccaaaac tctttcctga   2160
gagttccgat ctctaccaac aaagaaatgt gattcttaca ggacccagtg tgatagggt    2220 ggagaggccc taaccctccc atgcagtcac ttgtctgacc ttcaaatttt tcagggacaa   2280
tgcagacatc atctgggaat ggtcgaagag atttctcata gccataacct tgtggagaaa   2340
gttggggatt gctcaggact tagggttcac tgattgaaga ccccctagaa tccaaaggaa   2400
ctcctaggtg gagtgactct ccctgacagc aaggaccccc cccaccccaa aattaggagg   2460
ccttagccag gagaggaaga ggcgccttac ctatcacccc atcacctgga gagggccccg   2520
agaagccctc tgggtggagg tacattgatg cacaccctgg gacatctgcg ggaggaaaga   2580
aagggtgacg cgggtaaggg gctggtgagg ctgaggagca ggggaggaag aagccctgca   2640
cacattcaag aaactcatgc ctgctagcct gcagcccaga ctgccctttt cccgccacca   2700
aatgccaggg gaagttcccc cagagggagc tggaagcttg aagctctcgg tttgagggct   2760
gggacgaagg gcacgaggtg ggaagagcac ggggtgggg gggaggtggg gggcagcagc    2820
tggggctagg cagcctgttc cacaaggccc aagattccag ggagcagctg tttcctgtga   2880
gttcagggga aggaggggt gagagatgaa cctccggggg ttgggaaggg ttcggtaaga    2940
cttcctcgga atgggcacat gtccggtcag ccggtcaggt tccaaggcca gtacctctgt   3000
gtctctgtgt ctctctgtgt gtgtgtgtgt gtgtgcat gtgtgaacaa gtgagagagg    3060
agcgcagggg gtggagtggg ggccatctag agaaaaggca gcgggcactg ggctgttttt   3120
ttgtttgttt gtttgttttt tcgggtctaa gcggactcta cggcgttccc tgccatagaa   3180
ctgaaagctc ccagctccac ctagggaagg tgactgtgtg aaccacgctt caagtccaac   3240
```

```
cccttcccgc cccctccact cccacctatg aatgagccgc tgacacccga cacctcgggg   3300
gtggggggag gcaggaggga gggttcattc atgcctccat tttgtgaatg gaattcctga   3360
ctccattcag gaaagcggag ggaggcgggg aaggagttca agggcaagta acacgatccc   3420
cctccggtct ctagcctttg aaggtcagta actcagagca tctcttccag ccgccacttc   3480
accaggggcg atacagccag gtttgaggaa aggaagcaag cacctatcct gttctccctg   3540
gagcagctgg ggtttcgtgg ttcagccccc gaccaagaaa tactgtgctc atcaggaaaa   3600
gaaaaattct acagttctag actctcccct tctccattta ttttgagaca cggtctctgc   3660
agcccaggct ggcctgaaac tcattatgta gctcaggtta gtcttaaact catggccatc   3720
catctgcccc cacctcctga atgctggcat taatggaaag gcacaaccac agctcagttt   3780
tttgttttttt ttaatagaca ctagtccagg ctagcctttg cgttgctgat cactctgcca   3840
tcacttccca agggcttgga ttacatgggt acacatgttc agctcccttc atagttttaa   3900
gccattttg tatccttcaa ctgcatactc tagttccagg cacagtactc ttgtcttagt   3960
gggttaatta aaacccctaa acctcaaaca gaagtaaatg ccaacccttt tttattgtat   4020
aagggcaaag gtctatatac cttattattt tatctaaaaa aaaaaagtg agttgtatta   4080
tgaactgatg tatggaccac agaaaggcac aaaccttcta ggggtctttg cttaacctca   4140
ctgctcatag gagtacttgc cactccaccc tgtcaatccc agaaaaactc ctggaatccc   4200
cacaagagtc tcttacctga gtcataggcg aagtctgtgc gctcctgttt gatcaccacc   4260
cccgcccctg ggtacctgtg cccactgacc ccacccctggg tcgcagccgg ctggccagcc   4320
tgttcataca agggggtcgtg gtactcctgc ttgaagctct gctgggggta gggtgggcag   4380
ggctccgaca gctggtgttg gtaggggggct gggagaggtt cccggccccc tccctgagga   4440
gatgtgaagg agtggcacat atccaggggc tgctggaaga cagagctgga tgggataggc   4500
agagaaggaa gaaagagaa tcctccatta ggtcccctg agcctgtcac ttgctgaccg   4560
ggctctagag ggataacgag agtgtttctc tggttctcct tttctcccag ccaggtctct   4620
atagagaact agggaattgg gcccagactg cctggcgagg cctgggtccc ccggtactgt   4680
ctccttacct gtgctcacca aggtacccat ggccagggtg ggactgggag gagctggagg   4740
ttctcaggag gctctgctgc tgttctgccc tgggaagggg ctgcaggggt gactgtccag   4800
gggcaccggg ggcgggggac ttgatggcga tttgtctggg ggagtcatag gcactggggt   4860
tgaggggggag aggggaatga ggggacagag aagctaggtg accatctttt acccatcatc   4920
ccccaggaag tgattactac aattatagga gttagagggg ttggtcgaaa ttttatttat   4980
atatttttgt tttgttttgt ttttcaagac agggcttctc tctgtagtcc tggaactcct   5040
ctgtagacca ggctgacctc aaattcacag agatctgcct gcctctgtct cctgagtgct   5100
gggattaaag ggagcaccac cactgccaaa gcaattttgt ttgtttatcg tcttttttgag   5160
gtagggtttc tctatgtatc cctggctgtc ctagaactca ctctgtagac caggccggcc   5220
tatgcctccc cagtgctagg aaagtttttt gtttaaagta gggtctcatg taccccgtgg   5280
tggcctcaga ctctccgtat gtagccaaca atgacctcca acgccattct cctcacaagt   5340
gctgagcctg catgcacata atcacccgcc aggtttatgt agtgctgaca gtcaaatcag   5400
gatgtgctcc agaggctagc actctgccag ctcagctaca ttcccagcct ctaggcgaat   5460
tcttttttcct ctcctccaaa agggtcttgc tttgtacccc agcttgacct ggacctcccc   5520
atggagcgaa ggctatcctc aaacttacta tcctcctgtc tcaagcacat gccatcatat   5580
ttgtctaagt gacaacctct tagcttgaca acatctctcc aaagcacagc gtaactggtt   5640
```

```
tgagtaggac aagggcctcc aagtagaaac tcactgtgct caggtctctc agcacgctgg   5700
gggccatctg tccagtgtgt gctgcctcct gctaatactc acagggaacc ttgctagtac   5760
tacctacagg actaggaaac cctgttagcc acccttcatt gcgccctcag ctcacagccc   5820 cctcccccto aacaaagcct tgacctcctg acaccttgcc ccagacttca ccacacccac   5880
caaggccagg gctcacctgg agtaaaggca ctgctctcca tggtggtagg ggagtggtgg   5940
cttcctgctg caggacaggg ccggttctgt gcggggactc tggggttcct tcttgatcct   6000
ggtggtgggg ctatggaaag ctactgtggg gtaggacagt agaatagaac aaagccacag   6060
tgtcacatcg aggctgacag ggcttctgat aaagacctta gctttctgag ggctggctag   6120
gttactggca cagtgtcctc gctgctctca ttctctgaac accgaagttg acgatttcag   6180
aactagttac tcccagtatg tctagtttta tacatcagac taatgtctca tattaaccaa   6240
ggaaacatct aagaattcaa catgcacacc ccagctaagg aaacaccttc ctaagagtga   6300
gcatcttaga cccaggacct ctggcttttc tgagtgtcct gggaaactca agtgagggac   6360
atgttttctt gtttggggct atattctctg gttttctgag agagttgggc tattagccca   6420
cttgcatgtc agctgagaaa caaacacatg ctcccaatta tctgtgagga gcactggcct   6480
tttgggggcc ctttctgagt cctcaacgtc cagctaccac tgtggctgag ccctggtgta   6540
agtgacatcc tggcttcctg cagtcccatc atacgccctg gagtccacag ctctgatgtc   6600
tgctgttttc cattcttgtg actgttttat gtcatgagtg atgacatccg agagcagtac   6660
ctgatagcca acatcctttt cttcatactt tgctttttct tttttgtttt ttcaagacag   6720
ggtttctcta tgtagctctg gctgtcctgc aactcactct gtagaccagg ctggcctcaa   6780
attcacagaa atccacttgc ctctgcctca caagtgctgg gattaaaaca ccacactagg   6840
cattcttttt catttgaggc aaggcctcac tatgtatcca gactgctctc aaattcactg   6900
ttctccagat tacaggtgtg ggccacttta cctggccaag catcatttct caatagtgac   6960
attgaggtca gatttggcag gggcgggagg atgtcctgag cattgtagga ttttgcagt    7020 acccaacccc aaactctcca gagacactga caaatctttc ctggggcaat atcaccagca   7080
caaaagataa taacagaaaa acagagctgg atcctgctga gctgtctcaa gccccttgct   7140
ttggctgggg agagagcatc tgctccggcc ttcacatggc tacaactcca gaggggaacc   7200
aaggtcttca tctcccagtc actgccttgg tcttggagtc catattacag aatggggagc   7260
cttgaccttc accctgtctt taggtgagag caaactgctc ttctctggtg actctctgtc   7320
cccatgactc acttcctgtg gtaccctgac cctcatcccc caccccttgca cccagcactc   7380 actactcaca gttttctgaa tggaaatcag ggacaaactg ctcatcgctg tctggtacct   7440
gagctgcaga gagaggccag aggtgagtct ggggtgcaac cctgcaaagt ggcagcacca   7500
ggaagacacc actattgtca ccctgaagat cagcgtcagg agctttcctt agaccaggag   7560
tgattccacc ccaggccctg cactctccag ctccggctgc atgaagatgc atgaagatgg   7620
gggtgggggt tggcacaggg actgaacttg tctgagcaga ctccagtctt tgtctagatg   7680
ttttgtccct ggtccctcca ttttcctgaa gtgcgaatgg acctgccttt caaagtttcc   7740
aaagctttgt cagggctcac agcagagtgt catcaggggt gagcaggagt tacaaactgt   7800
ggggtcctgt ggacctggaa tcagatgagg aaaccctgaa gttgggaagg acccaggagt   7860
ctgctcttca gataatttcc taggtgcttt gggagacact caagcgttct agagcctagg   7920
aaaggaccgg agcaagggga gcagctgcag ggatgtgaga agagggtaaa aataggacag   7980
gaagaagttg gagacaccac ctcatcactg atgtgtagcc aagggaaagg agggctttcc   8040
```

```
aaacctggag gtctgcggag cattctccgg gggcgagcat ctctgtccca aagggcacct    8100
agatggactc cgcagtgttt gtttactttt gcctctctat caaggggggaa gaattacagc    8160 agaaagaaca gacacaaaga aggacctcct gattgtctag dacaatagtg ggtctgaagc    8220
aggacaatgg aactcgtgac ccaggagact ggactgccac tccctggagt ctgctctcaa    8280
actggacaat gtcaaaatgg caagataaaa gactcagact tcagagtggc tgatgaggct    8340
gtaagacgag ggttagggaa cactctacac ccaatctcat gtgagtacac aggcttagat    8400
cttggccata ggaccctgtg tttccctact cacccactcc aggccctgca gcccgcacag    8460
ccggcagggt gatctttgta caacagaaac caaatcactt tgctctctcg cttaaaatgt    8520
gaaatccgaa ctcctgtcct tggcttcctc tcatctctct ggcctgcctc tctttgctat    8580
catcacaccc tggcaccttg gtctccttta gttctcagtc ctgctgagct gagacctttc    8640
ccccagatcc tctgctctgt tctgggtctc actatgtagc ccaggctgcc ctaaaactca    8700
gcatcttcct gactctgcct ggaatgctga ggctacacat gggctccctg ccaagcttat    8760
tagaggcctt ctctgaccac ccaaagcaga actgtcccct ttggcttctg tctcagctag    8820
cagtaccccc tccaactccc tcttattaaa gtatatttgc aggttaatgt tcatctcttc    8880
accaggaagt taagctgtaa ggacaggggc tttgccttct tcagatgaca atctagcacc    8940
gagaacaggc tcctactcag atcagatact gaaatgattg ttatttatca gtaagcatcc    9000
gatgagactt gtcctcaggc tgggaggagc tagcaccaca gactctgaaa gcagagagac    9060
cctaagccag gcagaccttc ccttaccttt ccacacacca gctaccacca gcgctggcac    9120
accaccggaa aagctcatct tacaagaata ctcaagctgt gatcatatgc ttgcttcaaa    9180 tgtcaacgt actacgtggt tgacagacat aagtttgtag ttgatttta tttatttact    9240 tattgcaatg gtggggggttg aatcaaggtc cttttgaacc ctcagcccctt ggttttgtt    9300 tgtttggttt ggtttggttg tttgtttttg ttttttttgag acaaggtctt actatgtacc    9360
ccaggctggc ctgaaaattca ccatcttcct gcctcagctt cctaagggct gtgattaaag    9420
gcctatcagc accatgtctg gcttagatta tatttttttt agagagattg gggtgaggga    9480
gtttaagaac cagaagtctc cagtagttaa gaacttactt agatcagtgt actacatcaa    9540
tgggacacta catctctcca caaaaacata cataaatccc cagcgtgtgg aggcccaact    9600
acaatcccac agaagctgtc ctccagccag cctgactgaa cagtcacccg gctttgttat    9660
tgccacccag gttcccagtc ctcaaatctg taaagtcatt ctataagaca gaggtgggtc    9720
agacatccac atttgcaata aatgtccctg atgactggct catttggaaa acactagttc    9780
attcctgttt ggtcttctgc tcattctgac agacacctg aaggtggcag gagcaagctg    9840
gctgagcaat atttccctcc ctgctactta ggctaggagg gtcccaaggg caaggaaggg    9900
gtgcagaact tggcagaggg tagctgacgt attctggagt ccctcttggg gcctcattaa    9960
ctaccagttt ccagtgaggt aatgggctgg gggcatctcc tgctgacgcc actgggctag   10020
agagtcctgt gggtcatctg accttttcctc ctgcctcggg cttgaacatt tatccagaac   10080
ccctggaaga gacctctctt cagcacacag actatacccc caaagaagtg atgctgtcct   10140
cttcctagaa tggggagtga gccctactcc gtactcagct ctcccaatat tggccctctc   10200 ccaaagggt acagcagggc cctcagtcac ccagagacta tcactgagga tacaaatagg   10260
aacagaaaca gagccttgcg ttcctggaga gcagaagaaa ttttaattac catgtttggt   10320
cttgaacgtg caccattcta tttgttgact gggctgtgtt ttggctgctg agccactgtg   10380
ccaaagtctg ctccactggc actaaaaagg gactatctag gtggggacat ggcagatgat   10440
```

```
taaggtaggg tgtgtgtgtg tgtgtgtgtg tgtgtgtgtg tgtgtgttcg    10500
agcccgagtg catgcatact catgaattac actggccaca cacacacaca cacacacaca    10560
cagagtactc aggggctgtc ctgcaacaga gagcaagggg accccaaaga tgggctccag    10620
aataaatggg aagttcaacc agctaagctg tgaagcctat catgagcctg ctaccatgta    10680
tccccaaaag ggatgtcaac caccctctgg gtgtggggca aacccacata agagtgaatg    10740
gtagcattct tcagagcttt tgctctgttg tgttaccatt ggcttggggg ggctctcacc    10800
cacgccctgc ccccaccctg gcagcctcta tcttggaagg aaccagttct ctatctttgg    10860
aggggacatt cctctccagg gaccttctgg aaggggagga aatagaaaga tggaggaggc    10920
attgaactaa gaaagactag ggggaaaatt gaggtctaac cccttctccc aacagcctcc    10980
cccccagaca ccagggtgca tgcatacact ttcactcaaa ttccttgtac ttcactctga    11040
gaaaatatat gggtgaaagc accctctata tatgggtct ctcttttgga cctatatata    11100
gataaggagg ccaaggggcc aggggagggt agccctcttg gaggattatt tggctgcagt    11160
taattcttgt tgaaggatga gccacatcca tcccttaaaa ttctgataaa agctacaaac    11220
cattcccgtc ctagaaaaat ccatataatc accacatttg gtacacccct aacagtttta    11280
cacatagaac agcaatatta aggaccccga atctatccac aagtcttctg ggaattaaca    11340 gacgtccct ccccaacttc atacaaaggg cgtacacagc tcagtcagtg ttccccacta    11400
ccagagagac cacagaacca ttgtccccaa tggttcttga aggcccctga cagtcccaca    11460
aagggacccg ccatcagatc cacaaatctt ttacataacc agccacatct tggcgcagtc    11520
tgcctgagcc tgatccattt cccaacagct caaccgatca caggtaccca gaaaccagat    11580
gaccctctca gctcacttca tccttctctt acccagaaat atcctgaccc caaagatgtg    11640
tatgctgccg cagaagagcc tcaccaacac tcaccccca agcccagtca gcagcccaga    11700
tgccggaagc cacatccact cctctctaaa cctgctcagg tccagcctgg tcaccaccac    11760
cccgaaacct tcactgcccc acccacacta taagcattca ctgcttctct ccaaattgat    11820
gcttcaggaa gaaaccaagc cgagagaggt tgggctatgg gccccattcc tcctgatgtc    11880
ccccaccact ggcaagtttc caaaagagct cgtccctccc tggcaccct tcggattggg    11940 gggggcact gacctggtgg gaagaggcag gagaggagac tggggtggtg ttgggacggt    12000 gcaggggac aggaccccgg cagctgcatc tgtctccgaa gagagagtga ggagcgagtg    12060
gcctcagcat ccccccctca ggcctggccg tccatcgaca gctgggaacc tgagctgctc    12120
cctcaggagg aaggagaggg aaccaaggag atcccagccc ccttgcatt ccccaccccc    12180 tcctccccac ccattggatt taaatgtaca gggactccca aggcagcagt atgtaacaca    12240
cacatgcacg cgtgcgcaca tgcaagtgcg aaaccatttg ctgtcatact agcacacaca    12300
gacagacaca tggactgtca ccagacccac caccaagggg aggagcttcc aggttgggtg    12360
aagagagctt tttccatccc ttgtcatcca aatagatcaa gtactaccac aatgccaccc    12420
taagctaact cacagcctgg gagctaacca ctgtggggac cctcagctga tgggcaggga    12480
aaagaaccca gagagccaga ccaaaataaa aaaaaatca ggtggtaaga aaggaggtct    12540
ttaagagctc atggaaaccc tgagttcttc agcccagaa catggagcag ggaaagccca    12600
cccaacaaag ctcttcatgt aactaggagc tagacactca gctgaaggag atacacttga    12660
taccccagaa cccacacacc ccatgctaaa acagtcattc cctaacaaca acaacaacaa    12720
taatgtgtgg tttgagatgg tggccacgac agacctcatt ttacctcaga tctacctagt    12780 ggtcttttc ttttcacca agcactccta tagagaaaat cctgggagaa ggtgaattta    12840
```

```
agcttttaaa ttccaaaaga aaggtaccca gagtggagga atgggaaagc ccacaggaag    12900
agaaaagaca aaagacgtca agaaagagtt cactttcagt ttcttgcttt tcagattatt    12960
gatataaagg ggatgttagc taagatgggg ttgttaaccc ttcctgaatc acagggactg    13020
taagtcacca tgtctccttc tactggcagc cctctgccag tgacaccctt aggctaaata    13080
acctcaccaa aatacaccaa ctaggatcca actaggacac accgcccac ccagcccagg     13140 ctgggccact gaccccatcc tggccagctc acaagcaacc caccagcata caggaagggg    13200
ggcatttgcc tggggtgga ggtattcagg agggatggag ggaggaccag ttgccactgg     13260
aattataatc gaggctattt ggggaggcag ccctgagtct tctttgccaa agtgccaagg    13320
aaagaattat tgaaacttt gttgttattt tggctttggc agtaaattgg cccttggagt     13380
taggaagacg cgaaaggaag gcagtaaaaa ccaatgttcg agcaacttca gaagataggt    13440
aacaaattac ttatttctcc tgttcctcac tgctctcttt ctacatctca acacccaac     13500 actaccta ggcctggagc ctcctgccaa caaactttgc aaatgaaatt ttcaaccagg      13560
aaaaacgggc ctggggccaa gttccattca aataagcaaa taccccacac aatagtctga    13620
ttcatcccca ggcctagtta tacaagcctg gctcagggtg agaaaataaa tatggatata    13680
agtgtccaca ctgagcgctg ggaagagtga agtggttagg actggggag gggactgaag     13740 gactccttga gacagagaag accccctac acccccacttc taattccata aagacaacaa    13800
aactactcac cttcagcgag ccacgtctct tggaagtgac tgagatcctg gaagagatct    13860
gatgggtgaa tattggaatt ggtgatgagg tggagaggct acggggagag acctggcgag    13920 cccggttac agcctcccca ctgggataag ggaaggagaa ggatcagagt cctctaggtg     13980
gtttgacttt tggggaaacg tgggctgggg aggtccagta tagggctttg ggatgtgtgt    14040
gggttgagga gaggggtcgc agttagtctg gttctttacc ttctgagtcg gaaggcggca    14100
gggagcccgg gtccatgagc ttcccctgcg ggaccatcag cgcttcgccc aagctcccat    14160
ttccgggaga tttctgctgg aaggaggggg gagaatgccc cgaatcaccc taaggagtct    14220 agttttggg gggtgggtc ccggggcggc tcagggcta ggcctccctg accccactg        14280 agacccccg ggaggggct atgggcaag taggcggg gtgcgggcg ggcgggcg             14340 tggaggccgg cgcggcgctc acgctgcaga aggtgtaggg cactcgctgg tccaagtatc    14400
cgcctttcat cctccgctcc atccggccgc tccctccggc cacacggccg ggcccccgcg    14460
cggaggcaga gacctaggag gggggaggca gttcgtacac ggtcccggga gcgctgcggg    14520
ggggatgggg cgatcgagag gcttcgggtc ggacagtgaa acttctccga ctcgctggga    14580
cctgcgtggc caagtgccgc caccgccact cccctcccgc caaggaggt cccacctgct     14640 cccgcgagcc ggggtcggcg tgtctgcttt ctgcagccct gctcagcccg gctgggtta    14700 cataagacgt gtgtgtgcgc gcgtgtgagt gtgtgagtgt gtgagtgtgt gtgtgtgtgt    14760
gtgtgtgtgt gtgtgtgtgt gtgtgtgcgc gcgcgcgcaa gccgcacacc attcgcacgc    14820
ccataactca ggcgcccct ccagcccga atcccgacgc ctcccacccc cgcccgggaa      14880
tgtgcggaag cgggcaccga acggagagtg tggtgtgtgg gagacgaagc ggggaatcag    14940
acactctccc ttccttcccc ttccgcagct tcacctgagg cccgcgcgtc tgtgccggag    15000
ccgcgggggg atgctcagca tgcccggggg atgacacaac taagctggag gggctaggcc    15060
ggagcgaggc ggcctgagcc ccgcgtcccc agagcccgg cttgtttcc gggcgcagca     15120 gacagttgtg agcccagggg agcagctgat tggtgcattt cctttgcctc ggcctccgtt    15180
ctcgctctcc ccccaccca ccccggttc cctttgtttc attgactttt gtgaatgaaa     15240
```

```
ccccagggcc gggcacgccc gccaatccgc agactcgcct agcctggctt gagggcggag    15300
tttcccatcc acggaggcca atcagaatgt aggggctgtc tctcggcttc attcacttct    15360
tagactccca ttcataaaaa aataaactcc tttcggcccc agttcattca taaagaattg    15420
agaaaaaaag agggaagctg aggaccgggc agcttctcta ccggttccgg cgtggccttt    15480
gggtctgagg agccctgagc ccctccctct ggggttagca cacgcctctg tgcatacgtg    15540
ggagtgtgaa cacgtctgtg tgccctgggg ggagagggag gcaaacgaac ttgtgtgccc    15600
agaggaacta taataactag catttatgaa gagctctgcc tccacgtgct catttccttc    15660
ccataacctg gtgccatgga gctattgttt cctttttttt ttttttaaca agtgaaaatg    15720
gaagaaagct aagaaagaga tgttgcctct cacctgaggt aactcagcta atcaatactg    15780
ctgggcatta gagtctcaaa gccatcacca tcacctgtgt agccctgtga gaccatgagc    15840
tttagtgaat taagctaagt gaattatgca acagaggcac acttcgtgct cagtaaatgt    15900
aaaatagtat gaatacagtt ttctcctcaa gggcctgtga tttgtagagc tgctttatct    15960
gtgacctgct ttgtcattca tgtattgctg tgagaaccag aggctcaagg acaagtgatg    16020
ttccttctct ctgccatctt acttttttatc tgaaggcaag catcccagaa aaggaagaac    16080
tcccaagttc aaaggcatgg atgggcttca atttttgctc aataagttaa tcatagtgtt    16140
ttgtattcac tccctcattc aataaatatc tgctatgtca gacccaatgc tatgtggtga    16200
actgtgagaa agactacctc ccttggggtc tgggttgctc tagctgccac cacaaggacc    16260
caaaggccca tggagctgct ttcaaaatcc atctatctaa tcaaataccc ctactttaca    16320
ggtgaggcaa tgggggtctt gagaaggaca tgatacaggc aatctcttcc agcctgtagg    16380
agtcagagct gggacaagaa cgttaactcc ctggcaccga ataggactca ttctgcagca    16440
ccaactccct gcctgtccct tatctgccaa actgttcttt aaaattcaga cctgctgctc    16500
tctcccccag ggagccttc cttctacaag agcttgggtc agtccatacc cctggtgagg    16560
catcacttat tctgtttccg gttacagggg gctctgcagg gcccagagga ggatctattt    16620
gtaagacctc cttgagcctc actcattctc aagagtgtag aatgcctgtc aggtaaatag    16680
ctacaagaaa aagcaaagta atggagtttt gcaggcaccc tgcccaagga aggagaggca    16740
agcccaagca aatcccagct tggggtgggg tgtgagttcc taggccagga ggagtggggg    16800
aggaaggcag gcagttctag gaagagagct ctgatgtggt ctccacgaag gttcagttgg    16860
gtccctgaat gagcactggg tgctccagtt ggggcctgtc cagggctgcc tgtctggttc    16920
tgagttcttc atttctttgg agggccctgg ctactcaata ttccccctcc ttccctcacc    16980
ctccctaggc ctggcagaga ccaaaggagc ctacctccct gtctctggct cagcctgaag    17040
acccagtgag agaataaact gcagctgcag ctgccacacc tgtcttggcc tctgactgaa    17100
cacgaaggtt aagatcagtg acatttccca agggaacagg gtagcctctt ctccaatggg    17160
gccctaggta gttgaggaag gtgagaaagg ctggaggtgt ggactgggac tcacgttgtg    17220
gcttgaatga cattgaggga accagccttg tgtgcatatt cttcttcagt tcctgctacc    17280
tgccacccgc acttcatttt ataagaggtg acaatggggc cttaccaatg cacactagcc    17340
ccaaggggcc ccacgtacag attgaggata ccccagagag actcacttta aggaagcaca    17400
ggaggccgct tggaggacac tgccaagcct gacccgcacc gccaccactc agatgcagat    17460
tctcaggctt ccttaatgag tcgatatgct tcctgactcc tctaatatac ctccacgaga    17520
ggctgggcag gtaaatactc tcttcctcca gtagattggg gggctggact ctaacctgtt    17580
tcctagggtt taaattataa aatgtaaacg tggactttag agatgtaaat tttcatacaa    17640
```

```
aggcagccca tagcttgctg tgggagctgg gagacccaga gtacaggcat gggaaggaag   17700
gaaactgttt aaggtgcctg aatgcaacat catgctgact ctggagccat cagagaggtg   17760
gactctcccc acatagcttt tataatgttt tttatttatt tattttaatt atactttatt   17820
tatgtgtatg tataggtatg tgtgggtgtc tacaggggcc agaggcattg gatctcctga   17880
agctgcaggt taacaggcag ttgtgagcca tctggtgtgg gtgctgggaa cagaactcag   17940
gtcctctgga agagcagcaa gtgctctaaa ctgatgaaca tttctccagc tcatgttttg   18000
ttatggctct ctctctctct ctctctctct ctctctctct ctctctctct ctctctcttc   18060
tctcccttcc ttcctccctc ccttcttcct ttcctccttt ccccttttttg agacagggta   18120 tcatgactca ttctgactca gaactcctta tgtagctagg acggtcttaa aatgttgacc   18180
ctcctgcttt ggtgtactta tgatttgctt ggttttttgaa acagggtcag attctaggtg   18240
tctcaggctg gccttaaatt tctgatcctc tgccttgtct tcctagagtg ctggaattac   18300
aggtgaacaa cagcacacct agccctcata ggttttgggg gagtgaaagg cacggggctg   18360
gatttggtcc tcagagttgt gttagctggg gactttccag gggtaaccca tccagactga   18420
ctatttgcag ggtcagagaa acttggcttc tgcagaaact tggaaagcag tttcaggcac   18480
ttacagggag aattctgagg ataatgcaag gagactatag ttgtcttaag gtccagggat   18540
gataccaata ggatcccttt ggtgtctccc aggctatagc tttctccagg gagaatgaac   18600
cgagagcaga atctgtgttg gggttggggg ctgtgttaga tccttcccat gagctggtga   18660
tgagtctgta ccactaaagg caaaccaacc caactgtgtc acccttagac ttccttttgt   18720
ccttttcttc ctggcccagt ttctcttgct tccttccaac tgcaggggct ccagaccctc   18780
ctccatgcca tgaaatgaat gtgcacctca ggaaactaat tgcttgcatc agtgtgtgtc   18840
tgttcacctc actgaagaga gagtctatgg cttttatcag ggtcaccaca gagtagatct   18900
gtaatcaccc catccccact cttcaggtta gaaacatggc ccttgtgctt ttatctgcgt   18960
cttcacacta ctaaaaacag agcaagggtg cactatggta gagtaggatt agaggagggt   19020
gaaaaggctg actcccttt tccagctcac cttccactag cctgagtgtt ccctatcccc   19080 acccccact cccatcccct accccacc tcgactccct tctcatggca gacctcaaac     19140
tcagtgtgta tcatcctgat ctttttactc catttgagtg ccgaggtcat aggtgtgcac   19200
tttgcccaga caaaccttct cttgagactc cactaaacaa gggctctcca gacagttagc   19260
agaagatgta atgggcccag aggagaggga tgagaacaat cttgcccaat ccctgggct    19320 tcctggtgga ggccaacagt ccctaaacaa aagtcctgga gatgaggact ctgtccctca   19380
ggtgatgcag ggctaggtgt cctcaagagc ctccatgaaa tcaggaggaa cccaaatgac   19440
tgttgaggca tctcctttgc aatcagtggt ctgatgtagg tccctggaga cacccccatt   19500
tgtgtgggac aattgcaaca tccccaggag tagagcgtgg acttttgtg gactgagcca    19560 atcccaagga ggatctgatc taaggactct gcaggaatgg gggctcaaag tttggggacc   19620
tataattcat acttgtaaat ctattgagtg cctgggtgag atggcttagt agatggtgtg   19680
cctgctgcta agcctggtga cttgatccct aggacccata tggctgaaag agaaccaact   19740
cctccaagta gtcctttgaa cacacacaca cacacacaca cacacacaca cacacacaca   19800
cacacacact gtgggggggg gcagggtgtg tgcatgttca aatataagta ggcacacgac   19860
gtgcatgagt gcctgtgcat atgtgtgtct gcaaatgtgg aagtctaaag ttgagaccag   19920
tatcttcctt gctgactcct atcttatttg ctgaagcaga gttctggct gaacttggag     19980 cttgccagct tggctagtgt agccagccag cttgcccacc tgacatgtcc gtgagtactg   20040
```

```
tgatctgaat ctggtcctca agcttgtgca ggatgctctt tactcacgga gccattcaca   20100 aaacccccaca ttttagcgtt ttaaaattgt taactgcatt tatttgttta tttatctgga   20160
gacacatgct tgctgcagaa tgcatgtgaa ggacagagga caatgcgcag ccctctttc    20220 cttctgccac atgggtgggg atcaaactcc cataggtggt caggtaggtg gtcaggctgg   20280
gcgagcccct caacctggtg cccaatctca ctggccccat gttagtattt ttaaacaaag   20340
cagaataggc actgccctcc ttttctttga aacactgtgt cgaatggaaa gcctgagcca   20400
ggaggccaga gaccagtggt ggccagagga aagcactttc tatttttaga aggtgctggt   20460
gactctagct ttccacattc cctgcctgca gcagctcagg actcccttga acacgcaaag   20520 ctcttttttat ttttggctct gtcctgtctc tccctgtcca tttagatttc cacctctgtt   20580
tctagaagta caggcattca cagatgagcc ctcccagaaa actgcaggag attttttgt    20640 ttgtcttcat ttcttttgtcc ttttggtggg agagagacaa acggacaaat gctggcagac  20700
tgaaggatca gaatggaatt ggagccagtt ggccagagtg caggactatc ccctttttaa   20760
ttaagtgtgg acttgaatta tgaggggcca tggctcctgc tgggcggggc tctgctgagg   20820
gaaggcagtc ttctctcttc acagattaag catcatttat tccacttagt ctctcctcag   20880
ttccctgaga gtgtctatat ttgttcttgt cagaaataat ggacagctct aagctcagcc   20940
agctaagggg tagagctagg gaactccagg gatgacaaaa cctggggacc attcctggaa   21000
attattttgg agggaatagt gaggtgtgtg tccttttgaa aaataattaa aaaaaaatat   21060
ttgagacaga gtctcataat tccagcctag ccttaactag acccacaatg tagttgagga   21120
tgaacgtgaa tttctgctcc tcctgcctct ctgtcttcag agtgatagaa ttgcaaactg   21180
caccatcaca gtcttcactc gggcctagat acagagccca ggctactcaa gcaccttgtc   21240
tgctgagctg tgtctccagc cccaggtttt acttccaaag gctcccccaa ccccacaaa    21300 agaagctctt tctttgccca tttctagccc ttaacggtcc caaagtcact aggcttctct   21360
tttagctcaa ggagctgact gcagctgcca attgatttct cctgtagatt ttcattggtc   21420
ccactggcca ctggagccta gactcatcag gtagtttaca gccatggttg tcagtttaca   21480
gtttgggaca gagctgatct cccagtcact ccttggggac gtgggtggag actaaatcag   21540
gaggacacac actgagagga cacggtgcct agccaggtgg agatcaggca ctcatgactt   21600
tgagttgaca ttccagaata aggtgtttgt gtgtgagctt taaacttcat tgtttcctga   21660
gcctttccag atgtgtcatc ttgtttcatt tcccctgtgc cctacaaagt gggtatctgg   21720
agttcagaga gcaattagct ttgcgccacc ttcagtgaga aagggacca aactctcatt    21780 tccacacacc cagggtctat ggctcatcct ccactagctc agaggttagt aattctaagc   21840
tggcagagag ggtagcaggt tgtttcttat tgttatttgt tttgttttttg agacagggtc  21900 tcatgtagtc caagctggcc ttgaattaga tatgtagtga agggtgaccc tgaactgaga   21960
aagaaaattg tttgttaaat attattcttt tgaaatttaa atgtaatgtg ttcccctgca   22020
tgtatgtctt tgtttcatgt atgtgcagtg cccctggagc ctagaaaagg gcactggatc   22080
ccctggaatt ccaattagag atgttgtgaa ccactgggta gacgccagga attgaacccc   22140
aggtcctctg gaagagcagc cagtgctctt aactgctgaa ccacccatct ccctagcacc   22200
caacttctga tcctcctgtc cctgcctcca gagtgctgct attaaaggcc tgtgacacca   22260
cacctggtct atatagtact ggggatggaa ccctgggcct catgaatgct agggcaacct   22320
atcaattgag ttataattcc agtctggcaa tagcaaattt taaaccaaaa aacaaacaac   22380
agcccccccc cccatacaca cagagttttg ttgtttaatt ttctaaatta tttttagaga   22440
```

```
tggaatctca ttatgttgcg cagtttgata tgatttccgg aattcagata ccttgaccct   22500
gcctaaccct cacctgcttg atagttccaa tttcttttcc cctcctataa gtcagtctca   22560
cttttctgtt aaggaacaca tgttaaggtc ttgctaattg tgtaccctct taggggtgc    22620 tctgatattt tcttaaattg tgcagcagac acgaatgtct ctcacaaagg gaaatctgat   22680
gaggagaggg gggagcattt tgctctctta aaaaaaattg agagtgtaaa gtatatttaa   22740
ttaaaatgat aaatctgatt ttcagttcgg tttttaacta ctgctaaaac gaatatattt   22800
tacgcacatt tgcaaagggc tgcagccatc acaccaagag ttagagctgc ttttcaggtc   22860
tgtttgtctg tctgaacctt tcatttattt tatcgacaaa aaactgagag gctcaggttg   22920
gagaccctga agccccaaca gtgagtgagc ggccaatgta aaggcagtca cagcagttct   22980
tcctctcccc tgttttaatt cctggtgcaa ccggggtggg aactgtcagg ctcttctttc   23040
taaaggctgt tactttcttg ggggtgaatg agtacttaga acacacagag ccctgctgtg   23100
ttctgtcctc agcagagctc atgctgggta tggatggtgg tacacacctg tgatcccagt   23160
aatcagaagg taaaagtagg gaaggaagga aggttcaagg ccagcctggg ctgaatgaaa   23220
ctcagtctca tttttttttt gtttgtttgt ttgttttcg agacagggtt tcgctgtgta    23280
gctttggagc ctatcctggc actccctctg gagaccaggc tggcctcgaa ctcacaagag   23340
atccatctgc ctctgcctcc caagtgctgg gattaaaggt gtgcgccacc aacgcccggc   23400
cttcattttt tttttttaag tggtctcccc taccatgcag acagactcca gcctctccca   23460
ccctcccagt ggatgacact cttctccagt tctctcttgt ttcttcttgt cctagcagag   23520
ctgaaagcag atgctattaa gttcatgttt cacattgtgc ttaaagctgc aggtgcaaac   23580
catttaccga ggaggtgaga catccatgtg ggaaccgaag tcaaaagtca tacaatgggg   23640
tgttcttccc tttgaccttc ccctactctt gggagtcctt aataaatcta catttgttct   23700
gccttaaaaa atattacagt gttcttcggt gaaattgtat ttattttgt agtctgggga    23760 tggaacccag agcatcaaat atgcaaggca agtagttagt acttcactat agagtcacac   23820
cttcagatcc agtgaaattg tattttaatg gtttattttt atcattagtg tttgattgga   23880
ggtgaacatg tgaaggtcag agaacaattt cctagtgagt ctttgcttcc acctttaca    23940 tggattctgg gcattaactc ctggttacca gccttctaag taatcaccta tacccactga   24000
gctctcgtta gtccaccact gagaatttat gattgttctc attcccattc ttgggagcag   24060
aaagagagat tccaggcctg cttatccagc tctgcacaca ccagtggctt tggactttgt   24120
cccagaactc aggcagcggg gtttccttga gtgcagcctg ggatgaatcc tccctggaga   24180
tttcaggacc ggctagtgac tgtcctcaaa cactggtgct tgtagaaaga actttatttt   24240
cctgtaccca ccagtttcca aagaaccaac acggagactc agtattaatt ataaatgttg   24300
ggttgatagc tcaagcttat tactaactag cccttacaac ttacattaac ccatttctat   24360
taatctatgt attgtcacgt ggtttatggc tttacctgtc tgttagcatg tctttctccc   24420
tctgggtctc ctggtgacta ctctgactct gcccttcttc ttcttcccag aattctccta   24480
gtttggcttt cctgtccaat ctctcttgca cagctatagg ccagtcagct tgttattaac   24540
caatgagagt aatacatatt tacaatgtac aaagattgtt ccacagcagg tgctaaggga   24600
gaggaagagg aagagtcagt tttcttcaca gacgtgtatc tgtgtactct ccttactagt   24660
tttggctgga cctctgcagt cttctgggat gcagtgaagc aagcttctgt caggggctcc   24720
atttggaagt ttagcagctc ctgccccaaa gtatgaacc  tcagagttag ggagctgggc   24780
caaatgggta aaagacttat tgaataagca aaaagacctg agttcagatc cccagcaccc   24840
```

```
aggtaaaaac ctagaaatgg tagggagcac tcagaagccc actgttggga ggaggatcac    24900
tggtgaattc caggcttagt gagaaactct gtctcaaaaa acaaggtgga gagcaataga    24960
ggctgacagt agacctctgg actccacata cacacacatg cttacgtggg catgtgtgta    25020
cacacacaca cacacacaca cacacacaca cacacacagg atgagccaca cacacacaca    25080
cacacacaca cacacacaca cacacacaca cacacacaca caggatgagc ctcaggcctc    25140
cagcctgggt ccttggcacc tatatcagtg cataataaat gcttgtgggt ggagaactga    25200
gtgagtgggt gccaggggag aaaattgtcc acagggatgt aaagcaggcc tgtacctgcc    25260
gacggcttcc tgtttagtca gggaggtggg tgggcctgaa agaattatgt ttactaataa    25320 cattttcct aactcaagct tgaggtacct ggaggccacc tggaggttgg gcgtgccaat    25380
tctagggtgg tggaagccac gcccactccc ggaagaggtg tggctacttc aggcccaagc    25440
tgctctgagc tactctctgt gctcagctac ggtgtatttc ctggagctct cgaagtttct    25500
cgtgccagca tctcgcttgg cttctgccac tctctgccaa ggatggacac tatgggccat    25560
gacctggtgc agagatgtca ctgataggtg tatgttctgc tggcactagt agtctccctg    25620 ggaaagggt ggggaggact tggcaactta tgttcctgcc gctccctcca ggagttgtgc    25680
aatttatttt cgcagtttag aagaagagtg atagagtgac tggatgcaaa aatgggctgc    25740 acttttttt tttttttga cagggtctc catgtagctc accatgcctg gcttttgtgg    25800
ctctggggat caaacccagg gcttccagcc cagggcttca tgtatgctag caaccactg    25860 gccagttgag ttacatcccc tattaacttt attttttaaa ttcatattat tattattagt    25920 tttttgaga cagggtttct tggtgtagcc ctggatgttc tggaactcgc tctgtagatc    25980
aggctggcct tgaactcaca gagatccact tgcctctccc tgccgagtgc tgggattaaa    26040
agtgagcgct gccaccacca cccagcaaaa ttttattatt tttatgtgta tgagtgtttt    26100
gcctgctgca tgtatgtata tgttccatgt acatgcctgg cgcaggcaga ggccagaaga    26160
gagcgtcagg tcctctggac ctggaattac agatgactgt gatccaccat gtgggtgttg    26220
ggacttgaac ccgggtcctc tggaagaaca tctagtcttc ctcacctctg acccacctct    26280
ccagcccttc acttatttct ttattgagca gctgctagat ggcaggtact tttaggaagt    26340
gggaacgaca gccagtcaca gcagcaagac ttcctttcag cactcattgt gtgccagact    26400
aaacgtttta cacatgttac tcatttattc ccacaccaca tgctcagaga agctaggaaa    26460
tgttcccaga gttactgagc tggtaagtca caagaggga cagccgagaa agctcactcc    26520
agcagccccc ccatcagagc tgggagaggt gtgctctgcg tgttctggga gagctgggcc    26580
agctgtgaca ggtgactcta ctttgggttc ggggaagggg ttttttaatc agcctgtgtt    26640
ggttgaaaga aatgacacca gtagcaagag gacagttatc cgggcgggag ggaacaatag    26700
gagggccttg gaaacttcaa gaatagctcg tccatgatcc tgtcctcagg cctatatttt    26760
tcccctcttg ccacatagat ttgatgtcat cattcaaccc agacagatgg ccaaggtatg    26820
atgtgttgct gatgaaaaca tgggctctgg aggctaaatt tttgtatatgt caccatcaag    26880 ctacgatagc ctaagttagc cttccttcct tcgttttaac tctgtatgta tgtgcgtgtt    26940
tgcatgtgtg agtaggcata gtttcatgtg tgtgtgcagg tatgggttcg cacgtgtgta    27000
tacagttacg gagatcagag gacatcccca cttttgttc ttcaggcatc atccggcttc    27060 tttttttggga catggtctca ctggcctgga tgtggccaag taggctaggc tggccagcca    27120 gagagccca gccatctgtc accagtctcc atctccccag ctcagggatt acaaatgtgt    27180
gccaccatgc ctggctcttt ccatgtgttc taactacaga acccagatcc tcacgcttat    27240
```

```
ggggcaaaca ctctattgac tgagcccagg ctcccttttt ggcttttgag accgggtctc   27300
aatctactgc ccaagctggc caaaaatgct tggtactcct acttctgctt ctcacgtgct   27360
gggattacag gcaagaccca ccacaccctg atgatttaaa cttctttctt taaaacttta   27420
aaatatttat ttatttattt gtgtgtgtgt gtgtgtgtgt gtgtgtgtgt gtgtgtttgc   27480
ataagtgagt gcaagtcagt atgtgtaggg gtcagaggtc agaggctaac tcttgggagc   27540
tggctctccc actgtgaggt caggtgttgc attcaaattc ctctacccac tgagccatct   27600
cactggcttg gcttaatctt tctttacctc aggttgctca cctgtaaaat agcactagga   27660
gtatgggtgt gaagataaaa cgagatgatt tagagtggca gaggctgtca gtaaggaacc   27720
ataggttatt attataattt taattttttg aggcagagtt tctctgtgtg gccttggctg   27780
tcctggaact cgctccatag acggtgctga cctcgaactc agagatctgc ctgcctctgc   27840
ctcttgagtg ctgggattaa aggcatgtgc caccaccaat ggcttcttag attctacttg   27900
ctattatcag atgtcactat caggattggt tccccacccc attcccaccc ccccatctg    27960 atctgattcc ctgctgctgt gatggacccc agcttccctg acagcctccc aaaatgcaag   28020 caccccgacct cacctcacca gccactctga tctcagcgcc ttccttccc ctcccctgtg    28080 attatactaa acccctggag ctagtgggca ggctcagctg ggcctcttgc ctctttgaag   28140
tcccaagcca aattcccagt cccacatact gacttctgag aaagctgctt gctatcaaat   28200
cctgccgcca aaaagacgcc cctcttaggt attcctgcca actccgtttt ataatctccg   28260
tgctgggagg gaggacagtg caggcacttt gtctgcagga aggaagcaat taaattatta   28320
gcactttgag aaattaaacg acataactta tggtggaata agtttagcaa aaagaaaaaa   28380 aaaaaacct tgtaatgtga gaaacaatt aaaagaatt atataaggtt gggctcgctc     28440
ctttatggca atagagttag cagttcattg attatcgtct tgttataatg cagcaggatg   28500
gtgcgggctg ccgtggtggc agcgatgttc aggaagctga gcgcttagct gggtcctgca   28560
agagggcacg gaggaggagg agctgaaagg ttttctgga gaggtggcag ggaggggcag    28620
tgaggtcagc ggaggagcac cagagtagcc cctcccgtgc tccctggctt ttctgcttcg   28680
ctaggtagac tcacggagtt tgtttctctc agcctgccca cttcctgtgc cccagcaact   28740
ctgcttctag ctattcatgc ctgtgaaata ggtacatgac tccacaagga ggcaaggatg   28800
gctgaccagc agaggaaccc tccctaggac ggtggaccag tgagcccggt ggatgctctg   28860
agatgcagcc tgaagcacag gaagcagcag attgggatgc acaaagagag gcgaccagaa   28920
gtcctcaaat ttgatgcccc agtagctgaa aagagcaaac ggcagcagtc tatgaccacg   28980
tagaagaatc tcctactcag gatggtggaa agaagcaagg caacatgaag caggagctgg   29040
ttagttgtgt agataaggtt agaacaaatt cacattgggc atggtggcac atgcctataa   29100
accccgagaa ttcatcgag aggtggaggc cagagttggt gggttcacgg ccagctatag    29160
ctacatagtg agtaggagac tagcctgggc cacatgaaat gctgtttcat tcctctctac   29220
cccccaaaaa gtcacaacaa aaggacaact ttaaccagag taataaacac cttgttgggg   29280
aaggagtgca gcttgctcac tgagaaaagg caccaaataa caaacaccct aagttagggg   29340
tggaactgct tttccttttt gttttctgt ggagaacaca gatatttacc gctgggccct    29400
gagatttgtt tcagggtccc ctgagggata cccacaatcc actgtgtagc atgaggtgca   29460
gtgttggggt ggtgcagagc atgaggttag ggcacctccc atttgcttac agtgtctaat   29520
cagtacaatg taaccattg ttcaggagaa aataaagaaa agtctccaca cgttttttt    29580 tttaaaggtg taatatcttc attctgtggt tggatttgtg gatatggaac ccatggttac   29640
```

```
agagggccaa ctgaacactg gtaaaaatca ccaagctttta aaggaaaggt caggggatgc    29700
cccttggtta ataatacttg atgctctttt ggaggaccag agtttgatac ccagattcca    29760 catcagggggg ctcatgagca ctgtaattcc agccccaggg catttgacac cctcttttgt   29820
catccgtggg catccgtggg cataaagtgt ccatgtgcac acacacacat ttaaaaatta    29880
agaaatttag ctgggtggtg cacgccttta atcccagcac tggggaggca gaggcaggtg    29940
gatctctgag tttgaggcca gtctggtcta cacagcaagt tccaggatag tcagggctac    30000
agagagaaac cctgtcttga aaatcaaat aaataaataa taaaaaattt aaaaaaattt     30060
ttaaatttta tttcatgtgc gtgagtgttt tgcctgattg ttgtaagtgt atcatgtttg    30120
tttgtgccgg gtacagaatg gaggtcagaa aaaggcatgg tattgggggcc tctggaattg   30180 gagtcctgga tggttgggaa ccaccaggag ggtcctagga actgaacccg ggtcctctgc    30240
aagagcaaca aatgctctga acccctgagc catccctcta gctctaaatt aaaaattaaa    30300
aataaacaaa tggaaagttg cattctacac atcttgctgt aggcacattg tgccccaaag    30360
ggagagagta aagagcaaaa atgtgaagtg aaaaacagta gggaatcaga agatgaacaa    30420
caagatactg ttgtgggata tttgtacact gtgtgattgg tgtaataaaa agctgaacgg    30480
caatagctag gcaggaggta tgggggggtac cctggcagag cgagaactca agaaaaaaaa  30540
aagtctccag ccaaactcaa aaaaaaaaa aaaagcaaaa tgaacaattc aaaaatatgg     30600
acaaattaac ttaaatcata aaagctggtt aaaaacaagc ctaagctaaa gccaagcttt    30660
cataattaat aataagtctc catgtcgtta tttataagct ggtggtccta acaaaaatat    30720
tgctacatga aactatttac atgaatttat attttactat aaacatttac tataaaaaac   30780
atgaatttat ttatgtaaat aatccaccca cttgtgaatg aaataactac tcaacaaaca   30840
cattatcaga cagaaacaga atttcaggat aaaggaatca atgtgtgctt gtatgaatga    30900
atgaagccaa gatgggggttt tgtatggaaa tttttaggaa agtacttccc aggggctggg    30960
cgtgtagctc tgctggtaga tacaggaagc cctgggtttg agcaacagca tggcatacac    31020
ctggcatggt ggtagataat gtaattccag tcctggggag gtggtggcaa gatgatcaga    31080
aattcaacac catccttagt gatgcagaga gaagccagtc tgggttgcat gagaccttgt    31140
aaaagcaaaa caacaaagac aaaagctgct tgttaattat accaggaagt ctttgggctg    31200
ggtatggtgg gggaggagag ttgagtattc tggtctgagg acaggtagag attcagttgc    31260
tgatacctgt tggatgggga caccattctt aggacttcag acttctttga agcgtgcaag    31320
tccatgatgc cctgttccct gccttagagc ctcctgcagg gaagcaggtc ccaggagtga    31380
gcagcacaga gttagcctgc ccaatactgt gtcctagcag gttaggttac gctctgtgta    31440
tcttggctgg gatggatggg aaagaatgat gaagagtacc aaagactggg cactgggatc   31500
agagggctga gagtaccatt taaaagaagg cttggcacac tttctcttta gagggccaga    31560
aggtaaatct cccaggctct gggtcctgag gtctctgtca cagctccgcc ggaagtggcc   31620
acagacgtag atgaacgggc atggctgtgt tccagcaaaa ctatatttat ggatccagac    31680
attcaaaatt catataaatt tcatatgtcc agaaggagta ttcttttgat tgttttgtct    31740
tttcttttct ctctctgttt ttggttcttg attgttttttc aaaccacttg aaaacggatg   31800
actgggtctt agctttcaag ctttgtgcat ccagcaggg gctggaattt gtggacctct    31860
ggtctcagag gagagatgtt tgatgcatgg gcaattactc aagggagcta cactattttc    31920 cttcttttctt tctttctttc tttctttctt tctttctttc tttctttctt tctttttttc   31980
tttctttctt cttgtttttc gagacagggt ttctctgtgg cttttgcaggc tgtcctggaa   32040
```

```
ctagcttttg tagaccaggc tggtctcaaa ctcacagaga tccacctgcc tctgcctcag    32100
agtgctagga ctaaaggtgt gcgccactac cgcctggctt atttcttc tttttaaaa    32160 attattttc gccaggcggt catggcacac acctttaatc ccagcatggg cggggggtg    32220 gggggggtgg ggggtgtggg tgtgggggt gtgggtgtgg ggggtgtggg tgtgggtgtg    32280 ggggggtgtgg tggtggggtg gggtgaggag gcaggcagat ctctgtgaga gttcagcctg    32340
gtctacaaaa gctagttcca ggacagcctc caaagccaca gagagaccct gtctcaaaaa    32400
atcccagaaa aaattatttt tcatttttaa tttatatgtg tacatgtata tctgccatgt    32460
atgtgagtac cccaaaagat ttgaagtctt ctgaacccct ggatttacag aaggttgtaa    32520
gccactgtgt gggtgctagg aactgaacct gggacctctt caacagcacc aagggctctt    32580
aactgcggag ccatctctca agtcctagag ctgtgctatt ttaattctca ctccactgtg    32640
gagataaaga ggccagggt ggaggctgaa gtggctcatt cagtgtcatc caggacatca    32700
cccactgtat cctagatctc ctgagtctgg atttagcatt ttgaacaaat tgctctctct    32760
ctctctctct ctctctctct ctctctctct ctctctctct gtgtgtgtgt gtgtgtgtgt    32820
gtgtactcat ccagtgtgct gtggatatga tgtatgaaga gtgtgtatgt agaaaaggac    32880
agtgcatata tatgtgaaag ccactttgaa aagaggacca caaacttccc tctcccttg    32940 gaatttagtt cggggacctc tcagggatct gtgtgggctt acaggtggag tatgacatgc    33000
agaggggtgg aatggtgggt tatgtgtctg tcacaagcac ccagtttctc agctgctctg    33060
gtgggcggcc agcctgtgtt tttacaatgc caacctctgc ctgctgtagg tgaatgcagg    33120
gaaaagggtt ttggtcattc tgggagaccc tttcagctg atgttcatct gggtggctct    33180
caggccatct gtgggttct ggatggtttg ctggaattct ctctgaaatg tgccaagctt    33240
cctgctcagg ggaagacatt cacctaattt atttaatctg gatgatttaa ttctctcatt    33300
cagttggagc aaaacacaaa ttttgcatta gaggggggtg atgaagagag agagagagag    33360
agagagagag agagagagag agagagagag agagagagag agaaagttga aaagcagtga tgtcactatc    33420
cttgtggcag aatgtctctc ccacagacta caggcacccc acacttgagc ttgacatttt    33480
ggaagctcaa agagcaacag cctggctgta gagccttccc atgcaaaaga attgttcttg    33540
tccgatagat ctgacaaagc atttctgtgc tttcacttca ggcttagacc cttgctgatt    33600
gtatttccta agtccctgtc ctctgccgcc agctgccctt gccctcctc ccttccctcc    33660 cttgaacttg agcgctctgg ttcagagaac attggccttg cctctgcgtg ctctctctgt    33720
tggctggccc tctaagccct gcgtgctcag tttaggcttt gcctttctag ctgctccctc    33780
atccggtccc tctcctgcct ccttccctcc ctccctgtg tcttgactgt ggtgctcagc    33840
acaccaagct gaaattcttg gtccacgtga ttctccccca catacagcca caagtttctt    33900
ctgggcagaa actgtcttgt tcatctgtga atcaccaggt cccagggcga tgctcaccac    33960
agagctgttg catgggccca actgttagaa gcttgctgaa tgaataaagg aacccacaaa    34020
tggaaaggac caactccaca ggcctcaaca cagacatgca ccaccttccc atctcattcc    34080
tcctgtgctg aagtcgtcac agaggtatcc accccacaa aagtcaaaag gccatcccaa    34140
gccatgctga tgatctgtac tctagctgtt tatgttctgc tcagtggccc tgtgctttca    34200
gaaggactct gcgtagccca ggccaacctt taacattgc acaggatgag ggagcagaga    34260
gggactgcag gggcagttca gtgtggccac caaggcaaag ctctggtgga aggacccagt    34320
gggctaccct gcctgtgcta acaggctggg gtggagggt gagggaataa agtcccggt    34380 aaggtaagtg acccagataa agatcaaagc ggtggggaca gatgagtgct cctgcaggta    34440
```

```
actggcttct ccagtctcca ctcctcactt aaactctagg gaacttccaa gtacccaatg    34500
tgttaatatg tgaatgcaca cacatccatg gatgctattt gacttcaggt acataatttc    34560
ccctccctcc ctgcctcctt ttcttccctc tttctcatct tttctccttc ccttttctcc    34620
ctccttctct tttccctcca tcccttttctt ttggacaggg tctcatatcc ccggtgaacc    34680
ttgaattttc tatgtagtca aagatgaatt tgaacttctg accatcctgc ctccgccttc    34740
cctcccaaat gctggaactg cagacacctg ctaccacact tgtttttatg ccaggctgag    34800
ggtggaaacc agggcttcct gaatactacc caagctttct acaagtgagc cctgccccca    34860
gcctgttccc accctctccc aatcccaatc tctcctttct tttctgggct gggaattgaa    34920
cccatggcct catgtatgtt aggcaagaac tgaatcactg gctaataat atcccagcct    34980 gttattttac attttttgagg tttacttttt tcccccactt atttttttttt aagatttatt    35040 tattttact tttactttat gtgtgtgaat gctttgctta catgcatgca tatgcaccat    35100
gtgtgcgcct ggtgtccatg gaggccagaa gaggggttg gatcttgtgg aactggaatt    35160
acagatggct gtgagccgct atgtgggtgc tgggaatgga acccaggtcc tctgggagag    35220
tagcaagtgc ttttaaccac tgggccatct ctccagttcc tttcctcgca cttataagga    35280 ggagggact gatgtagtta cctctaaggt ctctctggtt cttctaggcc ttttccccct    35340
ttgtcttctt agtggcctgg atcctgcaca gctgtaaata atcacctgct tacattaagt    35400
gtgactatgg ctgtgtacct gttcttagct gcttgagctc tcagaataga acaaccaata    35460
ttctgaatga ggttgaaaag tcttaggttt agtttttgaa ttccccactt gtgtgtgtgt    35520
gtgtgtgtgt gtgtgtgtgt gtgtgtgtgt gtgcgcgcgc gcacacgcgt gtgatatttt    35580
gggcaggctt ctttttaacc ttctgcctct tgtgcataaa gtgttaacaa ttattgtctt    35640
atttgtcact cagagttgta gcatgaagtg aacgatggat tcaagagttt cgccacctgt    35700
aaatgtcact aaggaattat gtatgacaag cccccacatt agggggcttgt aaatgctcac    35760 tcaacaaatg agtgactttc tggctttgtg tccatccttc ctgaatctcc acaggcttct    35820 cagttttttct cttaatggac tttacccagt gctgcagaga gcttgaagca gccagtagtt    35880
ccccattact ccataaaggc caccacctaa gtgcttcaac tttgtcctca ccctgccccc    35940
ccataagtca acagagtggg taggtggggg ctgggagggg gaaacaaagg agctgttagc    36000
aggtaagagc aagtcaccac caataaaacc caatcaatgc agccctttt aagttggttg    36060 gatcagtgac ccagaaaata gctcccctgc agcagaggaa atgatagtca ataaaccgag    36120
ccgtcaatgg gaaaaatcta ttaaagggag tgagatagca ggagacctct ggtgttaact    36180
gagacccttt ggaacagagc catggatcca agagacttcg ttaaccctct agactcaagg    36240
cccagagtag tcgcctctgt cgcagtgcag atgcctgagc ttatgcggct tccggtcccc    36300
tcagatggca tcggaagagt atgctatgtg ggatttgtgt gtgtgtgtgt gtgtgtgtgt    36360
gtgtgtgtgt gtgtgtgtgt gtgtgtgtgt gtgttgttta catggacaaa tgaacttcta    36420 ggggggccagt aggtgtatgg gacatccacc tgggatgcta cagagaggta gatgatccct    36480
tatagccagc ctacctggga aagcatctgg ggtctcttga acttcagata tagcttagtt    36540
gatggagtgt ctgaccagta tgaaggggggt cctgggttca attccagcac aatatagaat    36600
ttgggttgat agtgcaaact ggtaatccca aactcaggag gtagaggcag ggagatcaga    36660
ggttcaagct cttggctata cagtaagttc gaggccagtc tagtttccat gagatcctgt    36720
ctcaaaagat gaaatgaata tagaggtctc tattctctca tttatagcag ctatcctgac    36780
tggggtgttg ggaagcaggg gacatgcctc accccatgcc aggtggctgg tatcaccttg    36840
```

```
acagctagtg ggacttcctt cgtctggtat tgacaaagaa ggaaagtgac ttccaagaaa   36900
ctgggctttc ccccagtgta tactttcacc tctctgtctc ctagtgaggt ggggaccagg   36960
gacactatga taggctaaca ggtttcttga gaacgctgta ctgaacctag aaggacttgg   37020
acaagaaagc agttctcacc gtctggtcct aggaaagcca cagggcgcac cctagccctt   37080
catgccactt cttttgttgt caccactgat gccaagtcag aaaggttgta tccgcacgtg   37140
catctgcaaa gtgtgtcccc agagctcagg gtgctgtggc agaatgtccc ctttatatcg   37200
tgctgaagct catcttgaat taaggacacc tggtcatgct gatgtgtcac gggtcagtgt   37260
ggacatgtta aggtatatca aaggcagcat gttggtgcac agttgggatg actcagagag   37320
ggacaggctt tgggccaagg gctacagggg acaagacctt ggctgtgctg tggctgtgtt   37380
ctttgcctct gcatagatcc tttagggctt agttttgttc ttatgtgtct tgtacatatt   37440
gatcttactg ctttgcatac tcctttggga aggaaggccg tagtactatg ttattactcc   37500
catgtcaggg aaccacagga tagttgttgg cagcttcctg gtccgggggg acattaccag   37560
ggcccatggg tgggtgttta ttgtacaagt ggctaaagag tgcgtaagaa tgtgatgata   37620
ttctcatccc ctcccccccct ctgattgagt gtccaggctg gcctagacct cactgtatag   37680
tcaggtgacc ttaaattcct gatcttcctg catccaccta ccaagtgcta cgttgacagg   37740
tgtgtgccac cacaccatgc ttaagatgag tttgtggctg tgacaatcac tgataatatc   37800
cacagactag gggaaggtcc tcattgctac tctccttcct tttctcaggt ggacacttgc   37860
atgatttgtg ggacactagc tgctgccatt caggggaatg gtcacatcta gtgggaaggg   37920
aattatgaaa gacgttcttg aatattcacg aaggtaaatc ataagcaact ttaaaatacg   37980
attttttagag ctgagttcac cttgtttctt tgtcaagaag ggaaatgctt tcccaagaat   38040
atgagaatca gacggcaact gtcctcattg gccacctcag gttggagcag cttctagact   38100
ggagagacag ggcttcctat tcctattaga ggagtgggta gacacagaga catgtgagtt   38160
gagttttttgg ttcttgtgaa tcatgggcta atgcctttta aaggatcagg tggtttctct   38220
ggcatttcac agaacatcca gaaagtatcc gatgtgcccc aagtctgtct gacaacccca   38280
gaacccccatt aaggctctat ctactccctc tcttttttgt caccttcagc tcagtgacct   38340
ctctcaattc aagacttgtg acggttgagt cctacacagc tgagaaaaat gaactattca   38400
ttcctagggg agcagtgtca ggaaagattg taggtggagt ctttcctcag gacctccagc   38460
cagctcccaa ataaccacac agagcttatt attaattata aatgctcggc tgatagctga   38520
ggcttgttac taactagctc ttacacatgg cagtaccttt tttccagctt tgcacatcta   38580
tcttcccttt ctctgtgtct cctgacagtc acaccttctt ctatcccatg ctctcttttt   38640
gtcccaccta accttttcct gcccagctat tggccagtca gctctctatt aaccaatgca   38700
agtaacacat atcctcagtg tactaaaaga ttgctcttca gagtttcagg gtaatctcat   38760
cactttagct gtgtgactct ggacaagtca cttcactggc atgagcatta gttttgtttg   38820
taaaatgagg gtcaataatg tctttaggac caaacttgac aaggtatgcc cagtagagca   38880
tgtttagcac cataactggt gcacacgagg gacctggaag taggtgaaat cttgaggctg   38940
gggagatgtc tttgttggta gagcgcttga tatgcaaaca ccaagacctg agtttgatct   39000
ccagtgtcca tgtaaaaaaa tttggataca atctggtggt gcacgccttt aatcccagca   39060
ctcagcaggc agaagcaggc agatctctgt gagtttgagg ccagcctggt ctacagaggg   39120
aattctagac agccagggct atacagagaa attctgtcag ggtgtggtgg gtaggggaca   39180
gggagccgga tgcagtggct gtttgcacct gtaacccccag caccatggag gtggagagag   39240
```

```
gaggatcctt ggaactcact ggctagacag cctagcccaa tcagcgagct ttaagctcag   39300
tgagagactc tcttctctct ggtggactgc tcttgaggag tgacactgga agctgacctc   39360
aggcctctac acacctggat acacatacat gtgcaaccca cacataaaaa gtgaatggat   39420
ttttagaatt acatttttat atctatatat ttatcatcca tccatcaatc catttctggg   39480
ggcgagggaa agtgtgtgtg ggggattaat gtaccactgc attcatgtgg aggtcagagg   39540
ttactcctac catgtgggtg tccctcagct agaattcaag ttgtcatatt tgctgtaagt   39600
gtctttatcc cacactgaat catcttgcca gaccaattat atgttaaaat ggacaccta   39660 tgctgtaaac tgccagggat ttctttgggg ggagtgtggt tctgggagtg caatccaggg   39720
cccagtgtct cagacatact aaggtcaccc cctttccact gagccacaac cccagtcaaa   39780
gagagtgatt tgaaacaaaa caagataaaa cataaactca gggttgggga gattgttcag   39840
tggttggtgt attctgcact tgcagaggac atgaatacag ctcctaaggc ctctctctcc   39900
ctacctttgg gaaactcaca gctactcgtc tccatttcca agggatctga tgcctctcgt   39960
ctctccagac acctgcatgc atgtgtacat accccacacc cacataatta atataaaata   40020
aaagtttgat aacgttatta acaagaagga cgataataaa cacctagagt cactctgctg   40080
acgggagtct ctgttgtcgc tcgcaaaagt gagtgcccag actacgagcc cagaaacgcc   40140 actgagttg tgttgctgac accagtggc agtgttggca agcacactgc aacgctcgct   40200
gctgccaggc cctaacagga agatacccc acagaccacc taattcaacg tgtctttacc   40260
tcaggagacg gaggccagag aggggaagta cccggccggc tggcagggga agtaccctgc   40320
cagcatcgca ggccattgca cctccatgtt ctggttgggg gcagggcggg gcagggaatg   40380
acaggagctt gagaatctca ggttcaattt ttagcatcac aatttacaga gaagcacgtg   40440 ggacccccg aaaaagctta tctgactacc tgagaaaaac ttccctggag tctacaaaac   40500
ctgaactgaa agtcccgtgc ctccattatg ggttgttcgt catctggtgt cagtcagagg   40560
ctatgaaaaa ccattatgcc ccctcaacct caaggacccc cccctccctc cctccgtccc   40620
tcctctcccc tctccagtgc atccttttac ctccatctcc aaattcgaaa gttgcaggca   40680
agtaccacta tgcctgactt aggcagtgct ggagaacaaa cccagggctt ccaccatgct   40740
gtcaggcacc ctaccaactg agccacatcc ccagccttt cttttcttag tcttttgag   40800 acaggatttc actatatact tcagactggc ctggaattca ctatgtagac caggtggccc   40860
cacagccaca gcaattgcct tgcctcaggc ttcatagagc gcgtgtgaca cgcgggccac   40920
tacatctggc tagtattcta agacaaggtt ctgtctttca taggacgggc gacaggaccc   40980
ctgtcttgca gtacatgtta gaaggctctt gggcctgtgt gatgcctcag cctgtaaagt   41040
tgctcgctgc caagcttgag ggacccacat aacgggagga gagaatcggc tcccacaaaa   41100
tgttctgtga cctccacaac ttcattgggg gcatgcatcc tccatacata gaataaatta   41160
aaatgcaatt tttaaaaaga aggctctgtg tgcagcttgg cgcgctaacc tttaccctca   41220
ctggtcacaa aggaggtga ttatactcag cttagctgag accacagggg gccagggagg   41280
gaagcagctc accttgggtc acacaggatt tgctgagtct gagctttttt gctctttggg   41340
agctgattgg aagggagaag gcggccacc ttcgtggttt gtaacctcgg gtgggtcctt   41400
tgtcctgcct gggagagtag ggcagtgcgg aaccgcttgc tctgcgcagg ctccgagcct   41460
cctcgcccgt tccccactg cagatcccca tgagttcctc tccagagcat tcactgagta   41520
ggttgctagt ggaaatgtgg ttttcaaatt tgggaaatct ccattaagtc cttttattta   41580
aggaggatgt cattatcacg cctccccgag gactattacg gttctattag gcaaggccgc   41640
```

```
agacttccta ggtactgtct ggggtctgat tcctgggcag gaaaatacga gacaggaaga   41700 ggggggcag ggagtgggag agagaaaacg ggatgcggag cgggcaggag agaggagagg   41760
agagggatga agaatcgcag agtgcaagag ggagcctgaa aggcgcgagg cagaggtaga   41820
gcgcgccccc tagtggtgga gagggaggac agggcgcccc ccgccacgtg gcccctcgaa   41880
cctcaaaaag gttcaaaatt tcactggact gaaaggtgcc tggattctgc cctctgcata   41940
ggcaaggagg gggacacagg ggagtccccg tgccctccag ctactgccca ccctcggagt   42000
ctaggagggg cctttagaat ggccagcgac aaagaaagag ttaactaggg aaggcagttc   42060
tgcaaacctg gcctgggctc agggtgcttt ctggcactct gagtcatcat ttgccctcct   42120
cttggagctt ctgggtgagc tccaggagag tttgacccct ctctctgctc tgtgctgtga   42180
cctttgacac ctcgtaggtg ctcagcgctg gctggcacgt ttgtgttaca actgagtgag   42240
gcagggaaat ggttcctcat cttgtctctt ctgtactcag agccaagtca tacggtttga   42300
gttactctta gcaaagcttg gtgaccctgg atgtcttcag ggtatcctac tgaggacccc   42360 taccccagc ccaccccagg ccacctcctg ggtagagttt aggcagggtc aggagctgca   42420
tggcaagcag ctgacagtgg tttggctaag cggcaaagag gaaaatatat gttcctctag   42480
ggaccgtgtg ttaggggtta ccagccaagg ctggaagcat tcatctccag gcaggaaggc   42540
tgctactcag aggagagcaa acatcctgac tgggcaatcc cctgcttgtg ggtccccggg   42600
gcctgggcaa cctcctgcca tgatccctgg tctctttagg gctgccttgg atcctgaggc   42660
caagacaccc ccctcccgac cctccttatc ctgtgagagc tagccctggg gtgccctgc    42720 cttggagctc ctgtgcagaa gtgattaatg aggcgggat aaaacctttc ttccccagct    42780
gtgtcaacaa gcccctgtgg cctttcaggc tgcaggggtg gggaagcagc cccagttccc   42840
taggcctgtt ctctctttac cctgggctcc tcagagacca ggagaggctg atactgacaa   42900
tgatgacaat gatgattatg attttatgat gcccacaaca cttgatattt tttgagagtg   42960
ctgagagggg aggaagagaa gtccccccccc cttttttttt cttctccact cctcagctgc   43020
atgaaccaca ggatatgaca gagctgtctt tagttgacaa ggaacaacgg tgcccgatgc   43080
cacattccct gcaaagcctt tcctgatggc acctggtggg cttcatatac tgcactcatt   43140
cctctccaag gctctgccag ctgtgggcac gtgagaggag gttgcctatt gtcatcactg   43200
ccccttatca gagaaggctg tgtggatttt tgaatcattc acttttttt tttttaactg    43260 ttgtgtgggt gccggggact gaactcaggg actcgaatat gttgcatatg ttaggcatgt   43320
ggtctgttgt tgagctcttt ccaagccttt cttaagcatc gatctttccc acaccccagt   43380
cttagagtgg cctggttccc tgcttagcct gttgttacga aatgaacgaa tgcccagtag   43440
acctagaatg atctgtggta caagggcttt ggttggtgat gtctgtagtt gtggctcaga   43500
cataccaggg accacacgcc ttgacccttc tctcagggtg tctgtggtgt cctaggatct   43560
tccacagaag gcttctgatg gagatgatct aagcctttgg gttgatggta ggttaggagc   43620
aggaagccag atgttgttac atgacattta ttttatttta tcttatccag attggtttgg   43680
cactaactat gtagtctggg ctggccttga actcatgctg ctcttcctgt ctcagctttt   43740
caagtgctgg aattacaggc atgagctacc atgtatggag atatttaaaa ataaactcat   43800
tagctttaca ggaagctgca ctaaggcttt ttactcagct tctcatcacc ataacccaca   43860
caaccaggca ctttgtgcaa aactgagaac tttataccga taatatatca tgatggttag   43920
ctttaagtgt caaggtgaca tagcctagaa ttgcctgtga agggagtctg agtgaaggac   43980
tgtctagatc aggttggctg tgaaccacca cacttaaaaa aacaaaaaac tggattaact   44040
```

```
gatgttagaa gatgcagcct gaatgtgggc tgcaccattc cccgggtggg ttgggtactg   44100
ggcagtaggt atggggagcc tgctgagcac aagaagcaac catgcattga tccattctct   44160
tggctcttga tttcagatgt ggcatgtgat atactagctg cttctggttt ctggttcccc   44220
ctgctttgat gtgttgtctg cttctggttc cccctgcttt gatgtgttgt ctgcttctgg   44280
ttcctgctga cttgacttcc tggccttagt ggactataac ctggaattgt gagcaaaagt   44340
aaacctatat tctctaaatt gtctttcacc agggtatttt actacagcca cagaaatgaa   44400
actagaatgg aaggcttcca ttagatttca ccagtgttcc cacgaatggc cttttgttga   44460
tttatttgtt tatttgagac aaagtttcac cctgtagcct aggctgctct tgaactcttg   44520
gagatcatcc tgactcagct tcctaagtac tggaattaaa ggcttggatt aacacatcct   44580
tttttctttt tttaggctgg atcttgctac gtagtgtatc ccagactgcc cttccttaaa   44640
cttaccagcc tcctcaacgg tgggcttaca gtgaatggaa ctacactagg gtttaaccaa   44700 tatgattta aaatggtgct ttacttaaca attcacacac agggctgagt gtagctcagg   44760
ggtaagccct tgcttagcat ccactggttt gattctcaat gccacaaaag gaaaaaaaa   44820 aggtaaatta tggtagtaat gtttaattcc aaggaaacaa tttgagttat ttcatggtaa   44880
gaataaaatg tgtacacagc caaatattct ggttaaatat tgccactatg gttatttctt   44940
tttgcttctc ccactctctt gcacaccacc ataggctctg tgtggagagt gaaacactgt   45000
ttttctttta aagatttgtt ttgatctatt ttgttgttgt ttctctgtgt agctttggaa   45060
cctgttctag aactcactct gtagaccagg ctctcctcaa actcacagag atccatgtgc   45120
ctctgcctcc caagtgtgta atgtatgtgt gtctgtgtgt aggtggatgc agtacagata   45180
gtagccagaa gagggcatca gatcctcctg gcaccttata tgggtgctgg gaactgaacc   45240
ctgcaagagc agcaagttct cttaactgct gagcggtttc tcctgcccct gaaacatcgt   45300
tttggaagga cactctcaag ctatattttg ctgtgctggg tagggcctga atccagggcc   45360
tcgaatttgt atgacaagca ctcaagctca gacctggaat cctgaccatt cattcattca   45420
ttcattcatt cattcatttt tttgtatatt gtttgttttg agatgaagtt tcactatata   45480
gccctggcaa tctggaattc accgtgtagt ccaaactgac gaggagcttg cagagatcct   45540
gctgtcattg ccttctccag tgctgagatt acagttctgg accacgacac cctcatcctg   45600
agatcctctt ctacatccat taccatctgt tgactgctgg tttgagcaag gagaagtgat   45660
ttctgggcca gtgaggatt gagaaaagca gacggagaac tggaaaggga gtagggctgg   45720
ggcagatccg tggaggagaa ggctctgtag gtatgagtgg accccgtcag ccctgcctcc   45780
ctgaaaagca gagctgtgca tttgggctga gagtaggatg aatgccctgg gctctctggt   45840
ccattgatca cagccagttt cctgtccctg tctctctccc cttggttacc catcttccac   45900
aggtgcatcc gtctgcagca ttacatgtgt cacagttgct tttggtcttg cttgctcttc   45960
tggcccactg aaataattag aatgaaaatt tcaattataa tgccaccaga tgctctgtta   46020
ataagagagg tgagcgttcc accctgctgt aaggaagaca ggatcttcct gtggagctaa   46080
gtctttggag gcccaaaggg ctggtggagg aataagcagg catgcaggtg ggccaaggag   46140
tcagttaagg tcgctgctct ttggcctctc cataggcggc tctccttctg ttctcaggtc   46200
tcagacaatg tccacggatg tcatcttcca cccttgttgg tttctaattc tctctgcttc   46260
aagagatagg ctggggactg gtgagccagc aagaggatgt gggaggtgag gcatttggaa   46320
tttggcttgg aattactttt ggaaggcgag acagtgactc ctgggagagt tctctgcagg   46380
ctgtccatct ggggaagggc agggcagtca gactgagaag gtaggagaaa agcagctgag   46440
```

```
actggagagc ccccccccac tccccgagca cgcacactga gggcaaggtg gcctgggagt    46500
agaggtccat ggacacccct tagacttcaa gtctgcgtct ctccaggctt cacacttgct    46560
tcaggaagat gtctggtagt gaagtgtgtg tgtgtgaggg ggggggggggg ggctttaagt   46620 gcagtggagg cttcttagcc ataggtggac ttttactcaa gactctgggt gctggaagct    46680
cataaaattc ctaccgagtc actggctcca ggttcttgtc tttcgaatac agaggaggaa    46740
tttcatggac aatggaagag tgaattcagg cgggagtttt cttggaggtt cataggtgga    46800
agtttaagat gaagaaggc agagcacctg tgtgaagcag gtcctagagg tagggcacca     46860
tcaagctgct gggccaggag cttttttct ttaaaaattt ttattatatt tgtttattta     46920
cttattgggg tgtgtgccac agcacacatg tggaagcctt ctcagaatgt cctgacagag    46980
ctgtctacac tcaatgcctc tacttcctcc ttctcacgat tcctcaaccc ttccccccca    47040
gtattccatg gaaaggatg tggtagttcc tgctgttttt ctgctgctac ctcggaataa     47100
cacagactgg gtaatttata aagaataaag gcttgtcccg gagagctggt ttggttataa    47160
agtgatcatt gcccaaacgt gaggacttga attggatgcc ccagaaccaa gaagtggcat    47220
gcacttgtaa taccagcact gggggccctg gccagatgga tgggatccct ggactcagtg    47280
gcctgcgagc ccagcctagt ccacgagctg caggaccgtg agagtcactg tctgaaaaaa    47340
acaaggtgaa tgttgtcttc ctaggcacta caccccaagtt gacctctggc ctccacatgc   47400
atgtgcaaac atgtagacat gcatatgtaa tgtgacaaag actaaaaaag aataaaggct    47460
cattcagctc ctagttcttg gggcaggaat gacaagaggg acaattcagg agacagagct    47520
aaacaggctt ttagtttaat ttttaaataa attcttttt aaaaattgaa aagctttaaa     47580
acagtatttc tattaacttt gaaaaggttt atgttttta catgtatgag tgtcttgctt      47640
gcacgtatgt acatgttcca tgtgcatgct ggagcctaca agagggcgtt ggagctcatg    47700
aaactggagt tatggaccgt tgtgagcctc catgtaaaca tctgaactga acccaggtcc    47760
tctggaagag cagccagtac tcttaaccac cgatctatcc ctccagcccc cacatttatt     47820
ttctaatttg tgtatatatg agttcaggta cctacagagg ccagaagagg atgtcagctc    47880
ccctggagtt ggagttacag gctgttgcaa caaccactct caagataagc ccattaatca    47940
tgaatgaact caatgctcat gaagaccttg gccctcagaa cctcattatc ccttagatcc    48000
cccccccatc tcctgtgtca tttcttaata cctcaaattg ggactgaatc ccaacacggt     48060
ttaatggaaa tgcagatttt ggccggtgtt gaaattcctt tagctaaaact cgcctacagc    48120 cagccggctc caagctgcag ttggctcttg tcttcatgcc ttcccatctg ccacgtggac    48180
tcttctcctc cagtgtgttg gctctcctgg tctcctagcc actcttttc tattcttcct     48240 tctccctgtc ttcctggcaa gccctcaacg atgctcggtt ctatttagtt attaaacaca    48300
ttccttttat ttatttattt ttaaactacg tgcatggctg tgttttctg tgaacatacg      48360 ccatgtgtat acaggtgctc ccagaggcca gaagaaggtc atcaaatctc cgggagctgg    48420
agtaacaggc agttgtgagc cacctaatga agatacctgg aagtgaactg aggtcctctg    48480
caagagcagt ttatgctctt aaccacagag ccctctctcc agctccgagg ctcatttcct    48540
gcacccatcc tctgtggcca ctcacctgga gttcttctca tactctctac ccaggcagct    48600
catggaccca ggtaccctct gcccacatcc tctgcccaca caacccaggg tcagtctgag    48660
catgccccaa gcctgagtc ctgagcccat catttctcag ttggtcatgt tgcctgaaca     48720
atctttcaca caccctagag ccacaagtcc acagttgagc acggccctgc tctccagttg    48780
cccctcctca cacttgctta aacacatgag gtacacattc acacaagagc acactcttac    48840
```

```
cacagtgcac aattgcccaa atctcaaaac tgcatcttga tctaaactcc tttttttttt   48900
tttttttttt tttttttttt tttttttttt tgccctccag ctctatactc actagcctgt   48960
gtagcttctg gtgtaaatgt ttttgattgc catccctgcc ccctgtgcct tccactaatg   49020
ccttgattcc gtcctttata atttcttctt tcattagtga aatatcccaa tgggattttc   49080
agttcctcct ctctgtggct gtgtttgttt gtttgtttgt ttttggtttt tccctaaaaa   49140
cagatcaagg ggctggtgag atggttgata gctccgtggg tgtcctagtt agcttttgt    49200
caacttgata caagctggag tcatctggga agtgggagcc tcagttgaga aagtattcct   49260
accagattgg cctgtggggc acttcttgc ttgactgttg atgtgtgatg ggctaactca    49320
actctgtgca gtgccacccc cagggaaggt ggtccggagt tttgtaagaa tgtaggctaa   49380
gcaagctggg agaagcagcc actaaggagc actcctccac agcctctgct ttgatttctg   49440
cctccaggtt cctgccttga ctcccttga tgatggcctg tgttgcggaa ctgtaagctg    49500
agacaagtcc tttccttccc aagttgcttt tggtcatggt gttctgttac agaaacagaa   49560
accccaagac agtgggtaaa ggcatttact actaaactgg accacttgag ttctatctct   49620
gggactcact ggatagaagg aaagttcaga ctcttttttg tttgtttgtt tttctgagac   49680
agggtttgtc catgtaggcc tgactgtcct agaacttact ctgtagacca ggttggcctt   49740
gaactcagag atccactgac ccttgcttcc caagtgctga gattaaaggc aagcgccacc   49800
accaccagat gagcactgac tcttgaaagt tgtcctctga ctcttataca cacacagtga   49860
gacatgtacc cacacaataa ataaaatgca atttagaact gaattgaaac ctgtcatttt    49920
atgcctaaaa gcttccagac ctttctcccc attgccaacc gaatgaactc caggttttta   49980
tcttatatta tgtagaagcc attcacagtc taagccaaac tatactttgt tcggtctctt    50040
ggcctctggt cacccactgt ctctcacact tggctatagc acacataggt tcttgtctta    50100
agagtactgg tccatctgtc tgccatagtt ttgcttatat ggaattcaag gccctgcttt   50160
gcaaaattct cccctgacta ccagctaaat gggtgacttc tttaaatccc cacattgcct   50220
cattgctcag gagtgtctag cactctgtac tgtgtcatct ttccctggct atctcatagt   50280
accgaattat aaatatctta aaattttta ttttatttta tgtgtatgag tattttggtt    50340
gtgtgtttgt ctgtgtgcca tgtgtgtgcc tggtgcacct ggaggccaga tgagggcatc   50400
aaatcccctg gaactggagt tataggcagt tgtgagccgc catgtgaatt ctgggagctg   50460
gacccaggtc ctctggaaga gtagccagtg ctctcttcc agcgcccaga ttatatattt     50520
tgagaccaaa gatcccatct tacttgacca gtggcctggc tgtgtttggc atcaataggt   50580
ggccttttaa aatagtaagt atagtggata cttattatcc actgaagtag aaacaaggaa   50640
tgagtaaata aatacattct tgtctcattt tgtagaccaa aggcatctta ggggaggagg   50700
tttatttag ctcaccacgg ttataggtta cagtctatca ttgcaaggta gtcacagtgg    50760
caggcaactg gccatgtcac acctatagac aagagcacag agaaactaat gcatactgct   50820
tatttggatg aagcatggtt tctgcacttt tttttttttt ttggtggggg gtggtttatg   50880
agacagggtt tctctgtgta gctttggagc ctggccttga actcacagag atttacctta   50940
ctctgcctcc ccagtgctgg gattaaaggt gtgccaccac tgcccagcag tttcagcact   51000
cttatactat tcagccaccc ccccccccag cgcctaagga atggtgctac ccagtgtggg   51060
ctgggccttt tcacatcaat taacttaata agacagtctt ctacaaacac gccctcaggc   51120
caagccaatg tagacaatcc ctcattgaga ctctcttcac aggtgagtct gtgttgtgtc   51180
aggttaataa ttaaagctaa ccataccaga atgaatgatt tctgtccctg ggtctggttt   51240
```

```
ttgttttttgt ttttgttttt aaatccttgg ggataagcta cagtcttggg aatacaggtc    51300
tcacattttg tttatctgtg ttgctctagg aaaagtctgg catgtggtac ccactccgtt    51360
ggaggactgg ttgtgcaaag gtcctgggtt tgggcaactt tgcttttcat gaactgaaag    51420
cattaaacat tactctttcc atttacaggg aaagcgactg agtttaggaa taacatttcc    51480
caggtgcaca ggaacatgag atagctctgt ggggctctcc gtgagggct gttggccaca     51540 gaggcttggt gatttccagc tgaattagag tgtgaactgt ttccgtggaa tattggtctt    51600
tcactggggt ttggagtcca ggaaaaggct ttttggccag ctttaggtat tgggtgaggg    51660
tgtaaagggg tcttcatggg tctaaaaatg taaggtacac cacaattctt tcaataatga    51720
atatcaataa aattaagggt tggagttgca gttgagtgat caagcctgcc tagagtaatt    51780
taagccttga attcaagaac tagcaccaca aaaaggggg gggaggagg agaagaaaga      51840 agaggaggag gaatagatga ggggagatag aggagatgga ggaggaaaaa tcgatgggag    51900
gaggaggaga tggggagaag ggtgcgatgg ggaagataag gaatgggaa ggagagagag     51960 agagagagag agagagagag agagagagag agagagagag agggagaggg agagggaaga    52020
agagggaggg agagagagag agggagagag agagagaggg gggagagaga gagggaggga    52080
gagggaggaa gagggaggga gagggagaga gagagaggga gagagaggga gaaagagaga    52140
gagagaatgt ttataggtca attgcctgtt tgttaaaata cagttgtttt tttgttttt     52200 gggtttttt ttgttgttgt tgttgttgtt ttcaagacag ggtttctctg tggctttgga     52260
ggctgccctg gaactagctc ttgtagacca ggctggtctc gaactcatag agatccgcct    52320
gcctctgcct cccgagtgct gggattaaag gcgtgcgcca ccaacgccca gcttaaaata    52380
aagttttatt gagaccaagt actaagctta attggggaga tggactgggc agggctagat    52440
cttctttttc ttcaaaattt tgatgttttg ttcattgtgg gatttttgtc tgtttgtgtt    52500
actgagtttt tgagacagtg tctctgtaag ccaggttgac ctccaccttc caagtgctgg    52560
gattgcagac atgccagatt ccttttggat tttgaggtta gttttgagtt ttcaaaattt    52620
ataatgggta gtgtgtagct tggattctgg gtatgaggca agatacttct tacattatgt    52680
gtctagacat cagtggctca ctggtgtatt agagcctttg ctcagtgtat tagaaacatt    52740
gagtcccaga tgggtatgg acaagccttc accaggtacc tggagctgac tggttagcta     52800
ggctggatgg ccagcatatc ccagaggtcc tccaggcttc gccactccag cagtaggatt    52860
tcaggtgtgc accaccatgc caaactttt agcaagtgct ggggatctgt tgtgggaact    52920
cattcagcca acagcctttg gggtaccagc ccattaaggt atggtctcag gtgctatgtg    52980
tggaatgata agtgggaaaa gaagcattct ctctctctct ctctctgtct ctctgtctct    53040
gtctctctct ctctctcttg ggtggtggtc agggattgga ttgaagcttc cagtgcccct    53100
ggtctcattc acgagtgact cccgaatgaa tatcagatat cccttatttt caggctcttg    53160
tgttctctct taccatcttc cttataggaa tcttaactca ggtcctcatg gttgtaccga    53220
aaacacttta ctgactgagt catctcccca actcctgtgg gttatttatt tatttatgta    53280
ttttgaggta agaaattgct atgtagccca gggtggcctt aaatttgtga ctctcttgct    53340
tagcatcccg agcgctgggt ttatggtaca cactaccata cccaggtcca ggcctgggac    53400
actgaatgtc ttctagacct tctcctcctg ttctccctgc ccagcttagc agctctcctg    53460
ctatctctcc tgattggccc ctcacctcca gccctaccct ttgcacccca gcttccacaa    53520
tggcatccag ggcacctgca catcttgtcc ctgtttctca actaaactttt cagcaccctc   53580 tgcacaaact ccctgttgct tgaatttaca tcaactcttt ttgaccaaac ttgagtcagg    53640
```

```
accctttggg actgccttttt gaccaaatct tgaccttggc tttgtcttcc aactatatag   53700
tcatatatat actatataca tatatatgga ggatgagaga gagagggaga gagagagaga   53760
gagagagaga gagagagaga gagagagaga gagagttctt ctgggtgaat ttagccaaat   53820
cccccattct tgactgaatg ctggtcaaat tccctcaccc cccaggcatc aggcatttca   53880
tcacccggct tgccttcaaa aggaatctca ctggccttga tgcttccact tactaatttt   53940
ctacccactg acactgccct gttctttggc tgtcagtctt caccatcctt gttgtgttca   54000
gagttgatca tcatctctct tccctattgc cagagcccac tgtggtagcc ttagcttcct   54060
tacaatctta tcatctttca ctttgagata cagtctcact aggtagctta ggctagcttt   54120
gaactctcaa acttttttgcc ctagcttctc atctttaaca attgccatga ataattcttt   54180 cttttttttca aaaatttat ttatttgtta ttggtgtttt gtctgtatat ctgttgaggg   54240
tgctggatcc tggagttaca gacagttgtg agctgtcatg taggtgctgg gaattgaacc   54300
caggtccttt ggaagagcag tcagtgctct taactgctga gccatctctc cagcccctct   54360
ttctttcttt taaaaatatt cattttattttt tatttttgtct gcatgtatat gtgccatgtg   54420
tgtgcaatgc ctgaagaggc ctgaagaggg catctgattc tctgggactg gaattacaga   54480
cttctttgag ctgccatgtg ggttctgggg accaaacctg ggacccaaac ctggggcccc   54540
tggaagagca gtcagcaccc ttaaccactg agccatctct taagtctttt ttaaaaaaca   54600
gaacaaacag cctgcctgag aaggcctagc cctccaatcc tctgcagtct ctctccagac   54660
ttcccatggt gtatgcatat cccttctttt tcctgattct ctcttcactc taggtcactt   54720
ccttggatgt gaccccccca cttgcctttg ttattttaaa cattagtttg tttatttggt   54780
gttagtctgt atttgtatgt ggtgctctga gggcagaact caggtcagca gtcttggctg   54840
caagcactct taccaagtaa gccatcttac tgaccctcac ctgacttttg aagtagcttc   54900
aatacccacc cccacctcag tatcccactg tgtctctgca ttttggctat ttatttactg   54960
ggctctgtga gctcctcaag cgcaggtcat accccttatta tatcgtctgc tctattccca   55020
cactctctat acagggcctg gcacaacacg ggcataaatg aatacgtgga tggatggcat   55080
gaacaccaca gcagaaagaa aaatcttttc ctcattgctt tccggccaaa tctgggcag   55140 aattcttacc cctgacctcg atccagagct cagaacatca gggtttggag gtctgggatc   55200
ctggtgcccc tagcccaagg aggacaataa aggccacctc tggagagctt ggccattcca   55260
gtggaggaaa ttaaaacaga attgaattaa ttattcctca tattgaaccc tgcttcttga   55320
gtgtgctaag tgtcggatta aacaaacaac cccaaaagat agattcgctc ccctatcatt   55380
tttcatagta agagaaaaaa aacaaagatg ttgatttaag atacatccca gagctggggg   55440
ctttggggaa aacccggtga aggctcttgt agtttggggt cggaggtcac aggagcagct   55500
gctgcctggg gatcaagctc aaggttctgg agagatggaa aaacctggcc agcgcttcct   55560
ccgcgggccc cttagctgct aacaggagcc agctgagcga acacaaacag aggcgctgtg   55620
accgacacag atcccagctt cctctgaaat ttccagcctc attttttcctg tcggattcca   55680 gacagatgaa actttcctgg ccctggcctg ttcctggcag catctctcct ttgaatcgcc   55740
ataaatcagg tctgggggtg agcaatgggc ttttcctgat tgacaagctg ctgccttggt   55800
aaaacggggt ctctgcttcc taggctaata aaataactgg ggagtgatgc ttgactaagt   55860
cgtcgtcgtc cctcgccacc ccccccccc gttctctgcc cgccccacca gaaccttcag   55920
gtatcccttc gtattttaaa gttttgattc tgtctatgat tattatttca tggagaaggg   55980
ctgcgtatgt acagatatgg gcctttgggg ggctctgtgg tcgtaagcag caccattgtt   56040
```

```
tgagggatca catggggggg ggctgtgcat tccttaaagg ctccatcatc catgagtccc   56100
caattaattt caatacaaac accggatctg gcctcctctg cgcctctgca gccataacac   56160
atgaggtcat gcagcttcgg ttaaccaaac cgaggaggtg tgggatggag ggggggggc    56220 ttccaagccc tcgggaggct ggggtatctg tcctgcctga ctccagcagg gttctttatt   56280 acaggggag ggtatcaagc atctatgttc ttctctgttt catagctggt tttacttacc    56340
ctacctcctc tcttcatctg gagccattca tctgcccaag tgccactctg tatttttgtt   56400
gtttgtttgt gacagggtct tgagtctctc aggctagcct tggacccctt atgtagtcaa   56460
ggaaggccat tgaacttctc tccctgtccc catctcctga gtcttgggat tacaggtgtg   56520
tgccattata ccttttttatg aggtcgggga ttgaacctag ggcttcatgc aagtacttta   56580
ccgactgagc tacatgctag ccctctcccc cttttatttt taggtgggg cagggtctga    56640 tgtatccaag aatgggaatg gcttcagact tgctgtggag ctgaggatga tcttgaactc   56700
ttgatcatct cttgagtgct gggattacag gcatgtacca ctacatctag ctggaactcc   56760
tggggatcaa acctagggct tgttcgtct atgcaagcat cctacccta  ccccactcct    56820 ccctgccata cccctgtcta ccctacctct cctgccttt tccccctt  ttttccccc     56880 acctccctt taaagatagg gtctcactgt gtaacccagc ctggtctcag cctcctggat    56940
acaggcatat actattacag gcttccatcc tgtagttctt tgaattcccc tcccccctcca  57000 tgccctgaaa tacacagctc tgtccacttg gggcgttgtg tgacctttta atctggctcc   57060
atcaagaagc ctgtccccat cacttcattc agggttaatt accatgctct gtggtcatac   57120
aaccattggt tctggtcaga atcacctgga aggtgtatga aagtgctgat tggtgggcct   57180
gctccagagt tctggattag ctgacttgga ttagagcctg caaatgtgaa tttctaacaa   57240
gatctcaggg gacaaagatg ctaccacagc ccctgctgcc actttcccctt gatagcactt   57300 attctgttgg cttgcaacca ctcatttatt tgctgtgccc tcccctaggg acagctggga   57360
ctgtcggttt cctctctaag tctacggttt agaaagctgc gtgcacagtg aagcagttca   57420
ctggaggttt gtagattaag tgagttgtgg actcagagga gactggctga ctgccaagct   57480
caggagaagg cagaagaagg tacctatctc ttggaggagg ctgctgggca ggagggctgg   57540
tctttagggc tcatggttca ggccagtggt tcaggtgcca gaaggagaac tcaacctgat   57600
tttttcctct gagacccagg aaggccatat aatgaaagaa tacacggctc ttcttttgat   57660
cccatacagg gtgcacgtgt gtggtgcaca tgcaagtatt tgtgtgttgg ggatgtcctt   57720
ccgtatatgc ttctcttatt gattgatgaa tagaacactg ttaggccgat ggccaatgag   57780
acaggatgat agacgggact aggagaggag gagaagtctg ggaaaggtag gcaggagagc   57840
ctgccagaac agtcaccatg tagcaggcaa aggagttgca gatctggcat tctccggtaa   57900
gccaagacca cgtggaaata catagattag tagttatgtg ttaataatta agacagagct   57960
agccaataag aagcccatgg gccaacggtt taataatata aatctctgag tgttcattcg   58020
gggctgggaa gtggcggtgg gaaccttttg ttacatttgt gtgtatgtat gcgtctgtgt   58080
gtgcaagtat atgtgtgtgt agaccagaaa tcaatgttct ttttttttatt tgtttttttca  58140 aagacaaggt ttccctgtgt aacagccctg gctatcttga aactccatgt gtagatctgg   58200
ctgaccttga actcacagag atccacctgc ctgtgcctct ctagtgctgg gattaaaggc   58260
atgtgccacc actgaaaaaa aagttttttgt gttttaatca ctctccatct tagttttga   58320 ggcagggtct ctcatttaac ctggagttca cagattaagc ctacttgctg accagcaaag   58380
cttagggatc ctcttgtgtc tgcctcccct gtgctaggat tacgggtagg gttttataga   58440
```

```
gtcccccccca tacataccta cctccctcac ttgacttagt gccccctcaa tctgctactg    58500
actgctctgg actcacagtc gggccagctc tcacccagac tatgatctcc ttgaggacac    58560
atctgcctca cagaaaccgc agcaggcaat tgtttgtttg atcttaacct ctgaattggc    58620
tccaacttac cagaccatac aaaatggagt cactcatact aaattctgca taatcaaacc    58680
gtagctttaa ggaggtagat agattctaaa acagatggac tcattcctaa aacaggggct    58740
tatatccgtt ctttttattt tttttaattt tttttattag ttcaaattag gaacaagctt    58800
gcttcacttg tcaatccctt ctccctctcc cttccctccc cccaccctat ccattctttt    58860
taacatcgta aggaaatcac ctttgattta gctgttgcat tagagtaact tgatgccagg    58920
cagtggtggc acacatcttt tatcccagca cttgggaatc agcagcaggc ccatctctga    58980
gttcaacacc agcctggttt acagagcaac ttccaggaca atgaggacta tacacgaaga    59040
gaccctgtct tgaaaaaaac aaaacaacaa aagaaaagag tgagtgcaag ctaattaaat    59100
tgggcttttt tttcccctac tgtacttgct tgtttccacc ttacaaagcc cacagttgtg    59160
ttgttgccca gcaaagctgt gtaatagaag ctccctttac tcatggatga acagtaaagc    59220
cgattcaagg gctggacacc ctttgtcttt tttttttttt tttttaatt tgttttttg    59280 agataggatt tctctgagta aattggctgt cctgggactt gctttgtaga ccaggctgac    59340
ctcaaactca gagatccacc tgcctctgcc tccaagtgct gggattaaag gatcttcttg    59400
tttttagagg tgggtttcag gtagcccata agtggtctca aacttgtcgt gttgtcaagg    59460
atgaccttaa actccagatt tcttgccca ttctcctgag tttggttata ggtaggtacc    59520
accatgcctc ttttctttct cttcgttgtt ttcctttatt tttgtttaac aaggcctcac    59580
catagcccag gctggccttg aacatgcaat ggtttttcta tgtcagcctc ccgaacactg    59640
agattctagg cacaacttat catgcctgct atatcctatc ttttaatcat ctctgtagct    59700
tacccttgct tctcctacag cagcttcaat gttctaccag gtctcagaga tcctaatagg    59760
agagggttca aagcctggtt ctgccactta accacacttg ccactgtcta cttagacgag    59820

ttataggttg tcaccaagcc cccattgctt cttcaagaaa atgggagtgc accccagcc    59880 ccatgctgca gtgaggactt aagacaatac accaggttcc agacacaggg tgtgccatga    59940
gttgcttctc ccttggacca gacttgaagc ctgaatctgg ctttcaagct ttgtctttac    60000
atgtcccaga tgtggccagc ttcctgcaca gcccttctaa ctccctgaca gtaactgagg    60060
acaacaggac aaaaggggtt ccatggagcc ggacacaggc тcтттттaccc aatctgagtt    60120 cagccggaaa gtcagacctc agacaggagg gaggaaaaat tattaaagga ttaagtccag    60180
aataatcctc tacatcccag gaggctcaga aagcaataag ccctagacta aaagtctgat    60240
ctgtggagtc atgggggtgg ccccaatgtt тcтcaggcagg gaggaggttt caagggtgca    60300
gtgtcgtagc caggtctttg ctaaaatacg gtctcattct ggacacttgg acagcatttc    60360

tccctcatct tgtcatggtt tttaattaat aaggagtgag ctgcaagagt agggggggacт    60420

ттттттттccc tgagattcca caaaaataaa aаaттттaaтт aaaacccaca agtcgtgaaa    60480

ттттcатcстт gtaaagtgag acatcttggg actcagcctc tagcagctct cactccaggg    60540
agctggggtt cacactggct cctcccggtc actgatggag gacaccggct ggataggtga    60600
cactggctct ggcatccagt agctctgaac tatctggggt gagggagatt cctgtgacct    60660
gcctagaaaa tccaggggat ctggatgagg ggacatttca agggcctgaa agtgggcccc    60720
agaatgtggg ctgtggaaga gactgaatgt ccagggtttg ggggacagaa aatgcagttt    60780
ccacaggaga cttggagcca agggtcttgt aatcttgtcc ctatgaagtc ataaactagc    60840
```

```
ttacaacatg gccaactcat ttccttatgg gcctcagtgt ccccatctag aaaatgagtt   60900
gagttagcta gataagggct ttcttacaag gtacgaggag gaggctcaca gattgcactg   60960
agcccttttc tgctactccc aggtgtctct gagggtcatc cccgccctc ccccccccac    61020
accatatccc atgaaggctt cctttgtct gcttcccaga ctgggttctc ctctgaggtt    61080
ttgctttaac aaagggtgct gaggctgagc atgctcacac acacccgagg acctctctgg   61140
tagagtagcc tgtgatccgc cctggcttct ctctggcagt gctccctcct tgcttccttc   61200
aggaaacgta gcttctccct ctcttttttt tctacctgtt ttctaggtct cagaaactgg   61260
agagaagctg gtgaaagcta ccagtcctct ccctggaaaa atacacatag gaaaagcaca   61320
tacagattgt ggggtggttg gttctctgaa atgcttagga caagaactat tttggtctac   61380
ccccccaatt ttggaatatt tgtgactata tagtgagata tcttggggat agtcatttac   61440
attttatatg catagcctga ggctggtttg taggcagaat ttttcgttgg gaccactggt   61500
cagctctgtc ccatctgcca gcttccccaa ataatcaaac agagacttgt tattaattat   61560
aaatgctcaa ccaatagctt aggcttgttg ctaactactc ttataactta aattaacctg   61620
tatttctctc tgctctacca tgtggtggtg ccttttttcca gcacagcgtg tccatcttct   61680
cgacacatcc ccggcaactc ccatgacctc gcctttcttc ttccccacat tctcttttg    61740
tctgcaagct ccacctaacc tttacctgtc tagctatggc catttagctg tttattagcc   61800
aatgagaata atacaaattc acagtgtacc acaagattgt tccattgcat tggttcattt   61860
tatactattt taaaatggta taaatggttg aagggaatat ttaaaatata cattttaaag   61920
aattctgtgc aagaagctga tttaaacatt ttaaattaat taattgttgt gtgtgtatgc   61980
atgtgtgcct gtgtgtatgt gcatgtgtat gtatgtgcat gtgtatgtgt attcattgtg   62040
tgtgtgtgtg tgtgtgtgtg tgtgtgtgtg catgaggaag tcagagaaca actcttccta   62100
gtaatgaaaa ttccagtgat cagtgttggc agcaagttct taacccactg agctgtcttc   62160
ctggttccca aatcaagata taaaactagc cagcatatct ggtatccttt ctgtctctgt   62220
ctctgtctct gcctgtctct ctgtgtatgg tcttactatg tagctctagc tgtcctagaa   62280
ctcactatgt agacaaggct tgtctccaac tcacagagat ccacctgcct ctgtcttttg   62340
agtgctggga ttaaaggtgt ttgcttggtt tctattttt tttttatcga atgttgaagg    62400
gaatagaaag ctatccattc caacatacac gtaacacaaa cacacacacc acctctacca   62460
ccaccaccac caccaccacc accaccacca ccaccaccga attcgagagg tctaaggatg   62520
tggctctgtg ggtaaagtac ttggctgcat caggacccga gtttggaccc ctggcaccca   62580
tgtaaaagtt gggcatgagg ctgctcacct gtaagcccag agttgggggg aaagagacaa   62640
gaggatccta ggggcttact tgtaggtgga gttttttgtt gggactgctg gatcccaaat   62700
aaccacacag agacttatta attataaatg ctcagctgat agcttaggct tgctactaac   62760
gaactctttc tacttaaagt acccctcccc ccccttttt ttggtttttc aagacagagt    62820
ttctctgtga aacagttcag gctgtcctgg aactcattct gtaaaccagg ctggcctcaa   62880
actcacagag atccacctgc ctttgcctct ggagtgctga gattaaaagc gtgcaccacc   62940
aaagcctggc tttaatccac atttctttc cctgctctac cacattgtgg tacttttca    63000
tcttgcttcc gtcagcagct cctggtgact ccacctcct ccttccctc actctctttt    63060
tgtccaaaag tcttgcctaa ctgctacctg cccagctgtt ggtcattcag cccttttatta 63120
gaccaacgag agcaacaaat attcaccatg tacaaaatga ttgttccata gcccttactg   63180
gccagccaga ctagctgaaa cactgagctc cagggtaaga aagagaccca tcaaaaaaaa   63240
```

```
atagagaaag acgataaaaa agaaaaggaa agcagcagag gctcccactg ttgacttctg   63300
acctctggct tctaccatgt atatgcaagt atgtgtacac ctgcacactg tacatgtgcg   63360
tgcagacccc ccccccccac atacacacaa tgactgtcta ttccttttgc agtttaagtt   63420
tgcaatgtgc ctgtagatga gtgatttttt aaatatttta attttactat gctgaatcat   63480
ggagaggatc tgaattctat ccaggtctac ttggagcagc agcagcatag ggttgtatct   63540
gtgggtagca gggaacagga tgatccccat ggtgaatcaa cttggatgac tatgaaacca   63600
gtgataacca ggatggtcat aggcctcaga atcccagggg ctgtcaggag ggcttcatgt   63660
tggatgtggt tggcaccgat tttatttcat cctaaaggat gggatgtttt agctgacgtc   63720
tgacttatat acatgagaca gtgcacacaa ttctgagatt taggatcttc tggaacccag   63780
gtggaggaga aggtaacaca gatggtctct gcccttttct cttgtctcat acacacacct   63840
ctcctcacat agcagatttg agggcccaca gtctcaccca taaccccagg cccctcctgg   63900
ccactctgag atgtcatctg tgcatttcca tgtgaacagt gtgaaatgat cccaaaggac   63960
tatggaggaa acctggcaca tggcatctgg accagttgtc tccatcagat gtaaacatcc   64020
cctgctgacc cccccaaccc tcccagccca ctgctgggga ttccaccctc cagatgatgt   64080
aatctctggc tcatggacct cggctaggag cagccgtggg tcacccattg taggcggctt   64140
ctagcagggg agctgctatg actccatcct gggcctcagc tgctgcagga tttatggcta   64200
cctgcttttc ttggagctga caactgtagc aagctggaga aaggagtttg aatttgtccc   64260
aaggaaataa ttcaaaagaa ggaaaacact ccaggcaaga aggtgtccag catcgtggca   64320
gcccacacgg gtcagatcag cctagaagtc tggcaatgac aatagatgac atttgcccca   64380
tgcttcatac tcccctgccc cctcccgccc ttcacagtta ccatgagcta agtagacccc   64440
tggctgaagt ttatgcaaca gtgtaaggca ggactaactt gaaactggaa ttcatttaaa   64500
cacatctatc acaatatgtc tgctacctga ttttttttct ttttctttt ttctttttt   64560 ttttagatta aagtctcact gtagcccagg ctggcttgaa ttcatgctgg gattaaaggc   64620
atgaaccacc actcctggtt tctgccacct gattttatca cttgctgtgt acacattaaa   64680
cttacaatgg atgcctgcct cccctacctc ctttgtggcc gctctaggga gtcaaaccag   64740
atcctcatgt ggtaagcata cgttcaccat cagctattgt accataatgc tatctgtctg   64800
tgtgtaccgc tcacctcctt ccccaagctc tgtgggatga attttttaaa aagattgatt   64860
tttcaaagtt aagtttgtaa ctgtgcgtct ttgtatatgt gcctgtgagt acagttgccc   64920
acagaggctg aagagggcat cagattcccc tggaactgga gagaaaggca gctgtgggcc   64980
acctagtatg agcactggga accaagctct ggtcctctgc aagagcagta tgagatttta   65040
accagctcct agaccaggct gaccttgaat tcacagagat ccacctgcct ctgtgttcct   65100
agtgctggga ttaaaggtgt gcaccaccac caccaccacc accaccacca ccatgcctgg   65160
ctcctgggtg ttgttttaaa gatgaggaaa ctgaggctcc aagtgagtga gttatttgcc   65220
cagagtcaca gatgtcctcc ttttaggttg tgttagatga ctgatgatta caatcaccac   65280
agctacaaac tgcatcatga ttctagattt tttttcccta aaaattattt tcttggaatg   65340
tatacacaca cacacacaca cacacacaca cacacacaca cacacaccaa   65400
cagcccacct ctaaatctct ctgacctcct ccccaatgc tggggttttg tgcttgctac   65460
tactgaggta tatgcctaac ccttgggttt ttgagaaagg ttctcacagt gtagcccagg   65520
ctagccttaa actcacaact gtcctgtttc agcctgctaa atgctggaat tacaggtata   65580
ttctgcccca tcttggtgag tttcttttt ccacatttgg ccctcaccac agagctttac   65640
```

```
acattctaga caagggctct tgtcactgag ccacaccccc ggcccctttg ctcatcatct    65700
tagacagcaa aatgggtcag agctgagtag atacacacac aaaatagttc agagttggtg    65760
tgtgtgtatg tgtgcgtgct cttggtggag gaggtggtca tatagaactc agcctatagg    65820
ctgcccttct ggcaagggca ggcagggaac tatttccaag agcactgtga tgtcctgtac    65880
ttgcatttga aaatcacttg gaaaggctgg ggtgatagct cagtgtttgc ctttcaagta    65940
tgagaacctg aattcaatct ccaggaaccc tatgaagaag ccaggcacag tggtgagcag    66000 ttgtaaccec agtgctgggg aggaagagac aggcagatcc ctggggattg ctggccagcc    66060
agcctagcct acatcataag attcaggtca gtgagaagcc ctcaaaacaa caacagacca    66120
acatggacag tgcctgagga atgacactgg aggttgttct ctgtcttcca cacatatgta    66180
catgtgagcg tttacacaga tcacacacac acacacacac acacacacac acacacacac    66240
acacactcgg cacaagttca caatggtgga cgattaggtt tttcttgtag cccaagggga    66300
cacagagggg ttttaggcaa tcaaaggtca gaacaaatca ccaatgagat agatatgccc    66360
atgaaagtac ccagagtatg tcaggtgata gtggacagtg tccatcacat ggaaggaagt    66420
agcttcactg tatgactgca tcctgtggcc tttacacgtg ttcacatagt gtacttgtgt    66480
acatatgtat acataagaac acacagaaaa taacgggggg gggtcccgtt cagccaggct    66540
gttgaaacta ctgggggta gggaactctc tattactggc tgtttctcag caaaagttgg    66600
aactttatag ggaagtggtg gagaaggttc tggatggagg ctggacagag tgcttccaac    66660
ccagagcctc tgactttctg ccatttggac tctcaggcat ttgaagttca ggaatgcttg    66720
caaatgaaat cattacccaa tcaaagaatc tatttaaaca gccaactttc tgcctttta    66780 aaaatagaac tcagtttaca gggtggtgga aaggaagtgg gactctgtgt ggccctgtga    66840
taggtcaggc attgtgtcat ttattcctac tgatgctcat acctggctgg ggaggaaatc    66900
caggtgcaaa gaggtggaca tgaagtggta agtgggtggg ttggcactcc agcctgtctc    66960
accaggtatg acggtgagct tgcttggacc aaggcagtct ctctggtcct aataagcagg    67020
cagcgggccc tagttggaag gtggtggact aggtctcttt cactgtcaaa cactgaatga    67080
atagcatcat tcaggcctgt ggccctgaat ataacttgta gcatctagct gccttgctgg    67140
tctgggggag tgtcctccac taggccactg caggcatgag atctacctgc cctggtgaca    67200
ttgtacactg gactgtactc cctccgggtt tgcctgtggt agctgccaga ctgccagatc    67260 cttttccagca caacaccttg cttttcagtg tatagtatct cccctaaaaa tatggactag    67320
agatagctgg ccagggtcct ggggacctgt gggctcactt catgagcata gtacatgcct    67380
cccgatccac gctgtcactc tttacagggt tttggctggc tttaacttat catcagtttg    67440
gtctgctgat tgtcccacct ggctttctaa cttccaccatg tccaccaagc tgggaaagtg    67500
aaggagttga ggagttaaaa gcattgactg atatttcaga ggagccacat ttagttccta    67560
gcacccaaaa agtggctcac aatcatctgt aattccacct ccagggatc tgatgttctc    67620 ttctgacctc cacagacccc aggcatgcac accatgtaca catatacagg caaaacacct    67680
atacaatcaa atcaaataaa tctttaaaaa gtcttaaaaa caaatttat aaagttgtga    67740 aactgacctg tagactttaa ttcactttac ttttaaacac tattcttgtg ctttgggttg    67800
aagtgaaacc ccagggaaaa cattggtgtg ccttggccag acgttggtgg cgcacgcctt    67860
taatcccagc actcggaagg cagaggcggg cggatctctg tgagttcgag gccagcttgg    67920
tctccagagt gagtgccagg ataggcgcca aagctacaca gagaaactct gtctcgaaaa    67980
accaaaaaaa caaaaaaaca aacaaacaaa caaaaaaccc caaaaacacc attggtgtgc    68040
```

| | |
|---|---|
| ttgcttcact atcctaccag agcagagcag cttttaaata tttgtttact tatttacttg | 68100 |
| tgtgtatctg tgtgtgcgca tgtgtacact tgaacatgtg cacaaaaatg ccacagcatg | 68160 |
| catatgaagg ccagagaaca acttgtaaga gtcagttctc ttcttctgtt atgtgagtcc | 68220 |
| tgggcattga actcaggttg tagggctttg caacaaatgc ctttacctga tgagccatct | 68280 |
| tgtcagcctc cagaatggct gaaaaaacat tttaattgat ttatagttgt atatttttta | 68340 |
| aaagaggatt acagaagggg ctgggaagat ggctcagtgg ttaagagcat tgttattctt | 68400 |
| tcagagaacc cagtttcaat tcccagcacc cacatggctg cttataacca tctaaactcg | 68460 |
| agttctaagg gctctgatgc tcttttctga actctgagga catcattcac agggcgcgcg | 68520 |
| cgagcgtgca cacgtgcata cacacacaca cacacacaca cacacacaca cacacacaca | 68580 |
| cacacacaca cgcaatccaa atgcccatac acataaaatc taactttgaa aagaggagtt | 68640 |
| ctgggaatga ttctagggtt ttgtgtgtgc taggtgtgtg ccaggtaaga gttcttccct | 68700 |
| gagctatatc cacagcccca ttgtagtttt tatcttgaga ctgggtctca tatgctgcct | 68760 |
| agattggttt tgaactttct gccacagcct cccgagtgca gggattgcag aactgcatca | 68820 |
| cccaggtctg acttatgggg tatgtgttta tggagttctg tgtgaaattt caatacatgt | 68880 |
| atgcaatgta taatgctcgg atcagggtca cgaatgtcat agcctgcctt ttctttgtgt | 68940 |
| tgggaacatc ctggcaattt tgaaattctc aacttgtcat caatagctgt agttacccca | 69000 |
| ccatgctatg gaacattagg agcaaaggga gattttggaa gaagattctg ttgttatcct | 69060 |
| catttggtag ttaaggaaac agaggcacag gaaaagacca ccatgggctc acagtcacga | 69120 |
| ctggctcagc agtgtgagca aagctcatgt ccgagagagg gcccttggca cttctgcttg | 69180 |
| cttccattgc ctctagcagt ctcatgactg aagctagctg taaggaggc tgggaagtat | 69240 |
| agtctgtaca gtgctttggg aagtatagtc tgttcagtgc ttgctttggg aagtatagtc | 69300 |
| tgtacagtgc ttgctttggg aagtatagtc tgtacagtgc tttgggaagt atagtctgta | 69360 |
| cagtgctttg ggaagtatag tctactatac tgagctgaac tcttcgctgt gacttacccc | 69420 |
| caggcagatg gctccggatc ccatatttaa gaagttatgt ggtatgtaaa gtgttggcac | 69480 |
| atggcaggtt ccgatcaggt tgctgagaga gaaagtgaat gaacgaattt ggactgtatc | 69540 |
| cagacccct tccccattgt gtcctgcagg ctgctaggct ctaggacaca ggtgttgctg | 69600 |
| gccctaagt tagaatgcag atttggctac cttctcagag atcccaagtt gattttccc | 69660 |
| ttttataaca gtccaagact agacacctgg gttcacacgg tagttccagt gtgctggag | 69720 |
| acaaccatcc ctctctccta ttgttcagca accaggaaca ttgcccttgg tctgtcattt | 69780 |
| agtcatttgg aaagtggcat ccttgtcagt gtggctgcag atggctctat accagctcta | 69840 |
| tattcacgtt caagatggaa gaagggttta tggagagccc tgactccatt ttggtgtttg | 69900 |
| tgtcatcttt atgtcccagc cctcactttc ctgcgcattc ctgtgtgctc cctccagtgg | 69960 |
| gcagcaggaa gctgaaactt tacttcagct ccatccccaa cttccagaga tctcaagcca | 70020 |
| gtccctgatc attctctaga aacctaggaa cctctattct gtgggtaaat aaatgtcttt | 70080 |
| gtaaccttt ggtgacatca tctgccttga tatctcaacc acatttgga tggggttcaa | 70140 |
| ttctgtctct ccaggtggtc acaaaacaac gggaaatgga tagagcttcc ttgcacccag | 70200 |
| aaggtagaca ttcttctctg gtttgttgac aatgcaccag tcacatgact gtatatagct | 70260 |
| gctagagagt caggaaatgt catctctgcc aggcttccat gtcctcagtg gaaattctag | 70320 |
| ggtctgttgt taagggaaga gaaaatggt ggctgctaga agtcacatca ccctttacag | 70380 |
| aagacacttg ggctgagtaa actcccaaga tggtagagtt agaaacccag gctcatctgc | 70440 |

```
tttgctggga gatatagcac tgtccccagg agactgttct ctgcatggag ggccatgtac   70500
ttttcttctc tagaggtcac ctagcaaatg cccaactaac actacctgtc ctttcaggct   70560
gtcactccca gctacttctg tagcagttcc tgaagtctgg tacttacttg ggacctagcc   70620
tcaagtttct ggatgggtgg gagggctgtg catggggact gggagtgaaa ggaacaatct   70680
gagctttccc tctgattcct actgcagaac gtactttact gtagtgtgta tttctgagtc   70740
tgtttcttcc tttgatccaa aggatctcaa atattctgga gcccagcatc cttaccagtt   70800
cctgacacat gacaggcatc tggtaaatga ttggtgacta tgtgagttaa tgaactcaag   70860
tggaggtcaa aggttgtgtg caggattggg agaatgccat agtgtcattc ataccagttt   70920
taactgcacc aacactccat agccaatcag cccaaaacaa tggctagcaa cacctgcgtt   70980
catgtgtttt ctccactcat gagcctgagg gctgcctggc tctacaggat ctggctgcac   71040
ataactctag accatgttca ggtatgttct agatatttct tcattttctt gagcaagttg   71100
ctatttggga catggctttc tcatggtaag tgattcaagt ggaaacatat gatggccttt   71160
caggcttggc ctagcaccac agtctgtcac ttctgctcat atcaccacgg gtcagatgac   71220
caggcctaat gtcactggag tagggaaata tattccattc attttctac tccaaggtca   71280 cttggataag tgagagtcaa gagttgaaca gcaatagatc acaccatcta tgaacaaagc   71340
ttagagcttc cttaatttct ccatctagaa tctcagggag aggggctgct gggccctgac   71400
ctttctctcc tcttggggat tatggcaaga agtgccaaag gccccccagtt ttttccattg   71460 ctaccttctt ttttagaagt agaatatttt aacatgatac acatgaggga ccacatttcc   71520
ccagctgttt ttgcagttgg gtttggtcaa gtggtgttga taaaagtggc agcaggtccc   71580
actgccactt ttcagcccca aataaacaca cagagatgct acattaatta ttaatctgtt   71640
ggctaatggc tatggcttct tattggctat ctctgtctta attactaacc cataactact   71700
aatctacgca tttctacatg gccttatctt actggagaac acctggagcg tcctagcctc   71760
ccagttcctc catggtatcc cttttctgcct accttttccca gaattctcct tgtctcctag   71820
tcccacctat tttcctgcct ctattggcca aacagtgttt tattcatcaa ccaataagtg   71880
aaacatacac agaaggactt ccccatcaaa gtggctcagc tgtggcccat gggatgatgg   71940
agaaatggac caaccacctt ctgatgaaaa ccatatggca agctccttgc cctggaatga   72000
acataaattt gcttggtgag atggccctgg ccatggctat acagatgaag actggctggt   72060
aatctggctt attatgtaat ggtgcttgct gccaaggcag atgacctgag cttgatccct   72120
gagacccaca tggtagaagg aaagaaccaa ctcccacagg ttttccactg actgccacag   72180
gtatactgta gcaggaatta cacaagccaa ataaataaaa tgtagcaaaa aattaaaaaa   72240
aacccactga actgtgaggc tgtcactttta ttttatttaa tttaatcttt taaatttttc   72300 ttttttatt ttaaggttta tttatttatt taatgcgcac cagtgttttg cctatatata   72360
ccctgtgtga gggcatcaga taccctggaa cttatgttac aggcagttgt aagctgccat   72420
gtgtatgctg ggaattgaac taaagtcttc tggaagggta gtcagtgctc ttaactactg   72480
agtcatctct ccagctctat ttattttttgg gggtgtggtg gttcaagaca gggtttctct   72540
gtgcaagagc catggctgtc ctcattctgt agaccaggtt ggcttgagct cacagagatc   72600
caccggtctc tgcctcctga gttctgggat taaaggagtg ctccaccact gctcagccac   72660
tcctttgtat ttttttgaatt ttcttacatt tatttattat tgttgcatttt acatattgta   72720 catgctctct ctgtctctgt ctctgtctct gtctctgtct ctctctcaca cacacacacc   72780
agtgctatgg tgagcatgtg ggagagtcag tggacaactt gagagaacca gttctctgtg   72840
```

```
tctactatgt gggtgcctgg aaaacaactc agattgtcag tattggtagg aagcaccttt   72900
acccatggaa ccatcttgct ggcaacactt tagggtagag ggagatcaca gttgaataga   72960
aaaatgccca cacgagctct tggaatttgc ctgctcacct gcccatccca gatccgagtg   73020
aaaggatggc agaacctccc ctgagctgta ttctcactgg ctcctgcatc ttagcctgtg   73080
cctctgaccc tcaagtcact cctttgccac tctgtgacat ccctgctcca acccacgagg   73140
acctctagtc tctcttctgt ccccattcac tgaagtgggg cctcaagcct cttttgattt   73200
ttccctggca aagttgagat gagatggatt aggaaaattt atgaatggca actagtagtc   73260
caaggaagtc aagaaatgaa gccttcaagt tcatactgta tagccactat gtaccaaagc   73320
agctgtgccc aggtgtgtac cccagtagac atggccaggg cagtctgatg ggacattcca   73380
cccagggaac tggaaatcag aggaatatga aatctagagc aataatgaca ataatagtga   73440
tattttttga gatataatat cattatgtct gatctggaac tcactatata gaccaggctg   73500
gcctcaaact cacatagatc tgcctgcctc tgcctcccga gtgctggcat taaaagtgtg   73560
caccatcatg ccccataaga atgacaaaat tttaaaatta ctttaaaaaa tttaaaatta   73620
catctaatga attgtgtgaa ccatgagaca cacatggagg tcagaggaaa acttgtggga   73680
gtcagttctc tccttccact gtgaaggacc tggaattgaa ctcaagtcat cagacttggc   73740
agcaatcacc tttactttct gagccttctc attggctcaa gaatgacagt gtttagaaag   73800
ttacagtgac ataccgatgg catattcatt ttttcactga catagaagct gagaaatttg   73860
gctcttccat aggaagcttc cagagggtct gttgttaata cacccgcct tgtgattcat   73920
agctggaaaa tcagagttgg ttggagggtg tttcagggcc tggcctgaag cagccaaatg   73980
ccagagctct gtgccttgca gaggtgactc actccatgga gtagtcacct tgtagaactt   74040
ccaactggtg cagctcggtg gccacctcct ggagtccctt gctctgggtt tcctaggctg   74100
ctcctctcca gccaacgtca cctgcttttcc tgctctctgt gacctggctg ccagccacag   74160
cagtcctttt ttgggaagga gcaggaaaat tccccaacgc cctggaacct cttaattcaa   74220
ttccgggctt agtttagaat ggcttgtgtc attcctaggc tattgccagg aatctgggga   74280
cgagaccaat aaataaccat gtctccatat ttcccagtgc cctgtgggaa tttgacattt   74340
gcaaattcaa ggtttcacaa tttcttttca ttttttcttt ctttcccac ctcctttctt   74400
tttgtgtata catgctcatg tgtgcatttg tgtgtaccaa tggtgttgaa tgtgtgtatg   74460
tatgtatgtg tgtgtgtatg actgtatatg tgtcaatagc atgtgtggtg tgtgtgtgtg   74520
tgatgctaat gcatgtgtgt gatgtatgag catgtgtgtc aatagcatat aagtgtgtgt   74580
gtaggccaga agtcaacctc aggcgttaaa aaaataattt atttaacttt attttatgtg   74640
cattggtatg aaggtgtcag atcccctgga atcagagtta cagatagttt taaactgcct   74700
tgtgaatgct gggatttgaa cctgggtctc tggaagagca gtcagtgttc ttaactgctg   74760
agctatctct ccaggcccca ccttgatttt ttttttaagg tttatttta tgtgtatgtg   74820
tgtgtgtctc tgtgtgtatg tgtatgtgtg tgtgagtacc caaggaggcc acaagtgtca   74880
gatcctctgg aaccaaagtt acaggacttt gtgagctcct gccatgggtg ctgggaaccc   74940
agctcaggtc ctcgggaggg gccacaagta cccctaactg ctgagccagc cctttgctt   75000
tgttttgaaa ataaattaaa aattatattt ctttatttat attagtgtgt gtgtgtgtgt   75060
gtgtgtgtgt gtgtgtgtgt gtgtgtgtgt gcatctgtgt aggcacacag gtgtcatgct   75120
gcacatgagg aggtcaaaga taacttgtag gaactgattc tctccttcca tcatgtagat   75180
ctaaggaatc aaacacaggt tgtcaggctt gatgccaaga gccttactc aaacacacca   75240
```

```
tttcactggc tcctaccttc tgttttgagg cagagtctct tattggcctg ggttcactga   75300
tttgactagg atagctggcc agtgagcccc aggggtttat ctgcctgtac ctccccagtg   75360
ctgacactat gattattgca tgcctccata cctagctttc tctttctttt gtgagacagg   75420
tcttatgtag cccacatggc cccgactgaa tactgagatt acatgtgtgt accaccaagc   75480
cccactcaca gttccttaat tatataatat cctttgtttc cacataaaga gaggaaggaa   75540
atactaaatg aacacctact aggggccaa gtatttaccc attttttcc ctaatctagc    75600 tgcaggataa tatggcaagt ggtgggcatt tggtcagaga cacaagaaga caggggcca    75660 aacggaaggg gcctcagatg accttggaag aggtgatgaa gagttctgct tcaacaaagg   75720
acttgggatc ctacgcgtgg aacctttctt tcacactgtg ctttctggaa acacccacat   75780
cccttcatga gatgagctca cccgtctttg gcactgactg cctctcagcg cagtcctggc   75840
tgggccaagc taccatttct acaggaggag tatagcaata acagcgatct catttttctc   75900
cttaaaataa tacctgtgtg ttctgccaac aagcaggag cggtcctgtg gaagcctgt     75960 tccctggccg ctaggattag actctacagg agccaacaaa ggcagccctc agacgacctg   76020
gaactcctgg ctgcagacct tccctgtctt tcctgtccct ggggaaaggg ggtgtcagct   76080
tcaagtcccc attcaggcct ctccagggca aagggatgct gttgtcatgg ttctattctc   76140
tgcccaccgg tgacttccct cctttttgcat ctctctggaa ttgggggcaa tgtgctatga  76200
ggaaaaggtc agtggaaaca atcattttac aggaagagtt taattttct tcctttcctt    76260 tcctttctcc ttttctttcc tcccatcctc ccttcttgcc ttccattctt ccttccttcc   76320
tctcttcctc ccttcctccc tcccctctct cttctttctt tctctttatt cccccaacaa   76380
acacccccct cctcccactt taaagtgaaa aaagttctca tttgcttaaa ggtctaagtg   76440
cctggaaatt tcttccctat gcgcacatta cccacttcct ggctggaggg acggaaggac   76500
tcagagaatt tgaaggatat taaccagatt cataatggac ccagcagtat aaacatgtct   76560
caagtgcaga cagaaatgcc acaagcccct attcagctta atgtaaaaca tatacccgtt   76620
gtgtctgtgc tcccatttca caaataagca aggtggagag atggactcag aaattgtccc   76680
tggagagcca ggtgcctccg ttcatggcaa tttggagact tctactgccc acaaataagc   76740
tagaaaagaa agcttaatgt agcattgcag acccctgcca agaggcagag caaataggag   76800
ccccgagcaa atgatgcact ggtcccaaca ttccagtgat ggcccaagtg gcagaggtgg   76860
ggctgaggac ccctcagttg gtgtagttga tgaaatgggt ccaagtagca tggtctatag   76920
aggttggtga atgtaggttc aagccctgct tttgtctcct cggccacagt tgtgggtcc    76980 ctgtatgcgt agctggcttc tcatgggaaa tgggacagcc attccagtct agaggctgtc   77040
actgcagggt tacaagggtg ccaggggtg agtgtgtcag tgtcctagaa gagaaggaaa    77100
atgatctcag gaatggtcac tttgtttatc cttgtttctt gccacaaatt cctgcaaatc   77160
tagacctaga gggactttgt ccccgtcaca aagtctaaac atgttgagac agggtcatgg   77220
gctcaaaggc aggggcacc agagtggact gtgagctgca taggtgggcc tggaggaagt    77280
tcagtcaatt cagctgcatg gtcaccgctg cagggatgtg taggtgtgag gaagatgaga   77340
gagattcaaa gtggaaggac aggcttggtc cagactccct gagtcctgct gtgtgatgag   77400
tcaaattcta gaaccctcct gagtcccagg atttttttt tttaatgaaa catcttttt     77460 ttttaaaaat atttatttct ttattatgta cacagtgttc tgcctgcatg tatgtctgca   77520
ggccagaaga ggacaccaga tttcattacg gatgattgtg agccaccatg tggttgctgg   77580
gaattgaact caggacctt ggaagagcag gcagtagtct taaccactga gccatctctc    77640
```

```
cagcccgagt gccaggattt taattgctgt gtaggaagca acagagtccc cctcagaagg   77700
gatttgaagg ctgaggatat gtactctagg ctacctgtgc agtgtactct agcctagctg   77760
tcctgtgcaa tgtactctag tctagctggc cagaaagctt cctcatgatt ctcttcctcc   77820
tgcctcccat ctgggcaaca gagctgggat tgcatttggt tgccaccaca tccttttttt   77880
cttttaaatg tgaattctgg ggattgaacg catgtcatta ggcttacatg gtctggtggt   77940
ttgactgaga atattccct gtagacttgg atctttgaac acttggttcc cagttggtgg    78000
cactgtctgg gaaggttgtg tggccttgtt gggggaagtg tattgctgga gcgggctttg   78060
agagtttata gccttgcccc aagtattagt tagggttctc taaaggagca gactgataga   78120
ccaaactaat acatataaag ggatttacta gaggggttta caggctgtag tctatgttgt   78180
tcaacaatgg ctgtccccct gacagaaaga taaaggatcc agtagttgtt cactacacga   78240
gcctggatgt ctcagcagtt ccaggtgctg gagttccaga taggtcttgg agatctgcca   78300
gtgttgagtc cacattggag tcctgaaggc gtaggttcta actctggtga aggagtgcct   78360
cagggtagat gagcttgcca gcaagaatga aggcaagcag gcaaaaccca aagcttcctc   78420
cttccatttc cttttctgtg ggctgccacc agaaggcgtg gcacacactt agggtgagtc   78480
ttctacttca aataatccaa ctggggaaaa tctctcacag acaggcccag ctgcttgggt   78540
tttaactgat tccagaagta gtcaagttgg caaccaagac tagccatcac acctcacaca   78600
tcactctcca cttccggttt gctctgtctg cttcatgctt gtggttgaag atgtgttcgc   78660
tcagcttcct gctcctgcca ccatgcctgc tctttgttgt caagcctccc agccatggag   78720
aactgtatct ctctggattc acaagccaaa gtaaactatc tctttataa gttgtcttta    78780 gtcagagtgt tttatcatga caaagaaaa gtaattcata tccatagcta gctgccactt    78840
ttaattactg agccatctct ccagccctca aatatcattt cagagacatc ttccaggcac   78900
tgttaccgtg gtgataatca ccatagggta ccattgactg actcctttct ttgtcccagg   78960
tacagggatt tatataacta aatctttact ttgaaaagaa cataccacta ttcccatttt   79020
acagatgagg aaacagaggg tcagagaagg gaagattttc aatccccatg gctgggagct   79080
ggcatcaaat gatctcgttt cccagaatgc acaccactgg ttcagccagg tccgggcacc   79140
tgctctcagc tcttggccca gacctcaggc atctctgtgt gactggctct ctgtgatctg   79200
atttggcctg agtgtgcagt cttttctgggt gttgggttca tagtacagga ggccttgggg  79260
tgcccaggca ggcagcacct cctttctcca ggtcctcttg gccaacactc attcttcact   79320
gggtttggat ccattcccca caggctttgg atatgtgctt ggctcaggct ctaaagattc   79380
tctgctctca gataataaat aacaagtttc taagtcttcc agcaatgagg gaagggagag   79440
gcttagcagc tcctgggtct gaggagcctt gaacctgacc caagcgttct tggcatcctg   79500
gtgcatctgt ccccaaggac ctctactctt ccacgcctct gatctgctgc tgtgtaaatt   79560
atccctgatc ttccctaaag gaaatataat aggagtgggg aatgggggag ggagcaagac   79620
cacaacctgg gggaggggga ggggccatga ccacaacctg ggggagggat gagttaagat   79680
aatccttccc attcaggaac tttatagcat caaacagtgt gcagtctttg tctaggcccc   79740
acacaggcaa tctgtcacag gatgtggagc ccatggggct gagaggatgt gacctgctga   79800
ggtagctctc tctgccccat actacgcaat cttagatctg tggcctttct tgccctgggg   79860
agccctgtaa cctcttctgg aagctataag ggcttttctt ctcaaaccca ccttcccaag   79920
atgccctgga gtgcatctct ggccgacaga tgtttggtgt gtgtgtgtgt gtgtgtgtgt   79980
gtgtgtgtgt gtgtgtgtgt ctagacatcg gggctggggt ggctagagct gccttgttca   80040
```

```
tcttcaggaa gccctcacaa tgtcctcgtg gggtgtgaag agaagagagg agtgggcatg   80100
ggacagagcc aaggatgacc cttcccagtg tgtggtacct catgctgctc tctcccacag   80160
atccaaatct agcttccaa gtaccctaaa atagctatct tttaaggtgg aggttagatg   80220
tatatatatg tatatatgta tatgtatatg tatatatata tgtatatata tatatatata   80280
tataaaatct cccaaagaac tgactcttat aatattttat tattttaatt atatgtatac   80340
gactttgctg gggagacagg gtatgtgaat gtgagtgcat gtgcccacag agagggcatt   80400
ggatcatctg gagttgagtt acaggcaact gagtcaccca tggacagggg tgctgggaat   80460
cgaactctgt cctctgaaag agcagaacac tctcaagcac tgagccatct cttcagcccc   80520
atgcactccc cccatttcat tatttcttcc ctgatattaa ttatttcttg gcatctattg   80580
ctttgggatt tggattcttc ttgtctttct agaaccttga gatgcagcct tagatggctg   80640
gaagtctttc tgatttctac ttgttcatag tttcgttccc ttccttctgt gctttagtgt   80700
aagtacctac tgttatactt tcttctgaga actgctttag ttgatcccga cgcttctggt   80760
aagtagtggt tccaagacat attaaatgtc tgttaaactt gacttttggt tcttgcttaa   80820
atgcatgtag acagttctcc atctgtgttc tcttccctcc aggggctgca attgttgagg   80880
ggtcctagtt tccagacccc tcttaatcca tatcttccca ccaagaaaaa acttccctta   80940
gtcactacag ttacacctac aagctaggta cacaatagtc ctttatccac aggggactct   81000
ttctcaggtg cccaaagaca cccgaagcag tgcctagtgc catgtcctac ctactactac   81060
atgcgaacaa caatgataaa attcaattta taaatggacc tcagtaagac agtgaagcta   81120
taactaaaat acaatagtca taacaatgta ctattataaa agctatttaa aacgtaagga   81180
ttatttctgg aaattttcac ttaatatttt tggatcatgg ctgaccaagg gtaactgata   81240
cctagagatg attgtaatta ttttcatata tgagtaaata ctcatcctgg gcatggtggc   81300
acatatgagt aatccctacc gtggaacagc aggagcagaa aaatcagaag ttcgtcaacc   81360
ttggctatat atcaagttca aagccagctt ggtctacatg agaccctgta tccaaacaac   81420
agatgcatga caacatcagg gtttgggagg tttcgatgct tgtctaggtg tggatagctg   81480
gaagaatagc cttcaacatt tatctggcct ttcgttttcc ttccccccat cttgccagaa   81540
gggttctgtc tcttttagga gggacttctg tgggagtcct tctgtgggac ttctgtggtc   81600
agtcagatgg aaggggacat ggatgggggct ctacgctgga gacatccaag aagagtgcct   81660
atacggaagg aaggacactc agaaggctgt ggcccatcag agtggcaggt cctgacagct   81720
caggtttcaa atccataacc tcactggccc tcccaaatct cccttctccc aacaagcaga   81780
gttttccatt gtagagaagg gaagaaatgc gactctaatc cctttgttcc atgatttcat   81840
ctctgctctt ttcaggggct gcaggcaagc agcgggagga aggaaagtgg ggcagagcag   81900
caggcagggc ttctgggggt ccccgggggc tttgggcagg agagaagagc tgaggggtaa   81960
atgcatcctc cccccagagt caacagctgg aaagacttcc aggaggcctt tctccccttg   82020
cttgctctct ggctcacagg acactgaatt cgcctcctga ctgtcccctg tgacccatca   82080
tcgataactg ctgcctgagc gcaggtctcc tcatgtcccg caggatttac tccagctgct   82140
gctgcggcct ccagagccca atgtgtctgt catggaccca tactccaccc agcaagtatt   82200
caccgggtta cttctcagca gccacagaat gaagcctggg ctccagcaag gcactcaaag   82260
tcctcctcgt ctttcccctc cttcgttcca actcagtggt tagtcgtaag ctcttgtaac   82320
tccagtaccc ccaggatcct ctggcactgg cttggcttct atagtatgga tcctgttgtt   82380
ttgcctcctt taggaaatca catatgtggc tggcacacac acacacacac acacacacac   82440
```

```
acacacacac acacacacag aggcacacac acagaggcac acacacacac acagacacac    82500
acacacagag gcacacacac acacacacac acacacagag gcacacacac acacacacac    82560
acacacagag gcacatacac acacacacac agaggcacat acacacacac acacagaggc    82620
acatacacac acacacacac agaggcacat acacacacac acacacacac agaggcacat    82680
acacacacac actcacacac agaggcacat acacacacac acacagagag gcacatacac    82740
acacacacac acacagaggc acacacacac acacaaacac acacacagag gcacacacac    82800
acacagaggc acacacacac acacacacac acacacacac acacacacac acacacacag    82860
tggtctacta cttcttgggt tcctgtacct tgttttcctt tcatttcttc ccctcctctc    82920
ttcttcttct cttcttct ctttttcttt taagacaggg tcttgtgtaa cccaggctgg    82980
ctttaaactt gctatgtagc tgagggtgac cttgaactct tggtcctccc acctttacct    83040
cctaaaggct agaactatag ctgtgtacca ccatgcctgg tttatgtggt gctgggatc    83100 agacccaggc actctgtcaa ctggactaca ttctcagcac tcccataccg tgtttacttc    83160
tatcctgtgc acttagtgtt ccctaccctg aagcatccac ttcctagtag gtagcggaag    83220
gggctggaac actgagctca tcattaaagt caattaaacc caataattag tttagtcact    83280
catcggggtt tgttaaatac tgccatgtgt gccaagctgt gcataccttg gaaactcagg    83340
ggctatcctc ctggtgagag aggaataagg ttcccaagta gatccgttca ggtaatgcta    83400
tccagggaag gccatgtctg gtggctcagg cctgtaatcc tgtctacttt ggaggctggg    83460
acaagaggat cacaagttca aggccagcct cggctccaga atgagttcaa gaccagccta    83520
agcacctgct tctgcccatc ccagagttct gctgacaggg ctggtgtgtg ttgggcagac    83580
cttcactcca ggtttgaggt aacataaggt ttctaagcaa gtgttactta aaaggaactg    83640
tcatccacag ccagacagtg gttaagtaag cttcctctgt ggaagtctaa atatatatgt    83700
tagatttggg agccaagagc aaaaccaagg atattata cttacatgac aacggaaaaa    83760
agcaacagct atccacaaat gcttcattaa caaagttgga aacataaaaa caattggggg    83820 gggaccttt tgtacacagg tctactaatg agaagaatcc attactttgg aagggctatg    83880 acatttgca taattgtagg gagttatgtg actcagcttt ccatccccat aacaatatac    83940
ctcaagcaat aaattgtgc acagaaaaac tattattta cttattcagt gaacacacac    84000
acatgcacac acactctata taagtaattt ttgagacagt tttgttatga atcctgggct    84060
ggcctagacc tcatgactca gccctcctga gtcctaggat gacaggtgtg agctaccaca    84120
cacagctcaa aagaaaaggc ttatttggc tcactgtact ggagactcag ttccaagaac    84180
aactgtctca ctgctgaagt ctctggcaag ggatgcttgt caaaggcaga gcctgtata    84240 gaacaaggct gctcatttg tgaaccagga agtgacagga agtgcaagaa accagaatct    84300
caaaattccc ctcagggta cagcccgtgg atctaaggac ctctcactaa gacccacctc    84360
ctaattgttc tactattccc caatatcacc atcctagaga ccatcccttt agctcctagg    84420
ctttgtgggg acatgaagat ggggcccata tgatggcatg agtgactttg taagaagagg    84480
aaggaaaaca tgagctggca cattcctgtg aactctcatg ctcttaggct tttctgcctt    84540
ccactatggg atgttgcagt ggaaaagcct tcaccagaca tagccccgca agggctcttg    84600
gtctgcagaa ctgtgagtca aataaacttc cgtgatttat aaatcaaccc agtctcagtt    84660
attgtaatgg actaaaatac caagggtcaa cccactatag tgtgctggta aaaaatggct    84720
atctggctct gtgaactaaa actgttttcc taggggctgg ctcctaggat gatagccag    84780 atgataaagt gattgctgtg caagcatgtg gacctgagtc tagatctcca gcacccacat    84840
```

```
aaaaagcaga gtgcagctgt gtacctacaa tctcagctct tgagaggcag agacaggagg    84900
attcctgggg atcctaaatg atggccattt aggattttgg tggaaaccat cttgcatttg    84960
ccagtgttct ccagagagaa aaccaacaga tggcagagat agatgtatgc atggctagat    85020
agatagatct agccaacccc ataagtcagc cacatgagag accagtctca aaatatgagt    85080
acagtgatta aagaagacac ccaacgttga tctctggcct ttatacacac acacacacac    85140
acacacacac acacacacac acacacacac acacgcatgt ttacatcaac ttggtcatac    85200
attttcaaaa ggagagattc tttcctaaat cacaatgcca catcataaat taatctctct    85260
ctgttcatgt ctcccaccct cccccctcca aacaaaattc agcagagtcc taacttggta    85320
gactgtcaga gatgaggtct gtgtgtaaga accagccatg agtaggtagg aggtttgtat    85380
agtgaaaact aaaaacatat tcctaaagga aaaaaaatat atatacatgt acatatacat    85440
atacatacat acatacatac acatacatat acatacatat taaagtcccc aacattcatg    85500
gattggatgg cttattatca ttcggatgtc gaccttctcg ctgagtggtc tatagatctg    85560
tgatggttaa ttttaggcat gagttgactg ggatacctgg agtctcagtt agggtttcta    85620
ttgctgcaat agagtagcat ggataaaaga aacttggaga ggaaagggct tatttcagtt    85680
tggttttgtt tttaaatcat ttcattattt tatgtgtacg agtatttggc ttgcatgcct    85740
gatgcctgct aaggtcagag agagtgttag atgccctgga actggagtta cagatgattg    85800
tgggttctga gaatcaaacc caagtcctct ggaagagcaa caagtctctc aaccactgag    85860
ccaactctcc agtccctgtt tgtttgtatt tttcaagaca gggtctcact tcataccact    85920
ggctgtccta gaacaggcta tatagaccga ctggccttga actcacagag atccacctga    85980
ctctatctcc taagtgctgg gattaaaggt gtgtgctgct atgcctggtt ttattcctgc    86040
tttcacgtgc tcatcagagt cttttcataaa aggaagtcag ggcaggaacc tggaggcaga    86100
aactgaagca gaggccatag agggaagtgc ttactggctt actccccatg gtttgctcag    86160
cctgccttct taacacccaa ggtgggggggt ggcactgtct cctgtgggat ggtcccatca    86220
gcatcaatca ctaattaaga aaatgcatca cagtttggag aaatggctca gcggttaaga    86280
gtactggctg agctgggcgt tggtagcgca cgcctttaat cccagcatgc ggaggactga    86340
ggcagaggac tgaggcaggc ggatctctgt gagtttgagg ccagcctggt ctccagagtg    86400
agtgccagga taggctccaa agctacacag agaaaccctg ttactggctg ctcttccaga    86460
ggtcctgggt tcaattccca gcaactacat atggatcaca accatctgtg atgagatttg    86520
atgccctctt ctggcctgca gggatacatg aagacagaac actgtacata ataaagaagt    86580
aaatgttaaa aaaggaaaag agaaagatag gaaggaagga aggaaggaag gaaggaagga    86640
agagagaaag aaagaaggga agaaagagag aaaggaagaa ggacacacat cacagattcg    86700
ctcacaggcc aatctgatgg gaacattttc tcagttgagg cttttctcata tgccaaatgg    86760 ccctagctta tggcaacttg acataaaaat tgccagcaca tagttacttc taggtacgtc    86820
tgtgaagatg tttccagaag agtttggatt gtgaatctgt ggactgagta aggaagacgc    86880
acggccccca ccagatctga aaggcttcac ccactgggct gagagtctga gataaacaaa    86940 ggagggagg aaagttctct ctcctctgga gccaggacac ccttctccag tccttggata    87000
ccagaactct aggttttctg gtctttggac ttgtatttgc accagttcat cccccatca    87060 agttcttagg catgggggtc acatgtcagg ccatgctttt agacttggat tgagccatag    87120
tgctggcttt gctggttctc cagcttgtgt atagcatgta gtgggacttc tcagtctctg    87180
gaatcacatg gtaaaaatca cctaatgaac ccttctcatc caccggtcgg tctatctatc    87240
```

```
tatctatcta tctatctatc tatctatctt catctatatt atctgtctac ctacctatcc   87300
ctccatttac ccatgcatct ttgttgccta ctgattctga agaacactga caaacacaag   87360
attcaatgct acttctatca caatctcaac agctgtttca ttagaaatga aatttgaggg   87420
ctggagagat ggctcagtgg ttaagagcac tggctgctct tccagaggtc ctgagttgaa   87480
ttcccagcat tcacatggtg gctcacaacc atctgtaatg agatctgctg cccattcctg   87540
acctacaggg acacatgcag agcattgtat acataacaaa taaatcttta aaaagaaat    87600 gaaaatttga attcttgact tcacatgaaa ttgtgataag ttttctgtca tgaaaacaat   87660
attgaaagaa aaaagttgaa agacacacag accaatggga cacaactgag agttttggct   87720
gggcgtgggg cacatgctgg gaatctgagc tcttgggagg ctgaggtgga agggcctcgt   87780
ctaattcaag gccaacaggg atacatagca agactgtgtc ttgacaacaa tgaaatattg   87840
aaaaaccggg ggaaaatgta tattttaact gattttcagc aaggttccca agactattcg   87900
gtgagcaaaa tagtcttatc agtgagtaat gctgggacaa ctacacacag aagagcagga   87960
tgaattctaa ccctgtgcag cactaactct atacagacat gtagcctaca taaaagtcaa   88020
aacatagaag aaaatagaag ggcaagtgtt catgacattg gacttggcag tggttttttag  88080 acttgacacc aaaggcgcag gcaacaaaaa tttggataaa tgagacatca tacaactaga   88140
gacatttgtc catcaaagag catcaagaag taagaggatt ggggctggag agatggttta   88200
gcagttaaga gcactgactg ctcttccaaa ggacacgggt tcagttccca gcacccacat   88260
ggcagcaact ccatgcagaa catgtctgta actccagttc caagggatct gacaccctca   88320
tatagacata catgaaggca aaaccccaat gcacattaaa taataatct taaaaaaaaa    88380 aggtgagatg acaacttaca gaatgggagg cagggtttgt gctttgatat tggtttagag   88440
cctgacaata taaagaactc ttacaactca acaacaaaaa ggttatccaa ttaaaatacg   88500
gcaatgaact tgaatggatg ttttttttaaa agaagataca cagatagtga gatcatgaag   88560
aaatagtcaa cgacagtgca ctctacggtt aagtgtgaaa tgtctcctat aggtgcatgt   88620
ctctgacagc ttggtcccag ctcatggtgc tgatgtggca gacagggaa tctttagggg    88680 gtgaagccta gctggaggaa ttggattact gggggcgcag attttagggg ttataacctg   88740
actgtgctac aatctaatct ttgcctttat ctctctccct ccctcttctg attggccaag   88800
atataagcaa gatatactcc tacccccagg aaaacggagt gtctccctgt catgaagctg   88860
tgagaaaaaa aataaatact ttcttcctga gttgctcctt gtcaggtgtt ttgccacaga   88920
aggaaaatgg caaaccccctt cacatctgct gagattgcta aaggagtaat acaacaactg   88980
tcgatgacgg aggaggagaa gggaagaagg ggaagaagaa gaaggaggag aaggagaaga   89040 aaagaagga ggaggaggag gaggaggggg aggaggagga ggaggaggag gaggaggagg    89100
aggaggagga gaagaagaag aagaagaaga agaagaagaa gaagaagaag aagaagaaga   89160
agaagaagaa gaagaagagg gtgcttgcaa ggatagggag aaattggcac ttctggtgag   89220
actagaaagt atggtggctg atttgaagaa tagtttggtg gtttctttaa aaagttaaac   89280
atgatccggg tggtggtggt gcacgccttt aatcccagaa ctcgggagtc agaggcaggt   89340
ggatctctgt gagttagaga ccaacctggt ttacaagagc tagttccagg acagcctcca   89400
atgctgtctt gaaaaaaccc tgtcttgaaa ccccccaaa aaacttaaaac ataaaattgt    89460 ttgtgataaa ttatatatcc aagagagaaa ttacccacaa ttctttttct ccttctattt   89520
ttcttcctct ttttaaaaga tagggtctct gtgcagtccc agatatcctg gaattttcta   89580
tgtacacctg tctagtctgg aactcacaga gatccacttg cctctgcctc ccaaatgctg   89640
```

```
gggttaaagg aatgtgccac cacatctggc acacaattct acttctaaaa tatattccta    89700
aaagtaataa aatatgtcca taccagaatt tgtacaagaa ttttttaata aaataagact    89760
agaaacaacc tgtgttcatc agcagatgaa tggataaatg caatgtagta tgtaaacaca    89820
atggaatatt accttgccat aaaatggaat gaagtgctaa tttatgctac agagtgagtg    89880
accccagaa ccatgtaaaa tgctaggagt ggtggcaccc acctttcatc ctcattactc     89940
agaaatggag tatcataagt tcaaagtcat cttagtgaga ccttgtgaca cacacacaca    90000
cacacacaca cacacactca cacgcgcaga aggaaccaga cacagacgac tacatgtttt    90060
ataattctct ctctctttct ctctgtgtgt gtgcgtgtat gtatgcatgt gtgtgtgtgc    90120
ctgtgtgagt tcacgtacat gcagtcaacc ttgaatgctg ctctttaggt attgtccaca    90180
ttccttttgt tttaaaagca tttttattta tgtgtgtgtg tgtgtgtgtg tgtgtgtgtg    90240
tacatgtgtg tgcataccac atgtatgctg atatcttagg aggccagaag agggcatcag    90300
atcccctaga aatagagttt cagacagttg tgaactactt gaggtaggtg ctgggaactg    90360
aacttgaatc atctgcaaga gcaccaagtg ctcttaactg ctaagccatc tctccagccc    90420
ctgccttctt atttgagaaa aggtctctca cttgccatat ggaatagact acttggccag    90480
caagccccag atgtccacct gcctccaact cccttgcact ggaattacaa gtatacctag    90540
gttttttgt ttttgttttt tgttttttt taaacacggg gttctgggga ttgaattcgg     90600
ggcctcacac ttgtatggca agcatttgat caactgatct ctcccctaa ccctataatt     90660
aattcctttt atatgaaaaa tccagaattg gcaaattcat aacccataca gacagaaaag    90720
agatcagtga aatgctagag ggtggaggaa gcaagcgtgg gtggtacctg gaggttatag    90780
aactttctgg agccatggaa aagctgaaat ctgtacctgg ttggccctgt ctacagtgtg    90840
gtcccacaga gaccacataa ggggccaatg gtggctgagt ggaaaataga tggccttgga    90900
gagctaaggg catgatgagg agaagtcctt cccaccctc tctccaccagc gtcatgtatc    90960
cagcaaggag agctgaccag atcctctgga agggaaggga aggggataaa ggaaaactct    91020
cttcccatct gttgagaatt aacctccgaa ccatttaacc aaacattggc ttctcctgtc    91080
atttgataag gtgcatccag cagagggaga tggggaaatt gggaggttat tctttcaaat    91140
tacatcagtg ggggtttgtt cctgcagctg agtccagcca gagtcccgtc tgggacatca    91200
catcaccagc aacacactca aggacaggtt caaatgcttt cctctgcttg ggagttcagg    91260
cattcacagg gatataaaaa aaaaaaatca agagggattt taaataaaag cccatactct    91320
ctgcaggctg tctgccccga gccagtgcag cagtgagggg tgattatgga ggaaggaatg    91380
gtttgtgtca ccgtcacacg gaaatgtcca atggcttttc tgcacagaca cacctctct    91440
gtcttccaga                                                          91450
```

<210> SEQ ID NO 27
<211> LENGTH: 34
<212> TYPE: DNA
<213> ORGANISM: Artificial Sequence
<220> FEATURE:
<223> OTHER INFORMATION: Synthetic

<400> SEQUENCE: 27
ccggatccga tgtacgggcc agatatacgc gttg        34

<210> SEQ ID NO 28
<211> LENGTH: 36
<212> TYPE: DNA
<213> ORGANISM: Artificial Sequence

```
<220> FEATURE:
<223> OTHER INFORMATION: Synthetic

<400> SEQUENCE: 28
ctggagctca taccacattt gtagaggttt tacttg                                    36

<210> SEQ ID NO 29
<211> LENGTH: 32
<212> TYPE: DNA
<213> ORGANISM: Artificial Sequence
<220> FEATURE:
<223> OTHER INFORMATION: Synthetic

<400> SEQUENCE: 29
gggctcgaga ggtgtgtgcc accacaccat gc                                        32

<210> SEQ ID NO 30
<211> LENGTH: 32
<212> TYPE: DNA
<213> ORGANISM: Artificial Sequence
<220> FEATURE:
<223> OTHER INFORMATION: Synthetic

<400> SEQUENCE: 30
gggatcgatc aggtttgcag aactgccttc cc                                        32

<210> SEQ ID NO 31
<211> LENGTH: 35
<212> TYPE: DNA
<213> ORGANISM: Artificial Sequence
<220> FEATURE:
<223> OTHER INFORMATION: Synthetic

<400> SEQUENCE: 31
gggctcgagt tcttgaatat tcacgaaggt aaatc                                     35

<210> SEQ ID NO 32
<211> LENGTH: 32
<212> TYPE: DNA
<213> ORGANISM: Artificial Sequence
<220> FEATURE:
<223> OTHER INFORMATION: Synthetic

<400> SEQUENCE: 32
gggatcgatt aactctttct ttgtcgctgg cc                                        32

<210> SEQ ID NO 33
<211> LENGTH: 34
<212> TYPE: DNA
<213> ORGANISM: Artificial Sequence
<220> FEATURE:
<223> OTHER INFORMATION: Synthetic

<400> SEQUENCE: 33
cccggtaccg aggctgggga gatgtctttg ttgg                                      34

<210> SEQ ID NO 34
<211> LENGTH: 34
<212> TYPE: DNA
<213> ORGANISM: Artificial Sequence
<220> FEATURE:
<223> OTHER INFORMATION: Synthetic

<400> SEQUENCE: 34
gggctcgaga actacagaca tcaccaacca aagc                                      34
```

```
<210> SEQ ID NO 35
<211> LENGTH: 31
<212> TYPE: DNA
<213> ORGANISM: Artificial Sequence
<220> FEATURE:
<223> OTHER INFORMATION: Synthetic

<400> SEQUENCE: 35
cccggtacct ccccgaggac tattacggtt c                           31

<210> SEQ ID NO 36
<211> LENGTH: 36
<212> TYPE: DNA
<213> ORGANISM: Artificial Sequence
<220> FEATURE:
<223> OTHER INFORMATION: Synthetic

<400> SEQUENCE: 36
gggctcgaga tgaaattcct cctctgtatt cgaaag                      36

<210> SEQ ID NO 37
<211> LENGTH: 38
<212> TYPE: DNA
<213> ORGANISM: Artificial Sequence
<220> FEATURE:
<223> OTHER INFORMATION: Synthetic

<400> SEQUENCE: 37
cccggtaccg aatcattcac ttttttttt tttaactg                     38

<210> SEQ ID NO 38
<211> LENGTH: 38
<212> TYPE: DNA
<213> ORGANISM: Artificial Sequence
<220> FEATURE:
<223> OTHER INFORMATION: Synthetic

<400> SEQUENCE: 38
gggctcgagc aaagttaata gaaatactgt tttaaagc                    38

<210> SEQ ID NO 39
<211> LENGTH: 26
<212> TYPE: DNA
<213> ORGANISM: Artificial Sequence
<220> FEATURE:
<223> OTHER INFORMATION: Synthetic

<400> SEQUENCE: 39
cgccctatag tgagtcgtat tacgcg                                 26

<210> SEQ ID NO 40
<211> LENGTH: 26
<212> TYPE: DNA
<213> ORGANISM: Artificial Sequence
<220> FEATURE:
<223> OTHER INFORMATION: Synthetic

<400> SEQUENCE: 40
atgacaatga tgattatgat tttatg                                 26

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
```
cattgtcagt atcagcctct cctgg                                              25

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42
cttctggttt ctggttcccc ctgc                                               24

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
agctagtata tcacatgcca catc                                               24

<210> SEQ ID NO 44
<211> LENGTH: 29
<212> TYPE: DNA
<213> ORGANISM: Artificial Sequence
<220> FEATURE:
<223> OTHER INFORMATION: Synthetic

<400> SEQUENCE: 44
gtacgggcca gatatacgcg ttgacattg                                          29

<210> SEQ ID NO 45
<211> LENGTH: 25
<212> TYPE: DNA
<213> ORGANISM: Artificial Sequence
<220> FEATURE:
<223> OTHER INFORMATION: Synthetic

<400> SEQUENCE: 45
cagactacat agttagtgcc aaacc                                              25

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
cagtgatgac aataggcaac ctcc                                               24

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
gctctcacag gataaggagg gtcg                                               24

<210> SEQ ID NO 48
<211> LENGTH: 24
<212> TYPE: DNA
<213> ORGANISM: Artificial Sequence

```
<220> FEATURE:
<223> OTHER INFORMATION: Synthetic

<400> SEQUENCE: 48
ctgagtagca gccttcctgc ctgg                                              24

<210> SEQ ID NO 49
<211> LENGTH: 25
<212> TYPE: DNA
<213> ORGANISM: Artificial Sequence
<220> FEATURE:
<223> OTHER INFORMATION: Synthetic

<400> SEQUENCE: 49
tcaaaccgta tgacttggct ctgag                                             25

<210> SEQ ID NO 50
<211> LENGTH: 35
<212> TYPE: DNA
<213> ORGANISM: Artificial Sequence
<220> FEATURE:
<223> OTHER INFORMATION: Synthetic

<400> SEQUENCE: 50
tagtccacta gtctccccga ggactattac ggttc                                  35

<210> SEQ ID NO 51
<211> LENGTH: 35
<212> TYPE: DNA
<213> ORGANISM: Artificial Sequence
<220> FEATURE:
<223> OTHER INFORMATION: Synthetic

<400> SEQUENCE: 51
acggacagat ctgctctcac aggataagga gggtc                                  35

<210> SEQ ID NO 52
<211> LENGTH: 34
<212> TYPE: DNA
<213> ORGANISM: Artificial Sequence
<220> FEATURE:
<223> OTHER INFORMATION: Synthetic

<400> SEQUENCE: 52
gtggactcga gctccccgag gactattacg gttc                                   34

<210> SEQ ID NO 53
<211> LENGTH: 34
<212> TYPE: DNA
<213> ORGANISM: Artificial Sequence
<220> FEATURE:
<223> OTHER INFORMATION: Synthetic

<400> SEQUENCE: 53
gtggacgtac ggctctcaca ggataaggag ggtc                                   34

<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
gtcccccggg ccgtccgcac cctcgccgcc                                        30
```

```
<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
ggcggcgagg gtgcggacgg cccgggggac                                      30

<210> SEQ ID NO 56
<211> LENGTH: 24
<212> TYPE: DNA
<213> ORGANISM: Artificial Sequence
<220> FEATURE:
<223> OTHER INFORMATION: Synthetic

<400> SEQUENCE: 56
gttaggccag cttggcactt gatg                                            24

<210> SEQ ID NO 57
<211> LENGTH: 37
<212> TYPE: DNA
<213> ORGANISM: Artificial Sequence
<220> FEATURE:
<223> OTHER INFORMATION: Synthetic

<400> SEQUENCE: 57
cccggatcca taccacattt gtagaggttt tacttgc                              37

<210> SEQ ID NO 58
<211> LENGTH: 44
<212> TYPE: DNA
<213> ORGANISM: Artificial Sequence
<220> FEATURE:
<223> OTHER INFORMATION: Synthetic

<400> SEQUENCE: 58
gagcagatct gcatgcacta gtcttcgtga ggctccggtg cccg                      44

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
ccagtttcac atcacactgg acac                                            24

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
gccacctctg acttgagcgt cg                                              22

<210> SEQ ID NO 61
<211> LENGTH: 44
<212> TYPE: DNA
<213> ORGANISM: Artificial Sequence
<220> FEATURE:
<223> OTHER INFORMATION: Synthetic

<400> SEQUENCE: 61
```

-continued cgcgtactag taagcatgcc cattcgccat tcaggctgcg caac     44

<210> SEQ ID NO 62
<211> LENGTH: 25
<212> TYPE: DNA
<213> ORGANISM: Artificial Sequence
<220> FEATURE:
<223> OTHER INFORMATION: Synthetic

<400> SEQUENCE: 62
cagctccagg agagtttgac ccttc     25

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
acccagaagc tccaagagga gggca     25

<210> SEQ ID NO 64
<211> LENGTH: 25
<212> TYPE: DNA
<213> ORGANISM: Artificial Sequence
<220> FEATURE:
<223> OTHER INFORMATION: Synthetic

<400> SEQUENCE: 64
accggggcct gggcaacctc ctgcc     25

<210> SEQ ID NO 65
<211> LENGTH: 25
<212> TYPE: DNA
<213> ORGANISM: Artificial Sequence
<220> FEATURE:
<223> OTHER INFORMATION: Synthetic

<400> SEQUENCE: 65
gacccacaag caggggattg cccag     25

<210> SEQ ID NO 66
<211> LENGTH: 22
<212> TYPE: DNA
<213> ORGANISM: Artificial Sequence
<220> FEATURE:
<223> OTHER INFORMATION: Synthetic

<400> SEQUENCE: 66
cgatcctgag gccaagacac cc     22

<210> SEQ ID NO 67
<211> LENGTH: 23
<212> TYPE: DNA
<213> ORGANISM: Artificial Sequence
<220> FEATURE:
<223> OTHER INFORMATION: Synthetic

<400> SEQUENCE: 67
aaggcagccc taaagagacc agg     23

<210> SEQ ID NO 68
<211> LENGTH: 25
<212> TYPE: DNA
<213> ORGANISM: Artificial Sequence

```
<220> FEATURE:
<223> OTHER INFORMATION: Synthetic

<400> SEQUENCE: 68
cagcttggtg accctggatg tcttc                                          25

<210> SEQ ID NO 69
<211> LENGTH: 25
<212> TYPE: DNA
<213> ORGANISM: Artificial Sequence
<220> FEATURE:
<223> OTHER INFORMATION: Synthetic

<400> SEQUENCE: 69
tgctaagagt aactcaaacc gtatg                                          25

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
ggattcttct gacacaacag tctcg                                          25

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71 agcttttgc aaaagcctag gcctcc                                          26

<210> SEQ ID NO 72
<211> LENGTH: 24
<212> TYPE: DNA
<213> ORGANISM: Artificial Sequence
<220> FEATURE:
<223> OTHER INFORMATION: Synthetic

<400> SEQUENCE: 72
ggacccggac cgccacatcg agcg                                           24

<210> SEQ ID NO 73
<211> LENGTH: 24
<212> TYPE: DNA
<213> ORGANISM: Artificial Sequence
<220> FEATURE:
<223> OTHER INFORMATION: Synthetic

<400> SEQUENCE: 73
acggtgtggc gcgtggcggg gtag                                           24

<210> SEQ ID NO 74
<211> LENGTH: 30
<212> TYPE: DNA
<213> ORGANISM: Artificial Sequence
<220> FEATURE:
<223> OTHER INFORMATION: Synthetic

<400> SEQUENCE: 74
gtcccccgcg ccgtccgcac cctcgccgcc                                     30
```

```
<210> SEQ ID NO 75
<211> LENGTH: 28
<212> TYPE: DNA
<213> ORGANISM: Artificial Sequence
<220> FEATURE:
<223> OTHER INFORMATION: Synthetic

<400> SEQUENCE: 75
gtcgtcgcgg gtggcgaggc gcaccgtg                                          28

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
ctgatgcggt attttctcct tacg                                              24

<210> SEQ ID NO 77
<211> LENGTH: 25
<212> TYPE: DNA
<213> ORGANISM: Artificial Sequence
<220> FEATURE:
<223> OTHER INFORMATION: Synthetic

<400> SEQUENCE: 77
ccattcgcca ttcaggctgc gcaac                                             25

<210> SEQ ID NO 78
<211> LENGTH: 37
<212> TYPE: DNA
<213> ORGANISM: Artificial Sequence
<220> FEATURE:
<223> OTHER INFORMATION: Synthetic

<400> SEQUENCE: 78
attcaggact agtcttcgtg aggctccggt gcccgtc                                37

<210> SEQ ID NO 79
<211> LENGTH: 35
<212> TYPE: DNA
<213> ORGANISM: Artificial Sequence
<220> FEATURE:
<223> OTHER INFORMATION: Synthetic

<400> SEQUENCE: 79
tctcagctag cagtcgagcc atgtgagcaa aaggc                                  35

<210> SEQ ID NO 80
<211> LENGTH: 35
<212> TYPE: DNA
<213> ORGANISM: Artificial Sequence
<220> FEATURE:
<223> OTHER INFORMATION: Synthetic

<400> SEQUENCE: 80
tctagatgat cattcccttt agtgagggtt aatgc                                  35

<210> SEQ ID NO 81
<211> LENGTH: 35
<212> TYPE: DNA
<213> ORGANISM: Artificial Sequence
<220> FEATURE:
<223> OTHER INFORMATION: Synthetic

<400> SEQUENCE: 81
```
cgtacgaagc ttttcacgac acctgaaatg gaaga        35

<210> SEQ ID NO 82
<211> LENGTH: 38
<212> TYPE: DNA
<213> ORGANISM: Artificial Sequence
<220> FEATURE:
<223> OTHER INFORMATION: Synthetic

<400> SEQUENCE: 82
agcttcgtac gcccgggacg cgtcaggcgg ccgcaagt        38

<210> SEQ ID NO 83
<211> LENGTH: 38
<212> TYPE: DNA
<213> ORGANISM: Artificial Sequence
<220> FEATURE:
<223> OTHER INFORMATION: Synthetic

<400> SEQUENCE: 83
ctagacttgc ggccgcctga cgcgtcccgg gcgtacga        38

<210> SEQ ID NO 84
<211> LENGTH: 34
<212> TYPE: DNA
<213> ORGANISM: Artificial Sequence
<220> FEATURE:
<223> OTHER INFORMATION: Synthetic

<400> SEQUENCE: 84
agtaagctag cctccccgag gactattacg gttc        34

<210> SEQ ID NO 85
<211> LENGTH: 59
<212> TYPE: DNA
<213> ORGANISM: Artificial Sequence
<220> FEATURE:
<223> OTHER INFORMATION: Synthetic

<400> SEQUENCE: 85
cgtccgaatt cggtcagtcg acctcagatc tgctctcaca ggataaggag ggtcgggag        59

<210> SEQ ID NO 86
<211> LENGTH: 34
<212> TYPE: DNA
<213> ORGANISM: Artificial Sequence
<220> FEATURE:
<223> OTHER INFORMATION: Synthetic

<400> SEQUENCE: 86
gtgaggatcc gctctcacag gataaggagg gtcg        34

<210> SEQ ID NO 87
<211> LENGTH: 35
<212> TYPE: DNA
<213> ORGANISM: Artificial Sequence
<220> FEATURE:
<223> OTHER INFORMATION: Synthetic

<400> SEQUENCE: 87
cagttcgtac gaccatggac aaagactgcg aaatg        35

<210> SEQ ID NO 88
<211> LENGTH: 39
<212> TYPE: DNA
<213> ORGANISM: Artificial Sequence

```
<220> FEATURE:
<223> OTHER INFORMATION: Synthetic

<400> SEQUENCE: 88
agatctgagg tcgaccttcg tgaggctccg gtgcccgtc                              39

<210> SEQ ID NO 89
<211> LENGTH: 26
<212> TYPE: DNA
<213> ORGANISM: Artificial Sequence
<220> FEATURE:
<223> OTHER INFORMATION: Synthetic

<400> SEQUENCE: 89
gtcgagccat gtgagcaaaa ggccag                                           26

<210> SEQ ID NO 90
<211> LENGTH: 39
<212> TYPE: DNA
<213> ORGANISM: Artificial Sequence
<220> FEATURE:
<223> OTHER INFORMATION: Synthetic

<400> SEQUENCE: 90
gaattcagga ctagtcagta caatctgctc tgatgccgc                             39

<210> SEQ ID NO 91
<211> LENGTH: 25
<212> TYPE: DNA
<213> ORGANISM: Artificial Sequence
<220> FEATURE:
<223> OTHER INFORMATION: Synthetic

<400> SEQUENCE: 91
ccattcgcca ttcaggctgc gcaac                                            25

<210> SEQ ID NO 92
<211> LENGTH: 35
<212> TYPE: DNA
<213> ORGANISM: Artificial Sequence
<220> FEATURE:
<223> OTHER INFORMATION: Synthetic

<400> SEQUENCE: 92
cagagctagc ccattcgcca ttcaggctgc gcaac                                 35

<210> SEQ ID NO 93
<211> LENGTH: 35
<212> TYPE: DNA
<213> ORGANISM: Artificial Sequence
<220> FEATURE:
<223> OTHER INFORMATION: Synthetic

<400> SEQUENCE: 93
gtcggacaga attcgctctc acaggataag gaggg                                 35

<210> SEQ ID NO 94
<211> LENGTH: 25
<212> TYPE: DNA
<213> ORGANISM: Artificial Sequence
<220> FEATURE:
<223> OTHER INFORMATION: Synthetic

<400> SEQUENCE: 94
acgctggctg gcacgtttgt gttac                                            25
```

```
<210> SEQ ID NO 95
<211> LENGTH: 26
<212> TYPE: DNA
<213> ORGANISM: Artificial Sequence
<220> FEATURE:
<223> OTHER INFORMATION: Synthetic

<400> SEQUENCE: 95
tgagcaccta cgaggtgtca aaggtc                                        26

<210> SEQ ID NO 96
<211> LENGTH: 25
<212> TYPE: DNA
<213> ORGANISM: Artificial Sequence
<220> FEATURE:
<223> OTHER INFORMATION: Synthetic

<400> SEQUENCE: 96
tggcaaagag gaaaatatat gttcc                                         25

<210> SEQ ID NO 97
<211> LENGTH: 24
<212> TYPE: DNA
<213> ORGANISM: Artificial Sequence
<220> FEATURE:
<223> OTHER INFORMATION: Synthetic

<400> SEQUENCE: 97
cttagccaaa ccactgtcag ctgc                                          24

<210> SEQ ID NO 98
<211> LENGTH: 28
<212> TYPE: DNA
<213> ORGANISM: Artificial Sequence
<220> FEATURE:
<223> OTHER INFORMATION: Synthetic

<400> SEQUENCE: 98
gcctccacca agggcccatc ggtcttcc                                      28

<210> SEQ ID NO 99
<211> LENGTH: 28
<212> TYPE: DNA
<213> ORGANISM: Artificial Sequence
<220> FEATURE:
<223> OTHER INFORMATION: Synthetic

<400> SEQUENCE: 99
tcatttaccc ggagacaggg agaggctc                                      28

<210> SEQ ID NO 100
<211> LENGTH: 40
<212> TYPE: DNA
<213> ORGANISM: Artificial Sequence
<220> FEATURE:
<223> OTHER INFORMATION: Synthetic

<400> SEQUENCE: 100
cgcaggtcta gaagctcagc tagcaccaag ggcccatcgg                         40

<210> SEQ ID NO 101
<211> LENGTH: 35
<212> TYPE: DNA
<213> ORGANISM: Artificial Sequence
<220> FEATURE:
<223> OTHER INFORMATION: Synthetic
```

```
<400> SEQUENCE: 101
gtccgtgatc atcatttacc cggagacagg gagag                          35

<210> SEQ ID NO 102
<211> LENGTH: 28
<212> TYPE: DNA
<213> ORGANISM: Artificial Sequence
<220> FEATURE:
<223> OTHER INFORMATION: Synthetic

<400> SEQUENCE: 102
ggccgcagga ctagtcttcg tgaggctc                                  28

<210> SEQ ID NO 103
<211> LENGTH: 28
<212> TYPE: DNA
<213> ORGANISM: Artificial Sequence
<220> FEATURE:
<223> OTHER INFORMATION: Synthetic

<400> SEQUENCE: 103
gctgtcagtc gacctcagat ctgctctc                                  28

<210> SEQ ID NO 104
<211> LENGTH: 31
<212> TYPE: DNA
<213> ORGANISM: Artificial Sequence
<220> FEATURE:
<223> OTHER INFORMATION: Synthetic

<400> SEQUENCE: 104
tcgttagctc agctagcacc aagggcccat c                              31

<210> SEQ ID NO 105
<211> LENGTH: 29
<212> TYPE: DNA
<213> ORGANISM: Artificial Sequence
<220> FEATURE:
<223> OTHER INFORMATION: Synthetic

<400> SEQUENCE: 105
attcgaacgt acgaagcttt tcacgacac                                 29

<210> SEQ ID NO 106
<211> LENGTH: 75
<212> TYPE: DNA
<213> ORGANISM: Artificial Sequence
<220> FEATURE:
<223> OTHER INFORMATION: Synthetic

<400> SEQUENCE: 106
gtacggccac catgaaacac ctgtggttct tcctcctgct ggtggcagct cccagatggg   60
tcctgtccca ggtgg                                                   75

<210> SEQ ID NO 107
<211> LENGTH: 75
<212> TYPE: DNA
<213> ORGANISM: Artificial Sequence
<220> FEATURE:
<223> OTHER INFORMATION: Synthetic

<400> SEQUENCE: 107
aattccacct gggacaggac ccatctggga gctgccacca gcaggaggaa gaaccacagg   60
tgtttcatgg tggcc                                                   75
```

<210> SEQ ID NO 108
<211> LENGTH: 28
<212> TYPE: DNA
<213> ORGANISM: Artificial Sequence
<220> FEATURE:
<223> OTHER INFORMATION: Synthetic

<400> SEQUENCE: 108
atcaaacgaa ctgtggctgc accatctg                                        28

<210> SEQ ID NO 109
<211> LENGTH: 29
<212> TYPE: DNA
<213> ORGANISM: Artificial Sequence
<220> FEATURE:
<223> OTHER INFORMATION: Synthetic

<400> SEQUENCE: 109
ctaacactct cccctgttga agctctttg                                       29

<210> SEQ ID NO 110
<211> LENGTH: 27
<212> TYPE: DNA
<213> ORGANISM: Artificial Sequence
<220> FEATURE:
<223> OTHER INFORMATION: Synthetic

<400> SEQUENCE: 110
tcccgggacg cgtcaggcgg ccgcaag                                         27

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
gtacgtagct tttcacgaca cctg                                            24

<210> SEQ ID NO 112
<211> LENGTH: 47
<212> TYPE: DNA
<213> ORGANISM: Artificial Sequence
<220> FEATURE:
<223> OTHER INFORMATION: Synthetic

<400> SEQUENCE: 112
tgcaggtcta gaaccaagct tgaaatcaaa cgtacggtgg ctgcacc                   47

<210> SEQ ID NO 113
<211> LENGTH: 35
<212> TYPE: DNA
<213> ORGANISM: Artificial Sequence
<220> FEATURE:
<223> OTHER INFORMATION: Synthetic

<400> SEQUENCE: 113
gtcaggtgat cactaacact ctcccctgtt gaagc                                35

<210> SEQ ID NO 114
<211> LENGTH: 28
<212> TYPE: DNA
<213> ORGANISM: Artificial Sequence
<220> FEATURE:
<223> OTHER INFORMATION: Synthetic

```
<400> SEQUENCE: 114
ccgcaggact agtcagtaca atctgctc                                          28

<210> SEQ ID NO 115
<211> LENGTH: 26
<212> TYPE: DNA
<213> ORGANISM: Artificial Sequence
<220> FEATURE:
<223> OTHER INFORMATION: Synthetic

<400> SEQUENCE: 115
ccgcccattc gccattcagg ctgcgc                                            26

<210> SEQ ID NO 116
<211> LENGTH: 35
<212> TYPE: DNA
<213> ORGANISM: Artificial Sequence
<220> FEATURE:
<223> OTHER INFORMATION: Synthetic

<400> SEQUENCE: 116
ccagatatct ggaagcttga atcaaacgt acggt                                   35

<210> SEQ ID NO 117
<211> LENGTH: 34
<212> TYPE: DNA
<213> ORGANISM: Artificial Sequence
<220> FEATURE:
<223> OTHER INFORMATION: Synthetic

<400> SEQUENCE: 117
acgcgtgaat tcttcacgac acctgaaatg gaag                                   34

<210> SEQ ID NO 118
<211> LENGTH: 74
<212> TYPE: DNA
<213> ORGANISM: Artificial Sequence
<220> FEATURE:
<223> OTHER INFORMATION: Synthetic

<400> SEQUENCE: 118
cgcgtgccac catggtgttg cagacccagg tcttcatttc tctgttgctc tggatctctg       60
gtgcctacgg ggat                                                         74

<210> SEQ ID NO 119
<211> LENGTH: 70
<212> TYPE: DNA
<213> ORGANISM: Artificial Sequence
<220> FEATURE:
<223> OTHER INFORMATION: Synthetic

<400> SEQUENCE: 119
atccccgtag gcaccagaga tccagagcaa cagagaaatg aagacctggg tctgcaacac       60
catggtggca                                                              70

<210> SEQ ID NO 120
<211> LENGTH: 35
<212> TYPE: DNA
<213> ORGANISM: Artificial Sequence
<220> FEATURE:
<223> OTHER INFORMATION: Synthetic

<400> SEQUENCE: 120
gcaggtgcta gctgaggaga cggtgaccgt ggtcc                                  35
```

-continued

```
<210> SEQ ID NO 121
<211> LENGTH: 35
<212> TYPE: DNA
<213> ORGANISM: Artificial Sequence
<220> FEATURE:
<223> OTHER INFORMATION: Synthetic

<400> SEQUENCE: 121
gactggcgta cgtctgattt ccagcttggt gcctc                              35

<210> SEQ ID NO 122
<211> LENGTH: 24
<212> TYPE: DNA
<213> ORGANISM: Artificial Sequence
<220> FEATURE:
<223> OTHER INFORMATION: Synthetic

<400> SEQUENCE: 122
tgagatctga ggtcgactga cagc                                          24

<210> SEQ ID NO 123
<211> LENGTH: 23
<212> TYPE: DNA
<213> ORGANISM: Artificial Sequence
<220> FEATURE:
<223> OTHER INFORMATION: Synthetic

<400> SEQUENCE: 123
actagcagtc gagccatgtg agc                                           23
```

EXPRESSION VECTOR FOR ESTABLISHING HIGHLY PRODUCTIVE CELL AND THE HIGHLY PRODUCTIVE CELL

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 139,959 bytes ASCII (Text) file named "707815ReplacementSequenceListing.txt." created May 9, 2011.

TECHNICAL FIELD OF THE INVENTION

The present invention relates to an expression vector to be used in a method where an expression vector into which gene of aimed protein has been inserted is transferred into host cells by means of gene recombination technique, and cells which express the gene of aimed protein in a high level are efficiently established from the transformed cells. It also relates to the transformed highly productive cells. The expression vector of the present invention is useful for the production of useful protein such as a drug in animal cells or, particularly, mammalian cells by a genetic engineering means.

BACKGROUND ART

Development of an expression system which produces a recombinant protein is important in providing a source of supply for protein which is used in research or therapy. As to the expression system, that based on prokaryotic cells such as *Escherichia coli* and that based on eukaryotic cells including yeast (genus *Saccharomyces*, genus *Pichia*, genus *Kluyveromyces*, etc.) and animal cells such as mammalian cells have been used. Among them, an expression system based on animal cells or, particularly, mammalian cells is preferred for the manufacture of protein for the therapy. That is because, since the posttranslational modification of protein which occurs in mammals such as human sometimes deeply contributes in bioactivity of the protein, and since posttranslational modification similar to that in the object to which protein is administered is possible in an expression system based on mammalian cells, efficiency of the protein for therapy is able to be enhanced by using the expression system based on mammalian cells.

As to a method for establishing the cells which produce a recombinant protein, it is general that a gene construct which expresses the gene of the aimed protein is transferred into host cells and, from the resulting transformed cells, the cells where the gene construct is stably transferred into the genome of the host cells are selected. At that time, a drug-resistant gene which acts as a drug selective marker has been previously inserted into the above gene construct so that said gene is expressed under a promoter which is same as or different from that of the gene of the aimed protein and then the cells survived by means of the drug selection are selected as the cells into which the gene of the aimed protein is stably transferred. Expression level of the aimed protein greatly varies depending upon the region of the host cell genome into which the gene coding for the aimed protein is transferred, but it is usually impossible to control the transfer region. Accordingly, even when gene transfer is carried out, most of the cells do not express the gene of the aimed protein or the expressed level is low. Therefore, in obtaining the transformed cells where the aimed protein gene is expressed in a high level, the operation of selection of one or two cell strain(s) from one thousand to several thousands of cell samples has been conducted repeatedly for several months to one year whereby quite a lot of labor and time have been needed for the selection of transformed cells which express the aimed protein gene in a high level.

Under such circumstances, a method of attenuating expression or function of a drug selective marker has been developed for an efficient selection of transformed cells which express the aimed protein gene in a high level. When expression or function of a drug selective marker is attenuated, the transformed cells where the drug selective marker gene is transferred into a low expression region in the host cell genome are unable to fully express the drug selective marker (drug-resistant gene) whereby they are dead and only the transformed cells where the drug selective marker gene is transferred into a high expression region survive by the drug selection. In the survived transformed cells, there is a high possibility that the aimed protein gene exists adjacent to the drug selective marker gene and, therefore, the aimed protein gene is also transferred into the high expression site in the host cell genome and there is a high possibility that the aimed protein gene is expressed in a high level. It is expected that, when that is utilized, transformed cells which express the aimed protein gene in a high level are able to be efficiently selected.

Examples of a method for attenuation of expression or function of the drug selective marker include a method where herpes simplex virus thymidine kinase (HSV-tk) promoter having a weak transcription activity is used for expression of the drug selective marker (Non-Patent Document 1) and a method where expression of the drug selective marker is suppressed using a variant type promoter where the transcription activity level is attenuated as compared with the wild type (Patent Documents 1, 2). However, when the present inventors carried out the follow-up studies of those methods, any of them rarely showed an effect in view of attenuating the expression of the drug selective marker. Therefore, it was thought to be difficult to efficiently select transformed cells which express the aimed protein gene in a high level using such a method.

Another method for the attenuation of expression or function of a drug selective marker is that mutation is transferred into the coding sequence of the drug selective marker such as neomycin phosphotransferase whereby the function of the drug selective marker itself is attenuated (Patent Documents 3, 4). The present inventors have carried out a follow-up study for this method and found that, when this method was applied, function of the drug selective marker was able to be attenuated to some extent and, as a result of the drug selection, small amount of cell strain exhibiting enhanced expression amount was able to be procured. However, the efficiency in terms of selection of transformed cells which express the aimed protein gene in a high level is not good and no significant effect was achieved by this method.

In establishing the highly productive cells, it is necessary to eliminate the influence from genome environment around the aimed gene-transferred site on the host cell genome for stably maintaining the expression of the aimed gene, in addition to the improvement in the cell selection art. Expression of the recombinant protein greatly varies depending upon the site of the host cell genome into which the gene coding for the recombinant protein is transferred. Usually however, control of the transfer site is impossible. Accordingly, even in the case of the cells exhibiting a sufficient expression upon screening, the expression sometimes lowers gradually as the cells are cultured continuously. In order to overcome such a position effect, a chromosome element (cis-acting DNA element) which mitigates the influence of the adjacent chromosome or regulatory element to the transgene has been utilized for the production of recombinant protein. One of the nucleic acid sequences having such a function is a sequence called an insulator and a DNAase I hypersensitive site of β-globin LCR of domestic fowls (cHS4; 1.2 kb length), etc. has been well analyzed for its function and utilized for the expression of recombinant protein (Non-Patent Document 2) but it has been reported that the increase in the protein expression in the CHO-K1 cells is not so significant (Non-Patent Document 3).

PRIOR ART DOCUMENTS

Patent Documents

Patent Document 1: U.S. Pat. No. 5,627,033
Patent Document 2: WO 2005/024015
Patent Document 3: WO 2001/032901
Patent Document 4: WO 2004/050884
Patent Document 5: Japanese Patent Application Laid-Open (JP-A) No. 2001-37478

Non-Patent Documents

Non-Patent Document 1: Niwa H, Yamamura K, Miyazaki J. (1991) Gene 108: 193-200
Non-Patent Document 2: Pikaart M J, Recillas-Targa F, Felsenfeld G. (1998) Genes Dev 12: 2852-2862
Non-Patent Document 3: Izumi M, Gilbert D M. (1999) J Cell Biochem 76: 280-289
Non-Patent Document 4: Bakheet T, Frevel M, Williams B. R. G, Greer W, Khabar K. S. A. (2001) Nucleic Acids Research 29: 246-254
Non-Patent Document 5: Lagnado C. A, Brown C. L, Goodall G. J. (1994) Molecular and Cellular Biology 14: 7984-7995
Non-Patent Document 6: Zubiaga A. M, Belasco J. G, Greenberg M. E. (1995) Molecular and Cellular Biology 15: 2219-2230
Non-Patent Document 7: Blasco M A (2007) Nat Rev Genet 8: 299-309
Non-Patent Document 8: Gonzalo S, Jaco I, Fraga M F, Chen T, Li E, Esteller M, Blasco M A (2006) Nat Cell Biol 8: 416-424
Non-Patent Document 9: Perrod S, Gasser S M (2003) Cell Mol Life Sci 60: 2303-2318
Non-Patent Document 10: Wakimoto B T (1998) Cell 93: 321-324
Non-Patent Document 11: Bao L, Zhou M, Cui Y (2008) Nucleic Acids Research, 36, D83-D87

DISCLOSURE OF THE INVENTION

Problem that the Invention is to Solve

An object of the present invention is to provide an expression vector which is effective in an efficient establishment of transformed cells which express the aimed protein gene in a high level and also to provide a highly productive cell.

Means for Solving the Problem

In order to solve the above problems, the present inventors have invented a cassette for expressing the drug selective marker into which mRNA destabilizing sequence is transferred and an element for gene expression stabilization. They have further constructed expression vectors equipped with the various kinds of expressing cassette for drug selective marker having mRNA destabilizing sequence and with the element for stabilizing the gene expression and analyzed the gene expression of host cells transformed by the above expression vectors in detail. As a result thereof, they have found that the rate of the cells which highly produce the aimed protein significantly increased whereupon the present invention has been achieved.

Thus, in accordance with the present invention, the followings are provided.

(1) An expression vector which is characterized in having a cassette for expressing the drug selective marker gene containing mRNA destabilizing sequence, at least one element for stabilizing the gene expression and a cassette for expressing the gene of the aimed protein.

(2) The expression vector according to (1), wherein the mRNA destabilizing sequence is derived from AT-rich sequence existing in the 3'-untranslated region of cytokine, interleukin or proto-oncogene.

(3) The expression vector according to (1), wherein the mRNA destabilizing sequence has a motif sequence of TTATTTA (A/T)(A/T).

(4) The expression vector according to (3), wherein the motif sequence is repeated for two or more times.

(5) The expression vector according to (4), wherein one or more base(s) of spacer sequence is contained between the repetition of the motif sequence.

(6) The expression vector according to any one of (2) to (5), wherein substitution, insertion or deletion of one to several base(s) is contained in the mRNA destabilizing sequence.

(7) The expression vector according to any one of (1) to (6), wherein the element for stabilizing the gene expression is derived from Chinese hamster genome.

(8) The expression vector according to any one of (1) to (7), wherein the element for stabilizing the gene expression consists of any one of the following (a) to (h) or any combination thereof:

(a) a DNA consisting of the sequence shown in SEQ ID No: 26;

(b) a DNA consisting of a partial sequence of the sequence shown in SEQ ID No: 26 and containing the sequence of the region from the 41820th base to the 41839th base of the sequence shown in SEQ ID No: 26;

(c) a DNA consisting of a partial sequence of the sequence shown in SEQ ID No: 26 and containing the sequence of the region from the 41821st base to the 41840th base of the sequence shown in SEQ ID No: 26;

(d) a DNA consisting of a partial sequence of the sequence shown in SEQ ID No: 26 and containing the sequence of the region from the 45182nd base to the 45200th base of the sequence shown in SEQ ID No: 26;

(e) a DNA consisting of a partial sequence of the sequence shown in SEQ ID No: 26 and containing the sequence of the region from the 91094th base to the 91113th base of the sequence shown in SEQ ID No: 26;

(f) a DNA consisting of the partial sequence of the sequence shown in SEQ ID No: 26 wherein, when it is aligned to be adjacent to the cassette for expressing the exogenous gene in the host cells, expression of the aimed recombinant protein from the exogenous gene contained in the cassette for expressing the exogenous gene is able to be increased or stabilized;

(g) a DNA which hybridizes under a stringent condition to a DNA consisting of the base sequence complementary to any of the DNAs in the above (a) to (f) and has a gene expression stabilizing function; and (h) a DNA which consists of the base sequence complementary to any of the DNAs in the above (a) to (g).

(9) The expression vector according to (8), wherein the element for stabilizing the gene expression consists of anyone of the following (i) to (k) or any combination thereof:

(i) a DNA containing the sequence of the region from the 41601st base to the 46746th base of the sequence shown in SEQ ID No: 26;

(j) a DNA which hybridizes under a stringent condition to a DNA consisting of the base sequence complementary to the DNA in (i) and has a gene expression stabilizing function; and (k) a DNA which consists of the base sequence complementary to the DNAs in the above (i) or (j).

(10) The expression vector according to (9), which is characterized in that the element for stabilizing the gene expression consists of any one of the following (l) to (n) or any combination thereof:

(l) a DNA containing the sequence of the region from the 41601st base to the 42700th base of the sequence shown in SEQ ID No: 26;

(m) a DNA which hybridizes under a stringent condition to a DNA consisting of the base sequence complementary to the DNA in (l) and has a gene expression stabilizing function; and (n) a DNA which consists of the base sequence complementary to the DNAs in (l) or (m).

(11) The expression vector according to any one of (1) to (10), wherein the element for stabilizing the gene expression is aligned on the upstream region of the cassette for expressing the gene of the aimed protein.

(12) The expression vector according to any one of (1) to (10), wherein the element for stabilizing the gene expression is aligned on both of the upstream and downstream regions of the cassette for expressing the gene of the aimed protein.

(13) The expression vector according to any one of (1) to (10), wherein the element for stabilizing the gene expression is aligned on both of the upstream and downstream regions of the cassette for expressing the gene of the aimed protein and of the cassette for expressing the drug selective marker gene.

(14) The expression vector according to any one of (1) to (13), wherein the drug selective marker gene is a gene which is resistant to the antibiotic substance of a protein synthesis inhibition type.

(15) The expression vector according to (14), wherein the drug selective marker gene is selected from the group consisting of puromycin-N-acetyltransferase, hygromycin-B-phosphotransferase and neomycin phosphotransferase.

(16) The expression vector according to any one of (1) to (15), wherein the cassette for expressing the gene of the aimed protein is equipped with a multiple cloning site for insertion of the aimed protein gene.

(17) The expression vector according to any one of (1) to (16), wherein the aimed protein is a heavy chain and/or light chain polypeptide(s) of an antibody.

(18) The expression vector according to any one of (1) to (17), wherein the cassette for expressing the gene of the aimed protein is an antibody gene expressing cassette containing a constant region gene of the light chain of the antibody and/or an antibody gene expressing cassette containing a constant region gene of the heavy chain of the antibody.

(19) A transformed cell, which is characterized in being obtained by transformation of the host cell by the expression vector according to any one of (1) to (18).

(20) The transformed cell according to (19), wherein the host cell is an animal cell.

(21) The transformed cell according to (20), wherein the animal cell is a mammalian cell.

(22) The transformed cell according to (21), wherein the mammalian cell is a Chinese hamster ovary (CHO) cell.

(23) The transformed cell according to (22), wherein the Chinese hamster ovary (CHO) cell is adapted to serum-free media.

(24) A method for selecting a cell group which expresses the aimed protein gene in a high level, characterized in that, the method comprises a step of subjecting the transformed cell according to any one of (19) to (23) to a drug selection.

(25) A cell group, characterized in that, it consists of the transformed cell according to any one of (19) to (23) and expresses the aimed protein gene in a high level.

(26) A method for producing a protein, characterized in that, the transformed cell according to any one of (19) to (23) is used.

(27) The method according to (26), wherein the protein is an antibody.

(28) The method according to (26), wherein the protein is a vaccine.

Advantages of the Invention

In the cassette for expressing the drug selective marker gene according to the present invention, an mRNA destabilizing sequence is inserted into it. Thus, expression of the drug selective marker thereby is attenuated as compared with the conventional cassette for expressing the drug selective marker gene having no mRNA destabilizing sequence. Therefore, unless the cassette is integrated into a highly expression region in the host cell genome, the transformed cell has a difficulty in surviving in the presence of a drug. Due to this reason, only such a transformed cell where the drug selective marker gene and the aimed protein gene are integrated in a highly expression region in the host cell genome is able to survive by means of drug selection. As a result, a highly expressing cell where the aimed protein gene is expressed in a high level is able to be efficiently selected.

In addition, the element for stabilizing the gene expression according to the present invention reduces the influence of the adjacent chromosome or regulatory element to recombinant protein gene in the cell genome and stabilizes the gene expression of the recombinant protein gene whereby high expression is able to be maintained for a long period. Therefore, when the attenuated cassette for expressing the drug selective marker and the gene expression stabilizing element of the present invention are used together, cells which very highly express the aimed protein gene in the cells obtained by drug selection are concentrated and, further, the expression in such highly expressing cells is able to be stably maintained due to the synergism thereof. In accordance with the present invention, a highly productive cell strain showing the very high level of protein productivity is able to be established quickly, easily and efficiently.

BRIEF DESCRIPTIONS OF DRAWINGS

FIG. 1 shows the construction of pBS-CMV-SNAPm2.

FIG. 2 shows the construction of pPUR.N4. Hereinafter, Pur in the drawings stands for puromycin-resistant gene. Also, iPCR in the drawings stands for inverse PCR.

Figure 49:
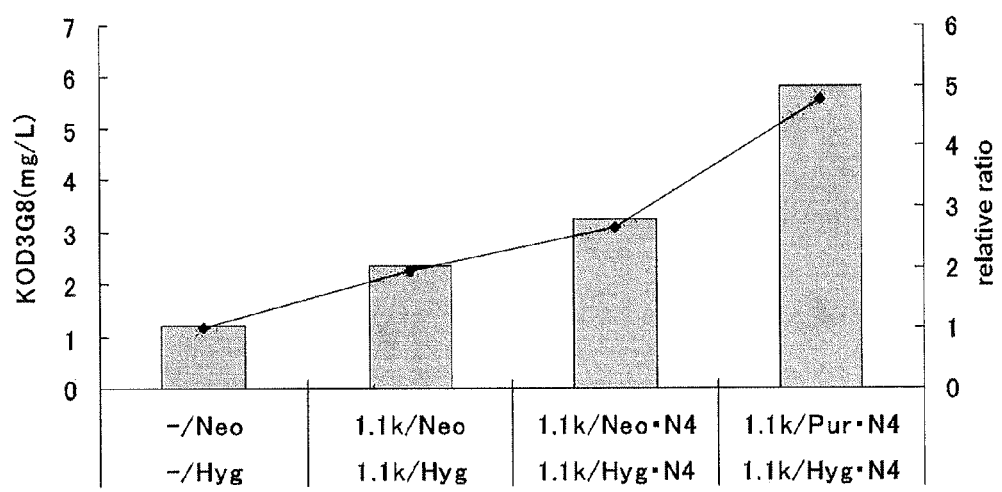

FIG. 49 is a graph where the thing containing no gene expression stabilizing element (−/Neo, −/Hyg); the thing into which gene expression stabilizing element CHO5Δ3-3 is inserted into both of upstream and downstream regions of the expression cassette (1.1k/Neo, 1.1k/Hyg); the thing into which gene expression stabilizing element CHO5Δ3-3 is inserted into both of upstream and downstream regions of the expression cassette followed by adding the mRNA destabilizing sequence (N4 sequence) to the drug-resistant gene (H chain: Neo; L chain: Hyg) (1.1k/Neo.N4, 1.1k/Hyg.N4); and the thing into which gene expression stabilizing element CHO5Δ3-3 is inserted into both of upstream and downstream regions of the expression cassette followed by adding the mRNA destabilizing sequence (N4 sequence) to the drug-resistant gene (H chain: Pur; L chain: Hyg) (1.1k/Pur.N4, 1.1k/Hyg.N4) were subjected to ELISA using the supernatant of the culture of polyclone and the calculated production amounts of the antibodies were plotted.

Figure 50:
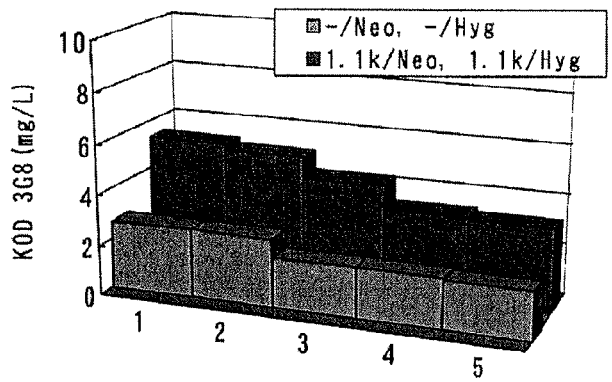
Figure 50:
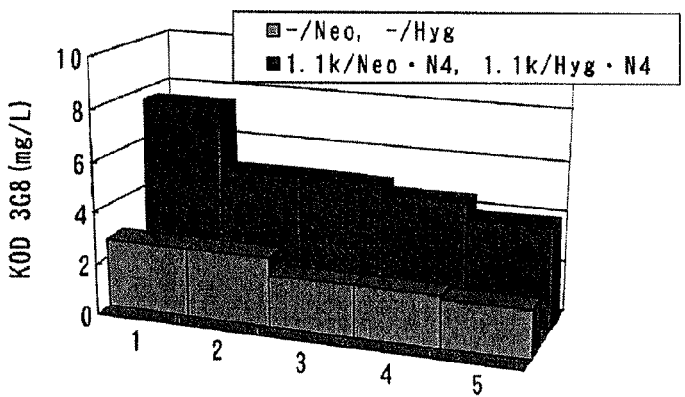
Figure 50:
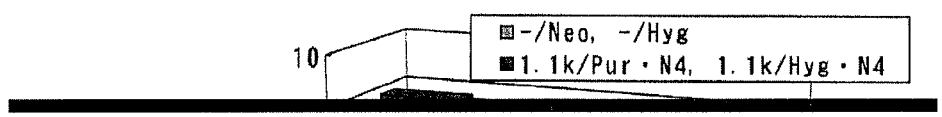

FIG. 50 is a graph where the production amounts of the antibodies by each clone calculated by conducting ELISA using the supernatant of culture of 6-well plate were plotted. With regard to each of the thing containing no gene expression stabilizing element (−/Neo, −/Hyg) and the thing into which gene expression stabilizing element CHO5Δ3-3 is inserted into both of upstream and downstream regions of the expression cassette (1.1k/Neo, 1.1k/Hyg); the thing containing no gene expression stabilizing element (−/Neo, −/Hyg) and the thing into which gene expression stabilizing element CHO5Δ3-3 is inserted into both of upstream and downstream regions of the expression cassette followed by adding the mRNA destabilizing sequence (N4 sequence) to the drug-resistant gene (H chain: Neo; L chain: Hyg) (1.1k/Neo.N4, 1.1k/Hyg.N4); and the thing containing no gene expression stabilizing element (−/Neo, −/Hyg) and the thing into which gene expression stabilizing element CHO5Δ3-3 is inserted into both of upstream and downstream regions of the expression cassette followed by adding the mRNA destabilizing sequence (N4 sequence) to the drug-resistant gene (H chain: Pur; L chain: Hyg) (1.1k/Pur.N4, 1.1k/Hyg.N4), the best five clones in terms of the production amount were plotted on the same graph.

Figure 51:
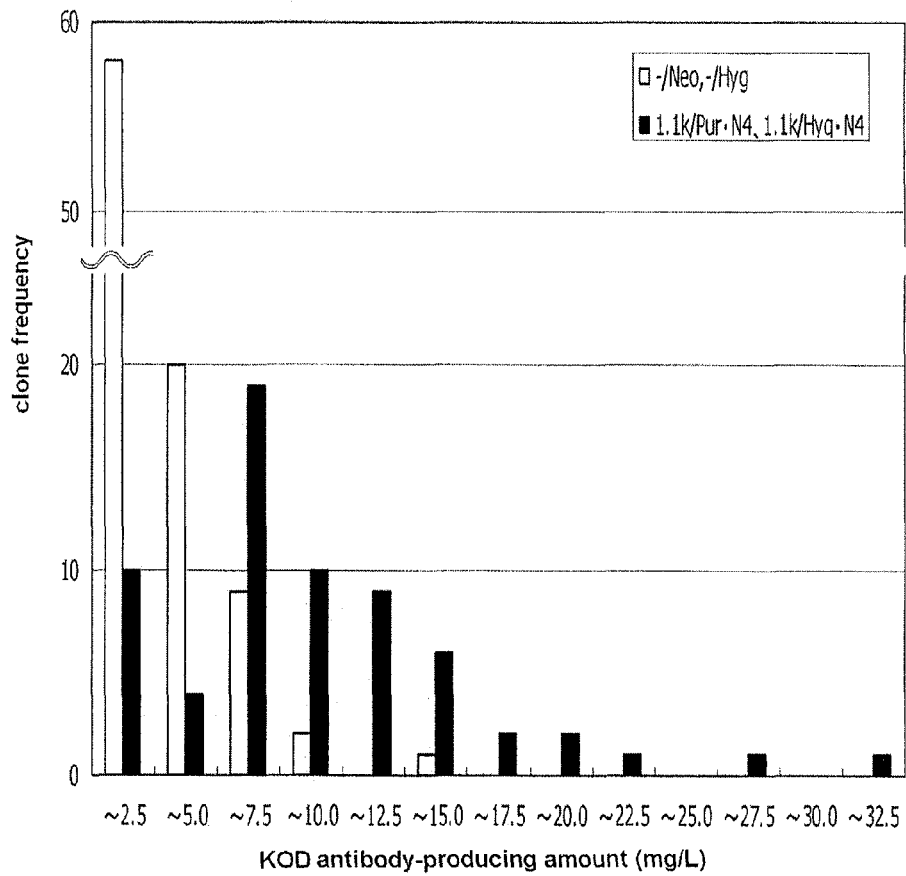

FIG. 51 is a graph where the thing containing no gene expression stabilizing element and no mRNA destabilizing sequence (−/Neo, −/Hyg); and the thing to which a gene expression stabilizing element and an mRNA destabilizing sequence were added whereby a high antibody productivity was noted (1.1k/Pur.N4, 1.1k/Hyg.N4) were incubated for two weeks in a 96-well plate and the frequency distributions of the antibody productivity resulted thereby were plotted.

Figure 52:
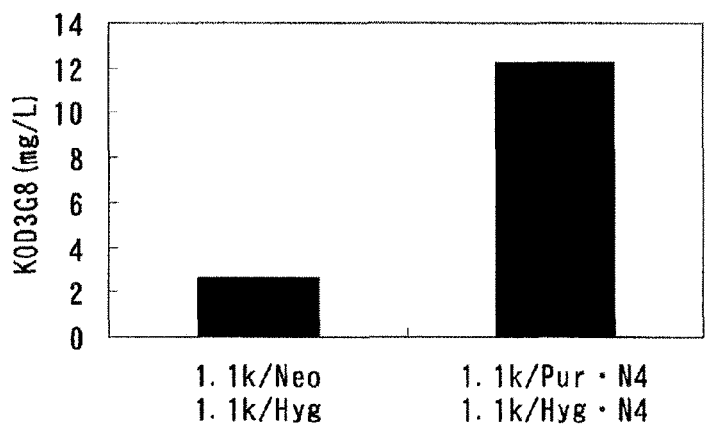

FIG. 52 is a graph where the thing into which gene expression stabilizing element CHO5Δ3-3 is inserted into both of upstream and downstream regions of the expression cassette (1.1k/Neo, 1.1k/Hyg); and the thing into which gene expression stabilizing element CHO5Δ3-3 is inserted into both of upstream and downstream regions of the expression cassette followed by adding the mRNA destabilizing sequence (N4 sequence) to the drug-resistant gene (H chain: Pur; L chain: Hyg) (1.1k/Pur.N4, 1.1k/Hyg.N4) were transferred to a serum-free adapted CHO-K1 cell and, after the drug selection, ELISA was conducted using the supernatant of the culture of polyclone and the production amounts of the antibodies calculated thereby were plotted.

Figure 53:
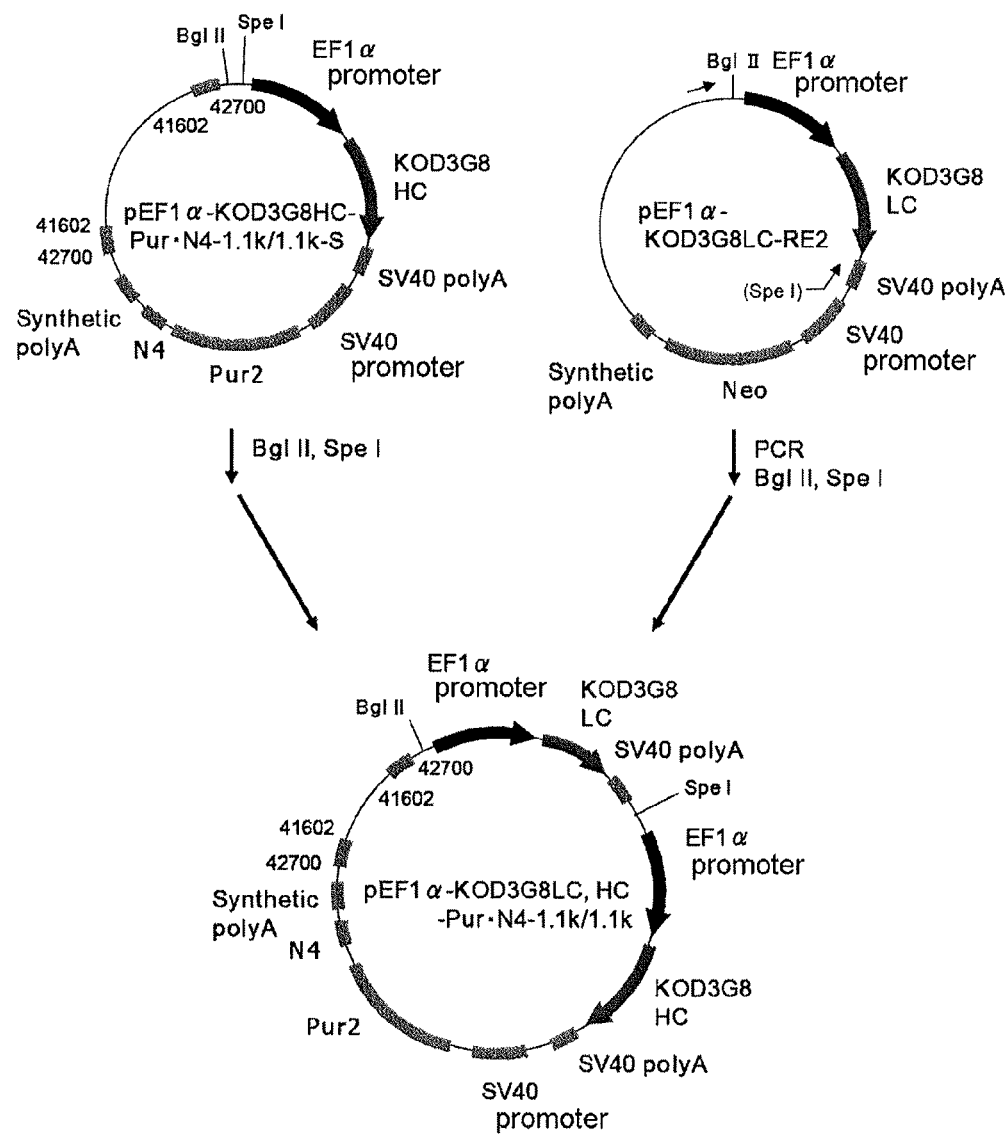

FIG. 53 shows construction pEF1α-KOD3G8LC and HC-Pur.N4-1.1k/1.1k.

Figure 54:
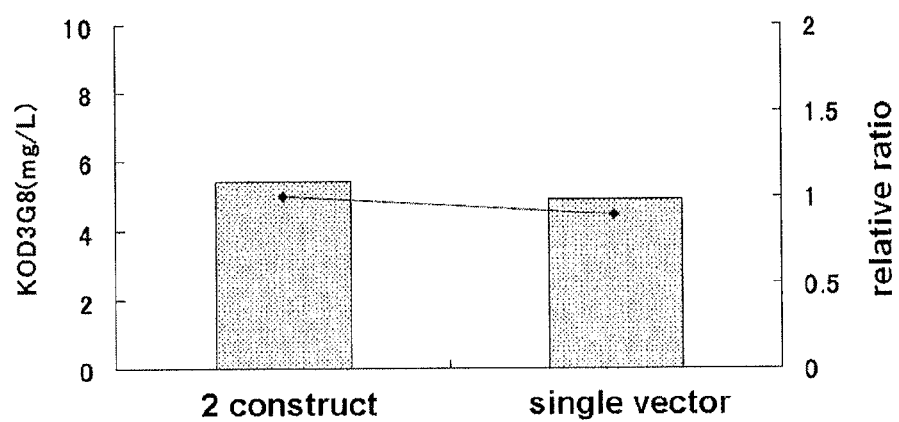

FIG. 54 is a graph where a two-construct antibody expression system and a single vector antibody expression system were subjected to ELISA using the supernatant of the culture of polyclone and the production amounts of the antibody calculated thereby were plotted.

Figure 55:
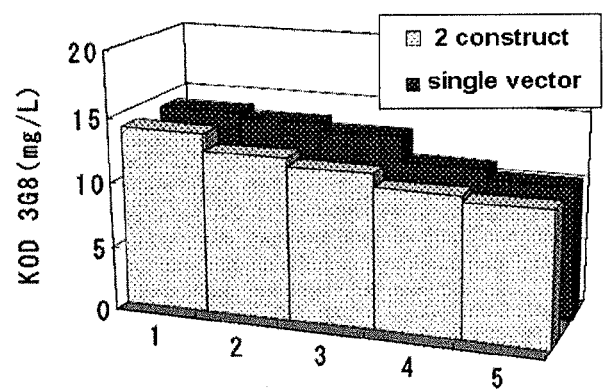

FIG. 55 is a graph where the production amounts of the antibodies by each clone calculated by conducting ELISA using the supernatant of culture of 6-well plate were plotted. With regard to each of the two-construct antibody expression system and the single vector antibody expression system, the best five clones in terms of the production amount were plotted on the same graph.

Figure 56:
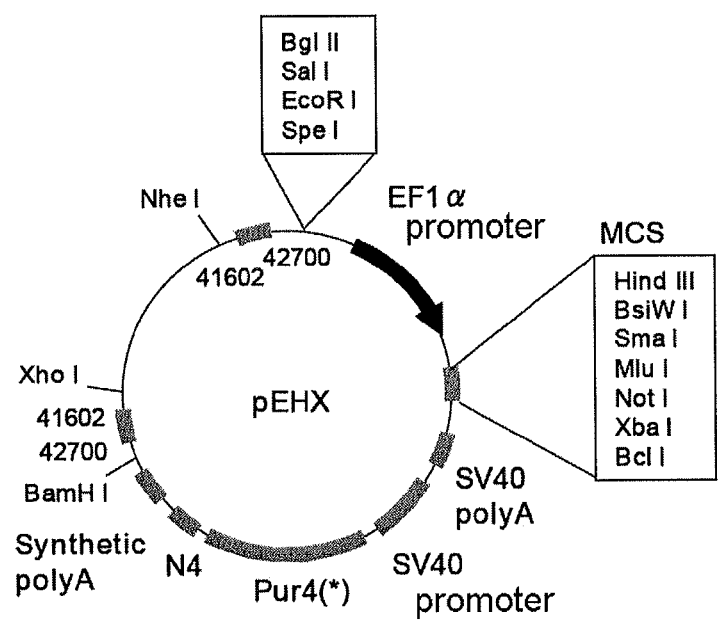

FIG. 56 is a chart showing a vector map of pEHX.

Figure 57:
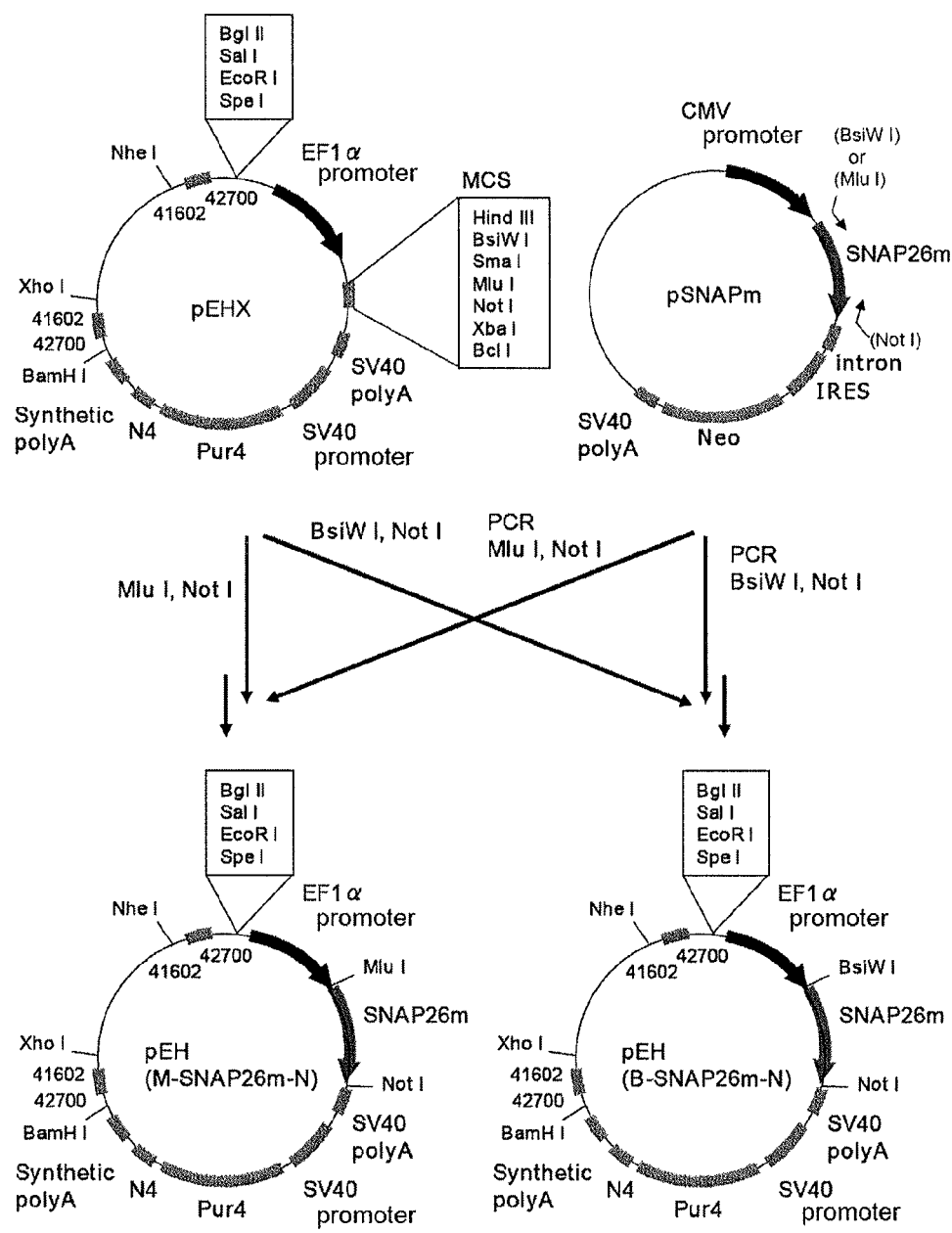

FIG. 57 shows the construction of pEH (M-SNAP26m-N) and pEH (B-SNAP26m-N).

Figure 58:
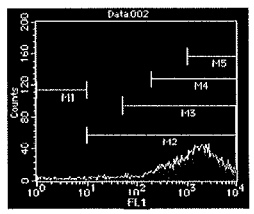
Figure 58:
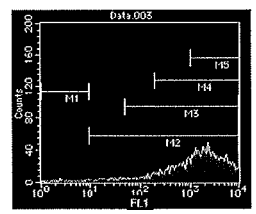
Figure 58:
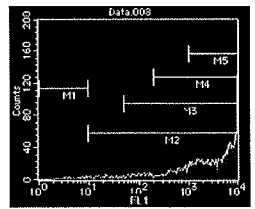
Figure 58:
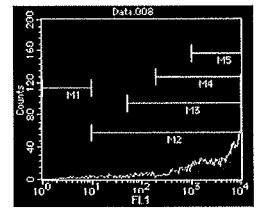
Figure 58:
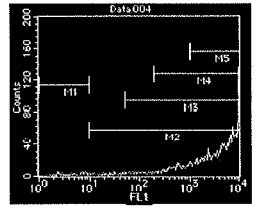
Figure 58:
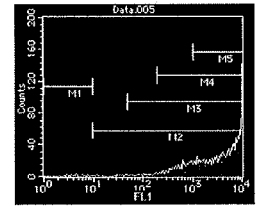

FIG. 58 shows the results of FACS analysis of the cell group which is transformed by pEF1α-SNAP26m-Pur.N4-1.1k/1.1k, pEH (M-SNAP26m-N), or pEH (B-SNAP26m-N).

Figure 59:
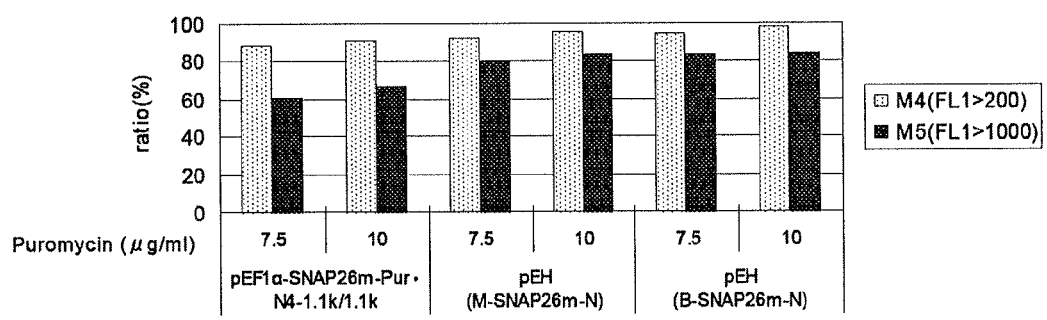

FIG. 59 is a graph where the rate of the cells which highly express SNAPm in the cells transformed by pEF1α-SNAP26m-Pur.N4-1.1k/1.1k, pEH (M-SNAP26m-N), or pEH (B-SNAP26m-N) is plotted.

Figure 60:
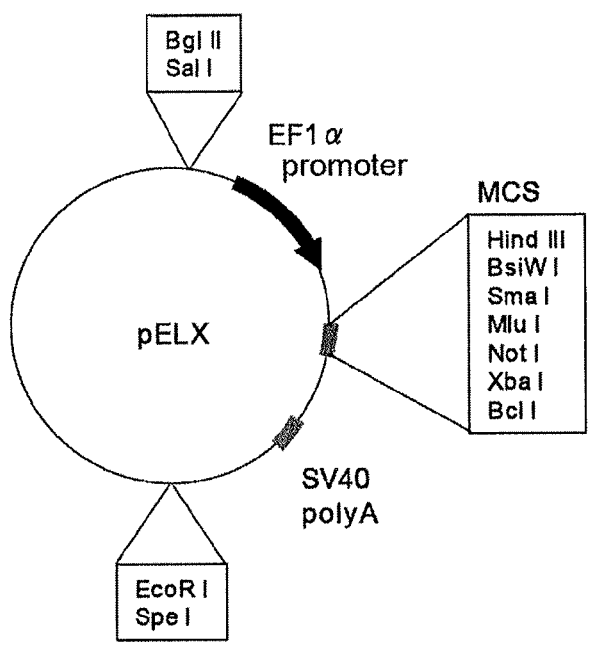

FIG. 60 is a chart showing a vector map of pELX.

Figure 61:
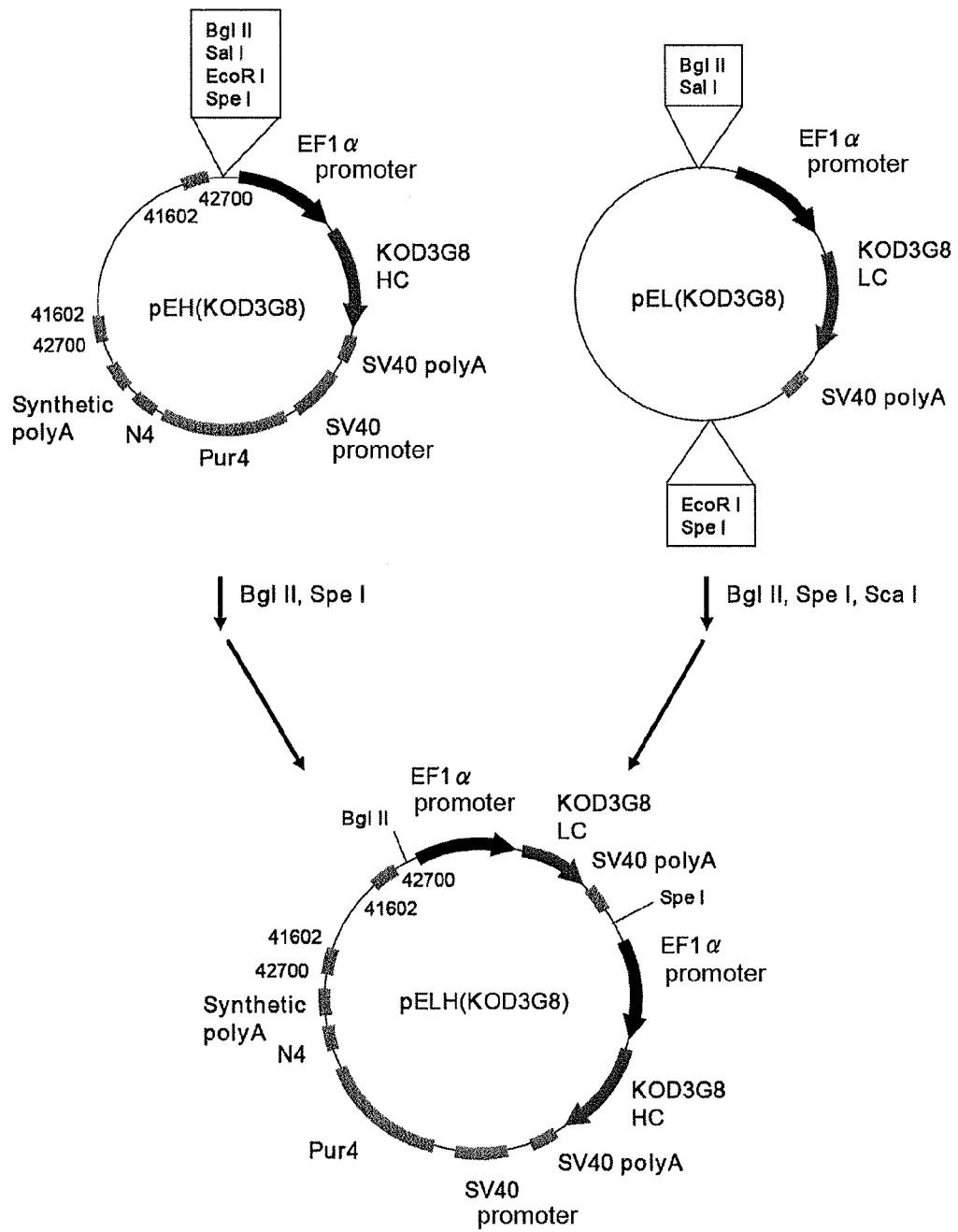

FIG. 61 shows the construction of pELH (KOD3G8).

Figure 62:
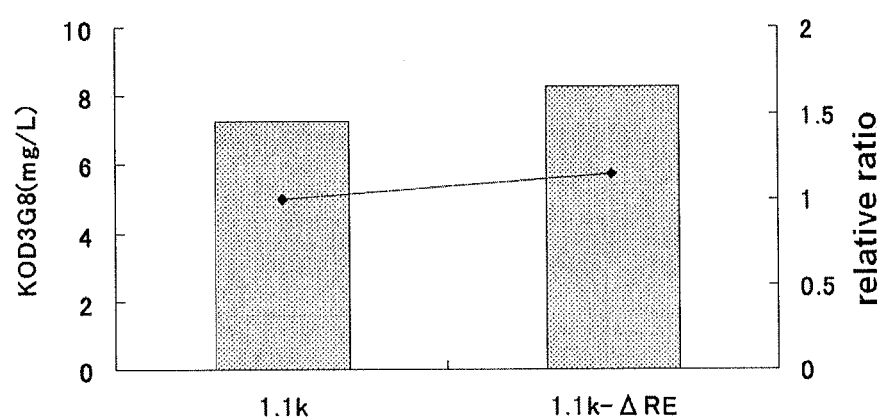

FIG. 62 is a graph where the thing in which a gene expression stabilizing sequence CHO5Δ3-3 wherefrom no restriction enzyme recognition sequence is deleted was inserted into both upstream and downstream regions of the expression cassette (1.1k); and the thing in which CHO5Δ3-3 wherefrom four restriction enzyme recognition sequences were deleted was inserted into both upstream and downstream regions of the expression cassette (1.1k-ΔRE) were subjected to ELISA using the supernatant of the culture of polyclone and the calculated production amounts of the antibody were plotted.

Figure 63:
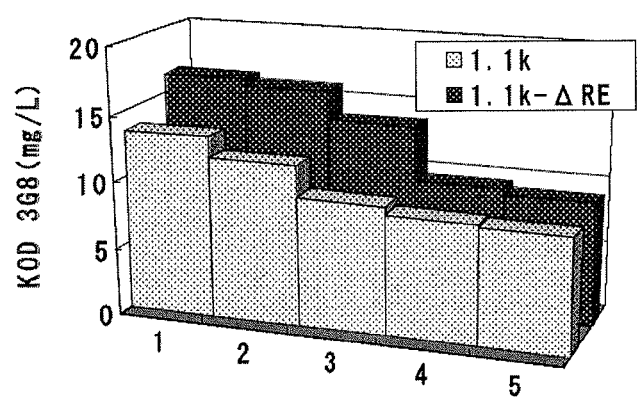

FIG. 63 is a graph where the production amounts of the antibodies by each clone calculated by conducting ELISA using the supernatant of culture of 6-well plate were plotted. With regard to each of the thing in which a gene expression stabilizing sequence CHO5Δ3-3 wherefrom no restriction enzyme recognition sequence is deleted was inserted into both upstream and downstream regions of the expression cassette (1.1k); and the thing in which CHO5Δ3-3 wherefrom four restriction enzyme recognition sequences were deleted was inserted into both upstream and downstream regions of the expression cassette (1.1k-ΔRE), the best five clones in terms of the production amount were plotted on the same graph.

Figure 64:
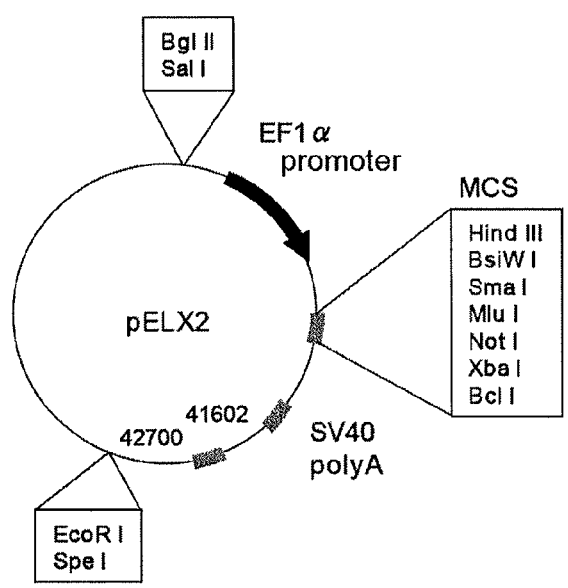

FIG. 64 is a chart showing a vector map of pELX2.

Figure 65:
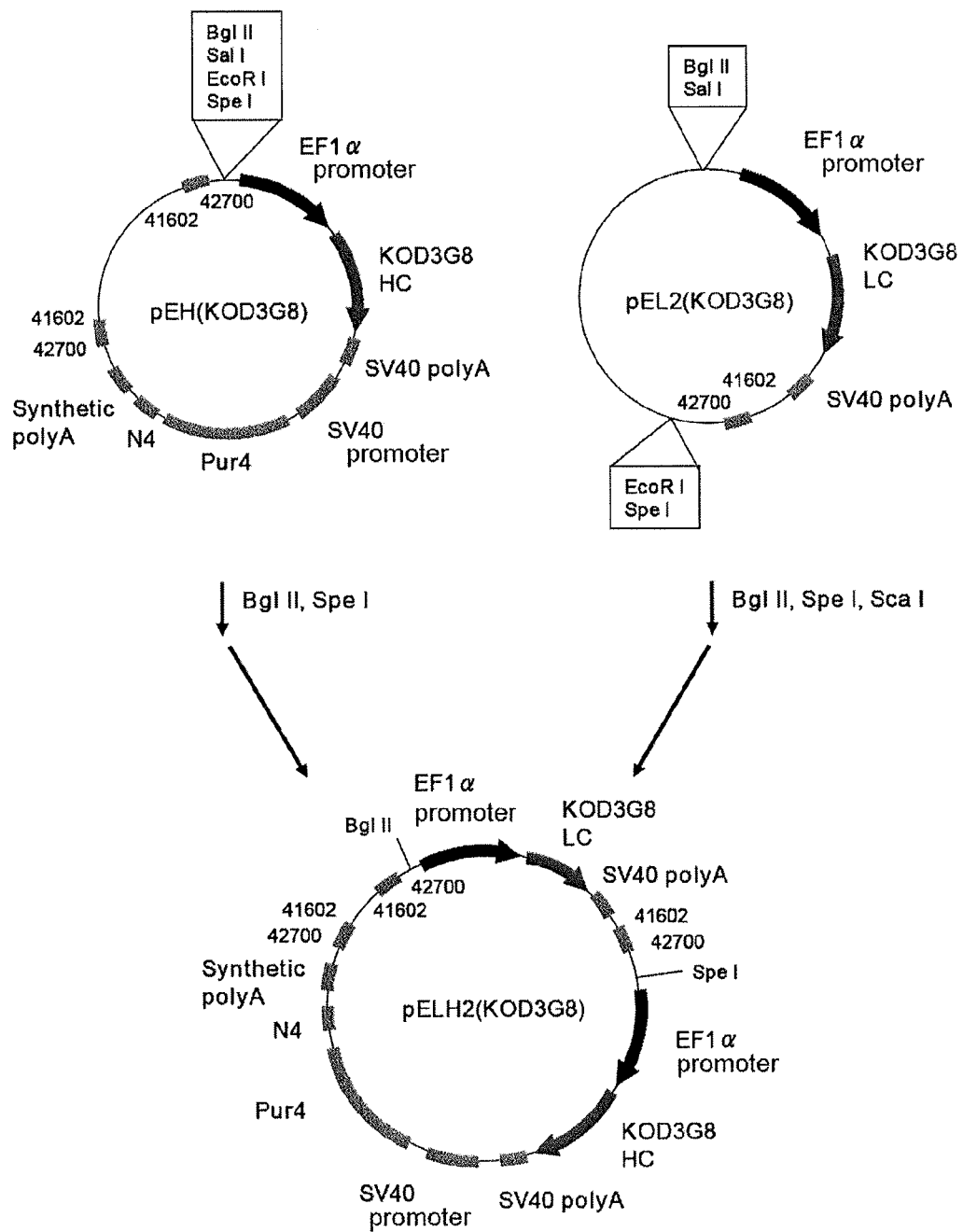

FIG. 65 shows the construction of pELH2 (KOD3G8).

Figure 66:
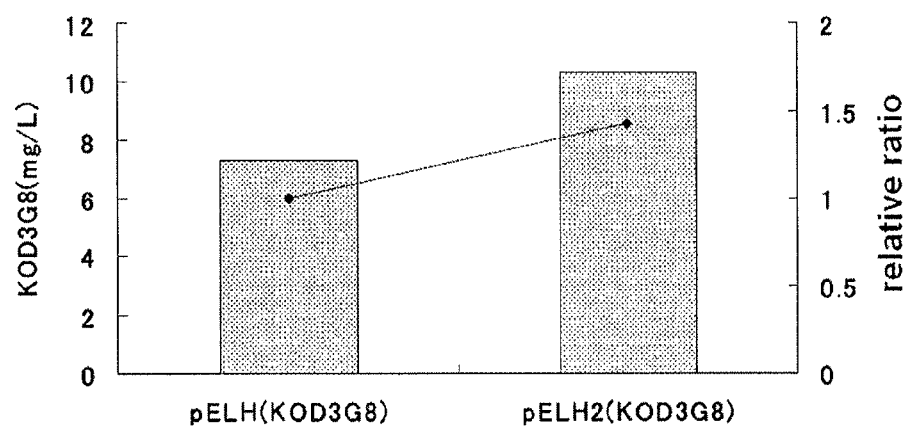

FIG. 66 is a graph where the thing in which CHO5Δ3-3 wherefrom four restriction enzyme recognition sequences were deleted was inserted into both upstream and downstream regions of the expression cassette (pELH (KOD3G8)); and the thing where CHO5Δ3-3 wherefrom four restriction enzyme recognition sequences were deleted was inserted into upstream and downstream regions of the expression cassette as well as the region between the L chain expressing cassette and H chain expressing cassette (three regions in total) (pELH2 (KOD3G8)) were subjected to ELISA using the supernatant of the culture of polyclone and the calculated production amounts of the antibody were plotted.

Figure 67:
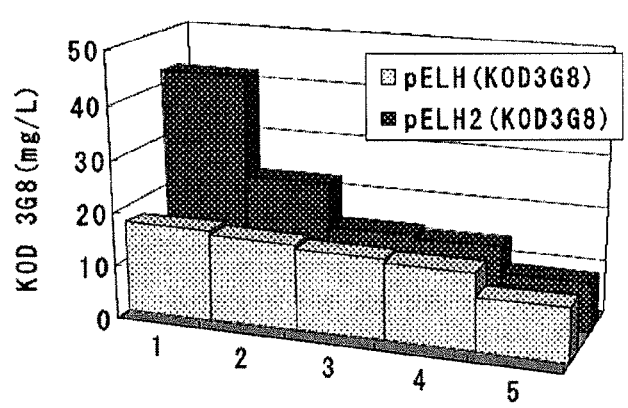

FIG. 67 is a graph where the production amounts of the antibodies by each clone calculated by conducting ELISA using the supernatant of culture of 6-well plate were plotted. With regard to each of the thing in which CHO5Δ3-3 wherefrom four restriction enzyme recognition sequences were deleted was inserted into both upstream and downstream regions of the expression cassette (pELH (KOD3G8)); and the thing in which CHO5Δ3-3 wherefrom four restriction enzyme recognition sequences were deleted was inserted into upstream and downstream regions of the expression cassette as well as the region between the L chain expressing cassette and H chain expressing cassette (three regions in total) (pELH2 (KOD3G8)), the best five clones in terms of the production amount were plotted on the same graph.

Figure 68:
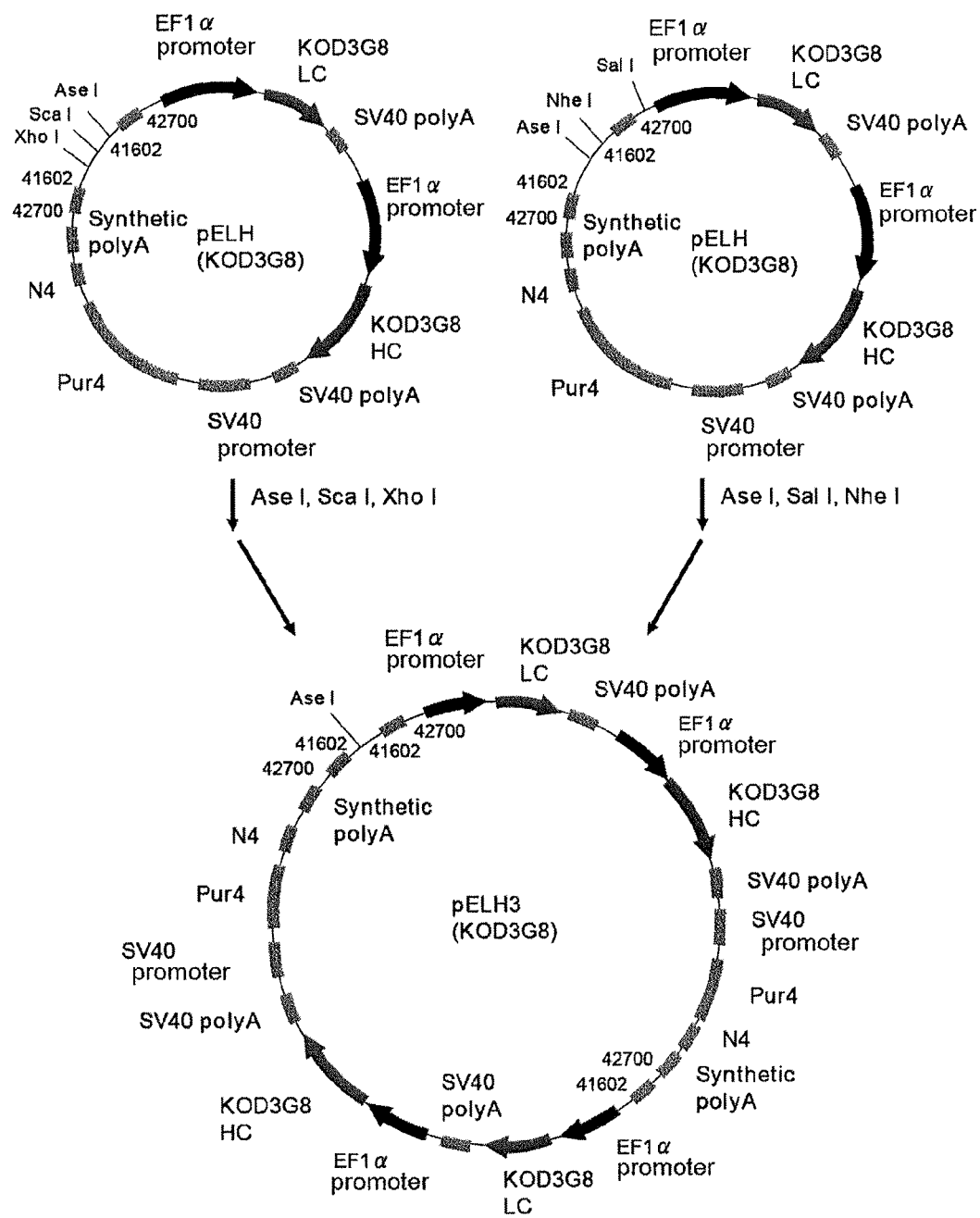

FIG. 68 shows the construction of pELH3 (KOD3G8).

Figure 69:
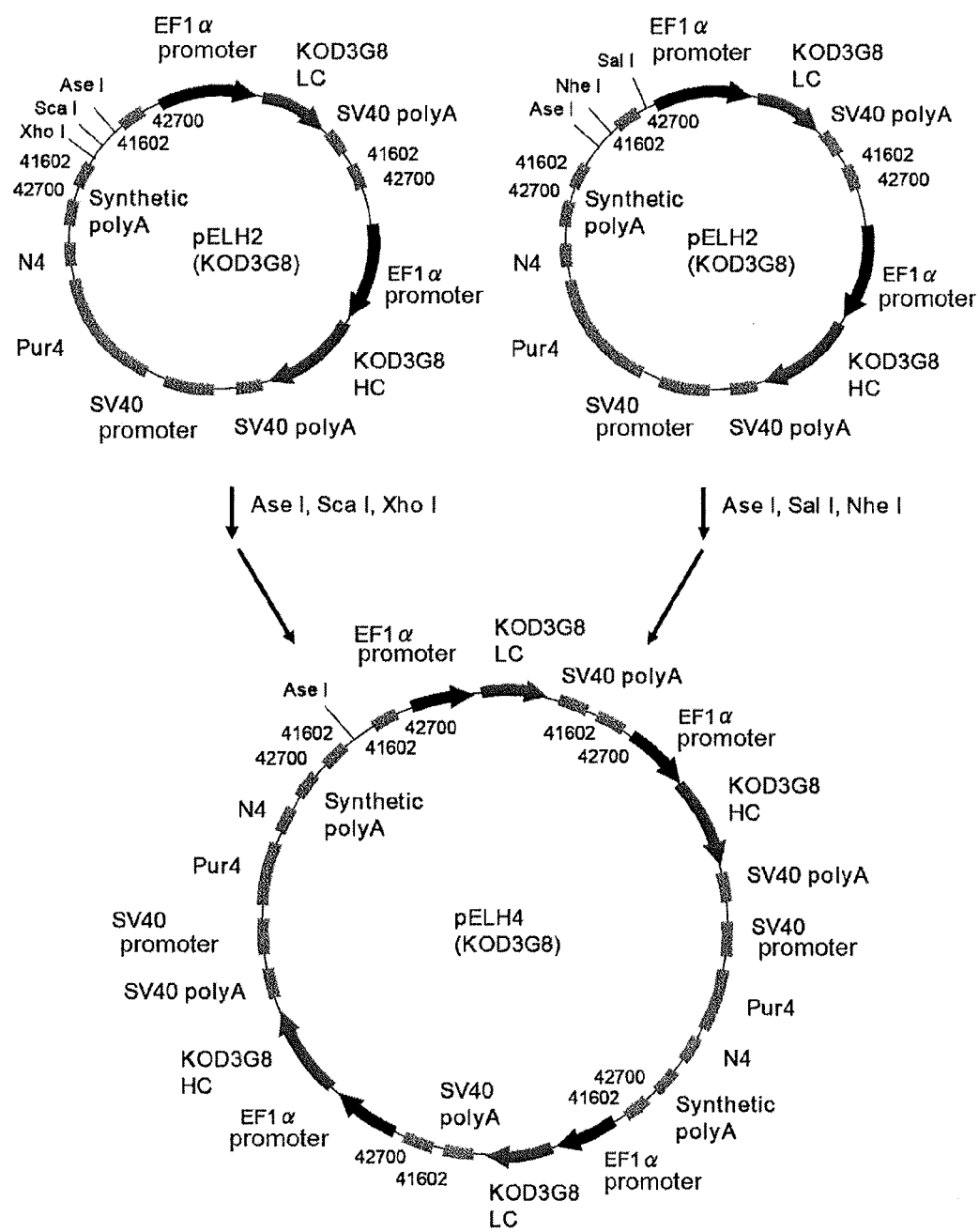

FIG. 69 shows the construction of pELH4 (KOD3G8).

Figure 70:
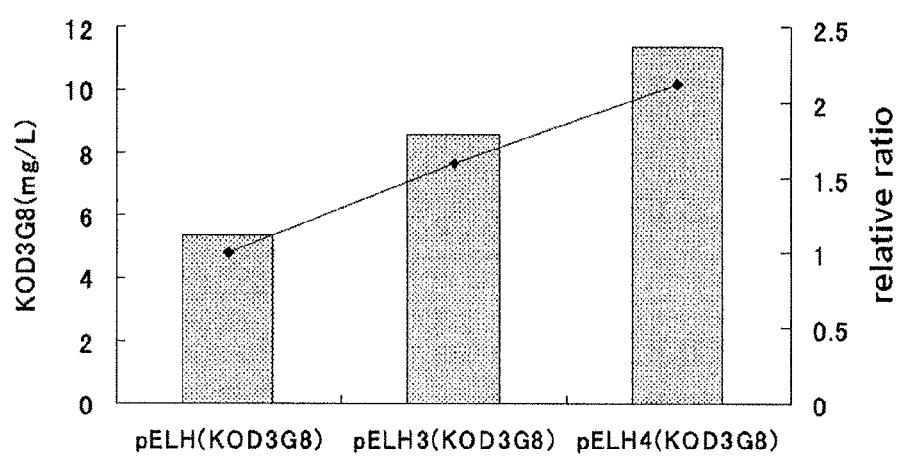

FIG. 70 is a graph where the thing in which each one copy of H chain expressing cassette and L chain expressing cassette of the anti-KOD antibody as well as Puromycin-resistant gene expressing cassette was coded (pELH (KOD3G8)); the thing in which each two copies of H chain expressing cassette and L chain expressing cassette of the anti-KOD antibody as well as Puromycin-resistant gene expressing cassette were coded (pELH3 (KOD3G8)); and the thing in which each two copies of H chain expressing cassette and L chain expressing cassette of the anti-KOD antibody as well as Puromycin-resistant gene expressing cassette were coded and, between the L chain expressing cassette and the H chain expressing cassette, the gene expression stabilizing element CHO5Δ3-3 was coded (pELH4 (KOD3G8)) were subjected to ELISA using the supernatant of the culture of polyclone and the calculated production amounts of the antibody were plotted.

Figure 71:
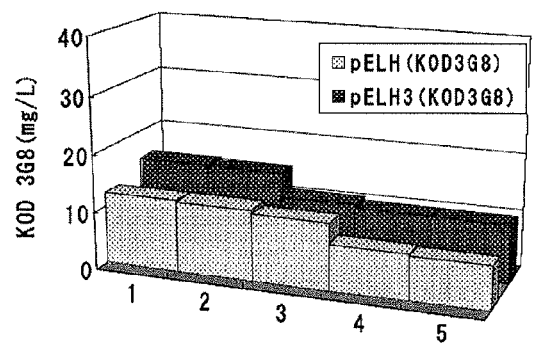
Figure 71:
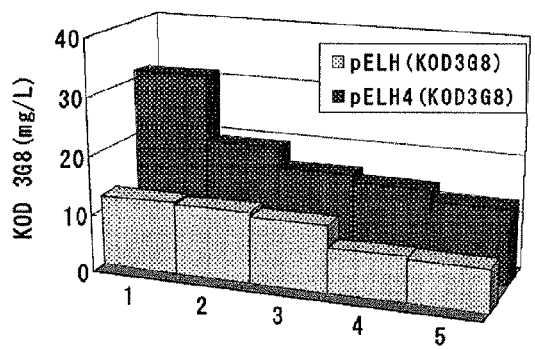

FIG. 71 is a graph where the production amounts of the antibodies by each cell strain in monoclones calculated by conducting ELISA using the supernatant of culture of 6-well plate were plotted. With regard to each of the thing in which each one copy of H chain expressing cassette and L chain expressing cassette of the anti-KOD antibody as well as Puromycin-resistant gene expressing cassette was coded (pELH (KOD3G8)); the thing in which each two copies of H chain expressing cassette and L chain expressing cassette of the anti-KOD antibody as well as Puromycin-resistant gene expressing cassette were coded (pELH3 (KOD3G8)); and the thing in which each two copies of H chain expressing cassette and L chain expressing cassette of the anti-KOD antibody as well as Puromycin-resistant gene expressing cassette were coded and, between the L chain expressing cassette and the H chain expressing cassette, the gene expression stabilizing element CHO5Δ3-3 was coded (pELH4 (KOD3G8)), the best five clones in terms of the production amount were plotted on the same graph.

Figure 72:
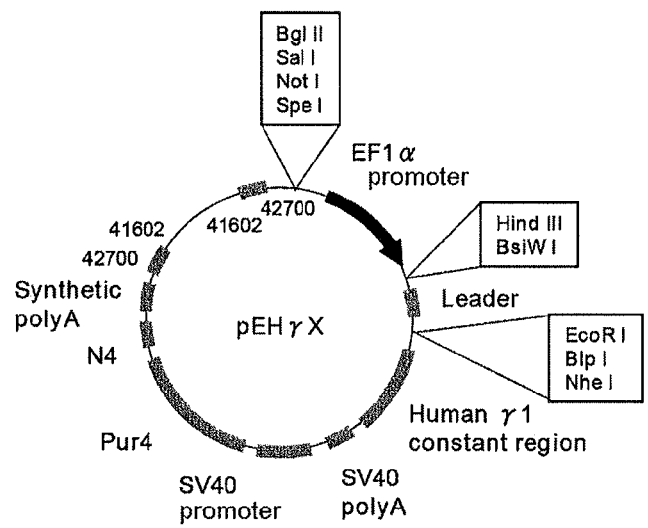

FIG. 72 is a chart showing a vector map of pEHγX.

Figure 73:
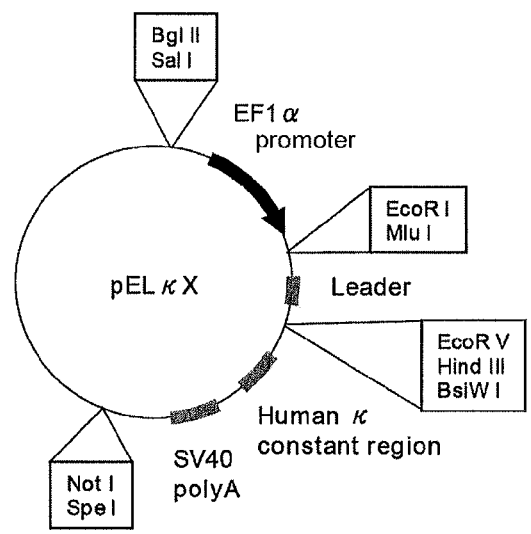

FIG. 73 is a chart showing a vector map of pELκX.

Figure 74:
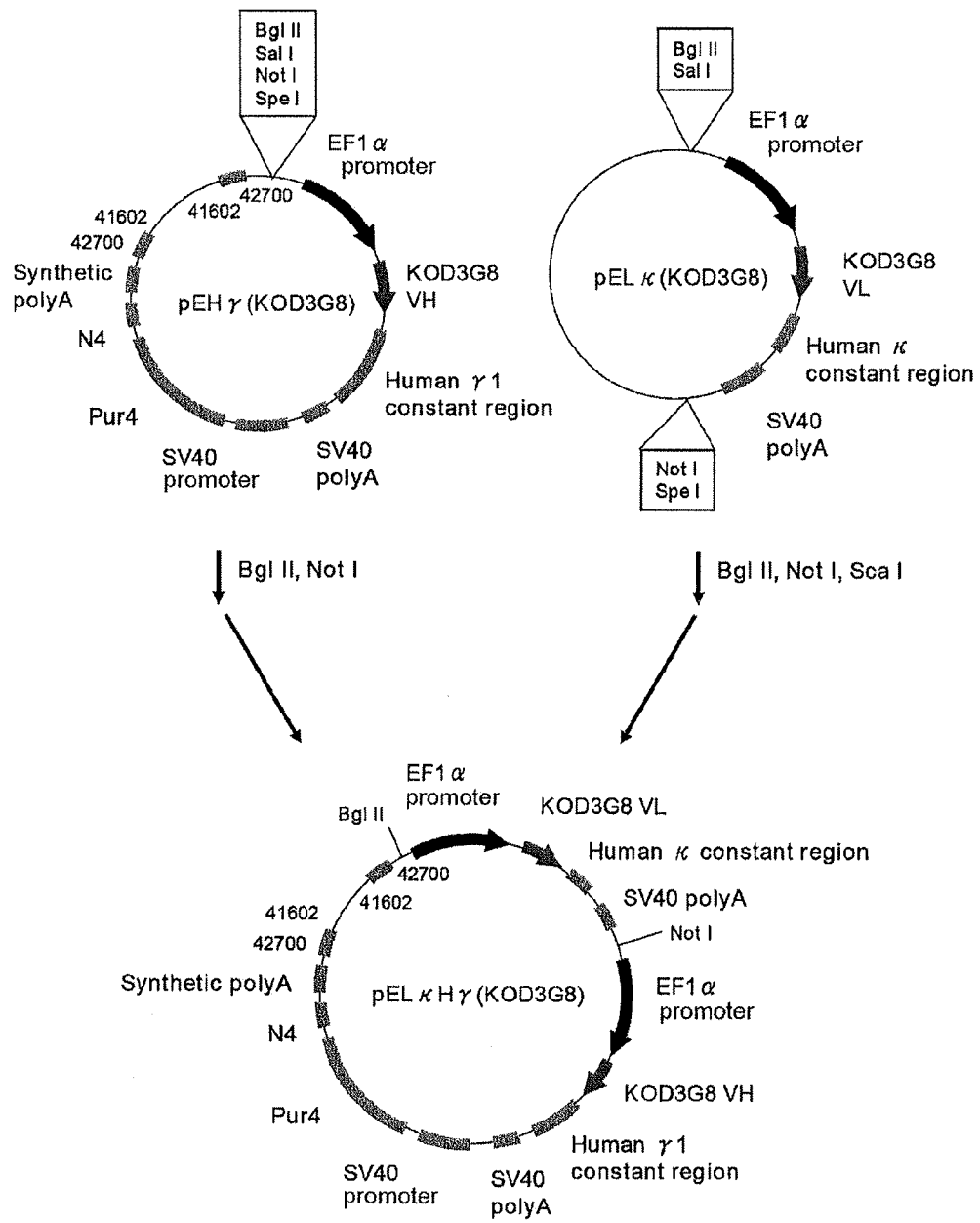

FIG. 74 shows the construction of pELκHγ (KOD3G8).

Figure 75:
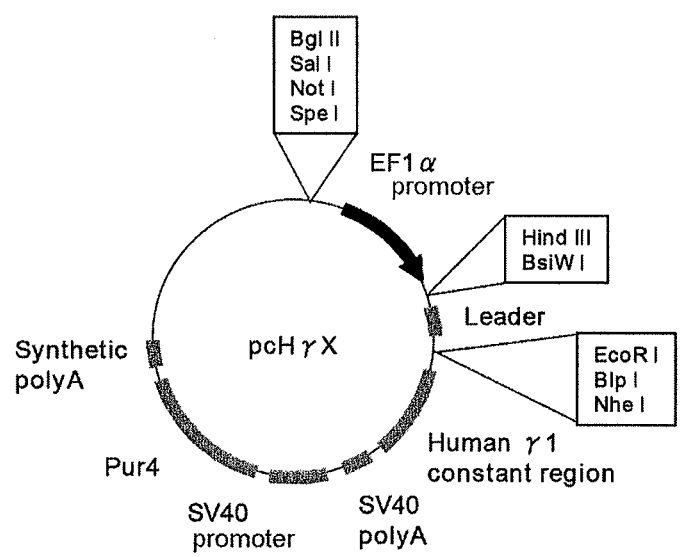

FIG. 75 is a chart showing a vector map of pcHγX.

Figure 76:
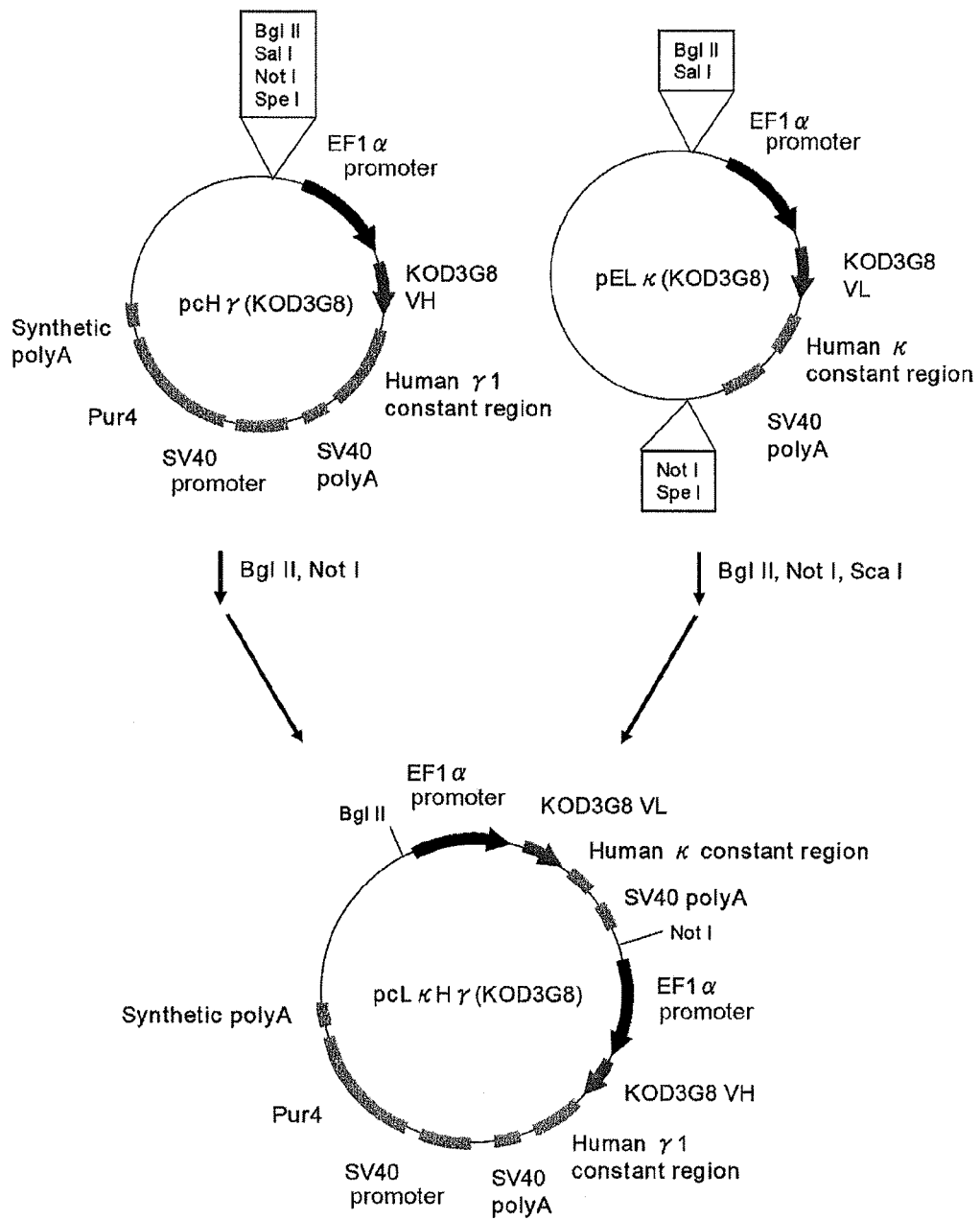

FIG. 76 shows the construction of pcLκHγ (KOD3G8).

Figure 77:
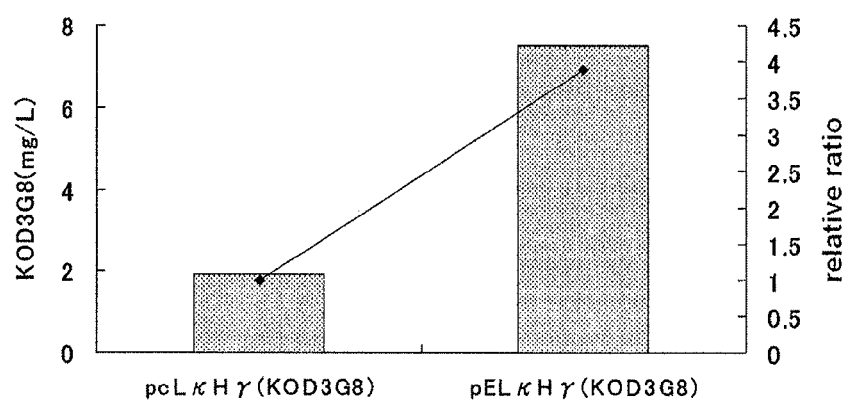

FIG. 77 is a graph where the thing in which no gene expression stabilizing element was contained and no mRNA destabilizing sequence was added to Pur-resistant gene (pcLκHγ (KOD3G8)); and the thing in which the gene expression stabilizing element CHO5Δ3-3 was inserted into both upstream and downstream regions of the expression cassette and an mRNA destabilizing sequence (N4 sequence) was added to the Puromycin-resistant gene (pELκHγ (KOD3G8)) were subjected to ELISA using the supernatant of the culture of polyclone and the calculated production amounts of the antibody were plotted.

BEST MODE FOR CARRYING OUT THE INVENTION

The present invention will be explained in detail hereinafter.

For the function analysis of protein and also for the production of useful protein, a method where gene of the aimed protein is transferred into cells or, particularly, animal cells using a gene recombination technique whereby it is expressed as a recombinant protein has been widely used. To be more specific, a method where gene of the aimed protein is inserted into a vector represented by a plasmid vector, then the vector is incorporated into the cells and then the aimed protein gene is integrated into the cell genome by means of recombination whereby the cell is transformed has been used frequently.

Genome of a cell is present on a chromosome while, in the chromosome, expression of gene is controlled by histone acetylation, high aggregation (heterochromatin), etc. and the expression level of the gene greatly differs depending upon the place in the chromosome into which the gene is inserted. In a method where the cell is transformed using a vector, it is not possible to control the place in the cell genome into which the aimed protein gene is transferred and, therefore, the expression level of the aimed protein gene in the transformed cell and, as a result, the production amount of the aimed protein are greatly different depending upon the cell strain.

There are also many cases where gene recombination does not proceed well and the aimed protein gene is not integrated with the cell genome.

Under such circumstances, there were conventionally conducted the following operations: a drug-resistant (drug selective marker) gene is inserted into the expression vector previously, this vector is then transferred to the cell, a drug is administered to the medium (drug selection), the cell where the transformation was successful is selected and, after that, the cell strains showing a high expression are repeatedly selected from the resulting cell group. In this method, however, much labor and time were needed since it is necessary to prepare many cell strains and further since a selecting operation for the cells which needs the culture for a long period is carried out repeatedly. Moreover, since the drug-resistant gene shows resistance to a drug even when it is expressed in small amount in many cases, the cell strains where the drug-resistant gene and the aimed protein gene are integrated in the low expression region in the cell genome and the expression amount of the aimed protein gene is small are also present in the living cells, which causes much more labor and time.

Even the cells which showed a sufficient expression upon the selection, not a few of them gradually lower the expression as the culture is continued. That will be due to the fact that the expression is suppressed by a gene silencing. Since it is usually impossible to control the transfer position of the aimed protein gene to the genome, prediction of the lowering of the expressed level by the effect of gene silencing is very difficult. Accordingly, it has been considered to be necessary to mitigate such a position effect so as to stably maintain the expression in a high level.

Thus, for solving those problems, the present invention makes it possible to procure the cells showing a high expression level by utilizing the drug selection and also makes it possible to maintain gene expression at high level by the gene expression stabilizing element regardless of the transfer site of the gene in the cell genome. The present invention exhibits a very significant effect in such a view that the cell strains where productivity of the aimed protein is high are able to be procured quickly, easily and efficiently.

In the present invention, an mRNA destabilizing sequence is utilized in the conventional drug resistance (drug selective marker) gene expression cassette whereby the expressing amount of the drug-resistant gene is greatly suppressed so that only the transformed cells where the drug-resistant gene is integrated in the highly expression region in the host cell genome are able to survive after the drug selection. Since the gene of the aimed protein is integrated near the drug-resistant gene, there is a high possibility that, in the survived cells, the aimed protein gene is also integrated in the highly expression region. Therefore, according to the present invention, it is possible to efficiently select only the cells of the following (iii) (i.e. the cells where the gene recombination was successful and, further, the drug-resistant gene and the aimed protein gene were integrated in the highly expression region of the host cell genome) by means of drug selection from the following cells (i)-(iii). Thus, (i): the cells where gene recombination did not proceed well whereby the aimed protein gene was not integrated in the cell genome; (ii): the cells where, although gene recombination was successful, the drug-resistant gene and the aimed protein gene were integrated in the lowly expression region of the host cell genome; and (iii): the cells where the gene recombination was successful and, further, the drug-resistant gene and the aimed protein gene were integrated in the highly expression region of the host cell genome. In the conventional selection method, although it is possible to select the cells of (ii) and (iii) by means of drug selection from the cells of (i) to (iii), it is not possible to select only the cells of (iii) from the cells of (ii) and (iii) by means of drug selection and, therefore, the expression level of the aimed protein gene was separately confirmed for the transformed cells being survived from the drug selection whereby the highly expressing cells of (iii) were selected. In accordance with the method of the present invention, it is now possible to immediately select the highly expressing cells of (iii) from the cells of (i) to (iii) only by means of drug selection and, therefore, said method is efficient and, as a result, the highly expressing cells are able to be quickly selected.

Moreover, in accordance with the present invention, a gene expression stabilizing element is utilized so that a lowering in the expressed level of the gene upon the continuous culture of the selected cells is prevented. The gene expression stabilizing element according to the present invention is not only useful for a stable maintenance of expression of the aimed protein gene but also, in case the effect is available for the drug-resistant gene, reduces the influence of the adjacent chromosome and regulatory element to the expression of the drug-resistant gene and helps the achievement of the function inherent to the drug-resistant gene whereby the synergism with the drug selection is achieved.

According to the first aspect of the present invention, an expression vector which is characterized in having a cassette for expressing the drug selective marker gene containing an mRNA destabilizing sequence, at least one element for stabilizing the gene expression and a cassette for expressing the gene of the aimed protein.

In the present invention, the expression cassette stands for the unit of gene expression from the promoter through the gene coding sequence and to the terminator sequence (polyadenylation signal). Moreover, it may also include introns, spacer sequences, translation enhancement regions, etc. Accordingly, in the case of "drug selective marker gene expression cassette" for example, it means that the gene coding sequence of the above-mentioned expression cassette is a coding sequence of the drug selective marker gene. Further, in the case of "aimed protein gene expression cassette", it means that the gene coding sequence of the above-mentioned expression cassette is a coding sequence of the aimed protein gene.

(Drug Selective Marker Gene Expression Cassette)

The drug selective marker gene expression cassette used in the present invention has the same constitution as the conventionally known drug selective marker gene expression cassette except that an mRNA destabilizing sequence is contained. Accordingly, the mRNA destabilizing sequence will be firstly illustrated.

The present invention is based on the finding that the mRNA destabilizing sequence is able to very effectively attenuate the expression of the drug-resistant gene. When an expression vector where a drug selective marker gene expression cassette containing the mRNA destabilizing sequence of the present invention is installed is transferred to the host cells, the surviving cell numbers after the drug selection or the colonies thereof decrease to an extent of $1/10$ to $1/100$ as compared with the case where no mRNA destabilizing sequence is contained. That is probably due to the fact that, since the mRNA of the drug selective marker becomes unstable and the expressed level of the drug selective marker lowers because of the presence of the mRNA destabilizing sequence, survival of the cells under the drug selection becomes difficult unless they are the cells where, in the genome of the host cells, said expression cassette is integrated in the highly expression region in which the transcription activity is high.

The term "mRNA destabilizing sequence" means a nucleotide sequence having a function of reducing the intracellular half life of the mRNA transcribed from the DNA having this sequence and, in the natural world, it has been found to be present in the early response genes, etc.

Although the mRNA destabilizing sequence is present in a coding sequence or in a 5'-UTR (untranslated region) in some genes, it is present in a 3'-UTR in many cases. AU-rich element (ARE), histone mRNA 3'-terminal stem-loop, iron-responsive element (IRE), insulin-like growth factor II (IGF-II), long stem-loop, etc. have been known as the mRNA destabilized sequence existing in the 3'-UTR. Among them, ARE is preferred as the mRNA destabilizing sequence used in the present invention since it is able to constantly destabilize mRNA.

ARE means "AU rich element" in mRNA or, in other words, a sequence or the region where adenine (A) and uracil (U) are contained in high rates. ARE is also used for designating "AT-rich element" in DNA coding for the above element or, in other words, a sequence or a region where adenine (A) and thymine (T) are contained in high rates.

ARE is found in cytokine gene such as hematopoietic cell growth factor gene, growth factor gene, interleukin gene or interferon and also in some proto-oncogenes (Non-Patent Document 4). In the drug selective marker gene expression cassette of the present invention, although the nucleic acid sequence corresponding to ARE in such a gene may be utilized as it is, utilization of TATTTAT (Non-Patent Document 5) and TTATTTA (T/A) (T/A) (Non-Patent Document 6) or the like known as a motif sequence in the ARE is highly convenient since insertion of unnecessary restriction enzyme recognition sequence into an expression vector is able to be avoided.

Examples of the gene having ARE include granulocyte-monocyte colony sitimulation factor (GM-CSF) for the hematopoietic cell growth factor, interleukin-1β, 2, 3, 4, 6, 8, 10, 11 for the interleukin, interferon-α for the interferon, and c-fos, c-myc, c-jun, c-myb, Pim-1 etc. for the proto-oncogene. Besides them, many genes such as tumor necrosis factor, cyclin D1, cyclooxygenase, plasminogen activator inhibitor type 2 have been known to have ARE and there is no limitation to the exemplified gene only.

With regard to the mRNA destabilizing sequence which is able to be used in the drug selective marker gene expression cassette of the present invention, the following ones are exemplified.

One motif sequence of ATTT or repetition thereof for two or more times.

One motif sequence of ATTTA or repetition thereof for two or more times.

One motif sequence of TATTTAT or repetition thereof for two or more times.

One motif sequence of TTATTTA (T/A) (T/A) or repetition thereof for two or more times. Here, (T/A) means any of T or A.

The sequences as such may contain substitution/insertion/deletion of one or more base(s) and those by natural variation such as error in duplication of DNA or mutation and those by transfer of artificial mutation may be expected. Moreover, a spacer sequence or a linker sequence comprising 1 to about 100 base(s) may be contained between the repetition of the motif sequences. In addition, the thing which contains inversion of the motif sequence may be available.

Although the number of repetitions of the motif sequence may be only one, the destabilizing effect on mRNA is able to be further enhanced when it is made two or more times or, more preferably, four or more times whereby the selection efficiency is able to be significantly increased.

Although there is no particular limitation for the upper limit of the number of repetitions, it is desirable that the expression vector becomes the length of 10 to 25 kbp at the highest in view of the incorporation of the vector into the cells. However, as the number of repetitions increases, the destabilizing effect on mRNA goes toward saturation and, when the number of repetitions is more than a certain level, no further significant effect is able to be expected. Although no upper limit will be decided, number of repetitions of 10 times or more is practically meaningless.

Although there is no particular limitation for the promoter in the drug selective marker gene expression cassette of the present invention so far as it is a promoter which is able to be expressed in animal cells or, particularly, in mammalian cells, examples thereof include that derived from virus such as cytomegalovirus (CMV) promoter of human or mouse, simian virus 40 (SV40) promoter or human herpes simplex virus-thymidine kinase gene (HSV-tk) promoter; that derived from nonviral cell gene such as phosphoglycerate-kinase 1 gene (PGK) promoter of mouse; and a hybrid of promoters of different origins. Here, the promoter is not limited to the core region of promoter but it may include an enhancer region. In order to attenuate the expression of the drug selective marker, that having a low transcription activity is more preferred. As a promoter having a low transcription activity, a promoter of a mutation type or the like may be utilized or Kozak sequence may be substituted therefor. In addition, it is one of the expected embodiments that the repeating number of the motif sequence of mRNA destabilizing sequence is made small and a promoter having a weak transcription activity is used together.

With regard to a drug used for the drug selection using the drug selective marker expression cassette of the present invention, blasticidin, geneticin (G418), hygromycin (Hyg), puromycin (Pur) may be exemplified as an antibiotic substance of a protein synthesis inhibition type. Examples of other drugs for the selection include methotrexate (MTX), MSX (methionine sulphoximine) etc. In addition, as to the drug selective marker gene in the drug selective marker gene expression cassette of the present invention, gene showing the resistance to the drug which is commonly used in the drug selection is used advantageously. When an antibiotic substance of a protein synthesis inhibition type is used as a drug, it is preferred to use the gene which is resistant to the antibiotic substance of a protein synthesis inhibiting type. Although there is no particular limitation thereto, examples thereof include neomycin phosphotransferase (aminoglycoside 3'-phosphotransferase) (Neo) derived from Tn5 as a neomycin-resistant gene (also having a function as a Geneticin-resistant gene), hygromycin-B-phosphotransferase (Hph; in Examples and drawings, it is mentioned as Hyg) derived from *Escherichia coli* as a hygromycin-resistant gene, puromycin-N-acetyltransferase gene (pac; in Examples and drawings, it is mentioned as Pur) derived from *Streptomyces* as a puromycin-resistant gene and blasticidin-resistant gene (bsr) derived from *Bacillus cereus* as a blasticidin-resistant gene. Among them, puromycin-N-acetyltransferase, hygromycin-B-phosphotransferase and neomycin phosphotransferase are preferred. Puromycin-N-acetyltransferase and hygromycin-B-phosphotransferase are more preferred, and puromycin-N-acetyltransferase is much more preferred.

As to the polyadenylation signal (terminator sequence) in the drug selective marker gene expression cassette of the present invention, examples thereof include late poly A signal derived from SV 40 virus, early poly A signal derived from SV 40 virus, poly A signal derived from HSV-tk, poly A signal derived from bovine growth factor gene and poly A signal derived from rabbit β-globin gene although they are non-limitative.

Although there is no particular limitation for the order of the arrangement of promoter, drug selective marker gene, mRNA destabilizing sequence and polyadenylation signal in the drug selective marker gene expression cassette of the present invention so far as expression of the drug selective marker gene is possible, it is usual that promoter, drug selective marker gene, mRNA destabilizing sequence and polyadenylation signal are arranged in this order from the upstream side to the downstream side. There is no need that those four elements are directly connected each other but, if desired, they may have introns, spacer sequences, translation enhancement regions, etc. between them.

(Gene Expression Stabilizing Element)

The term "gene expression stabilizing element" in the present invention means a nucleic acid region which solves the position effect and has a function of stabilizing the gene expression. The position effect is such that, in order to increase the productivity of the aimed protein, the aimed gene expression cassette is affected by the activating state of the transcription of genome near the site in the host genome into which the cassette has been inserted.

As to the nucleic acid sequence having a function of stabilizing the gene expression, there may be utilized insulator, scaffold/matrix binding region (S/MAR), locus control region (LCR), Ubiquitous chromatin opening element (UCOE), etc.

Examples of the insulator include 1.2 kb DNase I hypersensitive site (cHS4) derived from chicken β-globin LCR and URI derived from green sea urchin. Examples of the S/MAR include chicken lysozyme 5'MAR element, human β-globin MAR element and human interferon βSAR element.

The expression vector of the present invention has at least one gene expression stabilizing element. When the nucleic acid sequence having the function of stabilizing the gene expression as such is aligned either at upstream or downstream region or both of the expression cassette of the aimed protein, it is possible to stably maintain the gene expression and to increase the productivity of the aimed protein.

A plasmid vector is usually used as a gene construct for transferring the aimed gene into the host cell genome. The size of the gene expression stabilizing element is preferred to be as short as possible since the size of the plasmid vector is 10 to 25 kbp at the longest. Preferred size is 5 kbp or shorter and, more preferably, it is about 1 kbp.

The gene expression stabilizing element in the preferred embodiment of the present invention is a nucleic acid molecule which was identified by the present inventors from the CHO cell DR 1000L-4N strain (CHO cell-4N strain) mentioned in the Patent Document 5. Said strain is a clone cell of a telomere type which was obtained by such a manner that a human granulocyte microphage colony stimulating factor (hGM-CSF) gene as an exogenous gene was transferred into an expression vector having DHFR gene, the vector was transferred into a CHO cell DG 44 strain where DHFR gene was deficient, the transferred strain was cultured in a medium where 10% fetal bovine serum was added to an IMDM medium (containing no nucleic acid) to obtain a transformant, the resulting transformant was further selected by a medium to which an IMDM medium (containing no nucleic acid) and 10% dialyzed fetal bovine serum were added and further cultured in an IMDM medium containing 50 nM or 100 nM of methotrexate (MTX) and containing no nucleic acid until an increase of copy numbers of the transgene to an extent of 10 to 100 times was achieved by raising MTX concentration.

Genome of eukaryotic cell is classified into two classes of chromatins, i.e. euchromatin and heterochromatin. Sequences of centromere and telomere are main parts of the constitutive heterochromatin. Particularly, telomere consists of a repeated sequence of TTAGGG and a subtelomere region and is a gene-poor region having a striking conformation of heterochromatin (Non-Patent Documents 7, 8). In addition to its contribution to the stability of genome and to its protective role, telomere also affects the expression of gene transferred to the near site as a result of a phenomenon known as a telomere position effect (Non-Patent Documents 9, 10).

However, in spite of the fact that DR 1000L-4N strain is a clone cell of a telomere type, the exogenous gene transferred therein did not receive an influence of inactivation from the heterogeneous chromosome near the transferred site but maintained the high production of hGM-CSF in a stable manner in a culture for a long period. This suggests that a boundary element which strongly shuts off the progress of inactivation is present near the site to which the exogeneous gene is transferred whereby the expression of gene is made stable.

The present inventors have analyzed the sequence near the site to which the exogenous gene is transferred in the DR 1000L-4N strain and, as a result, they have found that DNA consisting of the sequence of about 91 kbp as shown in SEQ ID No: 26 in the Sequence Listing participates in stabilization of the gene expression.

Length of the gene expression stabilizing element contained in the expression vector of the present invention is preferred to be short. Accordingly, in order to narrow down the region having a gene expression stabilizing effect even in a smaller size, the present inventors have carried out further studies.

In order to further analyze the sequence of about 91 kbp shown in SEQ ID No: 26, a method where a library of fragments of about 3 kbp by a shotgun technique is prepared and each of the fragments is assayed one after another has been commonly used. However, in analyzing whether each fragment has a gene stabilizing effect, long time is needed for the transformation and the culture of the cell whereby a period of several weeks to several months are required for one assay. Accordingly, enormous time and labor are necessary for carrying out the total assay.

Under such circumstances, the present inventors have found a method where, in the sequence of SEQ ID No: 26, analysis is conducted laying stress on the site in which the boundary element of the gene expression sequence is expected to exist. As a result, they have found that, in the DNA consisting of SEQ ID No: 26, the regions near 42 kbp, 45 kbp and 91 kbp have a gene expression stabilizing function.

When the sequence was more precisely analyzed, it was found that, in the sequence, the four regions of (i) a region shown by from the 41820th base to the 41839th base, (ii) a region shown by from the 41821st base to the 41840th base, (iii) a region shown by from the 45182nd base to the 45200th base and (iv) a region shown by from the 91094th base to the 91113th base corresponded to the binding sequence motifs of the insulator binding protein CTCF. Accordingly, the neighbor of those regions including at least any of those four regions particularly participates in the stabilization of gene expression.

In the embodiments according to the present invention, any of the following (a) to (e) or a combination thereof is able to be used as a gene expression stabilizing element:

(a) a DNA consisting of the sequence shown in SEQ ID No: 26;

(b) a DNA consisting of a partial sequence of the sequence shown in SEQ ID No: 26 and containing at least the sequence of the region from the 41820th base to the 41839th base of the sequence shown in SEQ ID No: 26;

(c) a DNA consisting of a partial sequence of the sequence shown in SEQ ID No: 26 and containing at least the sequence of the region from the 41821st base to the 41840th base of the sequence shown in SEQ ID No: 26;

(d) a DNA consisting of a partial sequence of the sequence shown in SEQ ID No: 26 and containing at least the sequence of the region from the 45182nd base to the 45200th base of the sequence shown in SEQ ID No: 26; and (e) a DNA consisting of a partial sequence of the sequence shown in SEQ ID No: 26 and containing at least the sequence of the region from the 91094th base to the 91113th base of the sequence shown in SEQ ID No: 26.

Although those elements are isolated from the CHO genome and identified, the elements which are homologous to those elements are expected to be present in other mammalian cell genome as well. Therefore, (f) a DNA consisting of the partial sequence of the sequence shown in SEQ ID No: 26, wherein when it is aligned to be adjacent to the cassette for expressing the exogenous gene in the host cells, expression of the aimed recombinant protein from the exogenous gene contained in the cassette for expressing the exogenous gene is able to be increased or stabilized can also be used as a gene expression stabilizing element. The homologous elements as such are able to be easily isolated and identified by well-known techniques in this technical field such as interspecific hybridization or PCR.

It is also and of course possible to use (g) a DNA which hybridizes under a stringent condition to a DNA consisting of the base sequence complementary to any of the DNAs in the above (a) to (f) and has a gene expression stabilizing function, as a gene expression stabilizing element. The gene expression stabilizing element of the present invention comprises any one of those (a) to (g) or any combination thereof. Moreover, (h) a DNA which consists of the base sequence complementary to any of the DNAs in the above (a) to (g) also has a gene expression stabilizing function and is able to be used as a gene expression stabilizing element and, therefore, it is also included in the present invention.

A stringent condition is a condition of, for example, 40 to 50° C. in 0.2×SSC containing 0.1% of SDS or 55 to 65° C. in 2×SSC containing 0.1% of SDS, although it is different depending on the probe and labeling method used. More stringent condition is able to be decided based on the melting temperature (Tm value) of the nucleic acid to be bound. Further, as a washing condition after the hybridization, a condition of such an extent of "6×SSC, 0.1% SDS and the temperature of about 15 to 30° C. lower than the Tm value" may be exemplified. As a more stringent washing condition, a condition of such an extent of "2×SSC, 0.1% SDS and the temperature of about 5 to 15° C. lower than the Tm value" may be exemplified. As much more stringent washing condition, a condition of such an extent of "1×SSC, 0.1% SDS and the temperature of about 5 to 15° C. lower than the Tm value" may be exemplified. As still much more washing stringent condition, a condition of such an extent "0.1×SSC and 0.1% SDS", may be exemplified.

In the preferred embodiment of the gene expression stabilizing element of the present invention, the DNAs in the above (b) or (c) are a region from the 41601st base to the 46746th base of the sequence shown in SEQ ID No: 26; or a base sequence region which hybridizes under a stringent condition to a DNA consisting of the base sequence complementary to the sequence from the 41601st base to the 46746th base of the sequence shown in SEQ ID No: 26 and has a gene expression stabilizing function. A base sequence complementary to the DNAs consisting of these regions is also contained. In the more preferred embodiment of the gene expression stabilizing element, the DNAs in the above (b) or (c) are a region from the 41601st base to the 42700th base of the sequence shown in SEQ ID No: 26; a base sequence region which hybridizes under a stringent condition to a DNA consisting of the base sequence complementary to the region shown from the 41601st base to the 42700th base of the sequence shown in SEQ ID No: 26 and has a gene expression stabilizing function; or a base sequence complementary to the DNAs comprising these regions.

In this technical field, an expression vector equipped with a multiple cloning site is frequently used for a purpose of an efficient insertion of various aimed protein genes into the expression vector. When the recognition sequence for restriction enzyme used for the multiple cloning site is present in the sequence of the gene expression stabilizing element, said sequence is unable to be utilized for the multiple cloning site. Therefore, the restriction enzyme recognition sequence is deleted from the sequence of the gene expression stabilizing element without deteriorating the gene expression stabilizing function whereupon it is now possible to use said sequence for the multiple cloning site.

In the production of biopharmaceuticals, what is particularly demanded in recent years is an antibody molecule and, for the cloning of the antibody gene, it is preferred to use a restriction enzyme where no recognition sequence is present in the antibody gene as the multiple cloning site. Since the antibody for drugs is mostly occupied by IgG, the present inventors analyzed the base sequence of immunoglobulin heavy chain γ1 gene (for example, GeneBank Acc. No. AK057754), γ2 gene (for example, GeneBank Acc. No. BC062335), γ3 gene (for example, GeneBank Acc. No. BX538126), γ4 gene (for example, GeneBank Acc. No. BX640824), immunoglobulin light chain K gene (for example, GeneBank Acc. No. AY894991), λ1 gene (for example, GeneBank Acc. No. BC007782), λ2 gene (for example, GeneBank Acc. No. X57809), and pUC18 vector (except the multiple cloning site) used for the base of the expression vector construction. As the restriction enzyme which has no recognition sequence in any of the gene sequence and which forms the protruding end, a restriction enzyme such as AscI, BsiWI, BssHII, BstBI (Csp45I, NspV), CpoI, CspI (RsrII), FseI, HindIII, MfeI, MluI, NotI, PacI, PaeR71, SgrA1, SphI, XbaI, and XhoI were exemplified. In addition, BclI, BglII, BlpI, EcoRI, SalI, and SpeI are exemplified as an enzyme which cleaves one or two gene(s) but is able to be relatively easily utilized for gene recombination.

On the other hand, in the case of a restriction enzyme which forms a blunt end, it is able to be connected regardless of the sequence if the terminal end of the aimed protein gene is blunted and, therefore, it is preferred as a recognition sequence contained in the multiple cloning site. Examples of the restriction enzyme producing the blunt end as such include EcoR105I (SnaBI), EcoRV, NruI, PsiI, SmaI, and SrfI.

Thus, other preferred embodiment of the gene expression stabilizing element in the present invention is a sequence having a gene expression stabilizing function and being modified so as to delete the recognition sequence of at least one restriction enzyme selected from AscI, BsiWI, BssHII, BstBI (or called as Csp45I or NspV), CpoI, CspI (or called as RsrII), FseI, HindIII, MfeI, MluI, NotI, PacI, PaeR71, SgrA1, SphI, XbaI, XhoI, BclI, BglII, BlpI, EcoRI, SalI, SpeI, EcoR105I (or called as SnaBI), EcoRV, NruI, PsiI, SmaI, and SrfI.

For the purpose that the gene expression stabilizing element of the present invention achieves its expression stabilizing effect, it is necessary that the element is aligned at the position adjacent to the introducing site for the exogenous gene expression cassette in the host cell genome. Although there is no particular limitation for the term "adjacent to" in the present invention, it preferably means that the distance between the gene expression stabilizing element and the exogenous gene expression cassette of the present invention is 5000 by or shorter, and more preferably 500 by or shorter.

It is possible to achieve such an adjacent alignment by such a manner that a mixture of the nucleic acid sequence fragment containing the element of the present invention and the nucleic acid sequence fragment containing the exogenous gene expression cassette is transferred into the host cells by means of electroporation or transfection and the host cell clone showing high expressed level of the exogenous gene is selected. It is, however, desirable for surely achieving the adjacent alignment that the exogenous gene expression vector containing the gene expression stabilizing element of the present invention and the exogenous gene expression cassette which is adjacently aligned thereto are previously prepared and the host cell is transformed by this vector.

(The Cassette for Expressing the Aimed Protein Gene)

The cassette for expressing the aimed protein gene in the present invention comprises a promoter, a gene coding sequence and a terminator sequence (polyadenylation signal). It may further contain introns, spacer sequences and translation enhancing regions. With regard to the expression promoter for the aimed protein gene, it is preferred to have a transcription activity of as high as possible and examples thereof include that derived from virus such as cytomegalovirus (CMV) promoter of human or mouse or simian virus 40 (SV40) promoter; that derived from nonviral cell gene such as elongation factor 1 alpha (EF1α) derived from human, mouse or CHO, ubiquitin gene or β-actin gene; and a hybrid of promoter/enhancer where the origins are different such as CAG promoter.

In the present invention, the cassette for expressing the aimed protein gene is given in an independent form from the drug selective marker expression cassette. In the case of eukaryotic cells, although there is a means where a polycistronic expression is conducted in which the drug selective marker gene is connected to the aimed protein gene by the internal ribosome entry sites (IRES), mRNA of the aimed protein gene decreases when the above mRNA destabilizing sequence is inserted since coding sequences of the aimed protein gene and the drug selective marker gene are synthesized as one mRNA whereupon no highly expressing cell is able to be produced. Therefore, it is preferred in the present invention that the aimed protein gene expression cassette is aligned independently to the drug selective marker expression cassette. Although the aimed protein gene expression cassette and the drug selective marker expression cassette may be utilized in the forms of different vectors, it is more preferred that the aimed protein gene expression cassette and the drug selective marker expression cassette are aligned on the same vector.

In the aimed protein gene expression cassette, a multiple cloning site comprising a plurality of restriction enzyme recognition sequence is able to be aligned in place of the coding sequence of said protein gene. That is simple and convenient in the cloning operation upon transfer of coding sequence or cDNA of exogenous gene and is preferred.

Another embodiment is an aimed protein gene expression cassette in which the aimed protein is a polypeptide of heavy chain and/or light chain of an antibody. In that case, the aimed protein expression cassette may be aligned in plural or may be a polycistronic expression cassette where a plurality of polypeptide gene is connected by IRES.

A specific embodiment of the present invention being adoptable in the production of an antibody is an expression vector which is characterized in having a drug selective marker gene expression cassette containing an mRNA destabilizing sequence, at least one gene expression stabilizing element and an antibody gene expression cassette containing a constant region gene of light chain of the antibody and/or an antibody gene expression cassette containing a constant region gene of heavy chain of the antibody.

The antibody gene expression cassette in the present invention means an expression cassette for expressing the light chain polypeptide gene or the heavy polypeptide gene of the antibody molecule or for expressing the antibody molecule. The term "containing a constant region gene" stands for that gene of the constant region of heavy chain or light chain of the antibody is inserted as the gene coding sequence of the expression cassette. When the gene of the variable region of the desired antibody is inserted into the position to which control of the expression cassette governs, a complete antibody molecule is able to be expressed.

An antibody consists of light and heavy chains and, further, each of the light and heavy chains consists of constant region (also called "C region" or "constant part") and variable region (also called "V region" or "variable part"). The constant region of the light chain has two types of κ and λ while the constant region of the heavy chain is classified into the types of α, δ, ε, γ, and μ corresponding to the classes of immunoglobulin IgA, IgD, IgE, IgG, and IgM, respectively. Moreover, γ is further classified, for example, into γ1, γ2, γ3, and γ4 corresponding to the subclass of IgG. Although there is no particular limitation for the type of the constant region to be inserted, it is preferred in view of the production of IgG that the constant region of light chain is κ or λ while the constant region of heavy chain is γ, and it is more preferred that the constant region of heavy chain is γ1. A sequence coding for the gene of a leader peptide is able to be inserted into the antibody gene expression cassette to such an area which is downstream region of the promoter and upstream region of the constant region gene of the antibody. A leader peptide is a hydrophobic peptide comprising 15 to 20 amino acids and works for such a purpose that the light or heavy chain immediately after translation and synthesis passes through the membrane of the rough-surfaced endoplasmic reticulum and, at that time, it is cut off.

It is desirable that the variable region gene of the antibody is inserted into the upstream region of the constant region gene in the antibody gene expression cassette and, when a leader peptide gene is inserted into the antibody gene expression cassette, it is desired to be inserted into the downstream region of the leader peptide gene. When the expression vector has no leader peptide, it is preferred that a leader peptide is inserted together with the variable region gene. Although there is no limitation for the distance between the promoter and the variable region gene and between the variable region gene and the constant region gene, the distance between the promoter and the variable region gene is preferred to be 1.2 kbp or less, and more preferred to be 500 by or less. With regard to the variable region gene and the constant region gene, they are preferred to be just adjacent.

(An Expression Vector)

In the present invention, an expression vector is a vector which is utilized in gene engineering. The expression vector may be a plasmid vector but is not limited thereto but virus vector, cosmid vector, bacterial artificial chromosome (BAC), yeast artificial chromosome (YAC) and other non-plasmid vector may be used as well.

An embodiment of the expression vector in the present invention is an expression vector wherein a gene expression stabilizing element is aligned on the upstream or downstream region of the aimed protein gene expression cassette and the drug selective marker gene expression cassette. Preferably, it is the expression vector wherein a gene expression stabilizing element is aligned on the upstream region of the aimed protein gene expression cassette and the drug selective marker gene expression cassette. In that case, although any of the aimed protein gene expression cassette and the drug selective marker gene expression cassette may be in the upstream region, it is preferred that the aimed protein gene expression cassette is aligned in the upstream region.

Another embodiment in the present invention is the vector where a gene stabilizing element is aligned between the drug selective marker gene expression cassette and the aimed protein gene expression cassette. As to a specific embodiment, although any of the embodiment where the gene expression stabilizing element is aligned in a downstream region of the aimed protein gene expression cassette and the upstream region of the drug selective marker gene expression cassette and the embodiment where the gene expression stabilizing element is aligned in a downstream region of the drug selective marker gene expression cassette and the upstream region of the aimed protein gene expression cassette may be considered, a preferred one is a vector where the gene expression stabilizing element is aligned in a downstream region of the aimed protein gene expression cassette and the upstream region of the drug selective marker gene expression cassette.

A preferred embodiment of the expression vector in the present invention is the vector where a gene expression stabilizing element is aligned in the upstream and downstream regions of the aimed protein gene expression cassette and the drug selective marker gene expression cassette so as to sandwich those expression cassettes. Although the order of the aimed protein gene expression cassette and the drug selective marker gene expression cassette is not limited, it is preferred that the aimed protein gene expression cassette is aligned in the upstream region. It is also possible that the gene expression stabilizing elements are aligned in the upstream and downstream regions of the aimed protein gene expression cassette and of the drug selective marker gene expression cassette, respectively.

Another preferred embodiment of the present invention is the vector where the gene expression stabilizing elements are aligned in the upstream and downstream regions of the aimed protein gene expression cassette and, in the downstream region thereof, the drug selective marker gene expression cassette is further aligned.

It is also possible to carry out the expression vector where the aimed protein gene expression cassette is aligned in the downstream region of the drug selective marker gene expression cassette and the gene expression stabilizing element is aligned between the drug selective marker gene expression cassette and the aimed protein gene expression cassette and also in the downstream region of the aimed protein gene expression cassette.

The area between the gene expression stabilizing element and the drug selective marker gene expression cassette or the aimed protein gene expression cassette may be adjacent or a spacer sequence or the like may be inserted therebetween.

When the above drug selective marker gene expression cassette and the aimed gene protein expression cassette are aligned on the same vector, they may be adjacent or a spacer sequence is inserted thereinto. Although the aimed protein gene expression cassette is aligned in any of the upstream and downstream regions of the drug selective marker gene expression cassette, in case they are inserted in an adjacent manner, an alignment where the aimed protein gene expression cassette is in the upstream region is preferred. It is also possible that an insulator sequence for suppressing the transcriptional interference of the adjacent expression cassette is inserted as a spacer sequence.

Two or more drug selective marker gene expression cassettes may be contained in one vector. In that case, the same drug selective markers may be selected or the drug selective markers which are different each other may be selected. Each of the drug selective markers may be adjacently aligned or may be aligned apart.

When the aimed protein comprises a plurality of polypeptide such as in the case of heavy chain and light chain of the antibody, the aimed protein gene expression cassette may be aligned in plural or a plurality of polypeptide gene are connected by IRES to make into a form of a polycistronic expression cassette.

It is also possible that each of a plurality of polypeptide expression cassettes is inserted into the vectors which are different each other and then each vector is transferred into a host cell to prepare a transformed cell whereupon an aimed protein is able to be produced. In that case, a drug selective marker gene expression cassette is able to be aligned to each vector and, although the same drug selective marker may be used for each, it is advantageous to use the different drug selective marker in such a view that the cells where all of the polypeptides show high efficiency are able to be efficiently prepared.

In a comparison between the case where the heavy chain polypeptide gene and the light chain polypeptide gene of the antibody are inserted into different vector to express whereby an antibody is produced and the case where the heavy chain polypeptide gene and the light chain polypeptide gene of the antibody are inserted into the same vector to express whereby an antibody is produced, there is no difference between the two in terms of the productivity of the antibody. Accordingly, it is possible to obtain a cell strain showing a high productivity in any of the methods but, when expression is conducted by insertion of the heavy chain polypeptide gene and the light chain polypeptide gene of the antibody into the same vector, the outcome is that one kind of drug-resistant gene on the same vector is used and, therefore, the differences in the transgene numbers are able to be reduced, productions of the heavy chain polypeptide and the light chain polypeptide of the antibody are well-balanced and the productivity as an antibody consisting of two sets of two polypeptides of heavy and light chains is stabilized whereby that is preferred.

One of the specific embodiments of the expression vector in the present invention is an expression vector which is characterized in having a drug selective marker gene expression cassette containing an mRNA destabilizing sequence, three or more gene expression stabilizing elements and two or more aimed protein gene expression cassettes.

In that case, it is preferred that, among the three or more gene expression stabilizing elements, at least one is aligned between any of the two or more aimed protein gene expression cassettes. Thus, when there are two aimed protein gene expression cassettes, the gene expression stabilizing element is aligned between those expression cassettes. When there are three aimed protein gene expression cassettes, the element is aligned between the first and the second aimed protein gene expression cassettes, between the second and the third aimed protein gene expression cassettes or between the both. That is also the same when there are four or more aimed protein gene expression cassettes.

In this embodiment of the present invention where the expression vector has three or more gene expression stabilizing elements, the gene expression stabilizing element is aligned between the aimed protein gene expression cassettes in the case of preparing an expression vector which expresses protein consisting of two or more polypeptides such as immunoglobulin whereby it is possible to achieve further suppressive effect to the gene silencing. As a result, the cell strain where the production amount of the aimed protein significantly increases due to synergism is able to be obtained.

One of other specific embodiments of the expression vector of the present invention is an expression vector which contains two or more constitutions where the alignment is done to give such a position that [(gene expression stabilizing element)–(aimed protein gene expression cassette)$_n$–(drug selective marker gene expression cassette containing mRNA destabilizing sequence)] (where n is an integer of 1 to 4).

Hereinabove, (aimed protein gene expression cassette)$_n$ means that the (aimed protein gene expression cassette) in the numbers of n is continuously aligned and neither gene expression stabilizing element nor drug selective marker gene expression cassette containing mRNA destabilizing sequence is aligned between them. That is the same for (aimed protein gene expression cassette)$_m$, (aimed protein gene expression cassette)$_p$ and (aimed protein gene expression cassette)$_q$ as well.

Another one of other specific embodiments is an expression vector which contains two or more constitutions where the alignment is done to give such a position that [(gene expression stabilizing element)–(aimed protein gene expression cassette)$_m$–(gene expression stabilizing element)–(aimed protein gene expression cassette)$_p$–(drug selective marker gene expression cassette containing mRNA destabilizing sequence)] (where m is an integer of 1 to 4, and p is an integer of 1 to 4).

Still another one of other specific embodiments of the present invention is an expression vector which contains two or more constitutions where the alignment is done to give such a position that [(gene expression stabilizing element)–(aimed protein gene expression cassette)$_q$ (where q is an integer of 1 to 4), with a drug selective marker gene expression cassette containing an mRNA destabilizing sequence aligned in their downstream.

In those embodiments of the present invention, it is not intended that the expression vector does not contain the constitution elements other than those constitutions. For example, in addition to those, it is also possible that a gene expression stabilizing element is also aligned to the downstream region of the drug selective marker gene expression cassette containing the mRNA destabilizing sequence.

Further, when two or more aimed protein gene expression cassettes are aligned continuously in those embodiments, at least one gene expression stabilizing element may be additionally aligned between any of the aimed protein gene expression cassettes. Thus, if two or more aimed protein gene expression cassettes are aligned continuously, the gene expression stabilizing element is able to be aligned between the expression cassettes. If three aimed protein gene expression cassettes are aligned continuously, it may be aligned between the first and the second aimed protein gene expression cassettes or between the second and the third aimed protein gene expression cassettes or may be aligned between both. When there are four aimed protein gene expression cassettes, the alignment is the same.

Since the expression vectors of the present invention in those embodiments where a plurality of the constituting elements are aligned (concatemerized) is equipped with a plurality of aimed protein gene expression cassettes, a plurality of copies of the aimed protein gene expression cassettes are able to be inserted on the cell genome at one time and an increase in the expressed level of protein is able to be expected. Further, since a plurality of copies are inserted into the cell genome in the case of the drug selective marker gene expression cassette containing mRNA destabilizing sequence and gene expression stabilizing element as well, additional big contribution is resulted for establishment of the highly productive cell strain due to the synergism thereof.

According to the second aspect of the present invention, there is provided a transformed cell which is characterized in being obtained by transformation of the host cell by the expression vector according to the first aspect of the present invention.

Examples of the host cell in the transformed cell of the present invention include mouse myeloma cell (NSO), baby hamster kidney cell (BHK), human fibrosarcoma cell (HT1080) and COS cell which are derived from mammals in addition to Chinese hamster ovary cell (CHO) which is commonly used for the production of recombinant protein. However, they are non-limitative but the cells derived from animals such as human, mice, rats, hamsters, guinea pigs, rabbits, dogs, cows, horses, sheep, monkeys or swine are also widely made into the objects for the transfer. Further, it is also able to be applied to the protein production system using bacterial cells such as *Escherichia coli*, yeasts, insect cells, etc.

In general, in the industrial production of biopharmaceuticals for example, it has been demanded for excluding the contamination of harmful components such as virus that the produced cells are cultured in a medium containing no animal components or, more preferably, in a medium where the composition is chemically defined. For such a purpose, it has been said to be necessary that, after the highly productive cells are screened in a commonly used medium containing fetal bovine serum or the like, the cells are adapted to a medium containing no animal component or to a chemically defined medium during about one to two month(s) (serum-free adaptation). However, there may also be the case where the highly productive cells which were once obtained are not well adapted. Accordingly, when gene transfer is carried out to the cells which were subjected to a serum-free adaptation in advance, time for establishing the producing cells is able to be shortened by eliminating the serum-free adaptation and that is very effective. In order to achieve the problem as such, the host cells used for the present invention further include the cells which were already subjected to a serum-free adaptation in CHO cells, etc.

A method for the transformation of host cells may be appropriately selected if conducted by persons skilled in the art and examples thereof include a lipofection method, a calcium phosphate method, an electroporation method, a DEAF dextran method and a microinjection.

According to the third aspect of the present invention, there is provided a method for selecting a cell which expresses the aimed protein gene in a high level, characterized in that, the method comprises a step of subjecting the transfonned cell according to the second aspect of the present invention to a drug selection. Also, according to the fourth aspect of the present invention, there is provided a cell, characterized in that, it is obtained by the method according to the third aspect of the present invention and stably expresses the aimed protein gene in a high level.

A drug used for the drug selection is decided depending upon the type of the drug selective marker gene in the drug selective marker gene expression cassette. With regard to the concentration of the drug used, although highly expressing cells are able to be concentrated within a range of commonly used concentrations, a bit higher concentration is preferred. The optimum concentration varies depending upon the type of the host cells and the medium used. A method for setting the concentration has been known among persons skilled in the art and is able to be appropriately set. For example, when Chinese hamster ovary (CHO) cells being used as producing cells for industry are cultured in a Ham's F12 medium containing 10% of fetal bovine serum and a puromycin-resistant gene expression cassette is utilized, the concentration of puromycin is not lower than 5 µg/ml, more preferably not lower than 7.5 µg/ml and, still more preferably, not lower than 10 µg/ml. Concentration of hygromycin B when a hygromycin-resistant gene expression cassette is utilized under the same culture conditions is not lower than 200 µg/ml, more preferably not lower than 600 µg/ml, and much more preferably not lower than 800 µg/ml. Concentration of G 418 when a neomycin-resistant gene expression cassette is utilized under the same cultivating conditions is preferably not lower than 400 µg/ml, more preferably not lower than 800 µg/ml, and much more preferably not lower than 1,000 µg/ml.

In a selecting method of the present invention, rate of the cells which express the aimed protein gene in a high level becomes significantly high as compared with the cell group subjected to the conventional drug selection using the drug selective marker gene expression cassette without an mRNA destabilizing sequence. Accordingly, up to now, an operation for selecting the cell strain which expresses the aimed protein gene in a high level from the enormous samples after the drug selection had to be carried out repeatedly. However, in accordance with the present invention, numbers of the sample which is to be a candidate for the selection are able to be greatly narrowed down only by means of the drug selection including the destabilization of mRNA of the drug selective marker. When the selection method of the present invention is used, production amount of the aimed protein significantly rises in the state of a cell group (polyclone) being survived even after the drug selection and, when the cells are isolated from such a cell group followed by culturing, a cell strain (monoclone) showing a high expression is able to be easily procured. In an example of the embodiments of the present invention, the vector into which the drug selective marker gene expression cassette of the present invention is inserted is transferred to $4.0 \times 10^5$ cells, then 100 cell strains are randomly selected from the cell group resulted by subjecting to the drug selection and the expressed level of each cell strain is checked whereupon a highly expressing strain of the aimed protein is able to be easily obtained.

An expression level of the cell is able to be checked by an expressed level of the reporter gene and an example thereof is that an expression cassette containing a fluorescent protein gene such as SNAP26m gene (manufactured by Covalys) or GFP gene (green fluorescent protein) is transferred into the expression vector of the present invention and the fluorescence intensity is analyzed using a flow cytometer such as a FACS (fluorescence activated cell sorting) whereby a checking is able to be done. Another example is that an expression cassette containing a luciferase gene is transferred into an expression vector of the present invention, D-luciferin is then added to the cell lysate and the light-emitting amount is measured by a luminometer whereby a checking is able to be done. It is also possible to check the expression of the aimed protein such as an antibody by utilizing ELISA (enzyme-linked immunosorbent assay), enzyme immunoassay (EIA), etc. without using a receptor gene.

In accordance with the present invention, not only the steps and the time for the cell selection are able to be greatly shortened but also the rate of the cells showing a high expression rises whereby the cells which express the aimed protein gene in high level are able to be procured efficiently and within short time and, as compared with the prior art, a very remarkable effect is achieved.

For example, when the expressed level of SNAP26m is measured by FACS Calibur (manufactured by Becton, Dickinson and Company) at the fluorescence intensity of FL 1, the resulting effect in the present invention is that the ratio of the cells where FL1 is 200 or more or 1,000 or more is 1.1 times or higher or, in many cases, 1.5 to 2 times higher as compared with the cells obtained by using the drug selective marker gene expression cassette without an mRNA destabilizing sequence. Further, there is observed a tendency that an increasing rate of the ratio of the cell where FL1 is 1,000 or more is higher than an increasing rate of the ratio of the cell where FL1 is 200 or more and it supports the effect that the cell group selected by the present invention shows a higher expression than the cells obtained by using the drug selective marker gene expression cassette without an mRNA destabilizing sequence.

Further, in the cells which are transformed by an expression vector having a gene stabilizing element and an mRNA destabilizing sequence in accordance with the present invention, the ratio of the cells showing the high productivity is improved to an extent of 7 to 8 times as compared with the case using an expression vector having neither gene stabilizing element nor mRNA destabilizing sequence. In the cells which are transformed by an expression vector having only a gene expression stabilizing element, an excellent effect is noted where the ratio of the cells showing a high productivity increased to an extent of about two times but, in the present invention, far significant effect is achieved due to the synergism of the mRNA destabilizing sequence and the gene expression stabilizing element.

According to the fifth aspect of the present invention, there is provided a method for producing a protein, characterized in that, the cell according to the fourth aspect of the present invention is used.

In an embodiment, the produced protein is antibody. In that case, the heavy chain polypeptide gene and the light chain polypeptide gene of the antibody may be inserted into the same vector (single vector) or each of them may be inserted into different vectors forming two constructs.

It has been clarified already that, in the antibody of mammals, there are five kinds of classes including IgM, IgD, IgG, IgA, and IgE. In diagnosis, prevention and treatment of various kinds of human diseases, an antibody of human IgG class has been mostly utilized in view of the functional characteristics such as that the half life in blood is long, various kinds of effector functions are available, etc. Antibody is able to be purified from the supernatant of the culture of the transformed cells using a protein A column. Besides that, it is also possible to use a purifying method which has been commonly used for the purification of protein. For example, gel filtration, ion exchange chromatography, ultrafiltration, etc. are conducted in combination thereof whereby purification is able to be done. Molecular weight of H chain or L chain of the purified humanized antibody or of the antibody molecule as a whole is able to be measured by a two-dimensional electrophoresis, etc.

The antibody produced by the method of the present invention is able to be used as a drug. Although the drug as such is able to be solely administered as a treating agent, it is usually preferred to provide as a drug preparation manufactured by mixing the drug with one or more pharmacologically acceptable carrier(s) followed by subjecting any of methods which have been known in the technical field of pharmaceutical preparations.

With regard to the administering route, it is preferred to use that which is most effective for the treatment and examples thereof include oral administration and parenteral administration such as intraoral, intra-airway, rectal, hypodermal, intramuscular or intravenous. In the case of an antibody preparation, an intravenous administration is preferably exemplified. Examples of the dosage form include spray, capsule, tablet, granules, syrup, emulsion, suppository, injection, ointment and tape etc.

Examples of the preparation suitable for oral administration include emulsion, syrup, capsule, tablet, diluted powder and granules. A liquid preparation such as emulsion or syrup is able to be prepared using an additive such as water, saccharide (e.g., sucrose, sorbitol and fructose), glycol (e.g., polyethylene glycol and propylene glycol), oil (e.g., sesame oil, olive oil and soybean oil), antiseptic (e.g., p-hydroxybenzoate) and flavor (e.g., strawberry flavor and peppermint). Capsule, tablet, diluted powder, granules, etc. are able to be prepared using an additive such as excipient (e.g., lactose, glucose, sucrose and mannitol), disintegrating agent (e.g., starch and sodium alginate), lubricant (e.g., magnesium stearate and talc), binder (e.g., polyvinyl alcohol, hydroxypropyl cellulose and gelatin), surfactant (e.g., fatty acid ester) or plasticizer (e.g., glycerol).

Examples of the preparation suitable for parenteral administration include injection, suppository and spray. Injection is able to be prepared using a carrier, etc. comprising salt solution, glucose solution or a mixture thereof. It is also possible to prepare a powdery injection preparation by subjecting the humanized antibody to freeze drying by a conventional method followed by adding sodium chloride thereto. Suppository is prepared using a carrier such as cacao butter, hydrogenated fat or carboxylic acid. Spray is prepared from said compound per se or using a carrier or the like which does not irritate the mouth and the airway viscous membrane of the person to be administered and makes said compound dispersed as fine particles so as to make its absorption easy.

Specific examples of the carrier include lactose and glycerol. Depending upon the properties of said compound and of the carrier used, it is possible to prepare a preparation such as aerosol or dry powder. It is also possible even in such parenteral preparations to add the component which is exemplified as an additive for the oral preparations.

In another embodiment, the protein produced is vaccine.

As to vaccine, the protein consisting of the amino acid sequence of epitope of pathogen is able to be used as vaccine. It is also possible to produce not only all of the constituting proteins of viral body but also envelope protein, etc. and to use it as vaccine.

Vaccine is able to be made into a preparation for the administration by any route. Examples thereof include vaccine preparation for administration of mucous membrane type such as peroral route, intranasal route, intra-airway route, vaginal route or rectal route as well as for administration by non-mucous route such as hypodermic, intravenous or intramuscular administration.

According to the sixth aspect of the present invention, there is provided a method for producing an amino acid, characterized in that, the cell according to the fourth aspect of the present invention is used. Also, according to the seventh aspect of the present invention, there is provided a method for producing a nucleotide, characterized in that, the cell according to the fourth aspect of the present invention is used.

Production of amino acid is able to be conducted in such a manner that, at first, a polypeptide is produced in transformed cells and said polypeptide is then hydrolyzed. It is also conducted by producing the enzyme or the like which is necessary for an in vitro synthesis of amino acid in transformed cells. Production of a nucleotide is also able to be conducted by producing the enzyme or the like which is necessary for an in vitro synthesis of nucleotide in transformed cells.

EXAMPLES

Hereinafter, Examples will be exemplified so that the effect of the present invention is made clearer.

Example 1

Effect of mRNA Destabilizing Sequence in Puromycin-Resistant Gene (1) Construction of pBS-CMV-SNAPm-Pur and pBS-CMV-SNAPm-Pur.N4

Figure 1:
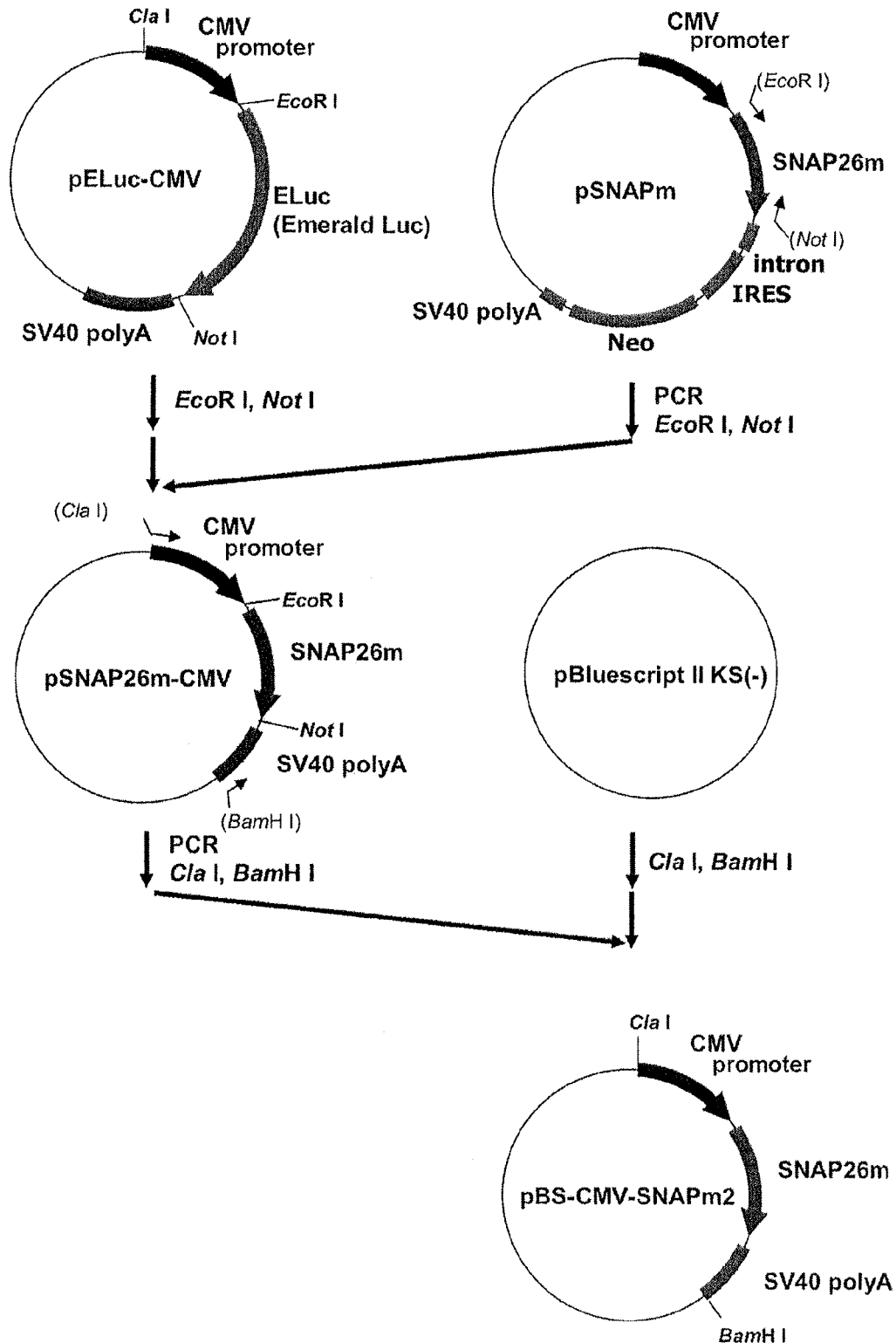

According to the scheme shown in FIG. 1, a plasmid pBS-CMV-SNAPm2 was constructed. Thus, firstly, Emerald Luc (Eluc) gene was excised from a pELuc-CMV plasmid where CMV promoter (SEQ ID No: 1) was transferred into the sites of restriction enzymes ClaI and EcoRI of Emerald Luc vector (pELuc-test) (manufactured by Toyobo), using restriction enzymes EcoRI and NotI. On the other hand, SNAP26m gene was amplified from SNAPm expression plasmid pSNAPm (manufactured by Covalys) by means of PCR using primers of SEQ ID Nos: 2 and 3 and transferred into the sites of restriction enzymes EcoRI and NotI of the pELuc-CMV plasmid to construct pSNAP26m-CMV. After that, CMV promoter/SNAP26 m/SV40 polyA was amplified from pSNAP26m-CMV by PCR using primers of SEQ ID Nos: 4 an 5 and transferred into the sites of restriction enzymes ClaI and BamHI of the plasmid pBluescript II KS (–) (manufactured by Stratagene) by means of partial digestion to construct a plasmid pBS-CMV-SNAPm2.

Figure 2:
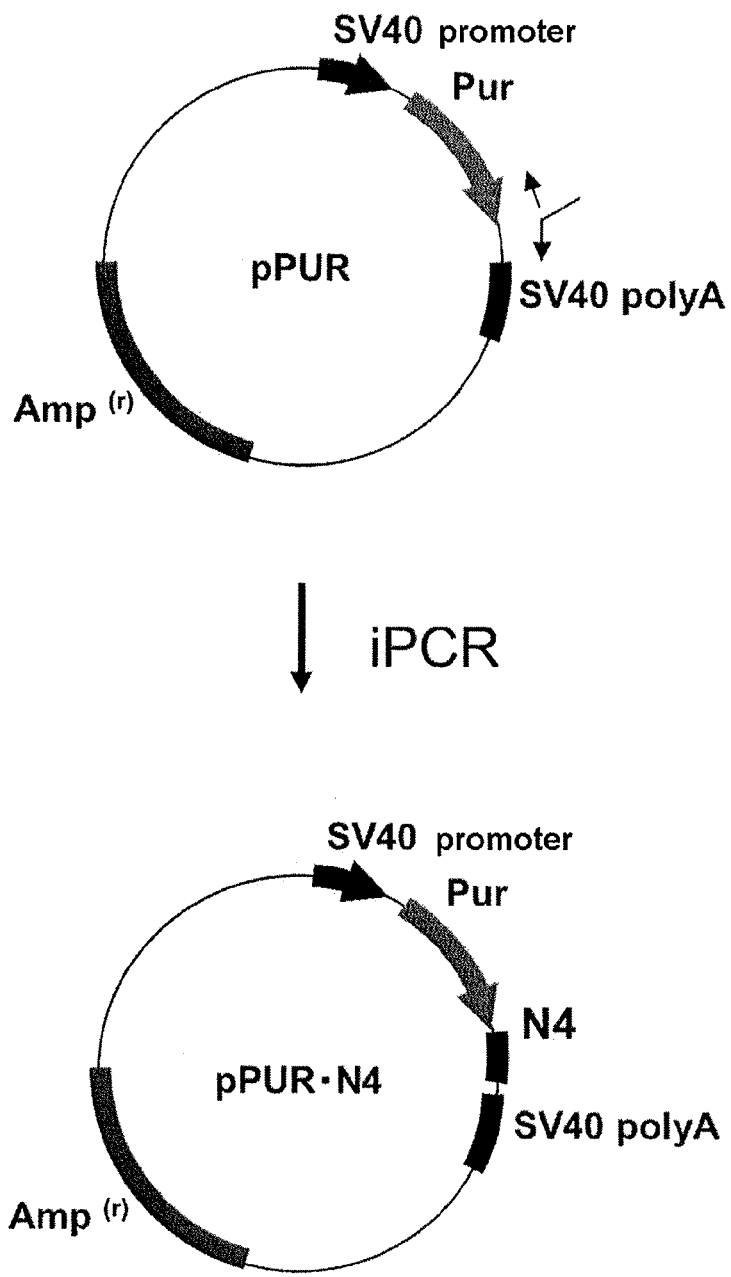

After that, according to the scheme shown in FIG. 2, a four-times repeated sequence of ARE sequence motif TTATTTATT (N4) was inserted into the 3' terminal of the coding sequence of puromycin-resistant gene of pPUR (manufactured by Clontech) by inverse PCR using primers of SEQ ID Nos: 6 and 7 and KOD-Plus-Mutagenesis Kit (manufactured by Toyobo) to construct pPUR.N4.

Figure 3:
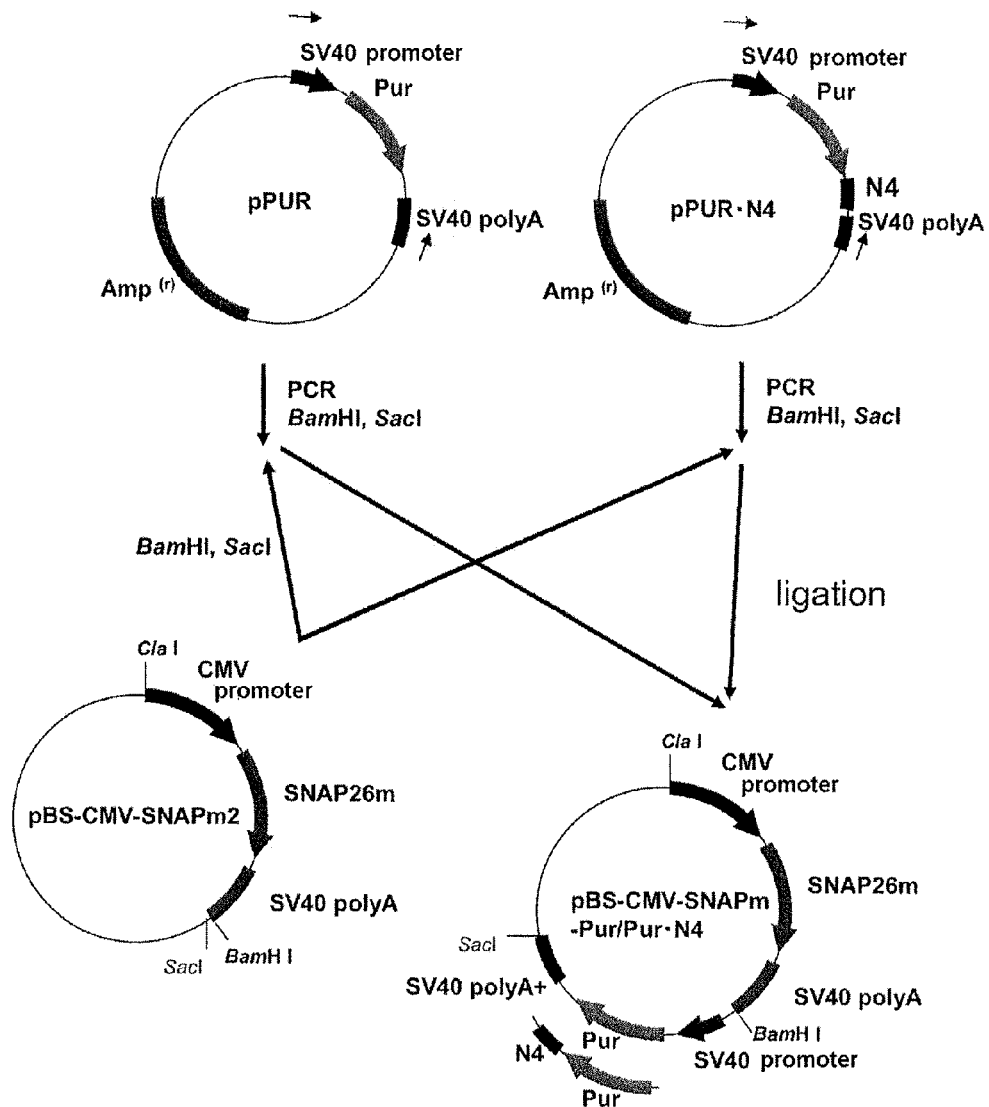
FIG. 3 shows the construction of pBS-CMV-SNAPm-Pur and pBS-CMV-SNAPm-Pur.N4.

Then, drug expression cassette fragments of SV40 promoter-Pur-SV40 polyA and SV40 promoter-Pur.N4-SV40 polyA were amplified by PCR using the primers of SEQ ID Nos: 8 and 9, KOD-Plus-ver.2 (manufactured by Toyobo), and pPUR and pPUR.N4 as templates. Each of pBS-CMV-SNAPm2 and the above amplified fragments were partially digested with the restriction enzymes BamHI and SacI, respectively and connected with each other whereupon pBS-CMV-SNAPm-Pur and pBS-CMV-SNAPm-Pur.N4 were constructed (FIG. 3).

Example 2

(2) Transfer of pBS-CMV-SNAPm-Pur and pBS-CMV-SNAPm-Pur.N4 into the Cells (1)

CHO-K1 cells (Riken Bioresource Center, No. RCB0285) were adjusted to $1 \times 10^5$ cells/ml, each 2 ml thereof was seeded to a 12-well plate on the previous day and cultivated for one night to prepare CHO-K1 cells for transfection. At that time, a Ham's F12 medium (manufactured by Nissui Seiyaku) to which 10% of fetal bovine serum was added was used as a medium.

Transfection was carried out in such a manner that 3 µl of GeneJuice Transfection Reagent (manufactured by Merck) was diluted with 100 µl of Opti-MEM I Reduced-Serum Medium (manufactured by GIBCO), 103 µl of this diluted liquid was added to 1 µg of pBS-CMV-SNAPm-Pur or pBS-CMV-SNAPm-Pur.N4 as a plasmid followed by being allowed to stand for 10 minutes and the mixture was added to the above CHO-K1 cells followed by cultivating for 24 hours. On the next day, the medium was removed and the cells were dispersed by treating with 2.5 g/l-trypsin and 1 mmol/l-EDTA solution (manufactured by Nakarai Tesk), transferred to a 90-mm Petri dish and subjected to a selective culture for three weeks in a Ham's F12 medium supplemented with 10% FBS and 6 µg/ml puromycin (manufactured by InvivoGen). During the selective culture, the medium was exchanged every three to four days. After finishing the selective culture for three weeks, the cells were dispersed by treating with 2.5 g/l-trypsin and 1 mmol/l-EDTA solution and $2 \times 10^5$ cells per well were seeded on a 12-well plate, 2 µM SNAP-Cell-505 (manufactured by Covalys) was added to 0.5 ml of a Ham's F12 medium on the next day and cultivation was conducted for 60 minutes at 37° C. After that, the above was rinsed with the Ham's F12 medium for three times and, together with exchanging the medium, cultivation for 10 minutes was conducted for three times to remove the unreacted fluorescent dye. The cells were treated with 2.5 g/l-trypsin and 1 mmol/l-EDTA solution to disperse, suspended in D-PBS(–) (manufactured by Nakarai Tesk) and the expression intensity of SNAP26m was analyzed using a flow cytometer BD FACS-Calibur (manufactured by Becton, Dickinson and Company).

Figure 4:
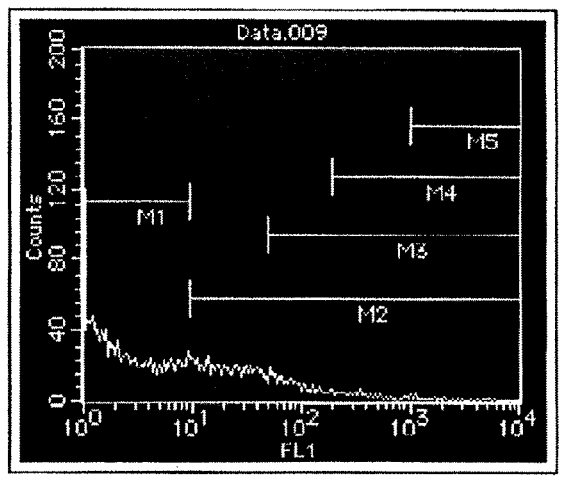
FIG. 4 shows the results of FACS analysis of the cell group which is transformed by pBS-CMV-SNAPm-Pur or pBS-CMV-SNAPm-Pur.N4.
Figure 4:
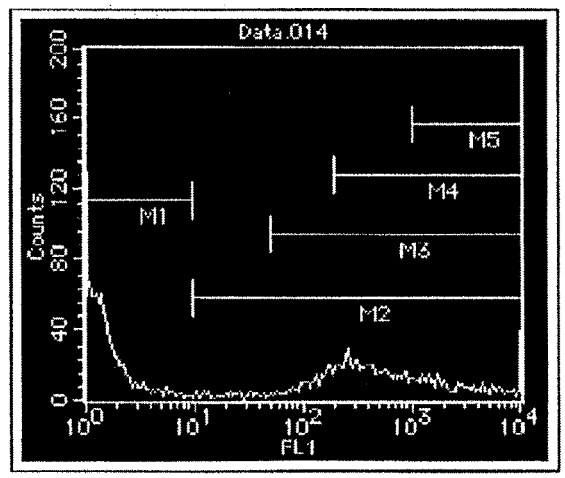
Figure 5:
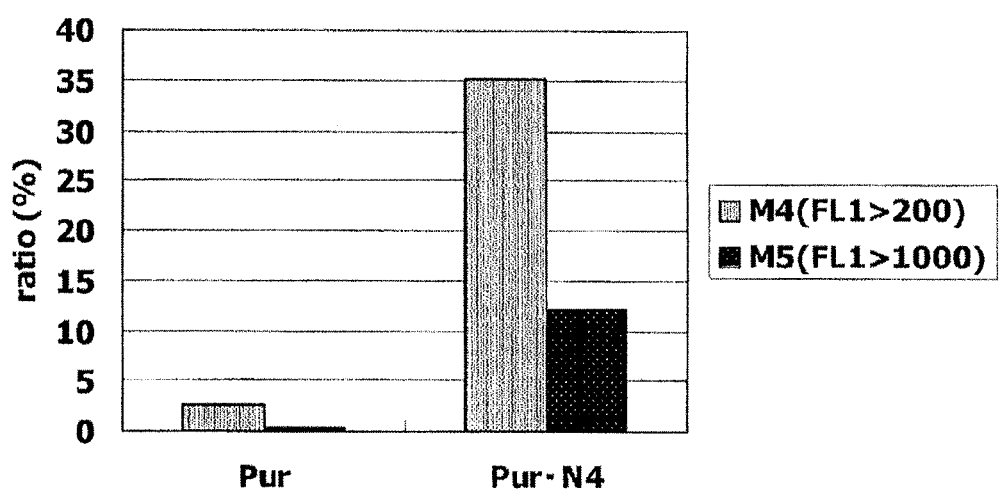
FIG. 5 is a graph where the rate of the cells which highly express SNAPm in the cell group transformed by pBS-CMV-SNAPm-Pur or pBS-CMV-SNAPm-Pur.N4 is plotted.

FIG. 4 shows the result of FACS analysis of the cell group generated after transfection of pBS-CMV-SNAPm-Pur or pBS-CMV-SNAPm-Pur.N4 and the drug selection. The abscissa shows intensity of fluorescence (FL1) and the ordinate shows count numbers of the cell. FIG. 5 shows plots of rates of cells where the fluorescence intensity FL1 is not less than 200 and not less than 1000 respectively. As a result, it is noted that, in the cell group transformed by pBS-CMV-SNAPm-Pur.N4 into which N4 which is an mRNA destabilizing factor is inserted, cells showing a high expression of SNAPm are significantly concentrated after the drug selection.

Example 3

Effect of mRNA Destabilizing Sequence in Puromycin-Resistant Gene in Cell Strain (1) Transfer of pBS-CMV-SNAPm-Pur and pBS-CMV-SNAPm-Pur.N4 into the cells (2)

After that, gene transfer was conducted by the same manner as in Example 2 and a selective culture was carried out for two weeks in a Ham's F12 medium supplemented with 10% FBS and 9 µg/ml puromycin. From the colonies formed thereby, 48 clones of pBS-CMV-SNAPm-Pur, and 20 clones of pBS-CMV-SNAPm-Pur.N4 were scraped using the front end of a pipette under a microscope and seeded on a 12-well plate. A labeling treatment with SNAP-Cell-505 was conducted, by the same manner as in Example 2, for 36 clones and 10 clones of the above where the growth was noted followed by conducting FACS analysis.

Figure 6:
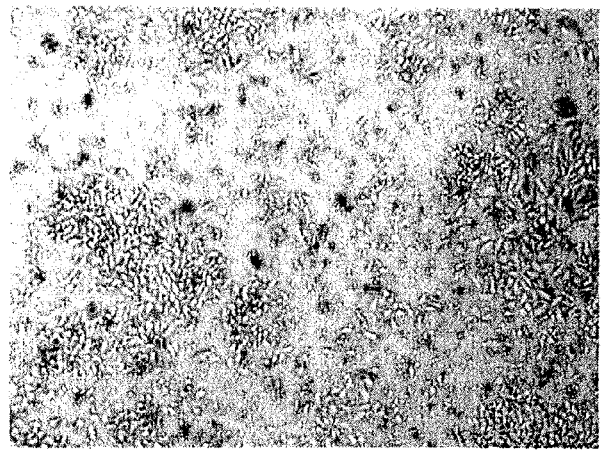
FIG. 6 is a bright visual field image when the cell group which is transformed by pBS-CMV-SNAPm-Pur or pBS-CMV-SNAPm-Pur.N4 is subjected to drug selection.
Figure 6:

FIG. 6 shows a bright visual field image of the cells after the drug selection. As a result, it is suggested that pBS-CMV-SNAPm-Pur.N4 shows a significant decrease in living cell numbers and in colony numbers as compared with pBS-CMV-SNAPm-Pur and that the selection effect is high.

Figure 7:
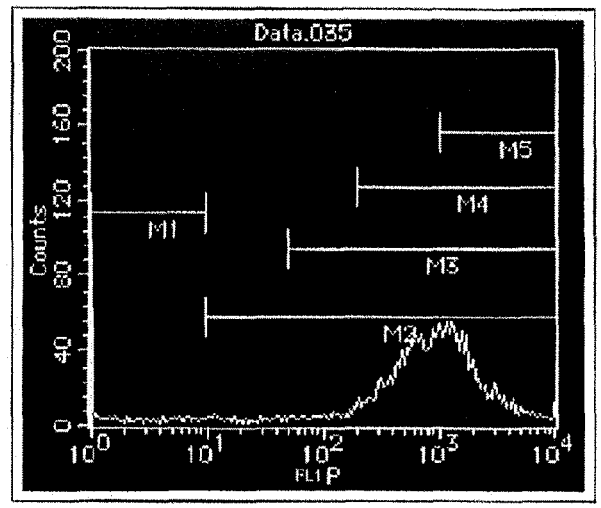
FIG. 7 shows the result where colonies of pBS-CMV-SNAPm-Pur were isolated and subjected to FACS analysis.
Figure 8:
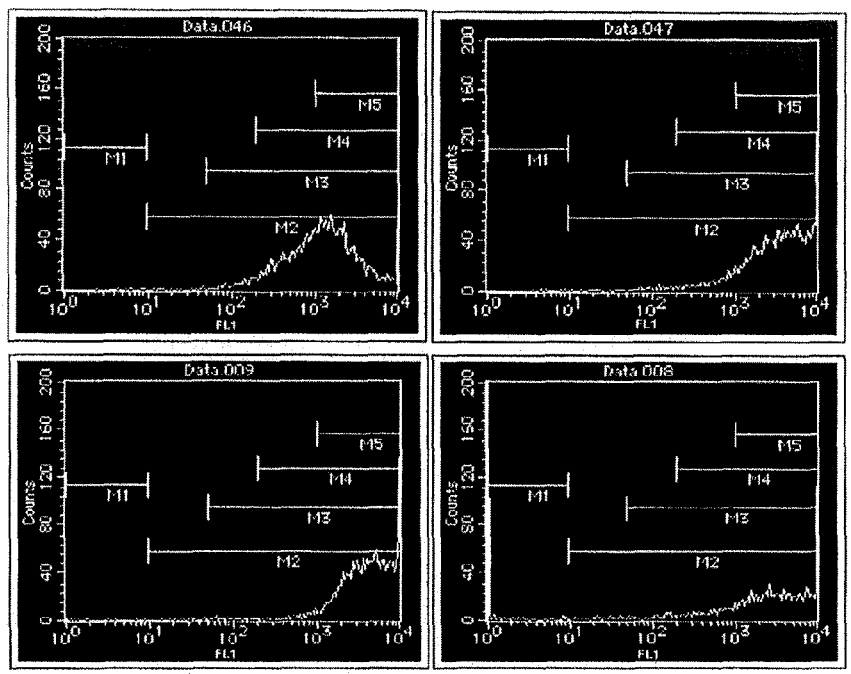
FIG. 8 shows the result where colonies of pBS-CMV-SNAPm-Pur.N4 were isolated and subjected to FACS analysis.

FIG. 7 shows the result of FACS analysis for pBS-CMV-SNAPm-Pur transformed cell clones in which the peak intensity is more than 1000 showing a particularly high SNAPm expression. FIG. 8 shows the result of FACS analysis for pBS-CMV-SNAPm-Pur.N4 transformed cell clones in which the peak intensity is more than 1000 showing a particularly high SNAPm expression. As a result, only one highly expressing clone (2.8%) was noted in 36 clones in pBS-CMV-SNAPm-Pur. However, in the case of pBS-CMV-SNAPm-Pur.N4, although the number of the procured clones is small, it was confirmed that the hitting rate of SNAPm highly expressing clone was as high as 40% (4 clones in 10) showing that the selection effect was very high. Further, it was confirmed from the result that, as noted in Example 2, there is a correlation between the fact that rate of highly expressing cells rises shown by FACS analysis of the cell group after the drug selection and the fact that procurement of the highly expressing clone is made efficient. Accordingly, in the analysis thereafter, confirmation of the effect was conducted by FACS analysis of the cell group.

Example 4

Effect of mRNA Destabilizing Sequence in Puromycin-Resistant Gene (1) Construction of pEF1α-SNAP26m-Pur.N4 and pEF1α-SNAP26m-Pur-RE2

Figure 9:
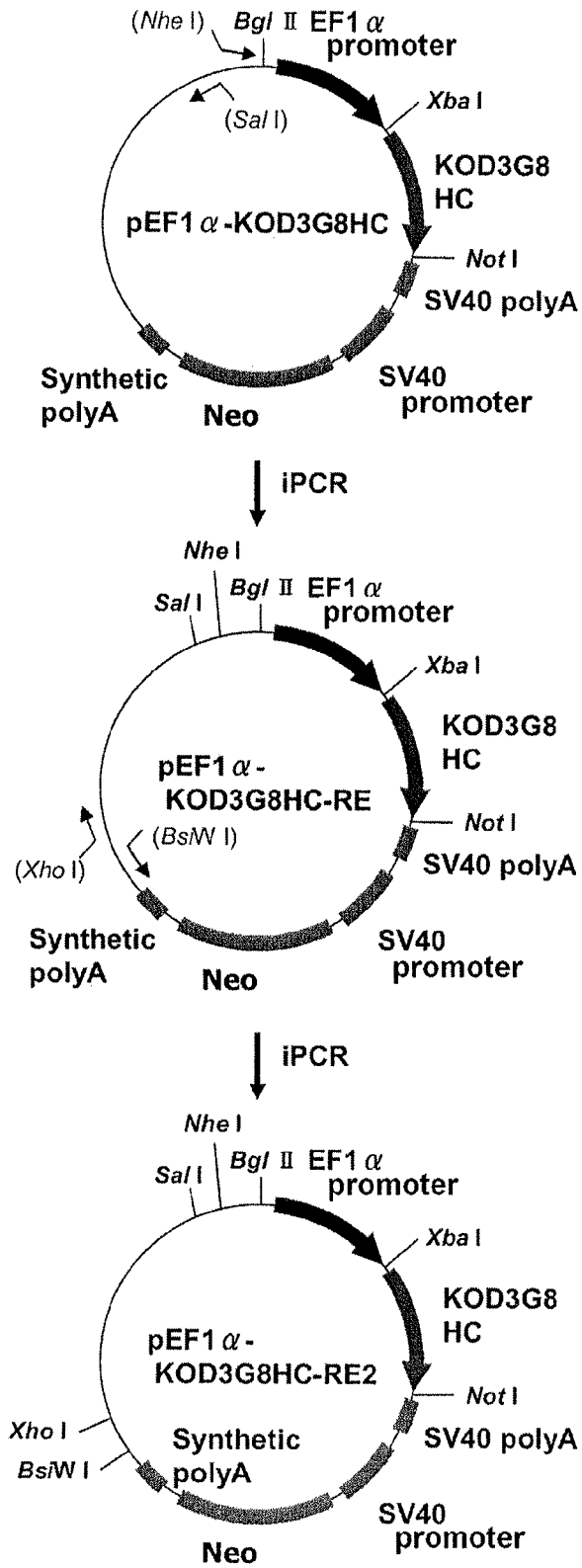
FIG. 9 shows the construction of pEF1α-KOD3G8HC-RE2. Hereinafter, Neo in the drawings stands for neomycin-resistant gene.

Then plasmids were constructed in order to investigate whether the same effect as above is also achieved when the promoter of the aimed gene expression cassette is substituted with an EF1α promoter. In this experiment, a plasmid pEF1α-KOD3G8HC-RE2 which was constructed according to the scheme shown in FIG. 9 was utilized. Thus, firstly, pEF1α-KOD3G8HC-RE to which sites of the restriction enzymes SalI and NheI were added to the upstream region of an expression cassette was constructed by inverse PCR using the primers of SEQ ID Nos: 10 and 11, a KOD-Plus-Mutagenesis kit, and pEF1α-KOD3G8HC plasmid where heavy chain of anti-KOD antibody was inserted into the sites of the restriction enzymes XbaI-NotI of pCI-neo plasmid (manufactured by Promega) in which a CMV promoter was substituted with an EF-1α promoter as a template. As to the heavy chain of the anti-KOD antibody, there was used that of an antibody prepared from mouse hybridoma cell line 3G8 (deposition number: FERM BP-6056; available from the International Patent Organism Depositary, the National Institute of Advanced Industrial Science and Technology) which produces an antibody specific to DNA polymerase derived from *Thermococcus kodakaraensis* KOD1 strain. A plasmid which was further constructed by addition of sites of restriction enzymes BsiWI and XhoI to the downstream region of the expression cassette by inverse PCR using the primers of SEQ ID Nos: 12 and 13, the KOD-Plus-Mutagenesis kit, and the present plasmid as a template is pEF1α-KOD3G8HC-RE2.

Figure 10:
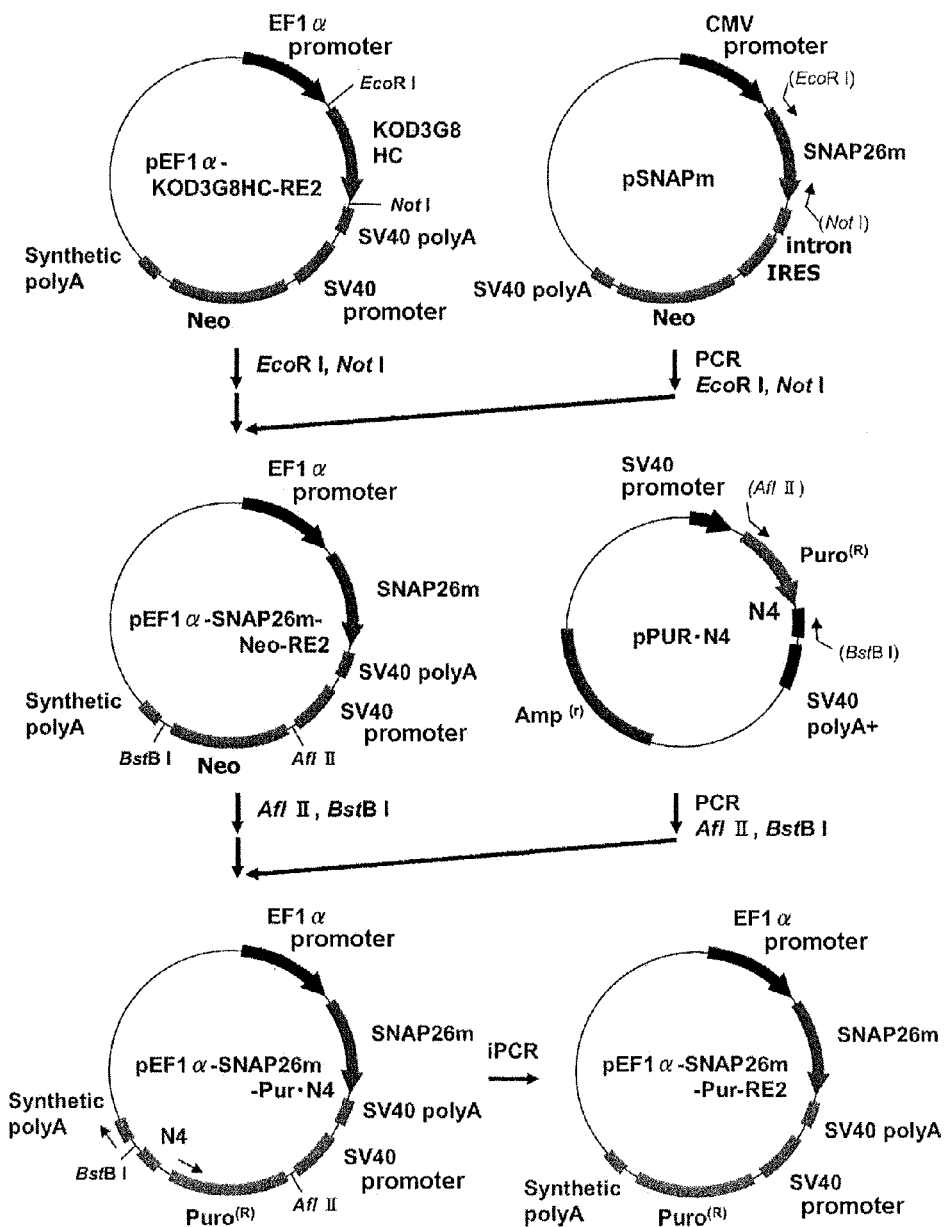
FIG. 10 shows the construction of pEF1α-SNAP26m-Pur.N4 and pEF1α-SNAP26m-Pur-RE2.

This pEF1α-KOD3G8HC-RE2 was used and, in accordance with the scheme shown in FIG. 10, plasmids pEF1α-SNAP26m-Pur.N4 and pEF1α-SNAP26m-Pur-RE2 were constructed. Thus, the heavy chain gene of the anti-KOD antibody was excised from the plasmid pEF1α-KOD3G8HC-RE2 using the restriction enzymes EcoRI and NotI. On the other hand, SNAP26m gene was amplified from the SNAPm expression plasmid pSNAPm by PCR using the primers of SEQ ID Nos: 2 and 3 and transferred into the sites of the restriction enzymes EcoRI and NotI of the pEF1α-KOD3G8HC-RE2 plasmid to construct pEF1α-SNAP26m-Neo-RE2. Neomycin-resistant gene was excised from this plasmid using the restriction enzymes AflIII and BstBI. On the other hand, from pPUR.N4, puromycin-resistant gene to which N4 sequence was added to the downstream region was amplified by PCR using the primers of SEQ ID Nos: 14 and 15 and transferred to the sites of the restriction enzymes AflIII and BstBI of pEF1α-SNAP26m-RE2 plasmid to construct pEF1α-SNAP26m-Pur.N4. After that, this plasmid was used as a template and inverse PCR using the KOD-Plus-Mutagenesis kit and using the primers of SEQ ID Nos: 16 and 17 was conducted to construct a plasmid pEF1α-SNAP26m-Pur-RE2 where the N4 sequence in the downstream region of the puromycin-resistant gene was deleted.

Example 5

(2) Transfer of pEF1α-SNAP26m-Pur-RE2 and pEF1α-SNAP26m-Pur.N4 into the Cells

CHO-K1 cells for a transfection was prepared by the method mentioned in Example 2. On the other hand, the SNAP26m expression construct constructed in Example 4 was linearized using a restriction enzyme AhdI (manufactured by New England Biolabs). Transfection was carried out in such a manner that 3 µl of GeneJuice Transfection Reagent was diluted with 100 µl of Opti-MEM I Reduced-Serum Medium followed by being added 1 µg of the above linearized plasmid and by being allowed to stand for 10 minutes and the mixture was added to the above CHO-K1 cells followed by cultivating for 24 hours. On the next day, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 5, 7.5, or 10 µg/ml puromycin. During the selective culture, the medium was exchanged every three to four days. After finishing the selective culture, the expression intensity of SNAP26m of the cell group was analyzed using the method mentioned in the Example 2.

Figure 11:
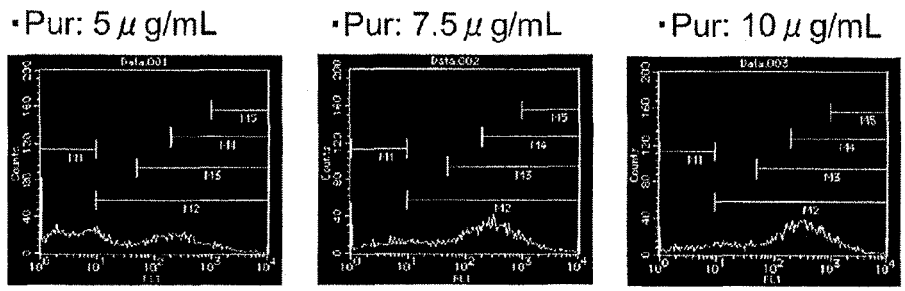
FIG. 11 shows the results of FACS analysis of the cell group which is transformed by pEF1α-SNAP26m-Pur-RE2 or pEF1α-SNAP26m-Pur.N4.
Figure 11:
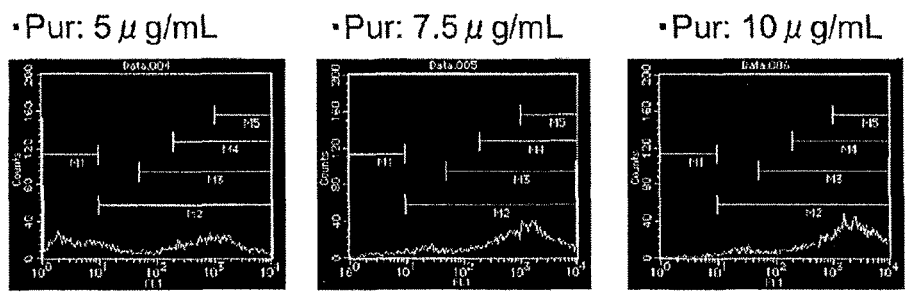
Figure 12:
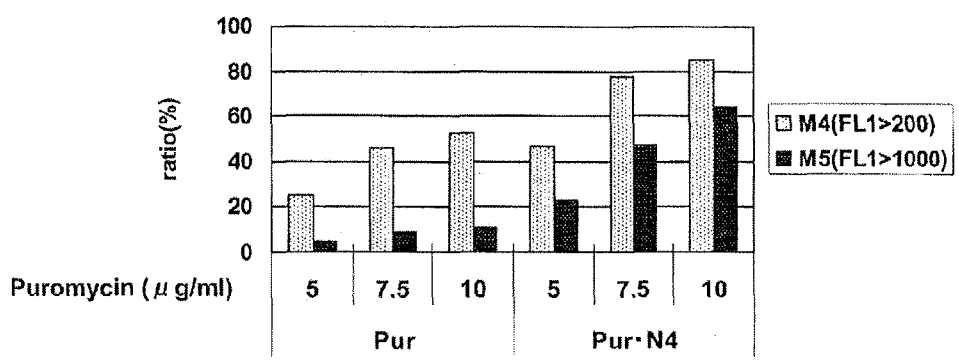
FIG. 12 is a graph where the rate of the cells which highly express SNAPm in the cell group transformed by pEF1α-SNAP26m-Pur-RE2 or pEF1α-SNAP26m-Pur.N4 is plotted.

FIG. 11 shows the result of FACS analysis of the cell group generated after transfection of pEF1α-SNAP26m-Pur-RE2 or pEF1α-SNAP26m-Pur.N4 and the drug selection. Also, FIG. 12 shows plots of rates of cells where the fluorescence intensity FL1 is not less than 200 and not less than 1000 respectively. As a result, it is noted that, in the cell group transformed by pEF1α-SNAP26m-Pur.N4 into which N4 which is an mRNA destabilizing factor is inserted, cells showing a high expression of SNAPm are significantly concentrated after the drug selection regardless of puromycin concentration during drug selection.

Example 6

Effect of mRNA Destabilizing Sequence in Hygromycin-Resistant Gene (1) Construction of pEF1α-SNAP26m-Hyg-RE2 and pEF1α-SNAP26m-Hyg.N4

Figure 13:
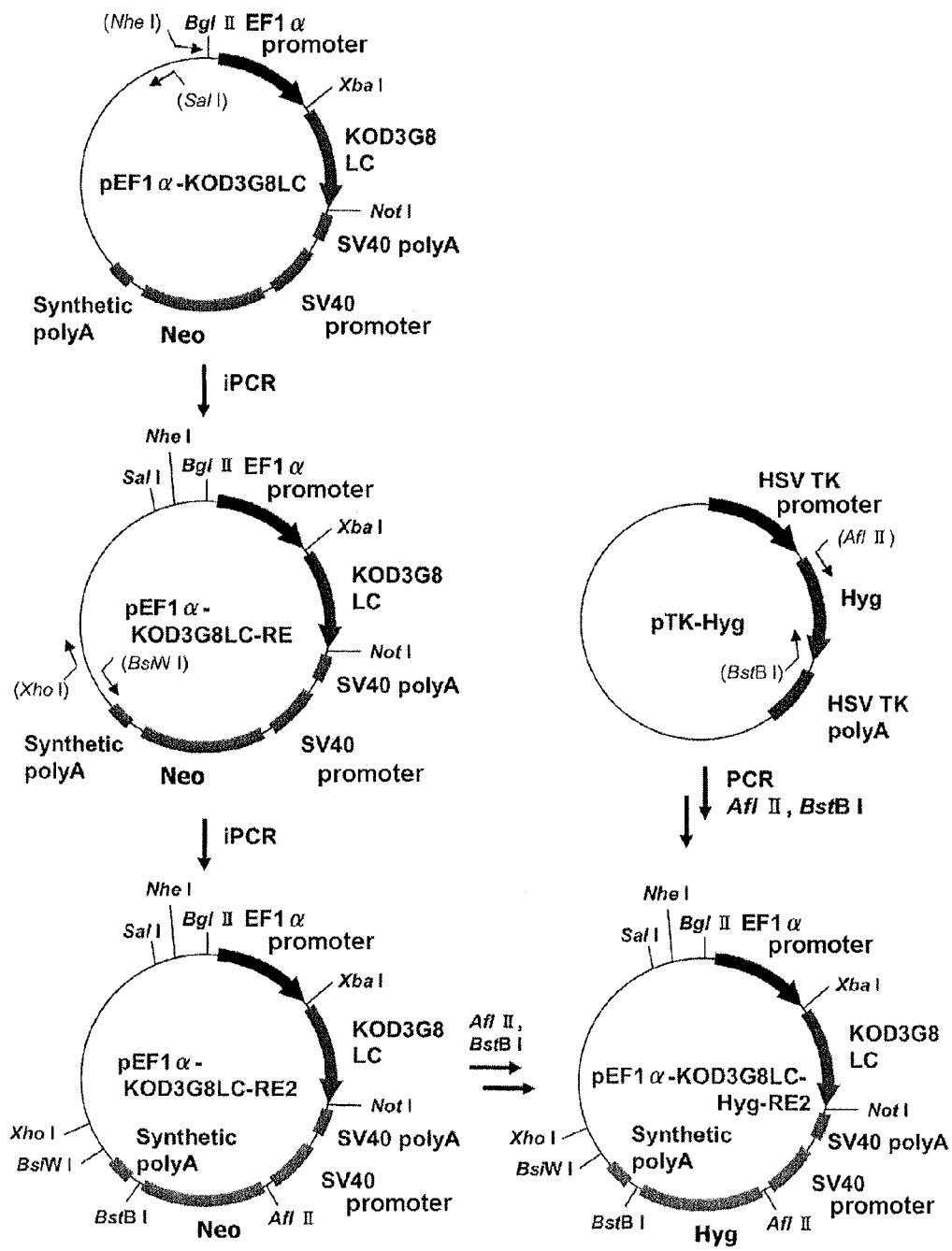
FIG. 13 shows the construction of pEF1α-KOD3G8LC-Hyg-RE2. Hereinafter, Hyg in the drawings stands for hygromycin-resistant gene.

Plasmids were constructed for investigating whether the effect of the mRNA destabilizing factor is also available when hygromycin-resistant gene is used. In this construction, a plasmid pEF1α-KOD3G8LC-Hyg-RE2 which was constructed according to the scheme shown in FIG. 13 was used. Thus, firstly, pEF1α-KOD3G8LC-RE to which sites of the restriction enzymes SalI and NheI were added to the upstream region of an expression cassette was constructed by inverse PCR using the primers of SEQ ID Nos: 10 and 11, a KOD-Plus-Mutagenesis kit, and pEF1α-KOD3G8LC plasmid where light chain of anti-KOD antibody was inserted into the sites of the restriction enzymes XbaI-NotI of pCI-neo plasmid in which a CMV promoter was substituted with an EF1α promoter as a template. As to the light chain of the anti-KOD antibody, there was used that of an antibody prepared from mouse hybridoma cell line 3G8 (deposition number: FERM BP-6056; available from the International Patent Organism Depositary, the National Institute of Advanced Industrial Science and Technology) which produces an antibody specific to DNA polymerase derived from *Thermococcus kodakaraensis* KOD1 strain. A plasmid which was further constructed by addition of sites of restriction enzymes BsiWI and XhoI to the downstream region of the expression cassette by inverse PCR using the primers of SEQ ID Nos: 12 and 13, the KOD-Plus-Mutagenesis kit, and the present plasmid as a template is pEF1α-KOD3G8LC-RE2.

Figure 14:
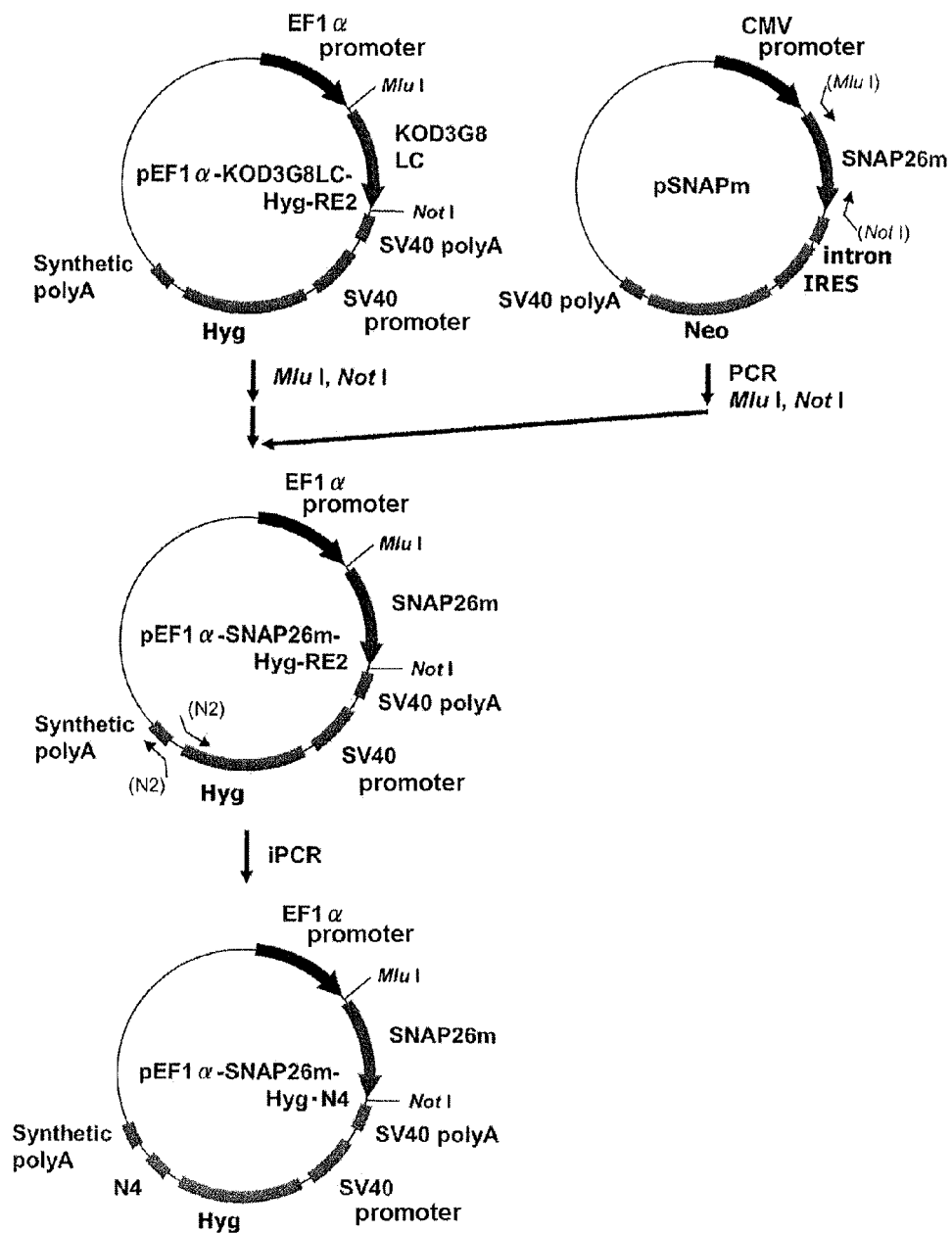
FIG. 14 shows the construction of pEF1α-SNAP26m-Hyg-RE2 and pEF1α-SNAP26m-Hyg.N4.

This pEF1α-KOD3G8LC-RE2 was treated with AflII and BstBI to excise the neomycin-resistant gene. On the other hand, from pTK-Hyg (manufactured by Clontech), hygromycin-resistant gene was amplified by PCR using the primers of SEQ ID Nos: 18 and 19 and transferred to the sites of the restriction enzymes AflII and BstBI of pEF1α-KOD3G8LC-RE2 to construct pEF1α-KOD3G8LC-Hyg-RE2. After that, plasmids pEF1α-SNAP26m-Hyg-RE2 and pEF1α-SNAP26m-Hyg.N4 were constructed according to the scheme shown in FIG. 14. Thus, from the plasmid pEF1α-KOD3G8LC-Hyg-RE2, light chain gene of the anti-KOD antibody was excised using the restriction enzymes MluI and NotI. On the other hand, from the SNAPm expression plasmid pSNAPm, the SNAP26m gene was amplified by PCR using the primers of SEQ ID Nos: 3 and 20 and transferred into the sites of the restriction enzymes MluI and NotI of pEF1α-KOD3G8LC-Hyg-RE2 plasmid to construct pEF1α-SNAP26m-Hyg-RE2. After that, this plasmid was used as a template, inverse PCR was conducted using a KOD-Plus-Mutagenesis Kit and the primers of SEQ ID Nos: 21 and 22 to construct pEF1α-SNAP26m-Hyg.N4 where N4 sequence was added to the downstream region of hygromycin-resistant gene.

Example 7

(2) Transfer of pEF1α-SNAP26m-Hyg-RE2 and pEF1α-SNAP26m-Hyg.N4 into the Cells

CHO-K1 cells for a transfection was prepared by the method mentioned in Example 2. On the other hand, the SNAP26m expression construct constructed in Example 6 was linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 800 µg/ml hygromycin HygroGold (manufactured by InvivoGen). During the selective culture, the medium was exchanged every three to four days. After finishing the selective culture, the expression intensity of SNAP26m of the cell group was analyzed using the method mentioned in the Example 2.

Figure 15:
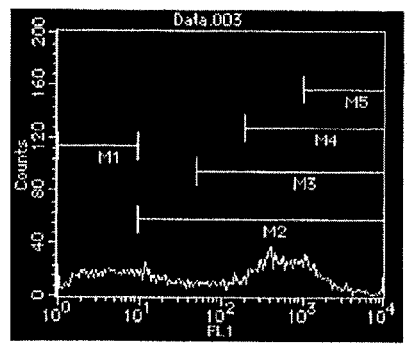
FIG. 15 shows the results of FACS analysis of the cell group which is transformed by pEF1α-SNAP26m-Hyg-RE2 or pEF1α-SNAP26m-Hyg.N4.
Figure 15:
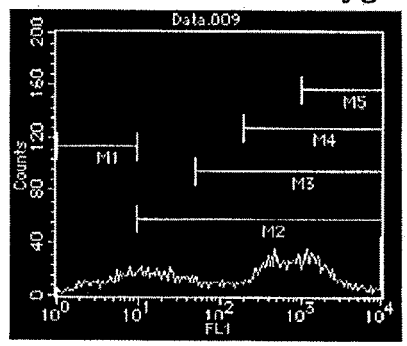
Figure 16:
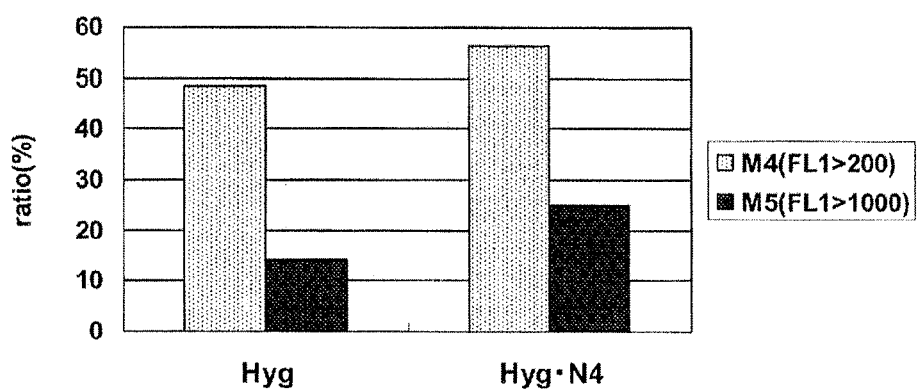
FIG. 16 is a graph where the rate of the cells which highly express SNAPm in the cell group transformed by pEF1α-SNAP26m-Hyg-RE2 or pEF1α-SNAP26m-Hyg.N4 is plotted.

FIG. 15 shows the result of FACS analysis of the cell group generated after transfection of pEF1α-SNAP26m-Hyg-RE2 or pEF1α-SNAP26m-Hyg.N4 and the drug selection. FIG. 16 shows plots of rates of cells where the fluorescence intensity FL1 is not less than 200 and not less than 1000 respectively. As a result, it is noted that, in the cell group transformed by pEF1α-SNAP26m-Hyg.N4 into which N4 which is an mRNA destabilizing factor is inserted, cells showing a high expression of SNAPm are significantly concentrated after the drug selection.

Example 8

Effect of mRNA Destabilizing Sequence in Neomycin-Resistant Gene (1) Construction of pEF1α-SNAP26m-Neo.N4

Figure 17:
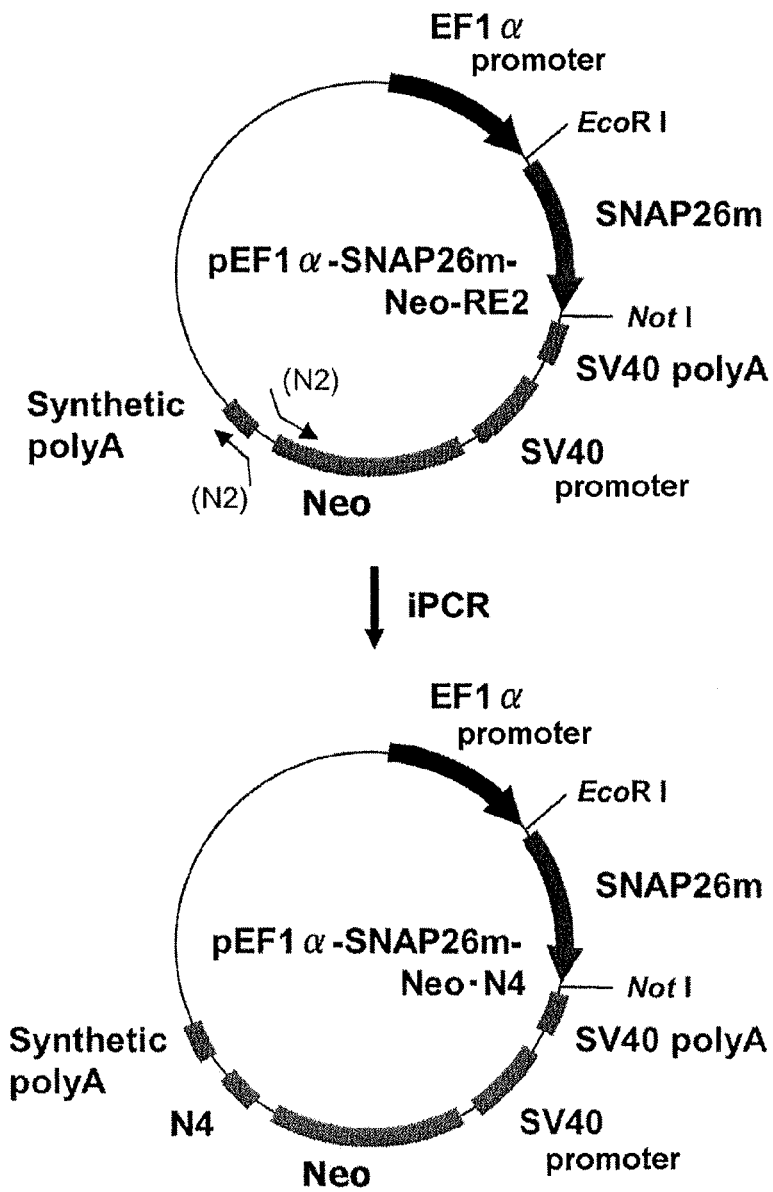
FIG. 17 shows the construction of pEF1α-SNAP26m-Neo.N4.

In order to investigate whether the effect of the mRNA destabilizing factor is also available when the neomycin-resistant gene is used, a plasmid pEF1α-SNAP26m-Neo.N4 was constructed according to the scheme shown in FIG. 17. Thus, the pEF1α-SNAP26m-Neo-RE2 mentioned in Example 4 was used as a template and inverse PCR using the KOD-Plus-Mutagenesis kit was conducted using the primers of SEQ ID Nos: 21 and 23 to construct pEF1α-SNAP26m-Neo.N4 where N4 sequence was added to the downstream region of neomycin-resistant gene.

Example 9

(2) Transfer of pEF1α-SNAP26m-Neo-RE2 and pEF1α-SNAP26m-Neo.N4 into the Cells

CHO-K1 cells for a transfection was prepared by the method mentioned in Example 2. On the other hand, pEF1α-SNAP26m-Neo-RE2 and pEF1α-SNAP26m-Neo.N4 were linearized using a restriction enzyme AhdI. Transfection was carried out by the method mentioned in Example 5, and on the next day of the transfection, the medium was removed and cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 1 mg/ml genetigin G418 (manufactured by Nakarai Tesk). During the selective culture, the medium was exchanged every three to four days. After finishing the selective culture, the expression intensity of SNAP26m of the cell group was analyzed using the method mentioned in the Example 2.

Figure 18:
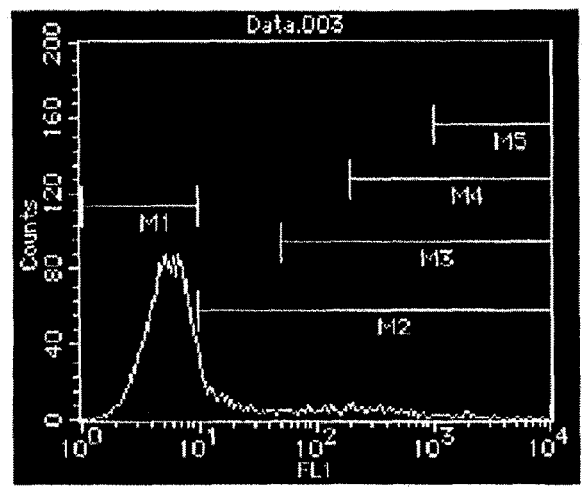
FIG. 18 shows the results of FACS analysis of the cell group which is transformed by pEF1α-SNAP26m-Neo-RE2 or pEF1α-SNAP26m-Neo.N4.
Figure 18:
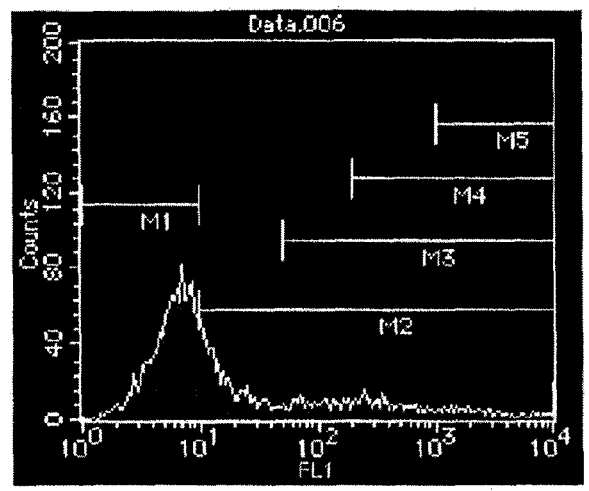
Figure 19:
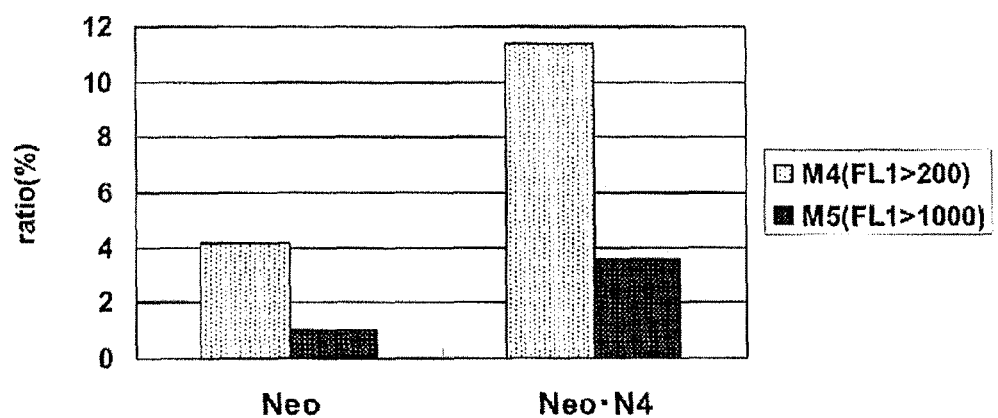
FIG. 19 is a graph where the rate of the cells which highly express SNAPm in the cell group transformed by pEF1α-SNAP26m-Neo-RE2 or pEF1α-SNAP26m-Neo.N4 is plotted.

FIG. 18 shows the result of FACS analysis of the cell group generated after transfection of pEF1α-SNAP26m-Neo-RE2 or pEF1α-SNAP26m-Neo.N4 and the drug selection. FIG. 19 shows plots of rates of cells where the fluorescence intensity FL1 is not less than 200 and not less than 1000 respectively. As a result, it is noted that, in the cell group transformed by pEF1α-SNAP26m-Neo.N4 into which N4 which is an mRNA destabilizing factor is inserted, cells showing a high expression of SNAPm are significantly concentrated after the drug selection.

Example 10

Investigation in Repeated Sequence Numbers of ARE Sequence Motif

Figure 20:
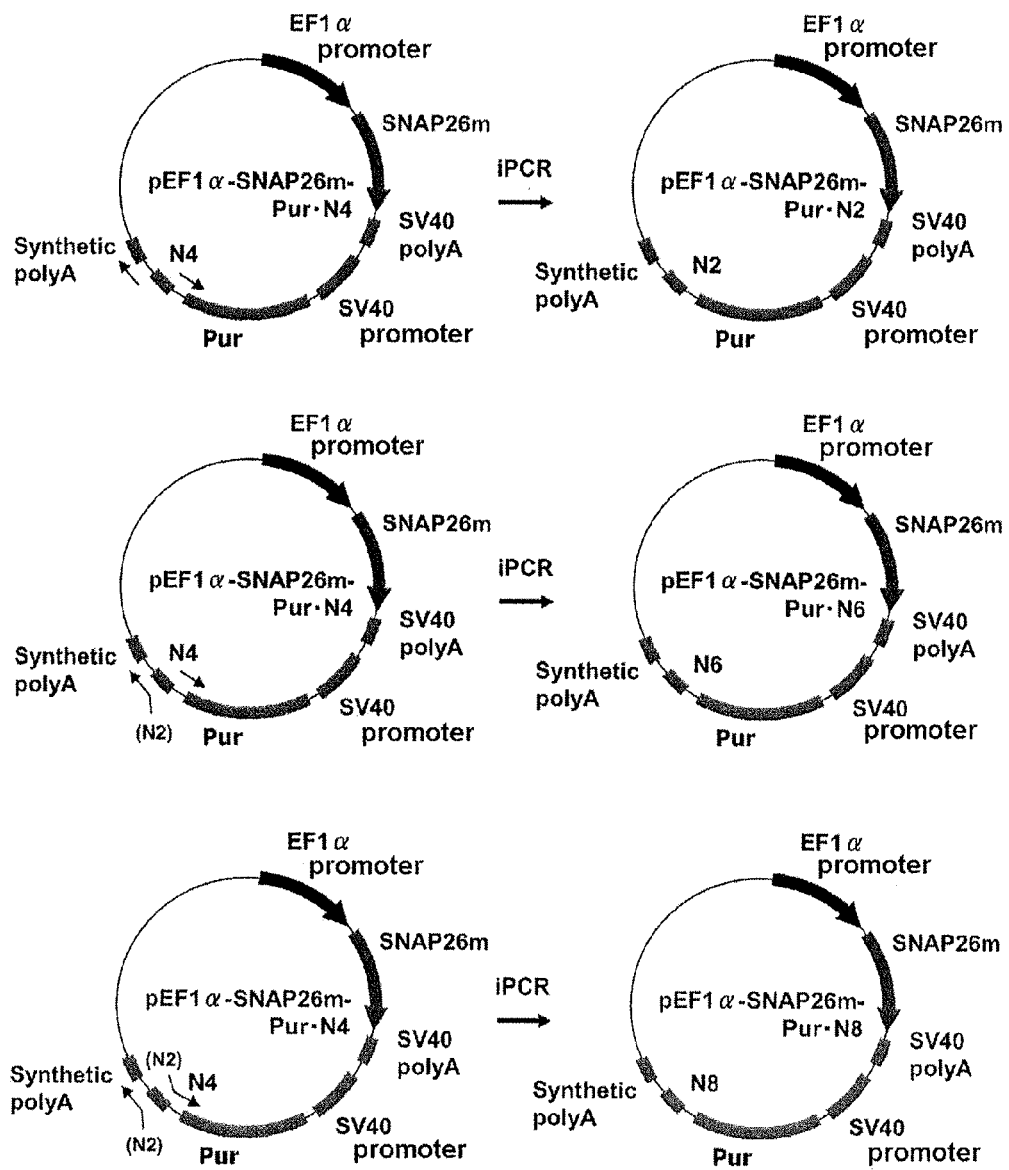
FIG. 20 shows the construction of pEF1α-SNAP26m-Pur.N2, pEF1α-SNAP26m-Pur.N6, and pEF1α-SNAP26m-Pur.N8.

Plasmid pEF1α-SNAP26m-Pur.N2, pEF1α-SNAP26m-Pur.N6, and pEF1α-SNAP26m-Pur.N8 were constructed according to the scheme shown in FIG. 20. The pEF1α-SNAP26m-Pur.N4 mentioned in Example 4 was used as a template and inverse PCR was conducted using KOD-Plus-Mutagenesis Kit and the primers of SEQ ID Nos: 16 and 24 to prepare a plasmid pEF1α-SNAP26m-Pur.N2 to which an N2 sequence (a sequence where the ARE sequence motif TTATT-TATT was repeated twice) was added to the downstream region of the puromycin-resistant gene. Also, using the primers of SEQ ID Nos: 7 and 24, a plasmid pEF1α-SNAP26m-Pur.N6 to which an N6 sequence (a sequence where the ARE sequence motif TTATTTATT was repeated six times) was added to the downstream region of the puromycin-resistant gene was prepared by the same method. Further, using the primers of SEQ ID Nos: 7 and 25 to prepare a plasmid pEF1α-SNAP26m-Pur.N8 to which an N8 sequence (a sequence where the ARE sequence motif TTATTTATT was repeated eight times) was added to the downstream region of the puromycin-resistant gene was prepared by the same method.

CHO-K1 cells for a transfection was prepared by the method mentioned in Example 2. On the other hand, each of the SNAP26m expression constructs of pEF1α-SNAP26m-Pur-RE2, pEF1α-SNAP26m-Pur.N2, pEF1α-SNAP26m-Pur.N4, pEF1α-SNAP26m-Pur.N6, and pEF1α-SNAP26m-Pur.N8 was linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 7.5 µg/ml puromycin. During the selective culture, the medium was exchanged every three to four days. After finishing the selective culture, the expression intensity of SNAP26m of the cell group was analyzed using the method mentioned in the Example 2.

Figure 21:
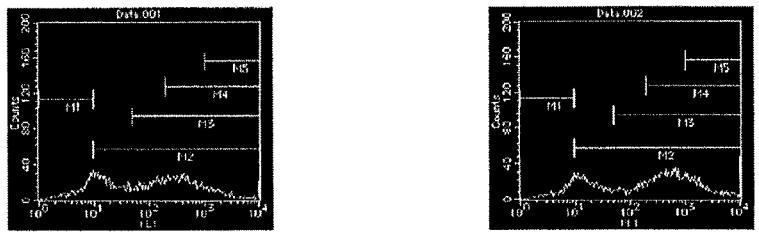
FIG. 21 shows the results of FACS analysis of the cell group which is transformed by pEF1α-SNAP26m-Pur-RE2, pEF1α-SNAP26m-Pur.N2, pEF1α-SNAP26m-Pur.N4, pEF1α-SNAP26m-Pur.N6, or pEF1α-SNAP26m-Pur.N8.
Figure 21:
Figure 21:
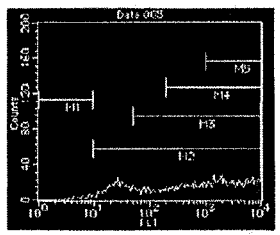
Figure 22:
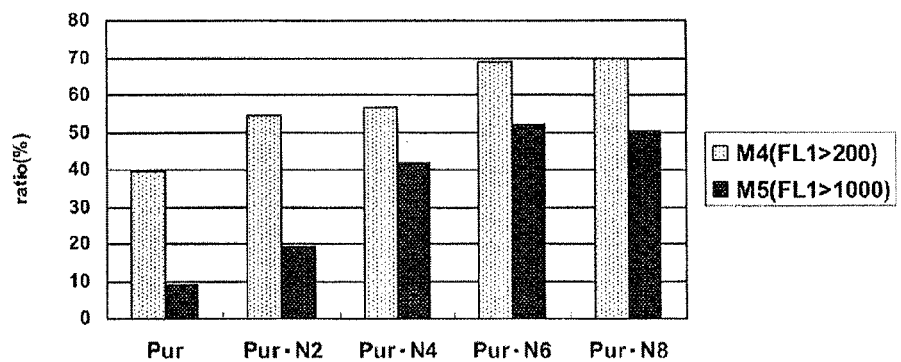
FIG. 22 is a graph where the rate of the cells which highly express SNAPm in the cell group transformed by pEF1α-SNAP26m-Pur-RE2, pEF1α-SNAP26m-Pur.N2, pEF1α-SNAP26m-Pur.N4, pEF1α-SNAP26m-Pur.N6, or pEF1α-SNAP26m-Pur.N8 is plotted.

FIG. 21 shows the result of FACS analysis of the cell group generated after transfection of pEF1α-SNAP26m-Pur-RE2, pEF1α-SNAP26m-Pur.N2, pEF1α-SNAP26m-Pur.N4, pEF1α-SNAP26m-Pur.N6, or pEF1α-SNAP26m-Pur.N8 and the drug selection. Also, FIG. 22 shows plots of rates of cells where the fluorescence intensity FL1 is not less than 200 and not less than 1000 respectively. As a result, the outcome was that, when a transformation was conducted using the plasmid pEF1α-SNAP26m-Pur.N6 or pEF1α-SNAP26m-Pur.N8 into which N6 or N8 having many repeated numbers was inserted, the rate of high expression cells of SNAPm was much more and the selecting efficiency for highly expressing cells was high as compared with pEF1α-SNAP26m-Pur.N4.

Example 11

Determination of Nucleic Acid Sequence

In a BAC library prepared from a DR 1000L-4N strain of CHO cell (CHO cell-4N strain), a clone Cg0031N14 containing an hGM-CSF expression cassette was isolated. A shotgun clone prepared from the Cg0031N14 BAC clone was subjected to 5',3' one-pass sequence to assemble the sequence information by Phred/Phrap/Consed whereupon the sequence of about 91 kbp of the genome sequence adjacent to the site in the CHO cells into which hGM-CSF expression cassette was transferred was determined. This sequence is shown in SEQ ID No: 26 of the Sequence Listing.

Example 12

Analysis of Nucleic Acid Sequence

Figure 23:
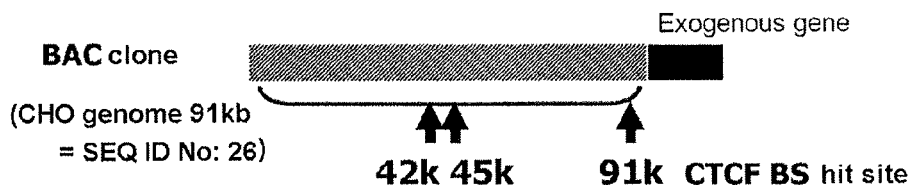
FIG. 23 shows the expected site of the binding sequence of the sequence of SEQ ID No: 26 to CTCF.

In order to check whether an insulator sequence is present in the nucleic acid sequence determined hereinabove, a search was carried out by retrieving of the binding sequence motif of an insulator-binding protein CTCF. As a tool for the analysis, the In silico CTCFBS prediction tool (insulatordb.utmem.edu/) (Non-Patent Document 11) was used. The motif sequences extracted by the above tool are shown in Table 1 and FIG. 23.

TABLE 1

| motif PWN | motif sequence | starting point of motif | motif length | orientation of motif | score |
|---|---|---|---|---|---|
| REN_20 | TCCACCACTAGGGGCGCGC | 41821 | 20 | − | 20.8898 |
| MIT_LM2 | TAGCCAGAAGAGGGCATCA | 45182 | 19 | + | 19.3604 |
| MIT_LM7 | CATCCAGCAGAGGGAGATGG | 91094 | 20 | + | 17.6996 |
| MIT_LM23 | CCACCACTAGGGGCGCGCT | 41820 | 20 | − | 15.4348 |

Example 13

Confirmation of Stabilizing Effect of Transgene Expression

Figure 24:
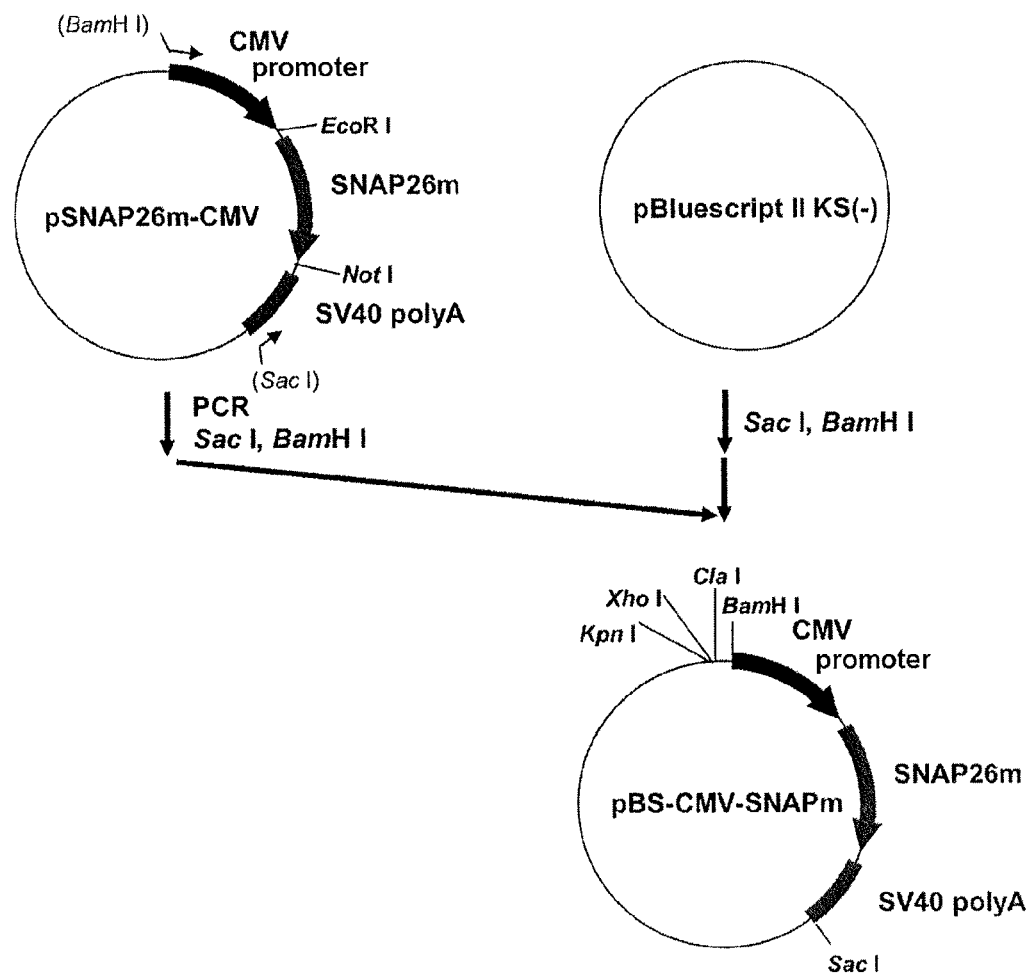
FIG. 24 shows the construction of a basic construct pBS-CMV-SNAPm used for the confirmation of a gene expression stabilizing effect of the nucleic acid sequence fragment.

From pSNAP26m-CMV constructed during the process of Example 1, CMV promoter/SNAP26m/SV 40 polyA was amplified by PCR using the primers of SEQ ID Nos: 27 and 28 and transferred into the sites of the restriction enzymes BamHI and SacI of a plasmid pBluescript II SK (−) by partial digestion to construct a plasmid pBS-CMV-SNAPm (FIG. 24).

Figure 25:
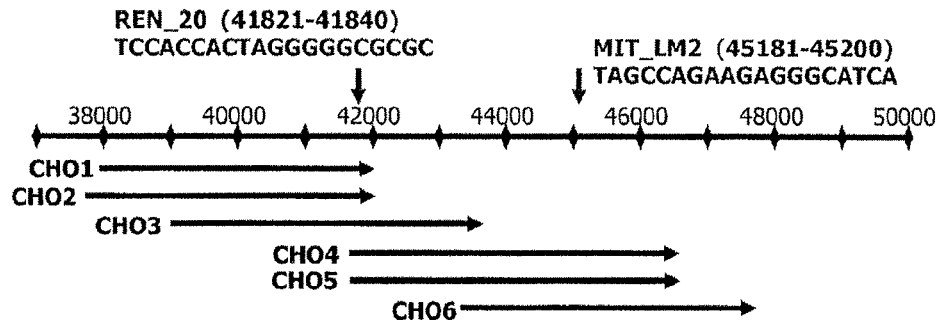
FIG. 25 shows the relation in terms of position among the sequence of SEQ ID No: 26, the CTCFBS and the nucleic acid fragment of the test sequence.

After that, in the clones of the shotgun library prepared in Example 11, a clone containing a CHO genome sequence near the binding sequence motifs of CTCF at the position 41820 or 45182 was extracted and a sequence derived from CHO genome (FIG. 25) was amplified by PCR and transferred into the sites of the restriction enzymes KpnI and XhoI or XhoI and ClaI of pBS-CMV-SNAP26m. The correspondence relationship between the shotgun library clone and the SNAPm expression construct into which said transferred sequence is integrated is shown in Table 2. Incidentally, (−) in the column of the SNAPm expression construct is pBS-CMV-SNAPm into which no genome sequence of CHO is transferred.

TABLE 2

| shotgun library clone No. | primer used for PCR | starting point of transferred sequence amplified by PCR (position at SEQ ID No: 26) | ending point of transferred sequence amplified by PCR (position at SEQ ID No: 26) | SNAPm expression construct |
|---|---|---|---|---|
| — | — | — | — | (—) |
| 1L24 | SEQ ID Nos: 29, 30 | 37738 | 42048 | CHO1 |
| 2O11 | SEQ ID Nos: 31, 32 | 37934 | 42043 | CHO2 |
| 2P05 | SEQ ID Nos: 33, 34 | 38934 | 43490 | CHO3 |
| 2B15 | SEQ ID Nos: 35, 36 | 41601 | 46746 | CHO4,5 |
| 1A02 | SEQ ID Nos: 37, 38 | 43232 | 47601 | CHO6 |

Those SNAPm expression constructs and pPUR were linearized using a restriction enzyme AhdI and mixed so as to make their ratio by weight 9:1 to prepare a mixed plasmid.

On the other hand, each 2 ml of the CHO-K1 cells adjusted to $1\times10^5$ cells/ml were seeded to a 12-well plate on the previous day and cultivated for one night to prepare CHO-K1 cells for the transfection. At that time, a Ham's F12 medium to which 10% fetal bovine serum was added was used as a medium.

Transfection was carried out in such a manner that 3 μl of GeneJuice Transfection Reagent was diluted with 100 μl of Opti-MEM I Reduced-Serum Medium, 103 μl of this diluted liquid was added to 1 μg of the above mentioned mixed plasmid followed by being allowed to stand for 10 minutes and the mixture was added to the above CHO-K1 cells followed by cultivating for 24 hours. On the next day, the medium was removed and the cells were dispersed by treating with 2.5 g/l-trypsin and 1 mmol/l-EDTA solution, transferred to a 90-mm Petri dish and subjected to a selective culture for three weeks in a Ham's F12 medium supplemented with 10% FBS and 6 μg/ml puromycin. During the selective culture, the medium was exchanged every three to four days. After finishing the selective culture, the cells were dispersed by treating with 2.5 g/l-trypsin and 1 mmol/l-EDTA solution and were seeded on a 12-well plate at $2\times10^5$ cells per well, 2 μM SNAP-Cell-505 was added to 0.5 ml of a Ham's F12 medium on the next day and cultivation was conducted for 60 minutes at 37° C. After that, the above was rinsed with the Ham's F12 medium for three times and, together with exchanging the medium, cultivation for 10 minutes was conducted for three times to remove the unreacted fluorescent dye. The cells were treated with 2.5 g/l-trypsin and 1 mmol/l-EDTA solution to disperse, suspended in D-PBS(-) and the expression intensity of SNAPm was analyzed using a flow cytometer BD FACS-Calibur.

Figure 26:
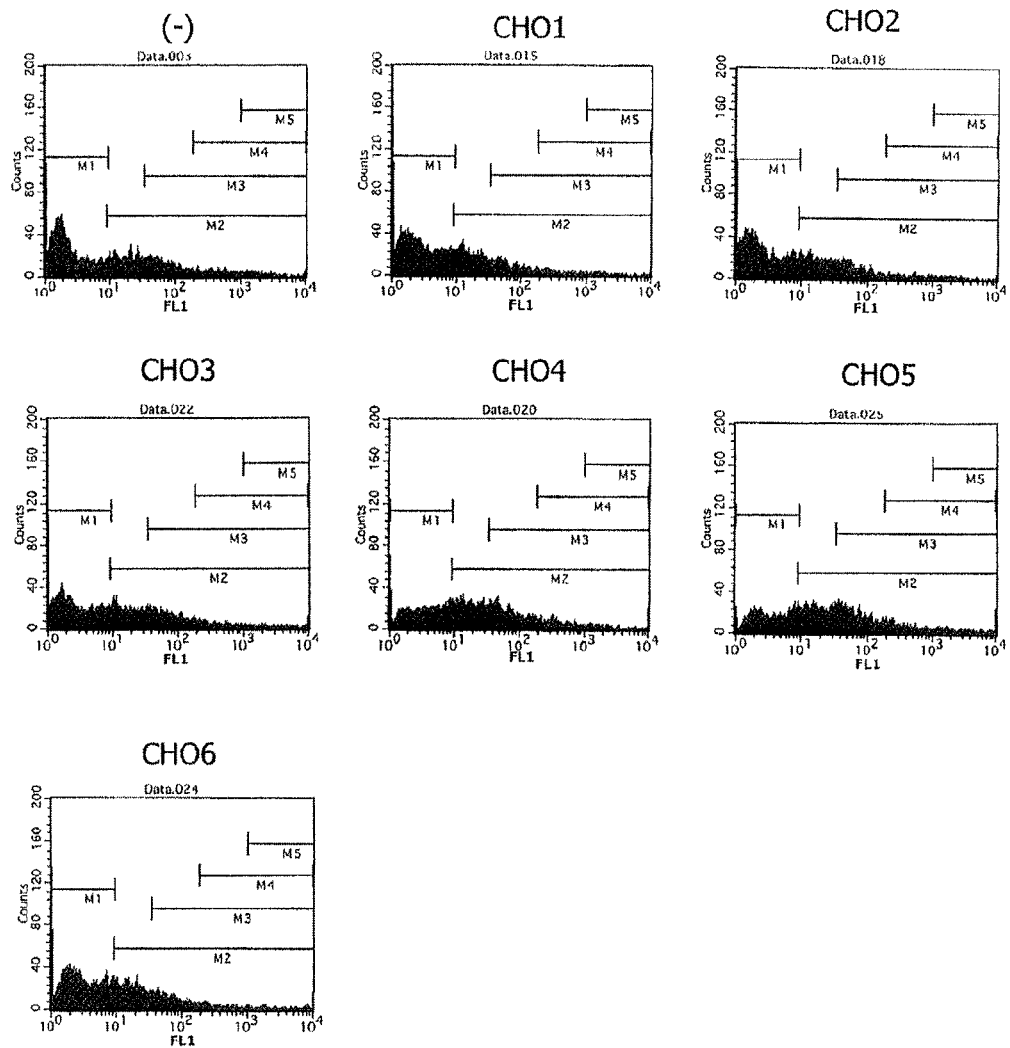
FIG. 26 is a graph which shows the distribution of cell numbers and SNAPm expression intensity obtained by FACS analysis of CHO cells into which SNAPm expressing construct containing fragment of each nucleic acid sequence are stably transferred.
Figure 27:
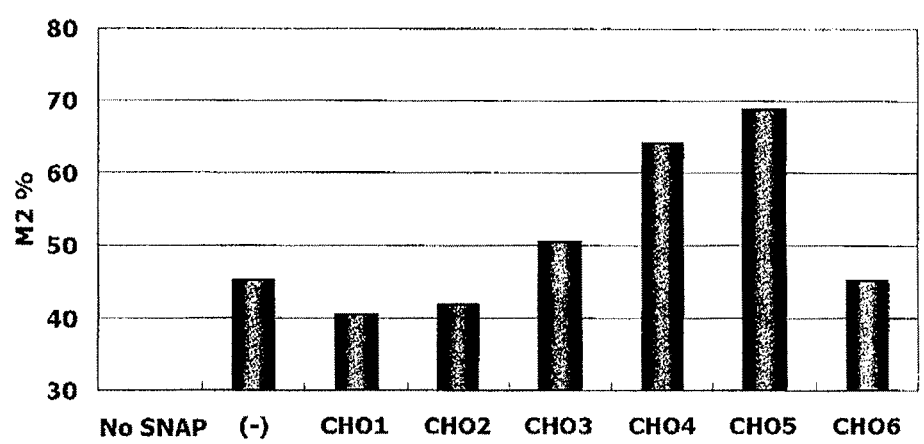
FIG. 27 is a graph where the rate (%) of the cells showing 10 or more SNAPm fluorescent signals by FACS analysis of CHO cells into which SNAPm expressing construct containing fragment of each nucleic acid sequence are stably transferred is plotted.

FIG. 26 shows the result of FACS analysis of the cell group transformed by an SNAPm expression construct into which each of test sequence CHO1 to CHO6 is transferred. FIG. 27 is a graph where, from the analytical result of the untreated CHO cell (No SNAP on the left of FIG. 27), the cell showing ten or more signals (M2 in FIG. 26) is adopted as the expression cell for SNAPm and the rates of said cell are plotted. As will be apparent from FIGS. 26 and 27, a significant rise of expression was achieved in the construct into which a part of CHO genome was transferred or, particularly, in CHO4 and 5 into which the positions 41601 to 46746 of SEQ ID No: 26 were transferred. Although the difference between CHO4 and CHO5 is believed to be within a dispersion among the samples, narrowing down of the optimum region hereinafter was carried out on the basis of CHO5.

Example 14

Narrow-Down of the Sequence Region Having a Gene Expression Stabilizing Ability (1)

Figure 28:
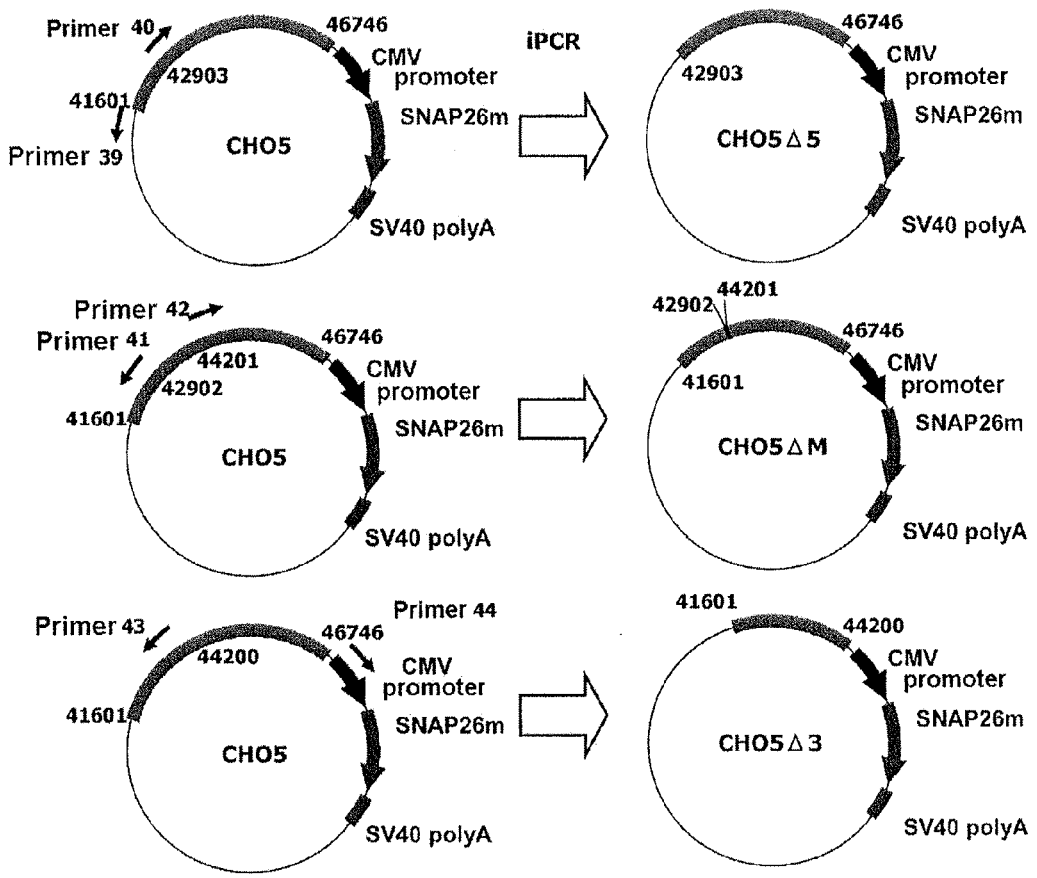
FIG. 28 shows the construction of deletion construct of CHO5 and the relation in terms of positions between said test sequences in SEQ ID No: 26.

Based on the construct CHO5 having the highest rise of expression hereinabove, inverse PCR using KOD-Plus-Mutagenesis kit was conducted. The primers of SEQ ID Nos: 39 and 40 were used to construct CHO5Δ5 in which the positions 41601 to 42902 of the test sequences were deleted. The primers of SEQ ID Nos: 41 and 42 were used to construct CHO5ΔM in which the positions 42903 to 44200 of the test sequences were deleted. The primers of SEQ ID Nos: 43 and 44 were used to construct CHO5Δ3 in which the positions 44201 to 46746 of the test sequences were deleted (FIG. 28).

Those SNAPm expression constructs and pPUR were linearized using a restriction enzyme AhdI and mixed so as to make their ratio by weight 9:1 to prepare a mixed plasmid.

The above mixed plasmid (1 μg) was transfected to CHO-K1 cells which were seeded on a 12-well plate on the previous day followed by cultivating for 24 hours. On the next day, the medium was removed and the cells were dispersed by treating with 2.5 g/l-trypsin and 1 mmol/l-EDTA Solution, transferred to a 90-mm Petri dish and subjected to a selective culture for three weeks in a Ham's F12 medium supplemented with 10% FBS and 6 μg/ml puromycin. During the selective culture, the medium was exchanged every three to four days. After finishing the selective culture, the cells were dispersed by treating with 2.5 g/l-trypsin and 1 mmol/l-EDTA solution and were seeded on a 12-well plate at $2\times10^5$ cells per well, 2 μM SNAP-Cell-505 was added to 0.5 ml of a Ham's F12 medium on the next day and cultivation was conducted for 60 minutes at 37° C. After that, the above was rinsed with the Ham's F12 medium for three times and, together with exchanging the medium, cultivation for 10 minutes was conducted for three times to remove the unreacted fluorescent dye. The cells were treated with 2.5 g/l-trypsin and 1 mmol/l-EDTA solution to disperse, suspended in D-PBS (-) and the expression intensity of SNAPm was analyzed using a flow cytometer BD FACSCalibur.

Figure 29:
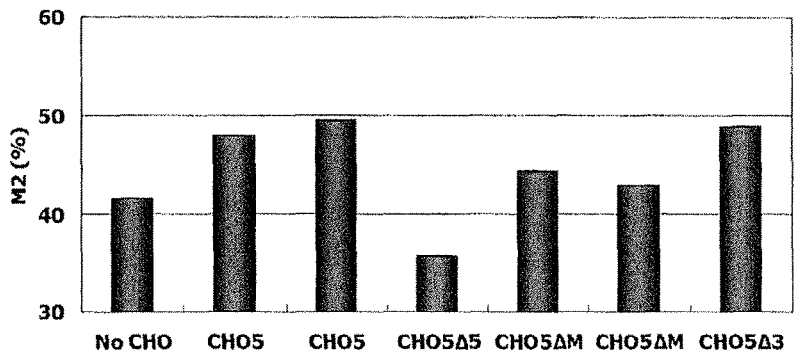
FIG. 29 is a graph where the rate (%) of the cells showing 10 or more SNAPm fluorescent signals as a result of FACS analysis of CHO cells obtained by stable transfer of CHO5 or CHO deletion construct thereinto is plotted.

FIG. 29 is that, as a result of FACS analysis of the cell group transformed by an SNAPm expression construct into which each of the test sequences CHO5Δ5, ΔM and Δ3 was transferred, rates of the cells showing 10 or higher signal value are plotted. As will be apparent from FIG. 29, CHO5Δ3 showed nearly the same expression intensity of SNAPm before the deletion while, in CHOΔM and Δ5, the effect of a rise in expression was apparently reduced. From the above result, it is believed that the part from 5' side to the first half area of the positions 41601 to 46746 of the sequence of SEQ ID No: 26 mainly participates in the stabilization of the expression.

Example 15

Narrow-Down of Sequence Region Having Gene Expression Stabilizing Ability (2)

Figure 30:
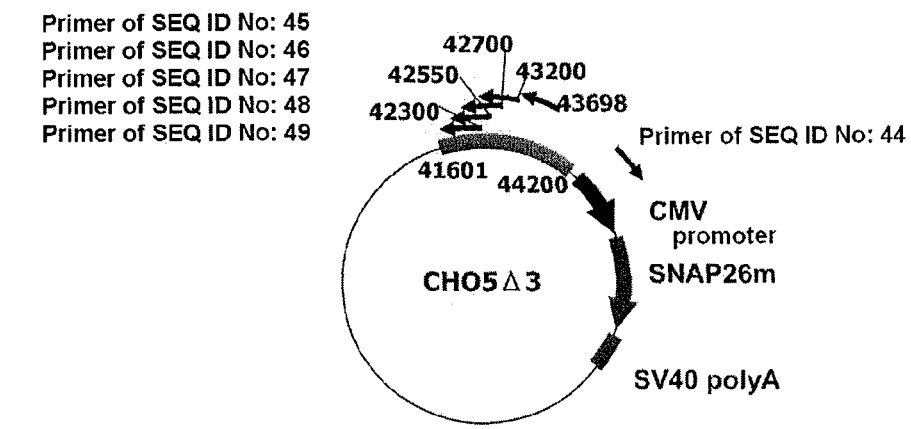
FIG. 30 shows the position relation of primers used for inverse PCR for the construction of 3'-deletion construct of CHO5Δ3 and the inserted test sequence obtained by the deletion.
Figure 30:
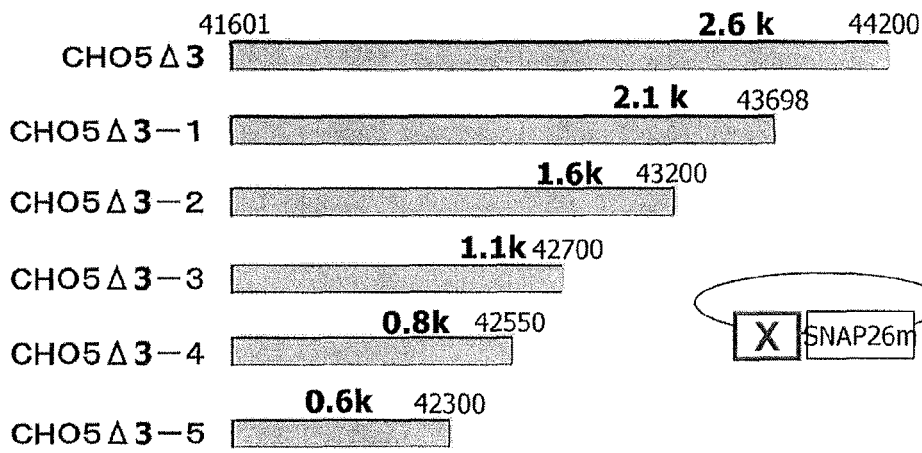

The primers of SEQ ID Nos: 44 to 49 were used and inverse PCR using the KOD-Plus-Mutagenesis Kit was carried out to construct an SNAPm expression construct where 3' of the test sequence of CHO5Δ3 was further deleted (FIG. 30 and Table 3).

TABLE 3

| SNAPm expression construct | starting point 5' of transferred sequence amplified by PCR (position at SEQ ID No: 26) | ending point 3' of transferred sequence amplified by PCR (position at SEQ ID No: 26) |
|---|---|---|
| CHO5Δ3 | 41601 | 44200 |
| CHO5Δ3-1 | 41601 | 43698 |
| CHO5Δ3-2 | 41601 | 43200 |
| CHO5Δ3-3 | 41601 | 42700 |
| CHO5Δ3-4 | 41601 | 42550 |
| CHO5Δ3-5 | 41601 | 42300 |

Those SNAP26m expression constructs were subjected to the same treatment as in Example 14 to analyze the expression intensity of the SNAPm.

Figure 31:
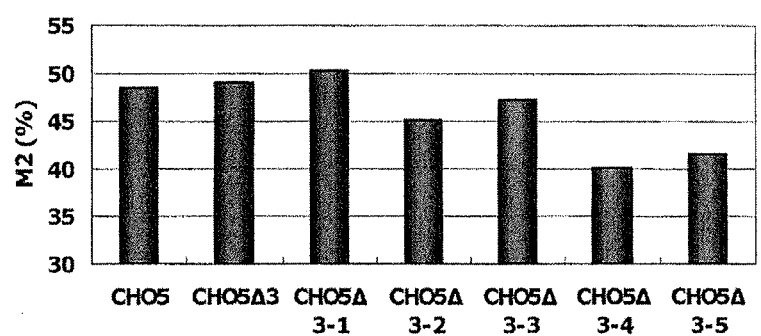
FIG. 31 is a graph where the rate (%) of the cells showing 10 or more SNAPm fluorescent signals as a result of FACS analysis of CHO cells obtained by stable transfer of CHO5Δ3 or 3'-deletion construct of CHO5Δ3 thereinto is plotted.

In FIG. 31, rates of the cells showing 10 or more signal values as a result of FACS analysis of the cell group transformed by the SNAPm expression constructs of the test sequences CHO5Δ3 and CHO5Δ3-1 to 5 were plotted. As will be apparent from FIG. 31, although there are dispersions among the samples for CHO5Δ3-1 to CHO5Δ3-3 containing the positions 41601 to 42700 of the sequence of SEQ ID No: 26, expression intensity of the SNAPm being nearly the same degree before the deletion was noted while, in the case of CHO5Δ3-4 and CHO5Δ3-5 where the 3' side of such a region was deleted, a rising effect of the expression was apparently reduced.

Example 16

Figure 32:
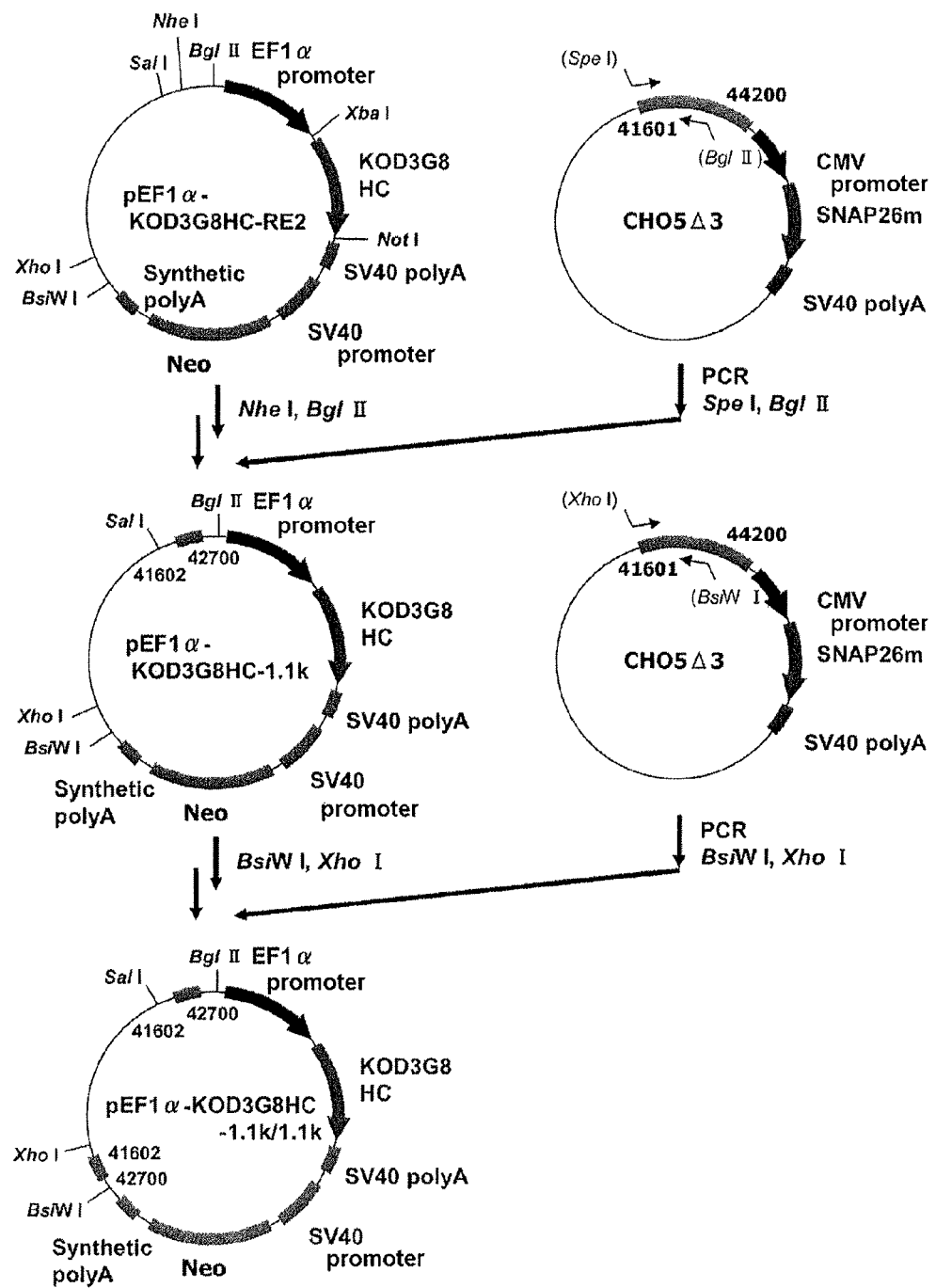
FIG. 32 shows the construction of pEF1α-KOD3G8HC-1.1k/1.1k.

Effect of Combination of an mRNA Destabilizing Sequence with a Gene Expression Stabilizing Element in the Puromycin-Resistant Gene (1) Construction of pEF1α-SNAP26m-Pur-1.1k/1.1k and pEF1α-SNAP26m-Pur.N4-1.1k/1.1k In order to investigate the effect of combination of N4 sequence with CHO5Δ3-3 which was noted of its gene expression stabilizing ability in Example 15 for the puromycin-resistant gene, a plasmid was constructed. In this experiment, the pEF1α-KOD3G8HC-1.1k/1.1k mentioned in FIG. 32 was utilized. Thus, firstly, a test sequence CHO5Δ3-3 (hereinafter, it will be referred to as 1.1k in the construct) amplified by PCR using a primer set of SEQ ID Nos: 50 and 51 was inserted into the sites of restriction enzymes NheI and BglII on the upstream region of the expression cassette of pEF1α-KOD3G8HC-RE2 constructed during the process of Example 4 whereupon a plasmid pEF1α-KOD3G8HC-1.1k was constructed. Further, a plasmid (pEF1α-KOD3 GHC-1.1k/1.1k) was constructed by inserting the test sequence CHO5Δ3-3 amplified by PCR using the primer set of SEQ ID Nos: 52 and 53 into the sites of the restriction enzymes BsiWI and XhoI of the downstream region of the expression cassette of the plasmid pEF1α-KOD3G8HC-1.1k.

On the other hand, the plasmids pEF1α-SNAP26m-Pur.N4 and pEF1α-SNAP26m-Pur-RE2 constructed in Example 4 were used as a template and inverse PCR using the KOD-Plus-Mutagenesis Kit was carried out using the primers of SEQ ID Nos. 54 and 55 to construct plasmids pEF1α-SNAP26m-Pur2.N4 and pEF1α-SNAP26m-Pur2-RE2 wherein the restriction enzyme BsiWI site existing in the puromycin-resistant gene was deleted.

Figure 33:
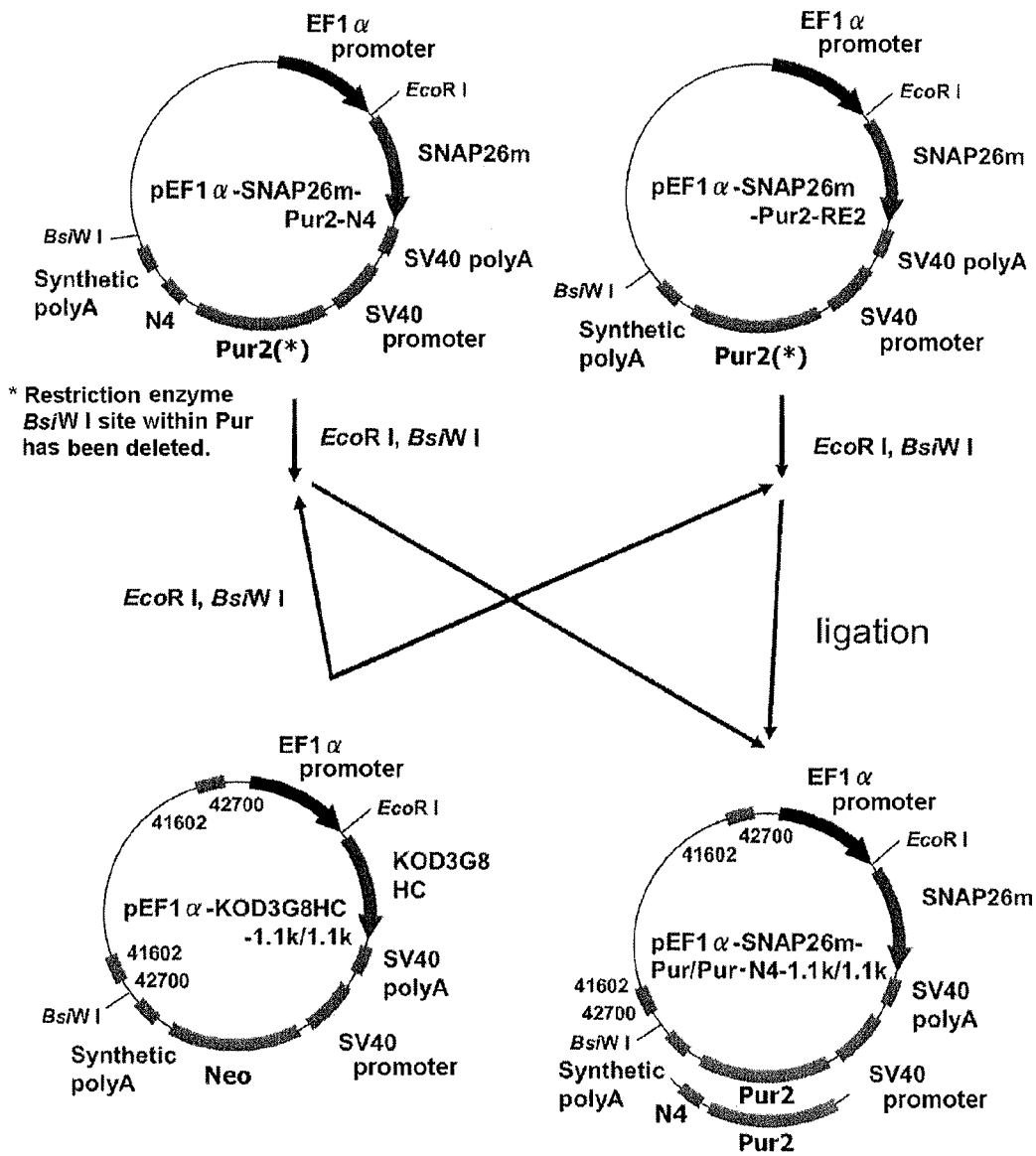
FIG. 33 shows the construction of pEF1α-SNAP26m-Pur.N4-1.1k/1.1k and pEF1α-SNAP26m-Pur-1.1k/1.1k.

After that, plasmids pEF1α-SNAP26m-Pur.N4-1.1k/1.1k, and pEF1α-SNAP26m-Pur-1.1k/1.1k were constructed according to the scheme shown in FIG. 33. Thus, SNAPm-pA-SV40 promoter-Pur2.N4-pA and SNAPm-pA-SV40 promoter-Pur2-pA were excised from pEF1α-SNAP26m-Pur2.N4 and pEF1α-SNAP26m-Pur2-RE2 using the restriction enzymes EcoRI and BsiWI and transferred into the sites of the restriction enzymes EcoRI and BsiWI of pEF1α-KOD3G8HC-1.1k/1.1k to construct pEF1α-SNAP26m-Pur.N4-1.1k/1.1k and pEF1α-SNAP26m-Pur-1.1k/1.1k.

Example 17

(2) Investigation of the Effect of Combination of N4 Sequence with CHO5Δ3-3 in the Puromycin-Resistant Gene CHO-K1 cells for a transfection was prepared by the method mentioned in Example 2. On the other hand, the SNAP26m expression constructs constructed in Example 4 and 16 were linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 5, 7.5, or 10 μg/ml puromycin. During the selective culture, the medium was exchanged every three to four days. After finishing the selective culture, the expression intensity of SNAP26m of the cell group was analyzed using the method mentioned in the Example 2.

Figure 34:
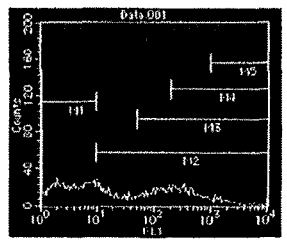
FIG. 34 shows the results of FACS analysis of the cell group which is transformed by pEF1α-SNAP26m-Pur-RE2, pEF1α-SNAP26m-Pur-1.1k/1.1k, pEF1α-SNAP26m-Pur.N4, or pEF1α-SNAP26m-Pur.N4-1.1k/1.1k.
Figure 34:
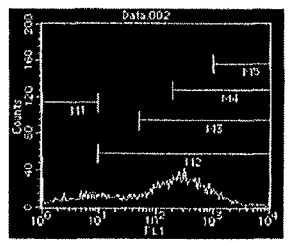
Figure 34:
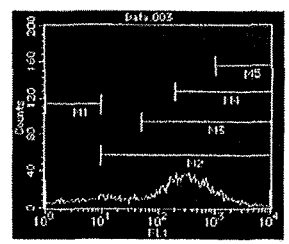
Figure 34:
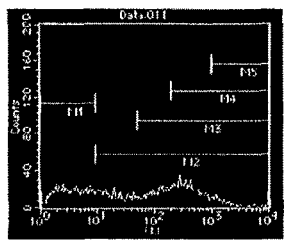
Figure 34:
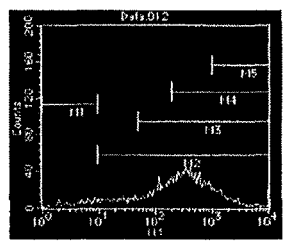
Figure 34:
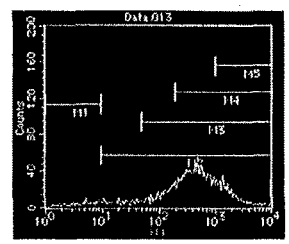
Figure 34:
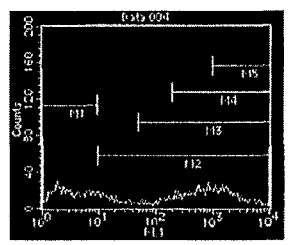
Figure 34:
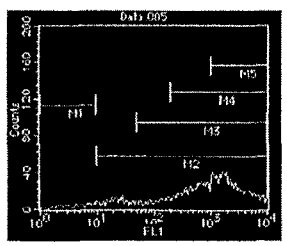
Figure 34:
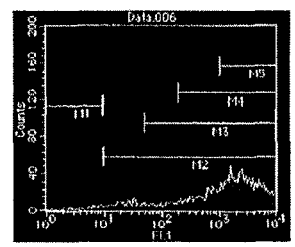
Figure 34:
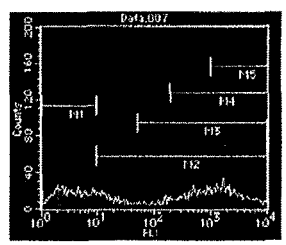
Figure 34:
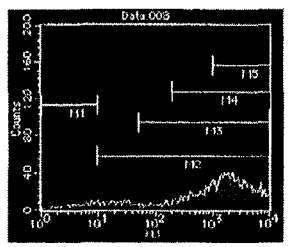
Figure 34:
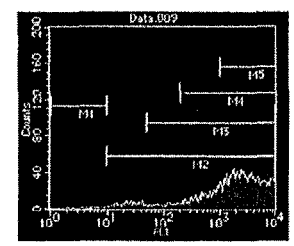
Figure 35:
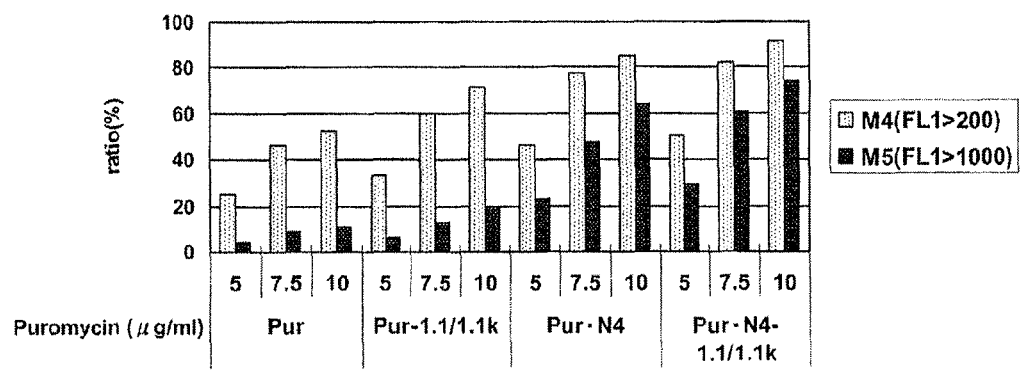
FIG. 35 is a graph where the rate of the cells which highly express SNAPm in the cell group transformed by pEF1α-SNAP26m-Pur-RE2, pEF1α-SNAP26m-Pur-1.1k/1.1k, pEF1α-SNAP26m-Pur.N4, or pEF1α-SNAP26m-Pur.N4-1.1k/1.1k is plotted.

FIG. 34 shows the result of FACS analysis of the cell group generated after transfection of pEF1α-SNAP26m-Pur-RE2, pEF1α-SNAP26m-Pur-1.1k/1.1k, pEF1α-SNAP26m-Pur.N4, or pEF1α-SNAP26m-Pur.N4-1.1k/1.1k and the drug selection. Also, FIG. 35 shows plots of rates of cells where the fluorescence intensity FL1 is not less than 200 and not less than 1000 respectively. As a result, it is noted that the higher the concentration of puromycin during the drug selection, the more the rate of the cells which highly express the SNAPm regardless of the presence/absence of the N4 sequence or CHO5Δ3-3. It is however noted that, when CHO5Δ3-3 or N4 sequence is used, the rate of the cells which highly express the SNAPm increases and, when they are used together, the rate of the highly expressing cells becomes the highest due to their synergism.

Example 18

Figure 36:
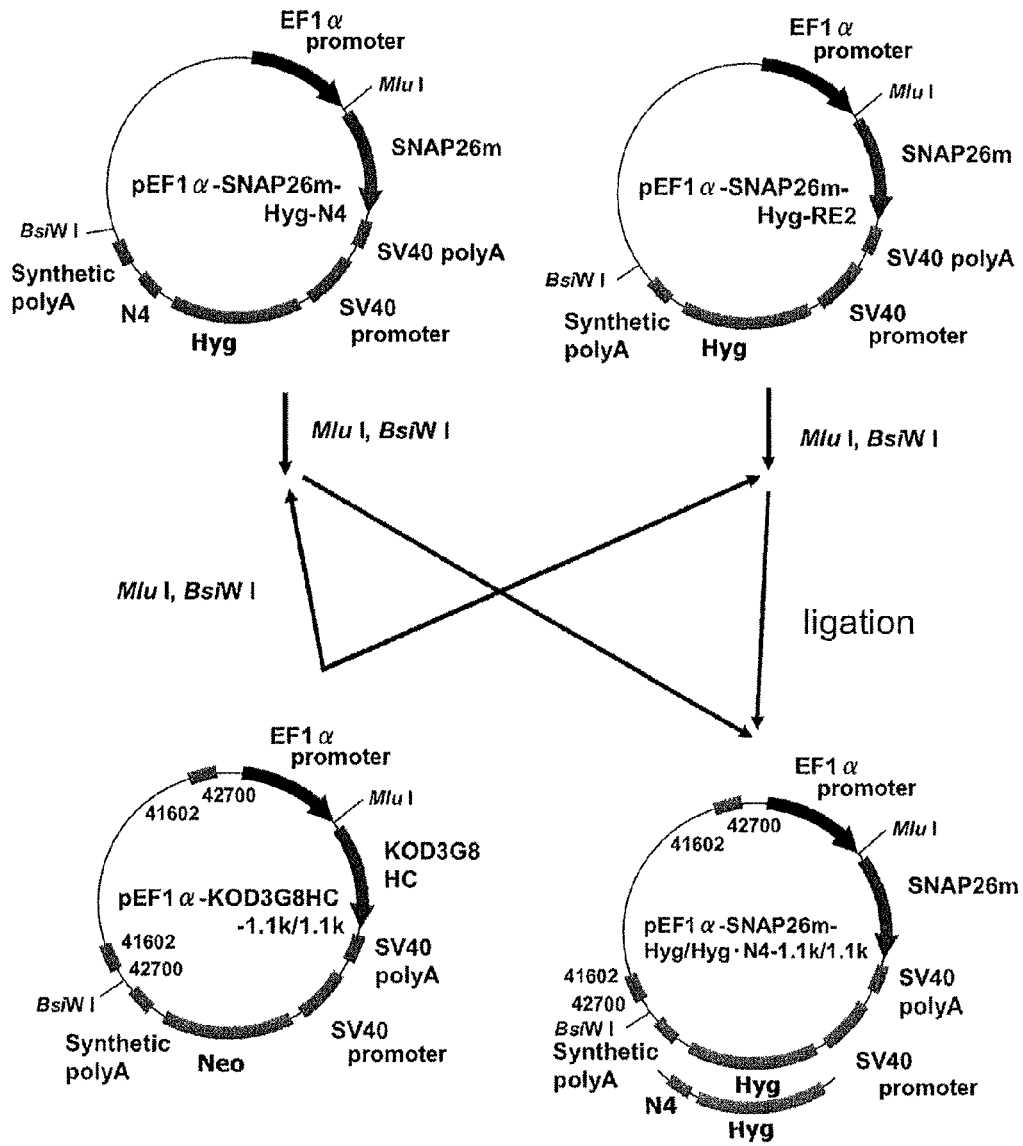
FIG. 36 shows the construction of pEF1α-SNAP26m-Hyg.N4-1.1k/1.1k and pEF1α-SNAP26m-Hyg-1.1k/1.1k.

Effect of Combination of an mRNA Destabilizing Sequence with a Gene Expression Stabilizing Element in the Hygromycin-Resistant Gene (1) Construction of pEF1α-SNAP26m-Hyg-1.1k/1.1k and pEF1α-SNAP26m-Hyg.N4-1.1k/1.1k In order to investigate the effect of combination of N4 sequence with CHO5Δ3-3 which was noted of its gene expression stabilizing ability in Example 15 for the hygromycin-resistant gene, pEF1α-SNAP26m-Hyg.N4-1.1k/1.1k and pEF1α-SNAP26m-Hyg-1.1k/1.1k were constructed according to the scheme shown in FIG. 36. Thus, SNAPm-pA-SV40 promoter-Hyg.N4-pA and SNAP26m-pA-SV40 promoter-Hyg-pA were excised from pEF1α-SNAP26m-Hyg.N4 and pEF1α-SNAP26m-Hyg-RE2 using the restriction enzymes MluI and BsiWI and transferred into the sites of the restriction enzymes MluI and BsiWI of pEF1α-KOD3G8HC-1.1k/1.1k to construct pEF1α-SNAP26m-Hyg.N4-1.1k/1.1k and pEF1α-SNAP26m-Hyg-1.1k/1.1k.

Example 19

(2) Investigation of the Effect of Combination of N4 Sequence with CHO5Δ3-3 in the Hygromycin-Resistant Gene CHO-K1 cells for a transfection was prepared by the method mentioned in Example 2. On the other hand, the SNAP26m expression constructs constructed in Example 6 and 18 were linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 800 μg/ml HygroGold. During the selective culture, the medium was exchanged every three to four days. After finishing the selective culture, the expression intensity of SNAP26m of the cell group was analyzed using the method mentioned in the Example 2.

Figure 37:
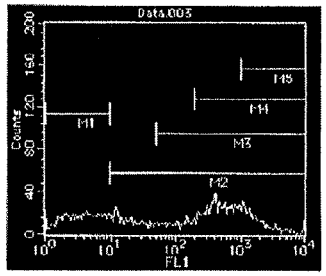
FIG. 37 shows the results of FACS analysis of the cell group which is transformed by pEF1α-SNAP26m-Hyg-RE2, pEF1α-SNAP26m-Hyg-1.1k/1.1k, pEF1α-SNAP26m-Hyg.N4, or pEF1α-SNAP26m-Hyg.N4-1.1k/1.1k.
Figure 37:
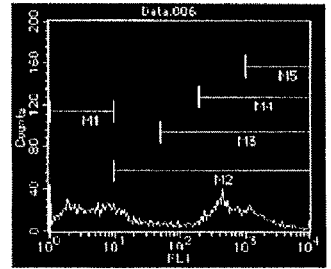
Figure 37:
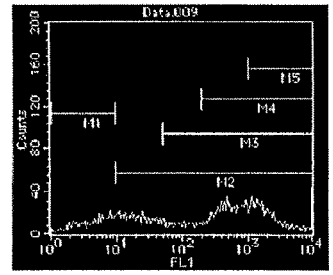
Figure 37:
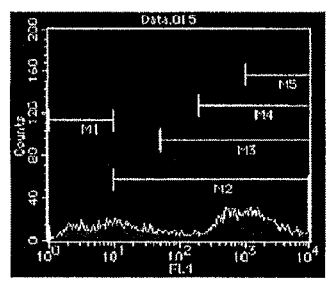
Figure 38:
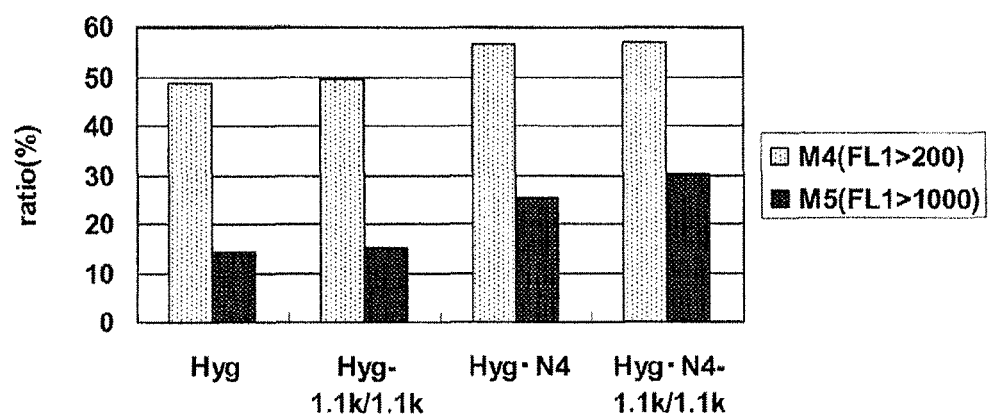
FIG. 38 is a graph where the rate of the cells which highly express SNAPm in the cell group transformed by pEF1α-SNAP26m-Hyg-RE2, pEF1α-SNAP26m-Hyg-1.1k/1.1k, pEF1α-SNAP26m-Hyg.N4, or pEF1α-SNAP26m-Hyg.N4-1.1k/1.1k is plotted.

FIG. 37 shows the result of FACS analysis of the cell group generated after transfection of pEF1α-SNAP26m-Hyg-RE2, pEF1α-SNAP26m-Hyg-1.1k/1.1k, pEF1α-SNAP26m-Hyg.N4, or pEF1α-SNAP26m-Hyg.N4-1.1k/1.1k and the drug selection. Also, FIG. 38 shows plots of rates of cells where the fluorescence intensity FL1 is not less than 200 and not less than 1000 respectively. As a result, it is noted that, when the N4 sequence which is an mRNA destabilizing factor is combined with the CHO5Δ3-3 which has a gene expression stabilizing effect, the rate of the cells which highly express the SNAPm further increases as compared with the case where the N4 sequence or the CHO5Δ3-3 is used solely and accordingly that the selection efficiency for the highly productive cells is enhanced.

Example 20

Figure 39:
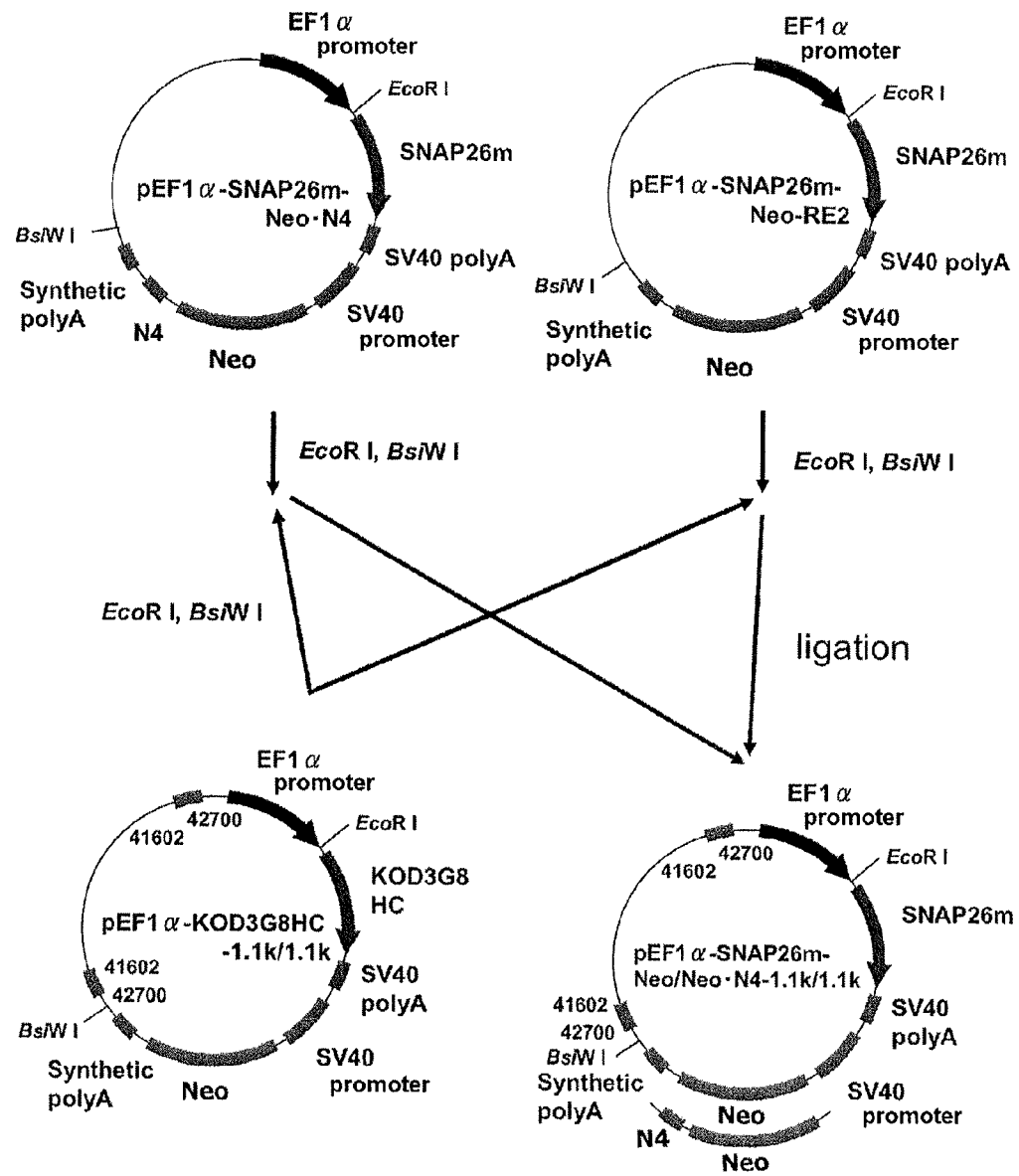
FIG. 39 shows the construction of pEF1α-SNAP26m-Neo.N4-1.1k/1.1k and pEF1α-SNAP26m-Neo-1.1k/1.1k.

Effect of Combination of an mRNA Destabilizing Sequence with a Gene Expression Stabilizing Element in the Neomycin-Resistant Gene (1) Construction of pEF1α-SNAP26m-Neo-1.1k/1.1k and pEF1α-SNAP26m-Neo.N4-1.1k/1.1k In order to investigate the effect of combination of N4 sequence with CHO5Δ3-3 which was noted of its gene expression stabilizing ability in Example 15 for the neomycin-resistant gene, pEF1α-SNAP26m-Neo.N4-1.1k/1.1k and pEF1α-SNAP26m-Neo-1.1k/1.1k were constructed according to the scheme shown in FIG. 39. Thus, SNAP26m-pA-SV40 promoter-Neo.N4-pA, SNAP26m-pA-SV40 promoter-Neo-pA were excised from pEF1α-SNAP26m-Neo.N4 and pEF1α-SNAP26m-Neo-RE2 using the restriction enzymes EcoRI and BsiWI and transferred into the sites of the restriction enzymes EcoRI and BsiWI of pEF1α-KOD3G8HC-1.1k/1.1k to construct pEF1α-SNAP26m-Neo.N4-1.1k/1.1k and pEF1α-SNAP26m-Neo-1.1k/1.1k.

Example 21

(2) Investigation of the Effect of Combination of N4 Sequence with CHO5Δ3-3 in the Neomycin-Resistant Gene CHO-K1 cells for a transfection was prepared by the method mentioned in Example 2. On the other hand, the SNAP26m expression constructs constructed in Example 8 and 20 were linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 1 mg/ml geneticin G418. During the selective culture, the medium was exchanged every three to four days. After finishing the selective culture, the expression intensity of SNAP26m of the cell group was analyzed using the method mentioned in the Example 2.

Figure 40:
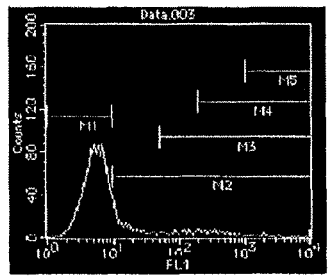
FIG. 40 shows the results of FACS analysis of the cell group which is transformed by pEF1α-SNAP26m-Neo-RE2, pEF1α-SNAP26m-Neo-1.1k/1.1k, pEF1α-SNAP26m-Neo.N4, or pEF1α-SNAP26m-Neo.N4-1.1k/1.1k.
Figure 40:
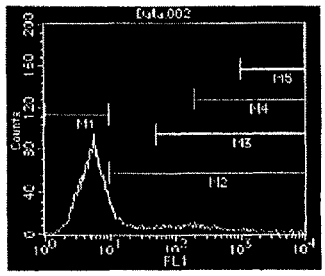
Figure 40:
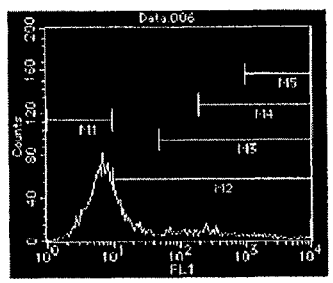
Figure 40:
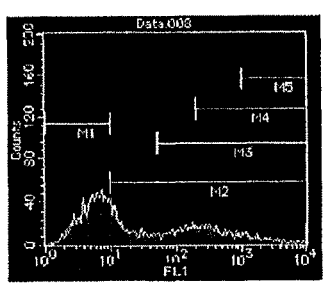
Figure 41:
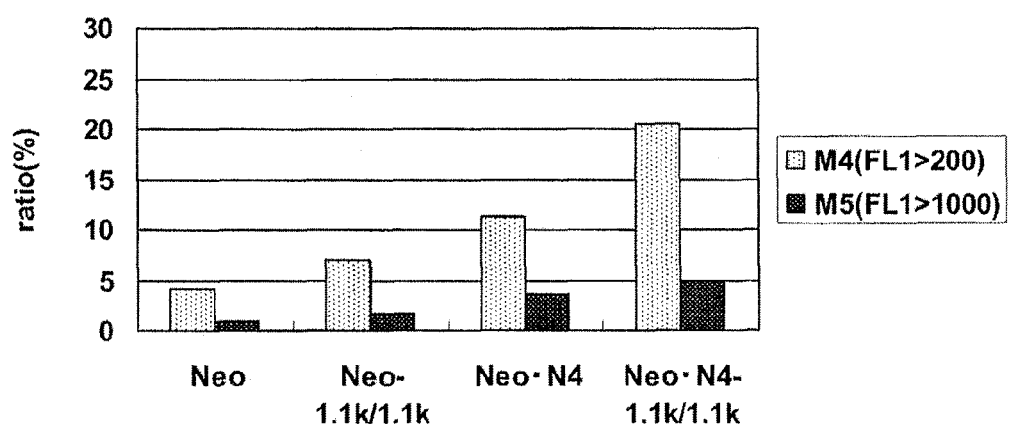
FIG. 41 is a graph where the rate of the cells which highly express SNAPm in the cell group transformed by pEF1α-SNAP26m-Neo-RE2, pEF1α-SNAP26m-Neo-1.1k/1.1k, pEF1α-SNAP26m-Neo.N4, or pEF1α-SNAP26m-Neo.N4-1.1k/1.1k is plotted.

FIG. 40 shows the result of FACS analysis of the cell group generated after transfection of pEF1α-SNAP26m-Neo-RE2, pEF1α-SNAP26m-Neo-1.1k/1.1k, pEF1α-SNAP26m-Neo.N4, or pEF1α-SNAP26m-Neo.N4-1.1k/1.1k and the drug selection. Also, FIG. 41 shows plots of rates of cells where the fluorescence intensity FL1 is not less than 200 and not less than 1000 respectively. As a result, it is noted that, when the N4 sequence which is an mRNA destabilizing factor is combined with the CHO5Δ3-3 which has a gene expression stabilizing effect, the rate of the cells which highly express the SNAPm further increases as compared with the case where the N4 sequence or the CHO5Δ3-3 is used solely and accordingly that the selection efficiency for the highly productive cells is enhanced.

Example 22

Investigation of Repeated Sequence Numbers of ARE Sequence Motif in the Presence of CHO5Δ3-3

Figure 42:
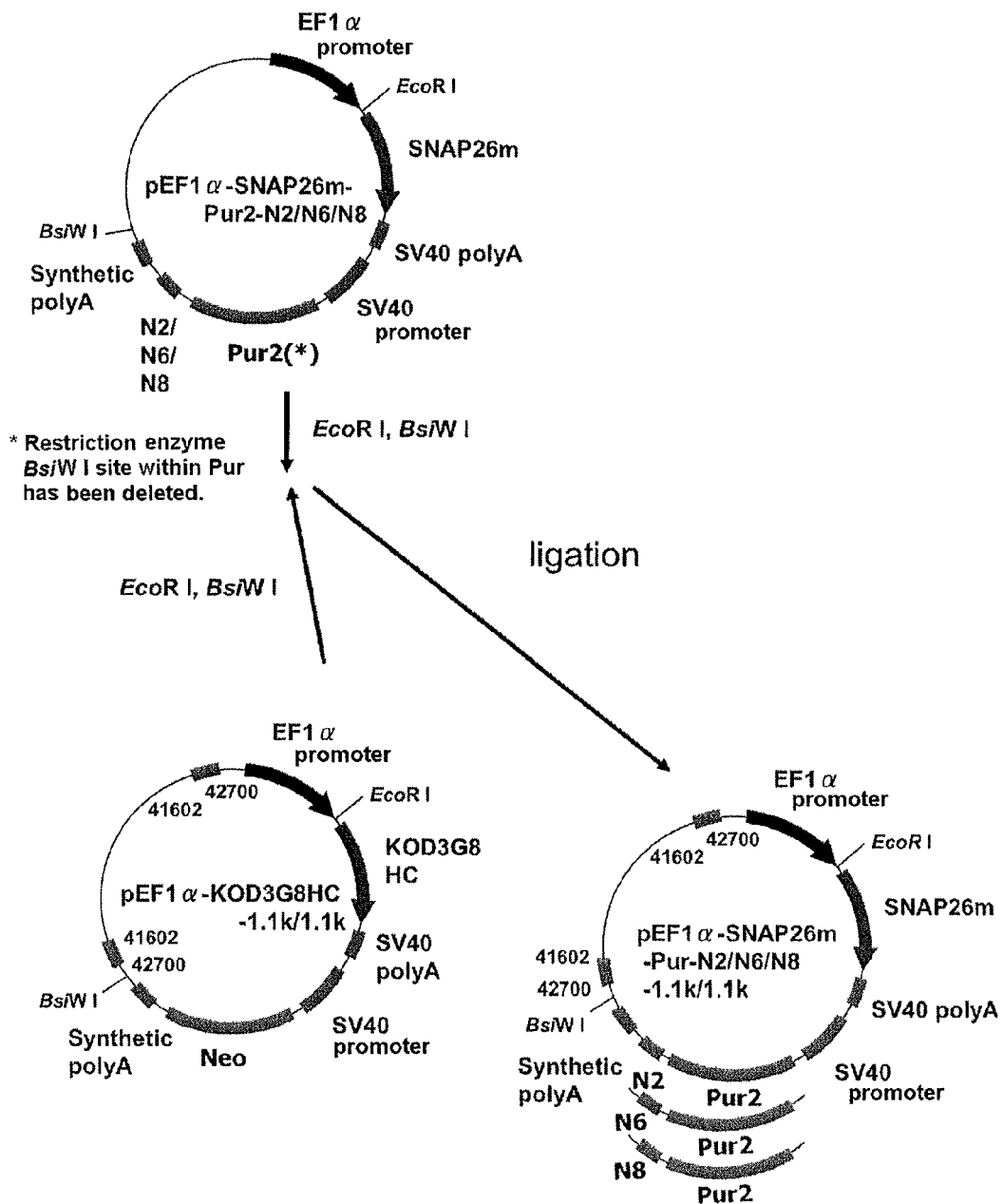
FIG. 42 shows the construction of pEF1α-SNAP26m-Pur.N2-1.1k/1.1k, pEF1α-SNAP26m-Pur.N6-1.1k/1.1k, and pEF1α-SNAP26m-Pur.N8-1.1k/1.1k.

Plasmids pEF1α-SNAP26m-Pur.N2-1.1k/1.1k, pEF1α-SNAP26m-Pur.N6-1.1k/1.1k, and pEF1α-SNAP26m-Pur.N8-1.1k/1.1k were constructed according to the scheme shown in FIG. 42. First, the plasmids pEF1α-SNAP26m-Pur.N2, pEF1α-SNAP26m-Pur.N6, and pEF1α-SNAP26m-Pur.N8 constructed in Example 10 were used as templates and inverse PCR using the KOD-Plus-Mutagenesis Kit was carried out using the primers of SEQ ID Nos. 54 and 55 to construct plasmids pEF1α-SNAP26m-Pur2.N2, pEF1α-SNAP26m-Pur2.N6, and pEF1α-SNAP26m-Pur2.N8 wherein the restriction enzyme BsiWI site existing in the puromycin-resistant gene was deleted. After that, a SNAP26m-pA-SV40 promoter-Pur2.N2-pA, SNAP26m-pA-SV40 promoter-Pur2.N6-pA, and SNAP26m-pA-SV40 promoter-Pur2.N8-pA were excised from pEF1α-SNAP26m-Pur2.N2, pEF1α-SNAP26m-Pur2.N6, and pEF1α-SNAP26m-Pur2.N8 using the restriction enzymes EcoRI and BsiWI and transferred into the sites of the restriction enzymes EcoRI and BsiWI of pEF1α-KOD3G8HC-1.1k/1.1k to construct pEF1α-SNAP26m-Pur.N2-1.1k/1.1k, pEF1α-SNAP26m-Pur.N6-1.1k/1.1k, and pEF1α-SNAP26m-Pur.N8-1.1k/1.1k.

CHO-K1 cells for a transfection was prepared by the method mentioned in Example 2. On the other hand, each SNAP26m expression constructs of pEF1α-SNAP26m-Pur-1.1k/1.1k, pEF1α-SNAP26m-Pur.N2-1.1k/1.1k, pEF1α-SNAP26m-Pur.N4-1.1k/1.1k, pEF1α-SNAP26m-Pur.N6-1.1k/1.1k, and pEF1α-SNAP26m-Pur.N8-1.1k/1.1k was linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for a week in a Ham's F12 medium supplemented with 10% FBS and 10 μg/ml puromycin. During the selective culture, the medium was exchanged every three to four days. After finishing the selective culture, the expression intensity of SNAP26m of the cell group was analyzed using the method mentioned in the Example 2.

Figure 43:
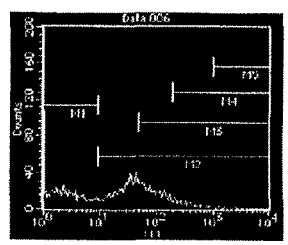
FIG. 43 shows the results of FACS analysis of the cell group which is transformed by pEF1α-SNAP26m-Pur-1.1k/1.1k, pEF1α-SNAP26m-Pur.N2-1.1k/1.1k, pEF1α-SNAP26m-Pur.N4-1.1k/1.1k, pEF1α-SNAP26m-Pur.N6-1.1k/1.1k, or pEF1α-SNAP26m-Pur.N8-1.1k/1.1k.
Figure 43:
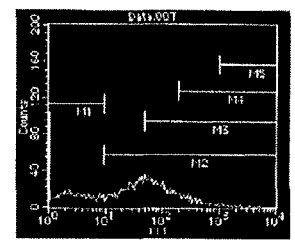
Figure 43:
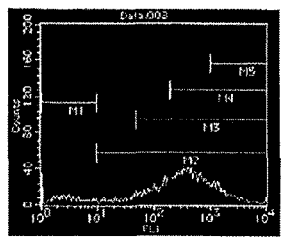
Figure 43:
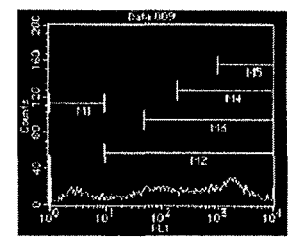
Figure 43:
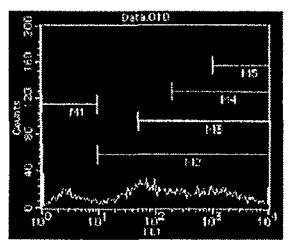
Figure 44:
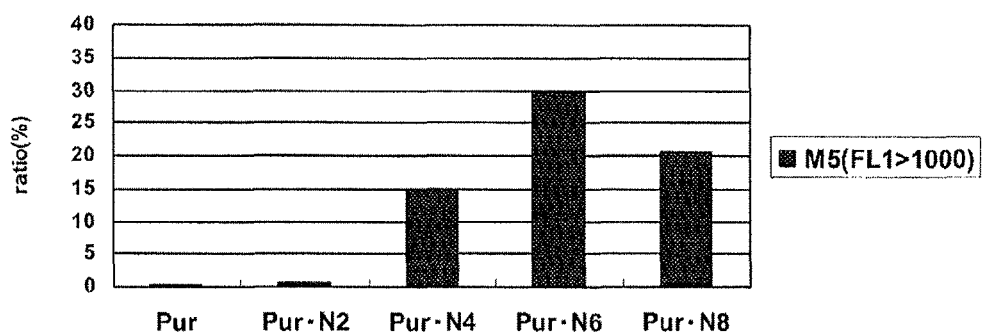
FIG. 44 is a graph where the rate of the cells which highly express SNAPm in the cell group transformed by pEF1α-SNAP26m-Pur-1.1k/1.1k, pEF1α-SNAP26m-Pur.N2-1.1k/1.1k, pEF1α-SNAP26m-Pur.N4-1.1k/1.1k, pEF1α-SNAP26m-Pur.N6-1.1k/1.1k, or pEF1α-SNAP26m-Pur.N8-1.1k/1.1k is plotted.

FIG. 43 shows the result of FACS analysis of the cell group generated after transfection of pEF1α-SNAP26m-Pur-1.1k/1.1k, pEF1α-SNAP26m-Pur.N2-1.1k/1.1k, pEF1α-SNAP26m-Pur N4-1.1k/1.1k, pEF1α-SNAP26m-Pur.N6-1.1k/1.1k, or pEF1α-SNAP26m-Pur.N8-1.1k/1.1k and the drug selection. When FACS analysis was carried out under the conditions until Example 19, fluorescence intensity FL1 of the cells was too strong and it was not possible to correctly calculate the rate of the highly expressing cells. Therefore, the fluorescence sensitivity of the flow cytometer was lowered and investigation was done once again. The result thereof is shown in FIG. 43. Further, FIG. 44 shows the plot of the rates of the cells where the fluorescence intensity FL1 is 1000 or higher. As a result, it was confirmed that, even in the case where the expression cassette was sandwiched by CHO5Δ3-3, when transformation was conducted using pEF1α-SNAP26m-Pur.N6-1.1K/1.1k or pEF1α-SNAP26m-Pur.N8-1.1K/1.1k (i.e. a plasmid into which N6 or N8 was inserted), the rate of the cells which highly express the SNAPm was much more and the selection efficiency of the highly productive cells was significantly enhanced as compared with the case of pEF1α-SNAP26m-Pur.N4-1.1k/1.1k.

Example 23

Figure 45:
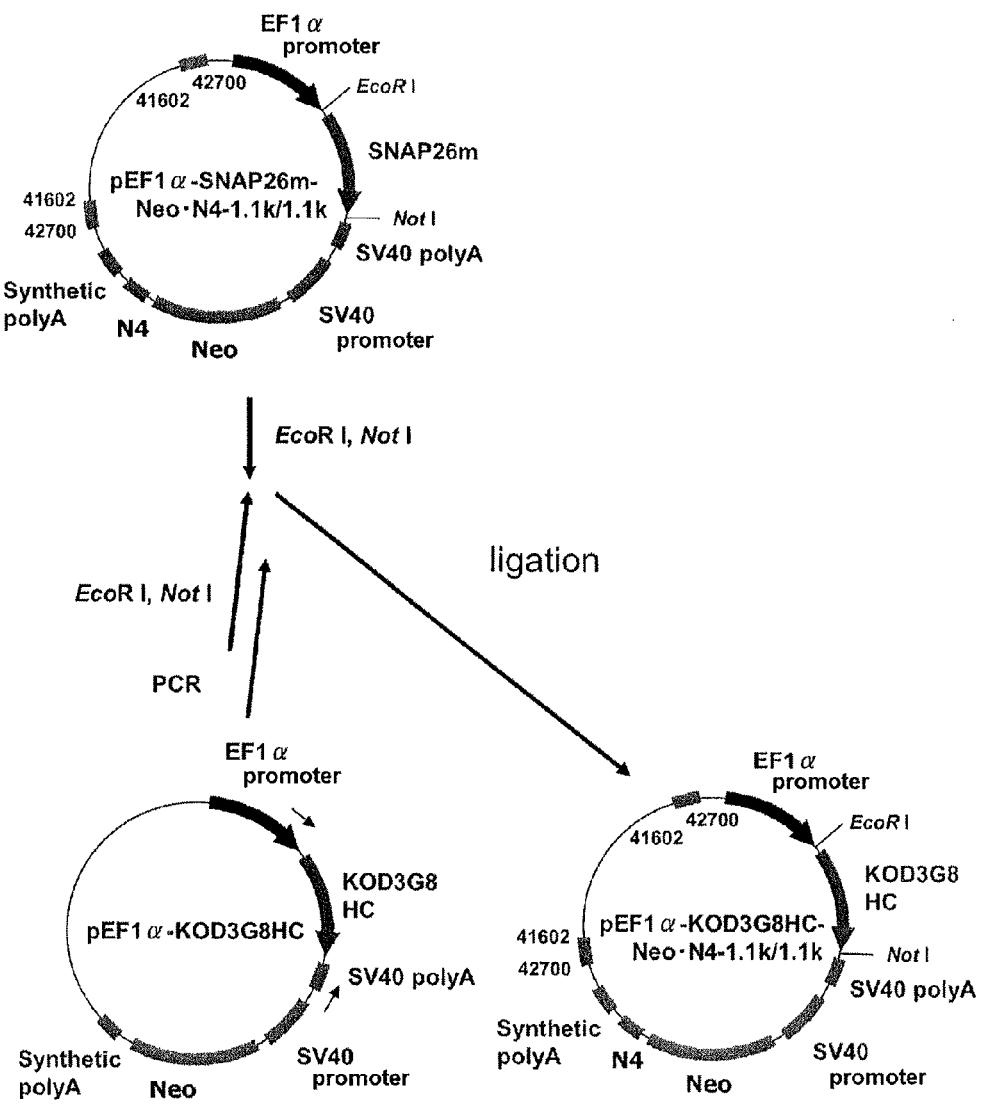
FIG. 45 shows the construction of pEF1α-KOD3G8HC-Neo.N4-1.1k/1.1k.

Effect of Combination of mRNA Destabilizing Sequence with Gene Expression Stabilizing Element in the Antibody Production System (1) Construction of pEF1α-KOD3G8HC-Neo.N4-1.1k/1.1k In order to investigate the joint use of the mRNA destabilizing sequence (N4 sequence) with the gene expression stabilizing element CHO5Δ3-3 which was recognized for its gene expression stabilizing effect in Example 15 in the antibody production system, pEF1α-KOD3G8HC-Neo.N4-1.1k/1.1k was constructed according to the scheme shown in FIG. 45. As to the antibody gene, the gene of the antibody (anti-KOD antibody) obtained from a mouse hybridoma cell strain 3G8 (deposition number: FERM BP-6056; available from the International Patent Organism Depositary, the National Institute of Advanced Industrial Science and Technology) which produces an antibody specific to DNA polymerase derived from KOD1 strain of *Thermococcus kodakaraensis* was used.

Thus, pEF1α-SNAP26m-Neo.N4-1.1k/1.1k mentioned in Example 20 was treated with restriction enzymes EcoRI and NotI to excise the SNAP26m gene. On the other hand, heavy chain gene of anti-KOD antibody was prepared from pEF1α-KOD3G8HC mentioned in Example 4 by PCR amplification using primers of SEQ ID Nos: 56 and 57 followed by treating with the restriction enzymes EcoRI and NotI, and this heavy chain gene was transferred into the sites of EcoRI and NotI of pEF1α-SNAP26m-Neo.N4-1.1k/1.1k to construct pEF1α-KOD3G8HC-Neo.N4-1.1k/1.1k.

Example 24

(2) Construction of pEF1α-KOD3G8LC-Hyg-1.1k/1.1k

Figure 46:
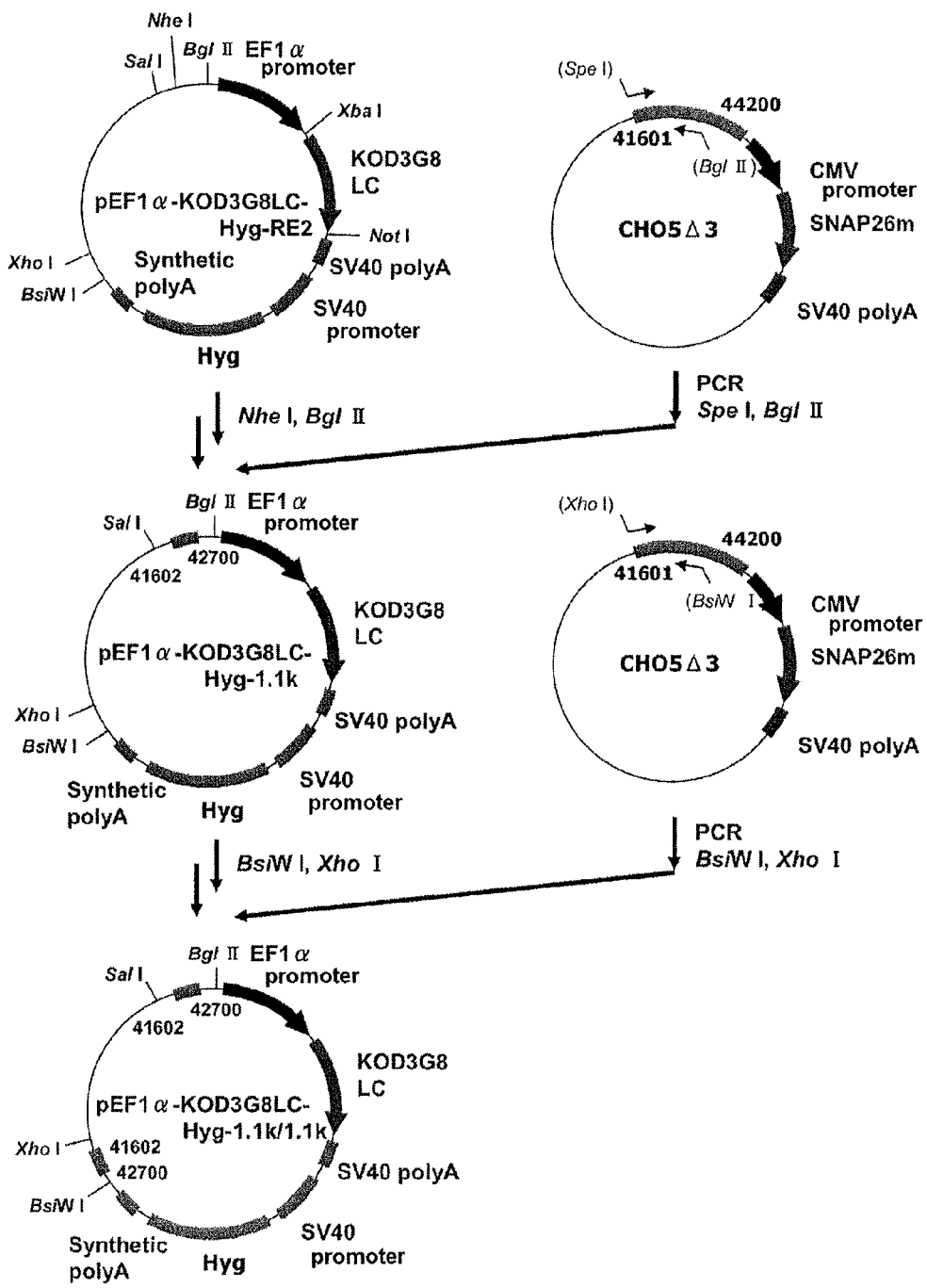
FIG. 46 shows the construction of pEF1α-KOD3G8LC-Hyg-1.1k/1.1k.

In order to investigate the joint effect of the N4 sequence with the CHO5Δ3-3 which was recognized of its gene expression stabilizing ability in Example 15 in the antibody production system, pEF1α-KOD3G8LC-Hyg-1.1k/1.1k was constructed according to the scheme shown in FIG. 46. Thus, firstly, a gene expression stabilizing element CHO5Δ3-3 (hereinafter, it will be referred to as 1.1k in the construct) amplified by PCR using a primer set of SEQ ID Nos: 50 and 51 was inserted into the sites of restriction enzymes NheI and BglII on the upstream region of the expression cassette of pEF1α-KOD3G8LC-Hyg-RE2 constructed during the process of Example 6 to construct a plasmid pEF1α-KOD3G8LC-Hyg-1.1k. Further, a gene expression stabilizing element CHO5Δ3-3 amplified by PCR using a primer set of SEQ ID Nos: 52 and 53 was inserted into the sites of the restriction enzymes BsiWI and XhoI of the downstream region of the expression cassette of a plasmid pEF1α-KOD3G8LC-1.1k to construct pEF1α-KOD3G8LC-Hyg-1.1k/1.1k.

Example 25

(3) Construction of pEF1α-KOD3G8LC-Hyg.N4-1.1k/1.1k

Figure 47:
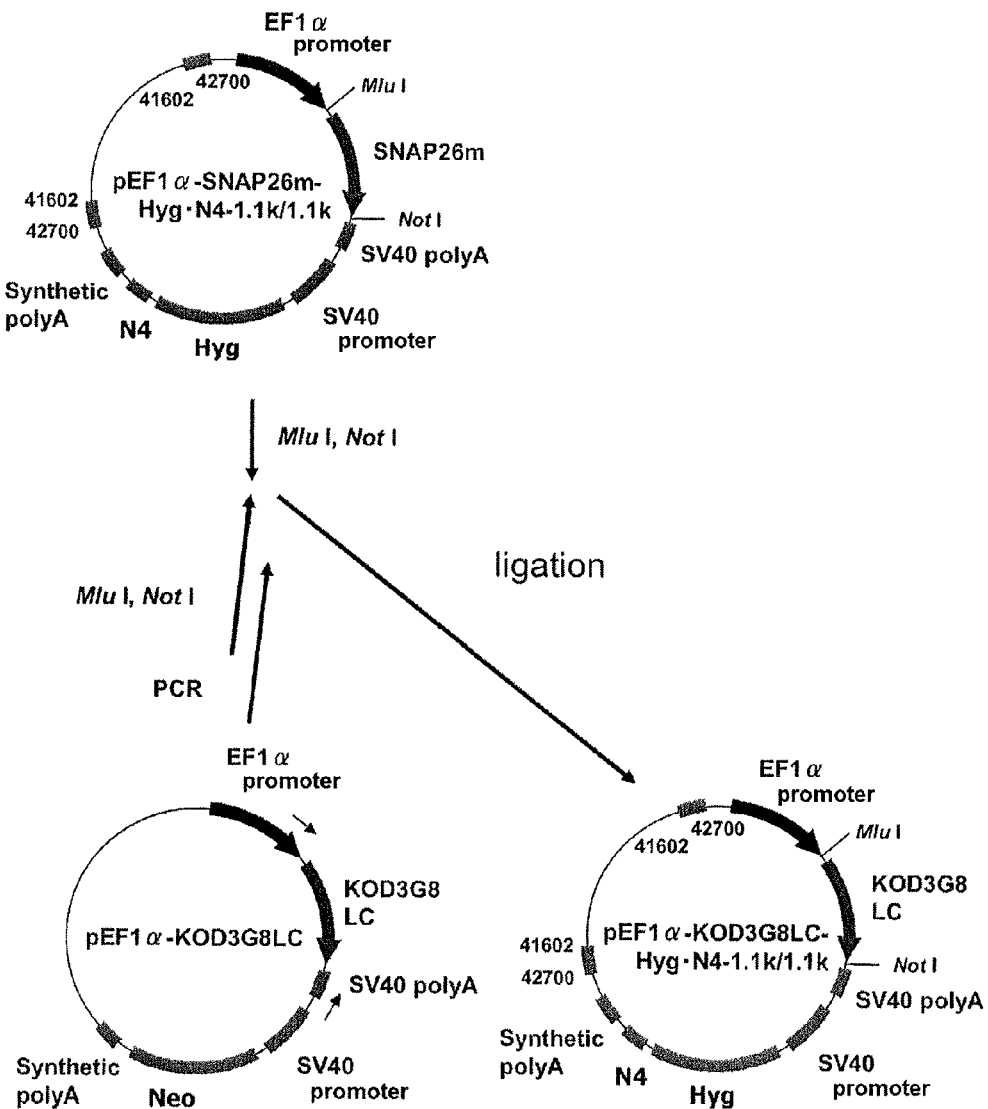
FIG. 47 shows the construction of pEF1α-KOD3G8LC-Hyg.N4-1.1k/1.1k.

In order to investigate the joint effect of the N4 sequence with the CHO5Δ3-3 which was recognized of its gene expression stabilizing ability in Example 15 in the antibody production system, pEF1α-KOD3G8LC-Hyg.N4-1.1k/1.1k was constructed according to the scheme shown in FIG. 47. Thus, pEF1α-SNAP26m-Hyg.N4-1.1k/1.1k mentioned in Example 18 was treated with the restriction enzymes MluI and NotI to excise SNAP26m gene. On the other hand, the light chain gene of the anti-KOD antibody was prepared from the pEF1α-KOD3G8LC mentioned in Example 6 by PCR amplification using the primers of SEQ ID Nos: 56 and 57 followed by treating with the restriction enzymes MlutI and NotI, and this light chain gene was transferred into the sites of the restriction enzymes MluI and NotI of pEF1α-SNAP26m-Hyg.N4-1.1k/1.1k to construct pEF1α-KOD3G8LC-Hyg.N4-1.1k/1.1k.

Example 26

(4) Construction of pEF1α-KOD3G8HC-Pur.N4-1.1k/1.1k

Figure 48:
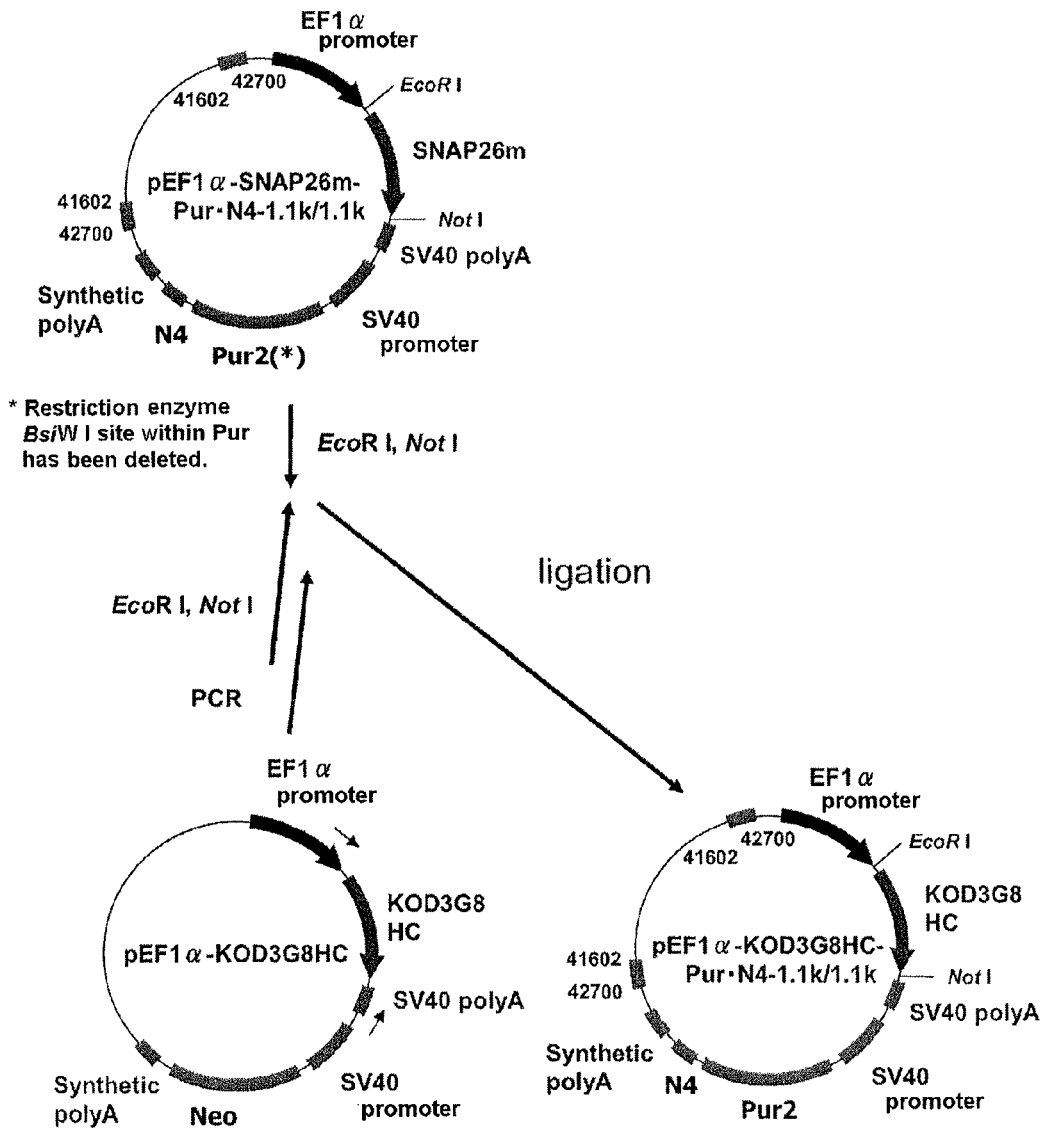
FIG. 48 shows the construction of pEF1α-KOD3G8HC-Pur.N4-1.1k/1.1k.

In order to investigate the joint effect of the N4 sequence with the CHO5Δ3-3 which was recognized of its gene expression stabilizing ability in Example 15 in the antibody production system, pEF1α-KOD3G8HC-Pur.N4-1.1k/1.1k was constructed according to the scheme shown in FIG. 48. Thus, pEF1α-SNAP26m-Pur.N4-1.1k/1.1k mentioned in Example 16 was treated with the restriction enzymes EcoRI and NotI to excise SNAP26m gene. On the other hand, the heavy chain gene of the anti-KOD antibody was prepared from the pEF1α-KOD3G8HC mentioned in Example 4 by PCR amplification using the primers of SEQ ID Nos: 56 and 57 followed by treating with the restriction enzymes EcoRI and NotI, and this heavy chain gene was transferred into the sites of the restriction enzymes EcoRI and NotI of pEF1α-SNAP26m-Pur.N4-1.1k/1.1k to construct pEF1α-KOD3G8HC-Pur.N4-1.1k/1.1k.

Example 27

(5) Investigation of the Effect by Combination of the N4 Sequence with the CHO5Δ3-3 in Polyclone in an Anti-KOD Antibody Expression System Each of the pEF1α-KOD3G8HC-RE2 (hereinafter, it will be referred to as −/Neo), the pEF1α-KOD3G8HC-1.1k/1.1k (hereinafter, it will be referred to as 1.1k/Neo), the pEF1α-KOD3G8HC-Neo.N4-1.1k/1.1k (hereinafter, it will be referred to as 1.1k/Neo.N4) and the pEF1α-KOD3G8HC-Pur.N4-1.1k/1.1k (hereinafter, it will be referred to as 1.1k/Pur.N4), which are heavy chain (HC) expression constructs of the anti-KOD antibody, as well as the pEF1α-KOD3G8LC-Hyg-RE2 (hereinafter, it will be referred to as −/Hyg), the pEF1α-KOD3G8LC-Hyg-1.1k/1.1k (hereinafter, it will be referred to as 1.1k/Hyg), and the pEF1α-KOD3G8LC-Hyg.N4-1.1k/1.1k (hereinafter, it will be referred to as 1.1k/Hyg.N4), which are light chain (LC) expression constructs of the anti-KOD antibody was linearized using a restriction enzyme AhdI. Then the heavy chain and light chain expression constructs were mixed for each of the followings so as to make the ratio by weight of the heavy chain expression construct of the antibody to the light chain expression construct of the antibody 1:1 whereupon a mixed plasmid was prepared:

(1) that where no gene expression stabilizing element was contained therein (−/Neo and −/Hyg);

(2) that where the gene expression stabilizing element CHO5Δ3-3 was inserted into both of the upstream and downstream regions of the antibody expression cassette (1.1k/Neo and 1.1k/Hyg);

(3) that where the gene expression stabilizing element CHO5Δ3-3 was inserted into both of the upstream and downstream regions of the antibody expression cassette and the mRNA destabilizing sequence (N4 sequence) was added to the drug-resistant gene (heavy chain: Neo; light chain: Hyg) (1.1k/Neo.N4 and 1.1k/Hyg.N4); and (4) that where the gene expression stabilizing element CHO5Δ3-3 was inserted into both of the upstream and downstream regions of the antibody expression cassette and the mRNA destabilizing sequence (N4 sequence) was added to the drug-resistant gene (heavy chain: Pur; light chain: Hyg) (1.1k/Pur.N4 and 1.1k/Hyg.N4).

The above mixed plasmid (2 μg) was transfected to the CHO-K1 cells which were seeded on a 6-well plate on the previous day and cultivated for 24 hours. On the next day, the medium was removed and the cells were dispersed by treating with 2.5 g/l-trypsin and 1 mmol/l-EDTA solution, transferred to a 90-mm Petri dish and subjected to a selective culture for two weeks in a Ham's F12 medium supplemented with 10% FBS as well as geneticin G418 and HygroGold, or puromycin and HygroGold. During the selective culture, the medium was exchanged every three to four days. For the case where no gene expression stabilizing element was contained therein (−/Neo, −/Hyg) and for the case where the gene expression stabilizing element CHO5Δ3-3 was inserted into both of the upstream and downstream regions of the antibody expression cassette (1.1k/Neo, 1.1k/Hyg), a selective culture was carried out using 600 µg/ml of geneticin G418 and 400 µg/ml of HygroGold. For the case where the gene expression stabilizing element CHO5Δ3-3 was inserted into both of the upstream and downstream regions of the expression cassette and mRNA destabilizing sequence (N4 sequence) was added to the drug-resistant gene (H chain: Neo; L chain: Hyg) (1.1k/Neo.N4, 1.1k/Hyg.N4), a selective culture was carried out using 400 µg/ml of geneticin G418 and 200 µg/ml of HygroGold. For the case where the gene expression stabilizing element CHO5Δ3-3 was inserted into both of the upstream and downstream regions of the expression cassette and mRNA destabilizing sequence (N4 sequence) was added to the drug-resistant gene (heavy chain: Pur; light chain: Hyg) (1.1k/Pur.N4, 1.1k/Hyg.N4), a selective culture was carried out using 7.5 µg/ml of puromycin and 400 µg/ml of HygroGold. After finishing the selective culture, the cells were dispersed by treating with 2.5 g/l-trypsin and 1 mmol/l-EDTA Solution and were seeded on a 6-well plate at 1.84×10$^5$ cells per well. After cultivating for three days, the supernatant of the culture was recovered and the production amount of KOD3G8 antibody in the polyclone was measured by means of ELISA (where DNA polymerase derived from *Pyrococcus kodakaraensis* KOD1 was made into a solid phase).

To be more specific, the supernatant of the culture was added to ELISA plate where DNA polymerase derived from KOD1 was made into a solid phase in a concentration of 30 µg/ml and cultivated at 35° C. for two hours. After that, it was washed with PBS-T (a phosphate-buffered saline containing 0.1% of Tween 20), 50 µl of anti-mouse antibody-HRP (manufactured by DAKO) diluted to an extent of 10,000 times was added followed by cultivating at 35° C. for one hour and it was further washed with PBS-T for three times and the mixture was made to react with TMB+ (3,3',5,5'-tetramethylbenzidine; manufactured by DAKO) for 5 minutes. After ceasing the reaction by addition of 50 µl of 1N sulfuric acid, its absorbance was measured using a plate reader (product name; SPECTRA CLASSIC, manufactured by TECAN Auctria) (main wavelength: 450 nm; subsidiary wavelength: 620 nm).

Concentration of the antibody was calculated on the basis of a calibration curve prepared from a standard substance. As to the standard substance, an antibody obtained from mouse hybridoma cell line 3G8 (deposition number: FERM BP-6056; available from the International Patent Organism Depositary, the National Institute of Advanced Industrial Science and Technology) which produces an antibody being specific to DNA polymerase derived from KOD1 was used. The result is shown in FIG. 49. As will be apparent from FIG. 49, the production amount of the antibody increased to an extent of about twice in the case in which the gene expression stabilizing element CHO5Δ3-3 was inserted into both of the upstream and downstream regions of the expression cassette (1.1k/Neo, 1.1k/Hyg) as compared with the case containing no gene expression stabilizing element (−/Neo, −/Hyg) while, in the case in which the gene expression stabilizing element CHO5Δ3-3 was inserted into both of the upstream and downstream regions of the expression cassette and mRNA destabilizing sequence (N4 sequence) was added to the drug-resistant gene (H chain: Neo; L chain: Hyg) (1.1k/Neo.N4, 1.1k/Hyg.N4), production amount of the antibody further increased to an extent of about thrice. In addition, when the drug-resistant gene of the heavy chain expressing construct was changed from Neo to Pur in the case in which the gene expression stabilizing element CHO5Δ3-3 was inserted into both of the upstream and downstream regions of the expression cassette and mRNA destabilizing sequence (N4 sequence) was added to the drug-resistant gene, production amount of the antibody significantly increased showing the antibody production of about five times higher as compared with the expression construct having neither gene expressing element nor mRNA destabilizing sequence.

Example 28

(6) Investigation of the Effect by Combination of the N4 Sequence with the CHO5Δ3-3 in Monoclone in an Anti-KOD Antibody Expression System After that, concerning each of the case containing no gene expression stabilizing element (−/Neo, −/Hyg), the case where the gene expression stabilizing element CHO5Δ3-3 was inserted into both of the upstream and downstream regions of the expression cassette (1.1k/Neo, 1.1k/Hyg), the case where the gene expression stabilizing element CHO5Δ3-3 was inserted into both of the upstream and downstream regions of the expression cassette and the mRNA destabilizing sequence (N4 sequence) was added to the drug-resistant gene (H chain: Neo; L chain: Hyg) (1.1k/Neo.N4, 1.1k/Hyg.N4), and the case where the gene expression stabilizing element CHO5Δ3-3 was inserted into both of the upstream and downstream regions of the expression cassette and the mRNA destabilizing sequence (N4 sequence) was added to the drug-resistant gene (H chain: Pur; L chain: Hyg) (1.1k/Pur.N4, 1.1k/Hyg.N4), cell group generated after the selection was subjected to a limiting dilution and the productivity in monoclone was compared.

To be more specific, polyclone cells of Example 27 which stably expressed the KOD3G8 antibody were treated with 2.5 g/l-trypsin and 1 mmol/l-EDTA solution to disperse the cells followed by sowing on a 96-well plate in a concentration of 0.75 cell/well. After cultivating for two weeks, the supernatant of the culture was recovered and the production amount of the KOD3G8 antibody was measured by ELISA according to the same manner as in Example 27. Antibody production amount of each clone was calculated on the basis of a calibration curve prepared from the standard substance. The clone showing the high expression amount in each of the case where no gene expression stabilizing element was contained (−/Neo, −/Hyg), the case where the gene expression stabilizing element CHO5Δ3-3 was inserted into both of the upstream and downstream regions of the expression cassette (1.1k/Neo, 1.1k/Hyg), the case where the gene expression stabilizing element CHO5Δ3-3 was inserted into both of the upstream and downstream regions of the expression cassette and the mRNA destabilizing sequence (N4 sequence) was added to the drug-resistant gene (H chain: Neo; L chain: Hyg) (1.1k/Neo.N4, 1.1k/Hyg.N4), and the case where the gene expression stabilizing element CHO5Δ3-3 was inserted into both of the upstream and downstream regions of the expression cassette and the mRNA destabilizing sequence (N4 sequence) was added to the drug-resistant gene (H chain: Pur; L chain: Hyg) (1.1k/Pur.N4, 1.1k/Hyg.N4) was subjected to an expansive culture. After that, cells were seeded on a 6-well plate at 1.84×10$^5$ cells per well. After cultivating for three days, the supernatant of the culture was recovered and the production amount of KOD3G8 antibody in monoclone was measured by ELISA according to the same manner as in Example 27.

FIG. 50 shows a graph where the antibody production amounts in each clone calculated on the basis of a calibration curve prepared from the standard substance are plotted. The result was that, the same as in the case where the productivity in polyclone was compared, the antibody production amount increased in the case where the gene expression stabilizing element CHO5Δ3-3 was inserted into both of the upstream and downstream regions of the antibody expression cassette (1.1k/Neo, 1.1k/Hyg) compared with the case containing no gene expression stabilizing element therein (−/Neo, −/Hyg). In the case where the test sequence CHO5Δ3-3 was inserted into both of the upstream and downstream regions of the antibody expression cassette and the mRNA destabilizing sequence (N4 sequence) was added to the drug-resistant gene (H chain: Neo; L chain: Hyg) (1.1k/Neo.N4, 1.1k/Hyg.N4), the antibody production amount further increased. In addition, in the case where the gene expression stabilizing element CHO5Δ3-3 was inserted into both of the upstream and downstream regions of the antibody expression cassette and the mRNA destabilizing sequence (N4 sequence) was added to the drug-resistant gene, the antibody production amount of each clone significantly increased when the drug-resistant gene of the heavy chain expression construct was changed from Neo.N4 to Pur.N4 whereby the rate of the clone showing a high antibody productivity becomes remarkably big. From the result as such, it was confirmed that the selection efficiency of the highly productive cells in the antibody production system significantly increases.

In order to further confirm the effect, the production amount of the KOD3G8 antibody calculated by the ELISA measurement after the above cultivation in the 96-well plate for two weeks was analyzed once again for the case where neither gene expression stabilizing element nor mRNA destabilizing sequence was contained (−/Neo, −/Hyg) and for the case where the gene expression stabilizing element CHO5Δ3-3 was contained and mRNA destabilizing sequence (N4 sequence) was further added to the drug-resistant gene (H chain: Pur; L chain: Hyg) (1.1k/Pur.N4, 1.1k/Hyg.N4) and the result was plotted in terms of frequency distribution. The result is shown in FIG. 51. Thus, as a result thereof, distribution of the clone to the production amount of KOD3G8 significantly shifted to the high production side in 1.1k/Pur.N4 and 1.1k/Hyg.N4 whereby the rate of the cells having a very high antibody productivity significantly increased. It was therefore confirmed that, due to the synergism, utilization of gene expression stabilizing element and drug selective marker gene expression cassette containing mRNA destabilizing sequence very greatly contributes in the procurement of a highly productive cell strain.

Example 29

Investigation of the Effect by Combination of N4 Sequence with CHO5Δ3-3 in Polyclone in the Anti-KOD Antibody Expression System Using Serum-Free Adapted CHO Cells CHO-K1 cells were subjected to a serum-free adaptation using a EX-CELL CD CHO Serum-Free Medium for CHO Cells, chemically defined (manufactured by SAFC Biosciences) according to the protocol attached thereto. The serum-free adapted CHO-K1 cells were suspended in a Opti-MEM I Reduced-Serum Medium (manufactured by GIBCO) in a concentration of $2.5 \times 10^5$ cell/ml and then each 1 ml of the suspension was seeded per four wells on a 24-well plate of a ultra-low attachment surface (manufactured by Corning Incorporated).

Each of the pEF1α-KOD3G8HC-1.1k/1.1k (hereinafter, it will be referred to as 1.1k/Neo) and the pEF1α-KOD3G8HC-Pur.N4-1.1k/1.1k (hereinafter, it will be referred to as 1.1k/Pur.N4) which are heavy chain (HC) expression constructs of the anti-KOD antibody, as well as the pEF1α-KOD3G8LC-Hyg-1.1k/1.1k (hereinafter, it will be referred to as 1.1k/Hyg) and the pEF1α-KOD3G8LC-Hyg.N4-1.1k/1.1k (hereinafter, it will be referred to as 1.1k/Hyg.N4) which are light chain (LC) expression constructs of the anti-KOD antibody was linearized using a restriction enzyme AhdI. Then the heavy chain and light chain expression constructs were mixed for each of the followings so as to make the ratio by weight of the heavy chain expression construct of the antibody to the light chain expression construct of the antibody 1:1 whereupon a mixed plasmid was prepared:

(1) that where the gene expression stabilizing element CHO5Δ3-3 was inserted into both of the upstream and downstream regions of the antibody expression cassette (1.1k/Neo and 1.1k/Hyg); and (2) that where the gene expression stabilizing element CHO5Δ3-3 was inserted into both of the upstream and downstream regions of the antibody expression cassette and the mRNA destabilizing sequence (N4 sequence) was added to the drug-resistant gene (heavy chain: Pur; light chain: Hyg) (1.1k/Pur.N4 and 1.1k/Hyg.N4).

Each 4 μl of the above mixed plasmid was diluted with 68 μl of the Opti-MEM I Reduced-Serum Medium. On the other hand, 15 μl of lipofectamine 2000 was diluted with 68 μl of the Opti-MEM I Reduced-Serum Medium, mixed with the above plasmid mixed solution and allowed to stand at room temperature for 15 minutes. After that, each half volume thereof was added to the cells in 2 wells.

On the next day, the cells were recovered, centrifuged at 800 g for 3 minutes to remove the supernatant and suspended in 4 ml of EX-CELL CD CHO Serum-Free Medium for CHO Cells, chemically defined. For the thing where the gene expression stabilizing element CHO5Δ3-3 was inserted into both of the upstream and downstream regions of the expression cassette (1.1k/Neo, 1.1k/Hyg), antibiotics comprising 400 μg/ml of G418 and 200 μg/ml of HygroGold were added thereto while, for the thing where the gene expression stabilizing element CHO5Δ3-3 was inserted into both of the upstream and downstream regions of the expression cassette and mRNA destabilizing sequence (N4 sequence) was added to the drug-resistant gene (H chain: Pur; L chain: Hyg) (1.1k/Pur.N4, 1.1k/Hyg.N4), antibiotics comprising 7.5 μg/ml of puromycin and 200 μg/ml of HygroGold were added followed by subjecting to a selective culture.

After finishing the selective culture, cells were seeded on a 6-well plate at $4 \times 10^5$ cells per well. After cultivating for three days, the supernatant of the culture was recovered and the production amount of the KOD3G8 antibody in polyclone was measured by ELISA according to the same manner as in Example 27. FIG. 52 shows a graph where the antibody production amounts calculated on the basis of a calibration curve prepared from the standard substance were plotted. As a result, it was confirmed that, in the case the serum-free adapted CHO-K1 cells were used, high productivity was achieved by using 1.1k/Pur.N4 and 1.1k/Hyg.N4, as in the case of the CHO-K1 cells which were not subjected to a serum-free adaptation, shown in Example 27. Generally, in an industrial production of biopharmaceuticals, etc., highly productive cells are screened and then subjected to a serum-free adaptation during one to two month(s). When gene is transferred to the cells which were subjected to a serum-free adaptation in advance, it is expected that the serum-free adaptation step is able to be eliminated. From the result of this Example, it was confirmed that, even in the serum-free adapted CHO cells, the cells having high productivity are able to be procured by the utilization of the gene expression stabilizing element and the drug selective marker gene expression cassette containing the mRNA destabilizing sequence of the present invention and it was confirmed that the cells having high productivity is able to be established within far shorter time.

Example 30

Comparison of 2-Construct Antibody Expression System with Single Vector Antibody Expression System in Anti-KOD Antibody Expression System (1) Construction of pEF1α-KOD3G8LC,HC-Pur.N4-1.1k/1.1k After that, in order to check whether highly productive cells are able to be procured even when the H chain expression cassette and the L chain expression cassette are aligned on one vector, pEF1α-KOD3G8LC,HC-Pur.N4-1.1k/1.1k was constructed according to a scheme shown in FIG. 53.

Incidentally, when the H chain (heavy chain) expression cassette and the L chain (light chain) expression cassette are aligned on different vectors, that is called "2-construct antibody expression system" or simply "2-contract" while, when the H chain expression cassette and the L chain expression cassette are aligned on one vector, that is called "single vector antibody expression system" or simply "single vector".

Firstly, pEF1α-KOD3G8HC-Pur.N4-1.1k/1.1k-S where a restriction enzyme site for insertion of the L chain expression cassette was inserted into pEF1α-KOD3G8HC-Pur.N4-1.1k/1.1k was constructed. Thus, pEF1α-KOD3G8HC-Pur.N4-1.1k/1.1k mentioned in Example 26 was treated with the restriction enzymes BglII and MluI to excise an EF-1α promoter. On the other hand, the EF-1α promoter was prepared from pEF1α-KOD3G8HC-1.1k constructed during the process of Example 16 by PCR amplification using the primers of SEQ ID Nos: 58 and 59 followed by treating with BglII and MluI, and this promoter was transferred into the sites of BglII and MluI of pEF1α-KOD3G8HC-Pur.N4-1.1k/1.1k to construct pEF1α-KOD3G8HC-Pur.N4-1.1k/1.1k-S where BglII, SphI and SpeI sites were inserted into the upstream region of the EF-1α promoter.

After that, pEF1α-KOD3G8HC-Pur.N4-1.1k/1.1k-S was treated with BglII and SpeI. On the other hand, the L chain expression cassette of anti-KOD antibody was prepared from pEF1α-KOD3G8LC-RE2 constructed during the process of Example 6 by PCR amplification using the primers of SEQ ID Nos: 60 and 61 followed by treating with BglII and SpeI, and this expression cassette was transferred into BglII and SpeI sites of pEF1α-KOD3G8HC-Pur.N4-1.1k/1.1k-S to construct a single vector pEF1α-KOD3G8LC,HC-Pur.N4-1.1k/1.1k.

Example 31

(2) Comparison of a 2-Construct Antibody Expression System and a Single Vector Antibody Expression System in Polyclone in the Anti-KOD Antibody Expression System Investigation was conducted in order to check whether a clone having a high antibody production amount is able to be obtained in the single vector antibody expression system the same as in the case of the 2-construct antibody expression system. As a 2-construct antibody expression system, the vectors in which a gene expression stabilizing element CHO5Δ3-3 was inserted into both of the upstream and downstream regions of the antibody expression cassette and mRNA destabilizing sequence (N4 sequence) was added to a drug-resistant gene (heavy chain: Pur, light chain: Hyg) (1.1k/Pur.N4 and 1.1k/Hyg.N4), for which the best result was achieved in Examples 27 and 28, were used. Then, a plasmid (already linearized with the restriction enzyme AhdI) where a heavy chain expression construct of the antibody and a light chain expression construct of the antibody were mixed to make their ratio by weight 1:1 was used for the transfection. Further, as a single vector antibody expression system, pEF1α-KOD3G8LC,HC-Pur.N4-1.1k/1.1k constructed in Example 30 was linearized by a restriction enzyme AhdI and used for the transfection. Each plasmid (2 μg) was transfected to the CHO-K1 cells prepared by the method of Example 2 followed by cultivating for 24 hours. On the next day, the medium was removed and the cells were dispersed using 2.5 g/l-trypsin and 1 mmol/l-EDTA solution, transferred to a 90-mm Petri dish and subjected to a selective culture for two weeks in a Ham's F12 medium supplemented with 10% FBS and 7.5 μg/ml puromycin and 400 μg/ml of HygroGold in the case of a 2-construct expression system while, in the case of a single vector system, in a Ham's F12 medium supplemented with 10% FBS and 10 μg/ml puromycin. During the selective culture, the medium was exchanged every 3 to 4 days. After finishing the selective culture, the cells were dispersed by treating with 2.5 g/l-trypsin and 1 mmol/l-EDTA solution and were seeded on a 6-well plate at $1.84 \times 10^5$ cells per well. After cultivating for three days, the supernatant of the culture was recovered and the produced amount of KOD3G8 antibody in the polyclone was measured by ELISA according to the same method as in Example 27.

Antibody concentration was calculated on the basis of a calibration curve prepared from the standard substance. The result is shown in FIG. 54. As a result, it was found that there was almost no difference in the producing amount of the antibody between the 2-construct antibody expression system and the single vector antibody expression system.

Example 32

(2) Comparison of a 2-Construct Antibody Expression System and a Single Vector Antibody Expression System in Monoclone in the Anti-KOD Antibody Expression System After that, concerning each of the 2-construct antibody expression system and the single vector antibody expression system, cell group generated after the selection was subjected to a limiting dilution and the productivity in monoclone was compared.

To be more specific, polyclone cells of Example 31 which stably expressed the KOD3G8 antibody were treated with 2.5 g/l-trypsin and 1 mmol/l-EDTA solution to disperse the cells followed by sowing on a 96-well plate in a concentration of 0.75 cell/well. After cultivating for two weeks, the supernatant of the culture was recovered and the production amount of the KOD3G8 antibody was measured by ELISA according to the same manner as in Example 27. Antibody production amount of each clone was calculated on the basis of a calibration curve prepared from the standard substance. The clones showing the high expression amount in each of the 2-construct antibody expression system and the single vector antibody expression system were selected. After the selected clones were subjected to an expansive culture, cells were seeded on a 6-well plate at $1.84 \times 10^5$ cells per well. After cultivating for three days, the supernatant of the culture was recovered and the production amount of KOD3G8 antibody in monoclone was measured by ELISA according to the same manner as in Example 27.

FIG. 55 shows a graph where produced amounts of the antibody of five clones showing the best expression amount calculated on the basis of the calibration curve prepared from the standard sample were plotted. As a result, it was found that, the same as in the result for the polyclone, there was almost no difference in the producing amount of the antibody between the single vector antibody expression system and the 2-construct antibody expression system. From this fact, it was found that, in the singe vector antibody expression system, it is also possible to procure the clone having high production amount of the antibody the same as in the case of the 2-construct antibody expression system.

Example 33

Confirmation of Effect by Deletion of Restriction Enzyme Recognition Sequence from Each Sequence Element in Expression Vector
(1) Deletion of Restriction Enzyme Recognition Sequence from CHO5Δ3-3

After that, a restriction enzyme recognition sequence was deleted from a gene expression stabilizing element CHO5Δ3-3. Firstly, there was constructed pEF1α-KOD3G8HC-1.1k-ΔRE where the restriction enzyme SadI site existing in CHO5Δ-3-3 was deleted by inverse PCR using the primers of SEQ ID Nos: 62 and 63, the KOD-Plus-Mutagenesis Kit and pEF1α-KOD3G8HC-1.1k mentioned in Example 16 as a template. Next, there was constructed pEF1α-KOD3G8HC-1.1k-ΔRE2 where the restriction enzyme SmaI site existing in CHO5Δ3-3 was deleted by inverse PCR using the primers of SEQ ID Nos: 64 and 65, the KOD-Plus-Mutagenesis Kit and pEF1α-KOD3G8HC-1.1k-ΔRE as a template. Moreover, there was constructed pEF1α-KOD3G8HC-1.1k-ΔRE3 where the restriction enzyme BamHI site existing in CHO5Δ3-3 was deleted by inverse PCR using the primers of SEQ ID Nos: 66 and 67, the KOD-Plus-Mutagenesis Kit and pEF1α-KOD3G8HC-1.1k-ΔRE2 as a template. Finally, there was constructed pEF1α-KOD3G8HC-1.1k-ΔRE4 where the restriction enzyme HindIII site existing in CHO5Δ3-3 was deleted by inverse PCR using the primers of SEQ ID Nos: 68 and 69, the KOD-Plus-Mutagenesis Kit and pEF1α-KOD3G8HC-1.1k-ΔRE3 as a template.

Example 34

(2) Construction of pEHX

There was constructed pEHX mentioned in FIG. 56 which contained multiple cloning site and the gene expression stabilizing element CHO5Δ3-3 prepared in Example 33 wherefrom four restriction enzyme recognition sequences were deleted. This sequence was aligned in the upstream and downstream regions of the expression cassette. To be more specific, there was constructed pEF1α-SNAP26m-Pur2.N4-ΔH where the restriction enzyme HindIII site existing in downstream of SV40 promoter was deleted by inverse PCR using the primers of SEQ ID Nos: 70 and 71, the KOD-Plus-Mutagenesis Kit and pEF1α-SNAP26m-Pur2.N4 mentioned in Example 16 as a template. Next, there was constructed pEF1α-SNAP26m-Pur3.N4-ΔH where the restriction enzyme SalI site existing in puromycin-resistant gene was deleted by inverse PCR using the primers of SEQ ID Nos: 72 and 73, the KOD-Plus-Mutagenesis Kit and pEF1α-SNAP26m-Pur2.N4-ΔH as a template. Moreover, there was constructed pEF1α-SNAP26m-Pur4.N4-ΔH where the restriction enzyme SmaI site existing in puromycin-resistant gene was deleted by inverse PCR using the primers of SEQ ID Nos: 74 and 75, the KOD-Plus-Mutagenesis Kit and pEF1α-SNAP26m-Pur3.N4-ΔH as a template. After that, there was constructed pEF1α-SNAP26m-Pur4.N4-ΔH-Δf1 where f1 origin of replication was deleted by inverse PCR using the primers of SEQ ID Nos: 76 and 77, the KOD-Plus-Mutagenesis Kit and pEF1α-SNAP26m-Pur4.N4-ΔH as a template.

After that, there was constructed pEF1α-SNAP26m-Pur4.N4-ΔH-Δf1-RE into which the sites of the restriction enzymes NheI, EcoRI and SpeI were inserted by inverse PCR using the primers of SEQ ID Nos: 78 and 79, the KOD-Plus-Mutagenesis Kit and pEF1α-SNAP26m-Pur4.N4-ΔH-Δf1 as a template. After that, there was constructed pEF1α-MCSpre-Pur4.N4-ΔH-Δf1-RE into which the sites of the restriction enzymes HindIII, BsiWI, XbaI, and BclI were inserted by inverse PCR using the primers of SEQ ID Nos: 80 and 81, the KOD-Plus-Mutagenesis Kit and pEF1α-SNAP26m-Pur4.N4-ΔH-Δf1-RE as a template. Then, there was constructed pEF1α-MCS-Pur4.N4-ΔH-Δf1-RE by inserting, into the HindIII and XbaI sites of pEF-1α-MCSpre-Pur4.N4-ΔH-Δf1-RE, the DNA fragments prepared by mixing the primer of SEQ ID No: 82 with the primer of SEQ ID No: 83 followed by annealing with a gradual temperature fall from 95° C. to 60° C. After that, there was constructed pEF1α-MCS-Pur4.N4-1.1k by inserting the CHO5Δ3-3 wherefrom four restriction enzyme recognition sequences were deleted which was prepared by PCR using pEF1α-KOD3G8HC-1.1k-ΔRE4 as a template and the primers of SEQ ID Nos: 84 and 85, into the NheI and EcoRI sites of pEF1α-MCS-Pur4.N4-ΔH-Δf1-RE. Furthermore, there was constructed pEHX by inserting the CHO5Δ3-3 wherefrom four restriction enzyme recognition sequences were deleted which was prepared by PCR using pEF1α-KOD3G8HC-1.1k-ΔRE4 as a template and the primers of SEQ ID Nos: 52 and 86, into the BamHI and XhoI sites of pEF1α-MCS-Pur4.N4-1.1k.

Example 35

(3) Construction of pEH (M-SNAP26m-N) and pEH (B-SNAP26m-N)

After that, in order to confirm the effect of deletion of the restriction enzyme sites from the element, SNAP26m gene was inserted into the multiple cloning site of pEHX. To be more specific, SNAP26m gene was amplified using pSNAPm as a template and a primer set of SEQ ID Nos: 3 and 20, and was inserted into the MluI and NotI sites of pEHX to construct pEH (M-SNAP26m-N). Similarly, SNAP26m gene was amplified using pSNAPm as a template and a primer set of SEQ ID Nos: 3 and 87, and was inserted into the BsiWI and NotI sites of pEHX to construct pEH (B-SNAP26m-N).

Example 36

(4) Investigation of the Effect by Deletion of Restriction Enzyme Recognition Sequence from CHO5Δ3-3 in a SNAP26m Expression System CHO-K1 cells for a transfection was prepared by the method mentioned in Example 2. On the other hand, the SNAP26m expression construct pEF1α-SNAP26m-Pur.N4-1.1k/1.1k constructed in Example 16 and the SNAP26m expression constructs constructed in Example 35 were linearized using a restriction enzyme AhdI. Transfection was carried out by the method mentioned in Example 5, and on the next day of the transfection, the medium was removed and the cells were dispersed by treating with 2.5 g/l-trypsin and 1 mmol/l-EDTA solution, transferred to a 90-mm Petri dish and subjected to a selective culture for two weeks in Ham's F12 mediums supplemented with 10% FBS and 7.5 or 10 μg/ml puromycin. During the selective culture, the medium was exchanged every three to four days. After finishing the selective culture, the expression intensity of SNAP26m of the cell group was analyzed using the method mentioned in the Example 2.

FIG. 58 shows the result of FACS analysis of the cell group generated after transfection of pEF1α-SNAP26m-Pur.N4-1.1k/1.1k, pEH (M-SNAP26m-N), or pEH (B-SNAP26m-N) and the drug selection. FIG. 59 shows a plot of the rates of the cells where the fluorescence intensity FL1 was not less than 200 and not less than 1000 respectively. As a result, it was noted that the rate of the cells which highly express the SNAPm was much more when a plasmid containing CHO5Δ3-3 wherefrom four restriction enzyme recognition sequences were deleted was used regardless of the concentration of puromycin during the drug selection. It was also noted that, when SNAP26m gene was inserted into pEHX, the rate of the cells which highly express the SNAPm was much more regardless of the restriction enzyme site used for inserting SNAP26m gene.

Example 37

Confirmation of Effect by Deletion of Restriction Enzyme Recognition Sequence from Each Sequence Element of Expression Vector in Antibody Production System
(1) Construction of pELX There was constructed pELX mentioned in FIG. 60 containing a multiple cloning site. To be more specific, there was constructed pEF1α-KOD3G8LC-Hyg-RE3 into which the sites of the restriction enzymes BglII and SalI were inserted by inverse PCR using the primers of SEQ ID Nos: 88 and 89, the KOD-Plus-Mutagenesis Kit and pEF1α-KOD3G8LC-Hyg-RE2 constructed during the process of Example 6 as a template. After that, there was constructed pEF1α-KOD3G8LC-RE4 where f1 origin of replication and expression cassette of hygromycin-resistant gene were deleted and into which the sites of the restriction enzymes EcoRI and SpeI were inserted by inverse PCR using the primers of SEQ ID Nos: 90 and 91, the KOD-Plus-Mutagenesis Kit and pEF1α-KOD3G8LC-Hyg-RE3 as a template. After that, there was constructed pEF1α-MCSpre-RE4 by inserting the sites of the restriction enzymes HindIII, BsiWI, XbaI, and BclI by inverse PCR using the primers of SEQ ID Nos: 80 and 81, the KOD-Plus-Mutagenesis Kit and pEF1α-KOD3G8LC-RE4 as a template. Then, there was constructed pELX by inserting, into the sites of the restriction enzymes HindIII and XbaI of pEF1α-MCSpre-RE4, the DNA fragments prepared by mixing the primer of SEQ ID No: 82 with the primer of SEQ ID No: 83 followed by annealing with a gradual temperature fall from 95° C. to 60° C.

Example 38

(2) Construction of Anti-KOD Antibody Expression Vector: pELH (KOD3G8)

Then, in order to confirm the effect by deletion of the restriction enzyme sites from the element in the anti-KOD antibody expression system, pELH (KOD3G8) was constructed.

Firstly, each of the heavy chain gene and the light chain gene of the anti-KOD antibody was inserted into the sites of the restriction enzymes MluI and NotI of pEHX and pELX to construct pEH (KOD3G8) and pEL (KOD3G8). To be more specific, the heavy chain gene of the anti-KOD antibody was prepared from pEF1α-KOD3G8HC mentioned in Example 4 by PCR amplification using the primers of SEQ ID Nos: 56 and 57 followed by treating with the restriction enzymes MluI and NotI, and this gene was transferred into the sites of the restriction enzyme MluI and NotI of pEHX to construct pEH (KOD3G8). Similarly, the light chain gene of the anti-KOD antibody was prepared from pEF1α-KOD3G8LC mentioned in Example 6 by PCR amplification using the primers of SEQ ID Nos: 56 and 57 followed by treating with the restriction enzymes MluI and NotI, and this gene was transferred into the sites of the restriction enzyme MluI and NotI of pELX to construct pEL (KOD3G8).

Then a light chain expression cassette of the anti-KOD antibody was prepared by treating the pEL (KOD3G8) with BglII, SpeI and ScaI according to the scheme shown in FIG. 61, and was inserted into the sites of the restriction enzymes BglII and SpeI of pEH (KOD3G8) to construct pELH (KOD3G8).

Example 39

(3) Investigation of the Effect by Deletion of the Restriction Enzyme Recognition Sequence from CHO5Δ3-3 in Polyclone in the Anti-KOD Antibody Expression System The effect by deletion of the restriction enzyme recognition sequence in CHO5Δ3-3 was investigated in the anti-KOD antibody expression system. The pEF1α-KOD3G8LC, HC-Pur.N4-1.1k/1.1k (1.1k) constructed in Example 30 was used as a single vector for expression of anti-KOD antibody where the gene expression stabilizing sequence CHO5Δ3-3 wherefrom no restriction enzyme recognition sequence was deleted was inserted into both of the upstream and downstream regions of the expression cassette. Further, the pELH (KOD3G8) (1.1k-ΔRE) constructed in Example 38 was used as a single vector for expression of anti-KOD antibody wherein CHO5Δ3-3 wherefrom four restriction enzyme recognition sequences were deleted was inserted into both of the upstream and downstream regions of expression cassette. Each plasmid (2 μg) linearized with the restriction enzyme AhdI was transfected to the CHO-K1 cells prepared by the method of Example 2 followed by cultivating for 24 hours. On the next day, the medium was removed and the cells were dispersed using 2.5 g/l-trypsin and 1 mmol/l-EDTA solution, transferred to a 90-mm Petri dish and subjected to a selective culture for two weeks in a Ham's F12 medium supplemented with 10% FBS and 10 μg/ml puromycin. During the selective culture, the medium was exchanged every 3 to 4 days. After finishing the selective culture, the cells were dispersed by treating with 2.5 g/l-trypsin and 1 mmol/l-EDTA solution and were seeded on a 6-well plate at $1.84 \times 10^5$ cells per well. After cultivating for three days, the supernatant of the culture was recovered and the produced amount of KOD3G8 antibody in the polyclone was measured by ELISA according to the same method as in Example 27.

Antibody concentration was calculated on the basis of a calibration curve prepared from the standard substance. The result is shown in FIG. 62. As a result, it was found that the producing amount of antibody was higher when there was used pELH (KOD3G8) (1.1k-ΔRE), which is a single vector for anti-KOD antibody expression where CHO5Δ3-3 wherefrom four restriction enzyme recognition sequences were deleted was inserted into both of the upstream and downstream regions of the expression cassette.

Example 40

(4) Investigation of the Effect by Deletion of the Restriction enzyme Recognition Sequence from CHO5Δ3-3 in Monoclone in the Anti-KOD Antibody Expression System After that, concerning each of the cases where the restriction enzyme recognition sequence in CHO5Δ3-3 was not/was deleted, cell group generated after the selection was subjected to a limiting dilution and the productivity in monoclone was compared.

To be more specific, polyclone cells of Example 39 which stably expressed the KOD3G8 antibody were treated with 2.5 g/l-trypsin and 1 mmol/l-EDTA solution to disperse the cells followed by sowing on a 96-well plate in a concentration of 0.75 cell/well. After cultivating for two weeks, the supernatant of the culture was recovered and the production amount of the KOD3G8 antibody was measured by ELISA according to the same manner as in Example 27. Antibody production amount of each clone was calculated on the basis of a calibration curve prepared from the standard substance. The clone showing the high expression amount in each of the cases where the restriction enzyme recognition sequence in CHO5Δ3-3 was not/was deleted was selected. After the selected clone was subjected to an expansive culture, cells were seeded on a 6-well plate at $1.84 \times 10^5$ cells per well. After cultivating for three days, the supernatant of the culture was recovered and the production amount of KOD3G8 antibody in monoclone was measured by ELISA according to the same manner as in Example 27.

FIG. 63 shows a graph where produced amounts of the antibody of five clones showing the best expression amount calculated on the basis of the calibration curve prepared from the standard sample were plotted. As a result, it was found that, the same as in the result in the case of polyclone, the producing amount of the antibody was higher when there was used pELH (KOD3G8) (1.1k-ΔRE), which is a single vector for the anti-KOD antibody expression where CHO5Δ3-3 wherefrom four restriction enzyme recognition sequences were deleted was inserted into both of the upstream and downstream regions of the expression cassette. From the above result, the conclusion will be that, when the restriction enzyme site was deleted from each sequence element of the expression vector, it was possible that, even in an antibody expression system, the process from cloning of the gene of aimed protein into the expression vector to construction of a highly expressive strain for aimed protein was carried out easily and efficiently.

Example 41

Confirmation of the Effect by Insertion of CHO5Δ3-3 Between the L Chain Expression Cassette and the H Chain Expression Cassette The effect by alignment of three or more gene expression stabilizing elements was tested. To be more specific, the effect by further insertion of gene expression stabilizing element between the two gene expression cassettes for the aimed protein in the expression vector where gene expression stabilizing element was aligned to the upstream and downstream regions of two gene expression cassettes for aimed protein and a drug selective marker gene expression cassette was tested by the following methods.

(1) Construction of pELX2 pELX2 shown by FIG. 64 was constructed where gene expression stabilizing element CHO5Δ3-3 wherefrom four restriction enzyme recognition sequences were deleted was aligned in the downstream region of the expression cassette of pELX constructed in Example 37. To be more specific, a restriction enzyme NheI site was added to the downstream region of the expression cassette using the primers of SEQ ID Nos: 90 and 92 by inverse PCR using the KOD-Plus-Mutagenesis Kit and the pELX constructed in Example 37 as a template to construct pELX-N. Then, there was constructed pELX2 by insertion of the gene expression stabilizing element CHO5Δ3-3 which was prepared by PCR amplification using the primer set of SEQ ID Nos: 50 and 93 and the pEF1α-KOD3G8HC-1.1k-ΔRE4 constructed in Example 33 as a template, into the NheI and EcoRI sites of pELX-N. In the gene expression stabilizing element CHO5Δ3-3 used in Examples 41 to 44, the restriction enzyme recognition sequences in four places were deleted.

Example 42

(2) Construction of Anti-KOD Antibody Expression Vector: pELH2 (KOD3G8)

After that, pELH2 (KOD3G8) was constructed in order to confirm the effect by insertion of CHO5Δ3-3 between the L chain expression cassette and the H chain expression cassette.

Firstly, the light chain gene of the anti-KOD antibody was inserted into the sites of the restriction enzymes MluI and NotI of pELX2 to construct pEL2 (KOD3G8). To be more specific, the light chain gene of the anti-KOD antibody was prepared from pEF1α-KOD3G8LC mentioned in Example 6 by PCR amplification using the primers of SEQ ID Nos: 56 and 57 followed by treating with the restriction enzymes MluI and NotI, and this gene was transferred into the sites of the restriction enzymes MluI and NotI of pELX2 to construct pEL2 (KOD3G8).

Then a light chain expression cassette of the anti-KOD antibody was prepared by treating the pEL2 (KOD3G8) with BglII, SpeI and ScaI according to the scheme shown in FIG. 65, and was inserted into the sites of the restriction enzymes BglII and SpeI of pEH (KOD3G8) constructed in Example 38 to construct pELH2 (KOD3G8).

Example 43

(3) Confirmation of the Effect by Insertion of CHO5Δ3-3 Between the L Chain Expression Cassette and the H Chain Expression Cassette in Polyclone in the Anti-KOD Antibody Expression System The effect by insertion of CHO5Δ3-3 between the L chain expression cassette and the H chain expression cassette in the anti-KOD antibody expression system was investigated during the stage of polyclone. The pELH2 (KOD3G8) constructed in Example 42 was used as a single vector for the anti-KOD antibody expression containing CHO5Δ3-3 between the L chain expression cassette and the H chain expression cassette. Further, as a comparative example, the pELH (KOD3G8) constructed in Example 38 was used as a single vector for the anti-KOD antibody expression containing no CHO5Δ3-3 between the L chain expression cassette and the H chain expression cassette. Each plasmid (2 μg) linearized with the restriction enzyme AhdI was transfected to the CHO-K1 cells prepared by the method of Example 2 followed by cultivating for 24 hours. On the next day, the medium was removed and the cells were dispersed using 2.5 g/l-trypsin and 1 mmol/l-EDTA solution, transferred to a 90-mm Petri dish and subjected to a selective culture for two weeks in a Ham's F12 medium supplemented with 10%. FBS and 10 μg/ml puromycin. During the selective culture, the medium was exchanged every 3 to 4 days. After finishing the selective culture, the cells were dispersed by treating with 2.5 g/l-trypsin and 1 mmol/l-EDTA solution and were seeded on a 6-well plate at $1.84 \times 10^5$ cells per well. After cultivating for three days, the supernatant of the culture was recovered and the produced amount of KOD3G8 antibody in the polyclone was measured by ELISA according to the same method as in Example 27.

Antibody concentration was calculated on the basis of a calibration curve prepared from the standard substance. The result is shown in FIG. 66. As a result, the use of pELH2 (KOD3G8), which is a single vector for expression of the anti-KOD antibody where CHO5Δ3-3 was also inserted between the L chain expression cassette and the H chain expression cassette showed the antibody production amount of about 1.5-fold higher as compared with the comparative example whereby the antibody production amount was significantly enhanced.

Example 44

(4) Confirmation of the Effect by Insertion of CHO5Δ3-3 Between the L Chain Expression Cassette and the H Chain Expression Cassette in Monoclone in the Anti-KOD Antibody Expression System After that, limiting dilution was conducted for each of the cell group transformed by an expression vector (pELH2 (KOD3G8)) having CHO5Δ3-3 between the L chain expression cassette and the H chain expression cassette, and the cell group transformed by an expression vector (pELH (KOD3G8)) having no CHO5Δ3-3 between the L chain expression cassette and the H chain expression cassette as a comparative example, and comparison in terms of productivity was carried out in monoclone.

To be more specific, polyclone cells of Example 43 which stably expressed the KOD3G8 antibody were treated with 2.5 g/l-trypsin and 1 mmol/l-EDTA solution to disperse the cells followed by sowing on a 96-well plate in a concentration of 0.75 cell/well. After cultivating for two weeks, the supernatant of the culture was recovered and the production amount of the KOD3G8 antibody was measured by ELISA according to the same manner as in Example 27. Antibody production amount of each clone was calculated on the basis of a calibration curve prepared from the standard substance. The clone showing the high expression amount in each of the cases where CHO5Δ3-3 is/is not contained between the L chain expression cassette and the H chain expression cassette was selected. After the selected clone was subjected to an expansive culture, cells were seeded on a 6-well plate at $1.84 \times 10^5$ cells per well. After cultivating for three days, the supernatant of the culture was recovered and the production amount of KOD3G8 antibody in monoclone was measured by ELISA according to the same manner as in Example 27.

FIG. 67 shows a graph where produced amounts of the antibody of five clones showing the best expression amount calculated on the basis of the calibration curve prepared from the standard sample were plotted. As a result, it was found that the use of pELH2 (KOD3G8), which is a single vector for expression of the anti-KOD antibody where CHO5Δ3-3 was inserted between the L chain expression cassette and the H chain expression cassette showed higher production of the antibody. Some cell strains showed twice or even higher production amount. From the result as such, it is apparent that the cell strain having far higher production of the antibody is able to be procured when the gene expression stabilizing sequence is also inserted between the L chain expression cassette and the H chain expression cassette.

Example 45

Confirmation of the Effect of the Expression Vector Made into Concatemer (1) Construction of Anti-KOD Antibody Expression Vector: pELH3 (KOD3G8)

In accordance with the scheme shown in FIG. 68, there was constructed pELH3 (KOD3G8) coding for each two copies of the H-chain expression cassette and the L chain expression cassette of the anti-KOD antibody and a drug selective marker gene expression cassette containing mRNA destabilizing sequence. Thus, into the sites of the restriction enzymes AseI and XhoI of the pELH (KOD3G8) constructed in Example 38, the DNA fragment consisting of the L chain expression cassette, the H chain expression cassette, the Puromycin-resistant gene expression cassette and gene expression stabilizing element CHO5Δ3-3 prepared by treating the pELH (KOD3G8) with the restriction enzymes AseI, SalI and NheI was inserted to construct pELH3 (KOD3G8).

Example 46

(2) Construction of Anti-KOD Antibody Expression Vector: pELH4 (KOD3G8)

In accordance with the scheme shown in FIG. 69, there was constructed pELH4 (KOD3G8) coding for each two copies of the H-chain and the L chain expression cassettes of the anti-KOD antibody and a Puromycin-resistant gene expression cassette and where gene expression stabilizing element CHO5Δ3-3 was inserted between the L chain expression cassette and H chain expression cassette. Thus, into the sites of the restriction enzymes AseI and XhoI of the pELH2 (KOD3G8) constructed in Example 42, the DNA fragment consisting of the L chain expression cassette, gene expression stabilizing element CHO5Δ3-3, the H chain expression cassette, the Puromycin-resistant gene expression cassette and gene expression stabilizing element CHO5Δ3-3 pprepared by treating the pELH2 (KOD3G8) with the restriction enzymes AseI, SalI and NheI was inserted to construct pELH4 (KOD3G8).

Example 47

(3) Confirmation of the Effect of the Concatemerized Expression Vector in Polyclone in the Anti-KOD Antibody Expression System The effect of the concatemerized expression vector was investigated in the anti-KOD antibody expression system. The pELH3 (KOD3G8) constructed in Example 45 and the pELH4 (KOD3G8) constructed in Example 46 were used as the concatemerzied expression vectors. Further, the pELH (KOD3G8) coding for each one copy of the H chain and the L chain expression cassettes of the anti-KOD antibody and Puromycin-resistant gene expression cassette constructed in Example 38 were used as the comparative example. Each plasmid (2 μg) linearized with the restriction enzyme AhdI was transfected to the CHO-K1 cells prepared by the method of Example 2 followed by cultivating for 24 hours. On the next day, the medium was removed and the cells were dispersed using 2.5 g/l-trypsin and 1 mmol/l-EDTA solution, transferred to a 90-mm Petri dish and subjected to a selective culture for two weeks in a Ham's F12 medium supplemented with 10% FBS and 10 μg/ml puromycin. During the selective culture, the medium was exchanged every 3 to 4 days. After finishing the selective culture, the cells were dispersed by treating with 2.5 g/l-trypsin and 1 mmol/l-EDTA solution and were seeded on a 6-well plate at $1.84 \times 10^5$ cells per well. After cultivating for three days, the supernatant of the culture was recovered and the produced amount of KOD3G8 antibody in the polyclone was measured by ELISA according to the same method as in Example 27.

Similar to Example 27, antibody concentration was calculated on the basis of a calibration curve prepared from the standard substance. The result is shown in FIG. 70. As a result, it was found that, when pELH3 (KOD3G8) or pELH4 (KOD3G8) which was an expression vector made into a concatemer was used, the production amount of the antibody was 1.5-times or even more higher in terms of relative ratio as compared with the control pELH (KOD3G8). Further, when the pELH4 (KOD3G8) where the gene expression stabilizing element CHO5Δ3-3 was also inserted between the L chain expression cassette and the H chain expression cassette was used, the production amount of the antibody was the highest and, as compared with the comparative example, twice or more higher production amount was achieved.

Example 48

(4) Confirmation of the Effect of the Concatemerized Expression Vector in Monoclone in the Anti-KOD Antibody Expression System Then, concerning the cells of polyclone procured by gene transfer in each of the expression vector pELH (KOD3G8), pELH3 (KOD3G8) and pELH4 (KOD3G8), cell group generated after the selection was subjected to a limiting dilution and productivity in monoclone was compared.

To be more specific, polyclone cells of Example 47 which stably expressed the KOD3G8 antibody were treated with 2.5 g/l-trypsin and 1 mmol/l-EDTA solution to disperse the cells followed by sowing on a 96-well plate in a concentration of 0.75 cell/well. After cultivating for two weeks, the supernatant of the culture was recovered and the production amount of the KOD3G8 antibody was measured by ELISA according to the same manner as in Example 27. Antibody production amount of each clone was calculated on the basis of a calibration curve prepared from the standard substance. The clone showing the high expression amount was selected for each of the cases transferred by the pELH (KOD3G8), pELH3 (KOD3G8) and pELH4 (KOD3G8) respectively. After the selected clone was subjected to an expansive culture, cells were seeded on a 6-well plate at $1.84 \times 10^5$ cells per well. After cultivating for three days, the supernatant of the culture was recovered and the production amount of KOD3G8 antibody in monoclone was measured by ELISA according to the same manner as in Example 27.

FIG. 71 shows a graph where produced amounts of the antibody of five clones showing the best expression amount calculated on the basis of the calibration curve prepared from the standard sample were plotted. As a result, it was found that, when pELH3 (KOD3G8) or pELH4 (KOD3G8) which was an expression vector made into a concatemer was used, production amount of the antibody was high as compared with the control pELH (KOD3G8) the same as in the case of the polyclone. Further, when the pELH4 (KOD3G8) where the gene expression stabilizing element CHO5Δ3-3 was also inserted between the L chain expression cassette and the H chain expression cassette was used, the production amount of the antibody was the highest. From the result as such, it is believed that, when an expression vector made into a concatemer is used for gene transfer, a cell strain having far higher production of the antibody is able to be quickly and efficiently procured.

Example 49

Preparation of Expression Vector Containing the Constant Region Gene of the Antibody and Investigation of the Effect of N4 sequence and CHO5Δ3-3 of Expression Vector Containing Constant Region Gene of the Antibody An expression vector containing the gene of the constant region of the light chain and/or the heavy chain of the antibody was prepared and the gene of variable region of the antibody was inserted into the expression vector to express the antibody molecule whereby the effect of the mRNA destabilizing sequence (N4 sequence) and the gene expression stabilizing element (CHO5Δ3-3) was confirmed.

(1) Deletion of Restriction Enzyme Recognition Sequence from CHO5Δ3-3

From the CHO5Δ3-3 wherefrom four restriction enzyme recognition sequences were deleted as constructed in Example 33, the restriction enzyme BlpI sites which were present in two places were further deleted. To be more specific, firstly, there was constructed pEF1α-KOD3G8HC-1.1k-ΔRE5 where one restriction enzyme BipI site existing in CHO5Δ3-3 was deleted by inverse PCR using the primers of SEQ ID Nos: 94 and 95, the KOD-Plus-Mutagenesis Kit, and the pEF1α-KOD3G8HC-1.1k-ΔRE4 constructed in Example 33 as a template. After that, there was constructed pEF1α-KOD3G8HC-1.1k-ΔRE6 where another restriction enzyme BipI site existing in CHO5Δ3-3 was deleted by inverse PCR using the primers of SEQ ID Nos: 96 and 97, the KOD-Plus-Mutagenesis Kit, and the pEF1α-KOD3G8HC-1.1k-ΔRE5 as a template.

Example 50

(2) Cloning of Human Heavy Chain Constant Region Gene Cγ1

Total RNA was extracted from human peripheral blood monocytes recovered from blood of healthy human treated with heparin using Sepasol RNAI Super (manufactured by Nakarai Tesk). Then, cDNA was synthesized by ReverTra Ace-α- (manufactured by Toyobo) using the total RNA as a template. After that, human γ1 constant region gene was amplified by PCR using the primers of SEQ ID Nos: 98 and 99 and the purified PCR product was subjected to a TA cloning to pTA vector (manufactured by Toyobo). Sequence of the constructed plasmid was confirmed by means of sequencing and the clone having the same sequence as the known sequence was named pTA-γ1.

Example 51

(3) Construction of pEHγX

A gene expression stabilizing element CHO5Δ3-3 wherefrom six restriction enzyme recognition sequences were deleted was aligned in the upstream and downstream regions of the expression cassette to construct pEHγX mentioned in FIG. 72 coding for human γ1 constant region gene. To be more specific, there was constructed pEF1α-MCS-Pur4.N4-1.1k-2 by insertion of CHO5Δ3-3 wherefrom six restriction enzyme recognition sequences were deleted prepared by PCR amplification using pEF1α-KOD3G8HC-1.1k-ΔRE6 constructed in Example 49 as a template and the primers of SEQ ID Nos: 50 and 51, into the sites of NheI and BglII of pEF1α-MCS-Pur4.N4-1.1k mentioned in Example 34. After that, there was constructed pEF1α-γ-Pur4.N4-1.1k by insertion of human γ1 constant region gene prepared by PCR amplification using pTA-γ1 mentioned in Example 50 as a template and the primers of SEQ ID Nos: 100 and 101, into the sites of XbaI and BclI of pEF1α-MCS-Pur4.N4-1.1k-2. After that, there was constructed pEF1α-γ-Pur4.N4-1.1k-RE where the EcoRI site of the upstream region of the EF1α promoter was substituted with NotI site by inverse PCR using the primers of SEQ ID Nos: 102 and 103, KOD-Plus-Mutagenesis Kit and pEF1α-γ-Pur4.N4-1.1k as a template. Moreover, there was constructed pEF1α-γ-Pur4.N4-1.1k-RE2 where the EcoRI site was inserted to the upstream region of the human γ1 constant region gene by inverse PCR using the primers of SEQ ID Nos: 104 and 105, KOD-Plus-Mutagenesis Kit and pEF1α-γ-Pur4.N4-1.1k-RE as a template. Then, there was constructed pEF1α-γ-Pur4.N4-1.1k/1.1k by insertion of CHO5Δ3-3 wherefrom six restriction enzyme recognition sequences were deleted prepared by PCR amplification using pEF1α-KOD3G8HC-1.1k-ΔRE6 constructed in Example 49 as a template and the primers of SEQ ID Nos: 52 and 86, into the sites of BamHI and XhoI of pEF1α-γ-Pur4.N4-1.1k-RE2. Finally, there was constructed pEHγx by inserting, into the BsiWI and EcoRI sites of pEF1α-γ-Pur4.N4-1.1k/1.1k, the DNA fragments prepared by mixing the primer of SEQ ID No: 106 with the primer of SEQ ID No: 107 followed by annealing with a gradual temperature fall from 95° C. to 60° C.

Example 52

(4) Cloning of Human Light Chain Constant Region Gene Cκ

Total RNA was extracted from human peripheral blood monocytes recovered from blood of healthy human treated with heparin using Sepasol RNAI Super (manufactured by Nakarai Tesk). Then, cDNA was synthesized by ReverTra Ace-α- (manufactured by Toyobo) using the total RNA as a template. After that, human κ constant region gene was amplified by PCR using the primers of SEQ ID Nos: 108 and 109 and the purified PCR product was subjected to a TA cloning to pTA vector. Sequence of the constructed plasmid was confirmed by means of sequencing and the clone having the same sequence as the known sequence was named pTA-κ.

Example 53

(5) Construction of pELκX

There was constructed pELκX mentioned in FIG. 73 coding for human κ constant region gene. To be more specific, there was constructed pELX-RE by deleting the sites of the restriction enzymes HindIII and BsiWI placed in the multiple cloning site by inverse PCR using KOD-Plus-Mutagenesis Kit, pELX mentioned in Example 37 as a template and the primers of SEQ ID Nos: 110 and 111. After that, there was constructed pEF1α-κ by insertion of human κ constant region gene prepared by PCR amplification using pTA-κ mentioned in Example 52 as a template and the primers of SEQ ID Nos: 112 and 113, into the sites of XbaI and BclI of pELX-RE. After that, there was constructed pEF1α-κ-RE where the EcoRI site of the downstream region of SV40 pA was substituted with NotI site by inverse PCR using the primers of SEQ ID Nos: 114 and 115, KOD-Plus-Mutagenesis Kit and pEF1α-κ as a template. Moreover, there was constructed pEF1α-κ-RE2 where the EcoRI, MluI, and EcoRV sites were inserted to the upstream region of human κ constant region gene by inverse PCR using the primers of SEQ ID Nos: 116 and 117, KOD-Plus-Mutagenesis Kit and pEF1α-κ-RE as a template. Finally, there was constructed pELκX by inserting, into the MluI and EcoRV sites of pEF1α-κ-RE2, the DNA fragments prepared by mixing the primer of SEQ ID No: 118 with the primer of SEQ ID No: 119 followed by annealing with a gradual temperature fall from 95° C. to 60° C.

Example 54

(6) Construction of Anti-KOD Antibody Expression Vector: pELκHγ (KOD3G8)

After that pELκHγ (KOD3G8) was constructed in order to confirm the effect of N4 sequence and CHO5Δ3-3 in a mouse-human chimera antibody expression system utilizing the variable region gene of the anti-KOD antibody.

Firstly, a heavy chain variable region gene of the anti-KOD antibody was prepared by PCR amplification using pEH (KOD3G8) mentioned in Example 38 as a template and the primers of SEQ ID Nos: 56 and 120 followed by treating with the restriction enzymes HindIII and NheI, and this gene was inserted into the sites of the restriction enzymes HindIII and NheI of pEHγX constructed in Example 51 to prepare pEHγ (KOD3G8).

After that, a light chain variable region gene of the anti-KOD antibody was prepared by PCR amplification using pEL (KOD3G8) mentioned in Example 38 as a template and the primers of SEQ ID Nos: 56 and 121 followed by treating with the restriction enzymes MluI and BsiWI, and this gene was inserted into the sites of the restriction enzymes MluI and BsiWI of pELκX constructed in Example 53 to prepare pELκ (KOD3G8).

Then a light chain expression cassette of the mouse-human chimera antibody was prepared by treating the pELκ (KOD3G8) with BglII, NotI and ScaI according to the scheme shown in FIG. 74, and was inserted into the sites of the restriction enzymes BglII and NotI of pEHγ (KOD3G8) to construct pELκHγ (KOD3G8).

Example 55

(7) Construction of pcHγX

Then pcHγX mentioned in FIG. 75 where N4 sequence and gene expression stabilizing element CHO5Δ3-3 were deleted from pEHγX was constructed. To be more specific, there was constructed pEF1α-7-Pur4-1.1k where N4 sequence was deleted by inverse PCR using the primers of SEQ ID Nos: 16 and 17, KOD-Plus-Mutagenesis kit and pEF1α-γ-Pur4.N4-1.1k-RE2 mentioned in Example 51 as a template. After that, there was constructed pEF1α-γ-Pur4 where the gene expression stabilizing element CHO5Δ3-3 was deleted by inverse PCR using the primers of SEQ ID Nos: 122 and 123, KOD-Plus-Mutagenesis Kit and pEF1α-γ-Pur4-1.1k as a template. Finally, there was constructed pcHγX by inserting, into the BsiWI and EcoRI sites of pEF1α-γ-Pur4, the DNA fragments prepared by mixing the primer of SEQ ID No: 106 with the primer of SEQ ID No: 107 followed by annealing with a gradual temperature fall from 95° C. to 60° C.

Example 56

(8) Construction of Anti-KOD Antibody Expression Vector: pcLκHγ (KOD3G8)

After that, in order to confirm the effect of the mRNA destabilizing sequence (N4 sequence) and the gene expression stabilizing element (CHO5Δ3-3), pcLκHγ (KOD3G8) where the mRNA destabilizing sequence and the gene expression stabilizing element were deleted in the mouse-human chimera antibody expression system utilizing the variable region gene of the anti-KOD antibody was constructed as a control.

Firstly, a heavy chain variable region gene of the anti-KOD antibody was prepared by PCR amplification using pEH (KOD3G8) mentioned in Example 38 as a template and the primers of SEQ ID Nos: 56 and 120 followed by treating with the restriction enzymes HindIII and NheI, and this gene was inserted into the sites of the restriction enzymes HindIII and NheI of pcHγX constructed in Example 55 to prepare pcHγ (KOD3G8).

Then a light chain expression cassette of the mouse-human chimera antibody was prepared by treating the pELκ (KOD3G8) constructed in Example 54 with BglII, NotI and ScaI according to the scheme shown in FIG. 76, and was inserted into the sites of the restriction enzymes BglII and NotI of pcHγ (KOD3G8) to construct pcLκHγ (KOD3G8).

Example 57

(9) Confirmation of the Effect of N4 Sequence and CHO5Δ3-3 in Polyclone in the Mouse-Human Chimera Antibody Expression System The effect of N4 sequence and CHO5Δ3-3 was investigated in the mouse-human chimera antibody expression system utilizing the variable region gene of the anti-KOD antibody. As a construct containing the N4 sequence and the CHO5Δ3-3, pELκHγ (KOD3G8) constructed in Example 54 was used while, as a construct containing no N4 sequence and CHO5Δ3-3, the pcLκHγ (KOD3G8) constructed in Example 56 was used. Each plasmid (2 linearized with the restriction enzyme AhdI was transfected to the CHO-K1 cells prepared by the method of Example 2 followed by cultivating for 24 hours. On the next day, the medium was removed and the cells were dispersed using 2.5 g/l-trypsin and 1 mmol/l-EDTA solution, transferred to a 90-mm Petri dish and subjected to a selective culture for two weeks in a Ham's F12 medium supplemented with 10% FBS and 10 µg/ml puromycin. During the selective culture, the medium was exchanged every 3 to 4 days. After finishing the selective culture, the cells were dispersed by treating with 2.5 g/l-trypsin and 1 mmol/l-EDTA solution and were seeded on a 6-well plate at $1.84 \times 10^5$ cells per well. After cultivating for three days, the supernatant of the culture was recovered and the produced amount of KOD3G8 antibody in the polyclone was measured by ELISA according to the same method as in Example 27.

Antibody concentration was calculated on the basis of a calibration curve prepared from the standard substance. The result is shown in FIG. 77. As a result, when pELκHγ (KOD3G8), which is the chimera antibody expression vector containing N4 sequence and CHO5Δ3-3 was used, production amount of the antibody was about four times higher than pcLκHγ (KOD3G8) which is a control. It has been clarified that, when an expression vector coding for the constant region gene of human antibody in addition to the N4 sequence and the CHO5Δ3-3 is used, the chimera antibody expression vector where the constant region is a human type and the vector which expresses the variable region gene procured by a phage display method, etc. as a complete antibody are able to be easily and conveniently constructed and further that the process until establishment of the highly antibody-expressing strain is able to be carried out easily and within a short period.

Industrial Applicability

By using an expression vector of the present invention which is equipped with the nucleic acid region having a stabilizing function of gene expression and the weakened drug gene expression cassette, the cell which highly expresses the aimed protein gene is able to be obtained efficiently. Accordingly, the expression system in mammalian cells using the expression vector of the present invention greatly contributes not only in the function analysis of protein of various animal cells or, particularly, mammalian cells but also in the industries of drug discovery and medical service as biopharmaceuticals.

The invention claimed is:

1. An expression vector comprising a cassette for expressing a drug selective marker gene containing an mRNA destabilizing sequence, at least one element for stabilizing gene expression and a cassette for expressing a gene encoding a recombinant protein, wherein the element for stabilizing gene expression consists of any one of the following (a) to (d) or any combination thereof:
  (a) a DNA sequence consisting of the region from the 41601st base to the 46746th base of the sequence of SEQ ID NO: 26;
  (b) a DNA sequence consisting of a partial sequence of the region from the 41601st base to the 46746th base of the sequence of SEQ ID NO: 26, wherein the partial sequence comprises the region from the 41601st base to the 42700th base of the sequence of SEQ ID NO: 26;
  (c) the DNA sequence of (a) or (b), wherein a recognition sequence of at least one restriction enzyme selected from the following group has been deleted:
  AscI, BsiWI, BssHII, BstBI (Csp45I, NspV), CpoI, CspI (RsrII), FseI, HindIII, MfeI, MluI, NotI, PacI, PaeR71, SgrA1, SphI, XbaI, XhoI, BclI, BglII, BlpI, EcoRI, SalI, SpeI, EcoR105I (SnaBI), EcoRV, NruI, PsiI, SmaI, SrfI, SacI, and BamHI; and
  (d) a DNA sequence consisting of the sequence complementary to the DNA sequence of (a), (b), or (c).

2. The expression vector according to claim 1, wherein the mRNA destabilizing sequence is from AT-rich sequence existing in the 3'-untranslated region of cytokine, interleukin or proto-oncogene.

3. The expression vector according to claim 1, wherein the mRNA destabilizing sequence has a motif sequence of TTATTTA (A/T)(A/T).

4. The expression vector according to claim 3, wherein the motif sequence is repeated for two or more times.

5. The expression vector according to claim 4, wherein one or more base(s) of spacer sequence is contained between the repetition of the motif sequence.

6. The expression vector according to claim 3, wherein substitution, insertion or deletion of one to several base(s) is contained in the mRNA destabilizing sequence.

7. The expression vector according to claim 1, wherein the element for stabilizing the gene expression is aligned on the upstream region of the cassette for expressing the gene encoding the recombinant protein.

8. The expression vector according to claim 1, wherein the element for stabilizing the gene expression is aligned on both of the upstream and downstream regions of the cassette for expressing the gene encoding the recombinant protein.

9. The expression vector according to claim 1, wherein the drug selective marker gene is a gene that encodes a protein which is resistant to an antibiotic substance which inhibits protein synthesis.

10. The expression vector according to claim 9, wherein the protein encoded by the drug selective marker gene is selected from the group consisting of puromycin-N-acetyltransferase, hygromycin-B-phosphotransferase and neomycin phosphotransferase.

11. The expression vector according to claim 1, wherein the cassette for expressing the gene encoding the recombinant protein comprises a multiple cloning site for insertion of the gene encoding the recombinant protein.

12. The expression vector according to claim 1, wherein the recombinant protein is a heavy chain and/or light chain polypeptide(s) of an antibody.

13. A method for selecting a cell, said method comprises: transforming a host cell with the expression vector according to claim 1 to produce a transformed cell, subjecting the transformed cell to a drug selection, and selecting a cell which expresses the gene encoding the recombinant protein in a high level.

14. The method according to claim 13, wherein the host cell is a Chinese hamster ovary (CHO) cell.

15. The method according to claim 14, wherein the Chinese hamster ovary (CHO) cell is adapted to serum-free media.

16. A cell obtained by the method according to claim 13.

17. A method for producing a recombinant protein, said method comprises culturing the cell according to claim 16 to produce the recombinant protein.

* * * * *